United States Patent
Wang et al.

(10) Patent No.: US 11,142,528 B2
(45) Date of Patent: *Oct. 12, 2021

(54) SUBSTITUTED PYRAZOLO[1,5-A]PYRIMIDINES AS BRUTON'S TYROSINE KINASE MODULATORS

(71) Applicant: BEIGENE SWITZERLAND GMBH, Basel (CH)

(72) Inventors: Zhiwei Wang, Beijing (CN); Yunhang Guo, Beijing (CN)

(73) Assignee: BEIGENE SWITZERLAND GMBH, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/739,447

(22) Filed: Jan. 10, 2020

(65) Prior Publication Data
US 2020/0148690 A1  May 14, 2020

Related U.S. Application Data

(63) Continuation of application No. 15/969,864, filed on May 3, 2018, now Pat. No. 10,570,139, which is a continuation of application No. 15/359,871, filed on Nov. 23, 2016, now Pat. No. 10,005,782, which is a continuation of application No. 14/951,494, filed on Nov. 25, 2015, now Pat. No. 9,556,188, which is a continuation of application No. 14/723,417, filed on May 27, 2015, now Pat. No. 9,447,106, which is a continuation of application No. PCT/CN2014/075943, filed on Apr. 22, 2014.

(30) Foreign Application Priority Data

Apr. 25, 2013  (CN) .................. PCT/CN2013/074728

(51) Int. Cl.
| | |
|---|---|
| A61K 31/519 | (2006.01) |
| C07D 487/04 | (2006.01) |
| C07D 487/14 | (2006.01) |
| C07D 471/14 | (2006.01) |
| C07D 471/20 | (2006.01) |
| C07D 519/00 | (2006.01) |
| A61K 31/5517 | (2006.01) |
| C07D 487/20 | (2006.01) |
| A61K 31/4188 | (2006.01) |
| A61K 31/435 | (2006.01) |
| A61K 31/437 | (2006.01) |
| A61K 31/527 | (2006.01) |
| A61K 31/55 | (2006.01) |
| A61K 31/551 | (2006.01) |
| A61K 45/06 | (2006.01) |
| A61K 31/438 | (2006.01) |

(52) U.S. Cl.
CPC ........ *C07D 487/04* (2013.01); *A61K 31/4188* (2013.01); *A61K 31/435* (2013.01); *A61K 31/437* (2013.01); *A61K 31/438* (2013.01); *A61K 31/519* (2013.01); *A61K 31/527* (2013.01); *A61K 31/55* (2013.01); *A61K 31/551* (2013.01); *A61K 31/5517* (2013.01); *A61K 45/06* (2013.01); *C07D 471/14* (2013.01); *C07D 471/20* (2013.01); *C07D 487/14* (2013.01); *C07D 487/20* (2013.01); *C07D 519/00* (2013.01)

(58) Field of Classification Search
CPC ........................... A61K 31/519; C07D 487/04
USPC ..................................... 514/259.3; 544/281
See application file for complete search history.

(56) References Cited

U.S. PATENT DOCUMENTS

| | | | |
|---|---|---|---|
| 7,393,848 | B2 | 7/2008 | Currie et al. |
| 7,514,444 | B2 | 4/2009 | Honigberg et al. |
| 7,718,662 | B1 | 5/2010 | Chen et al. |

(Continued)

FOREIGN PATENT DOCUMENTS

| | | |
|---|---|---|
| GB | 1412017 | 10/1975 |
| JP | H 07-278148 A | 10/1995 |

(Continued)

OTHER PUBLICATIONS

Extended European Search Report for European Application No. 14787642.9, dated Jan. 26, 2016, 5 pages.

(Continued)

*Primary Examiner* — Douglas M Willis
(74) *Attorney, Agent, or Firm* — Cooley LLP

(57) ABSTRACT

The invention is fused heterocyclic compounds of formula (I), and salts thereof, compositions thereof, and methods of use therefor. In particular, disclosed herein are certain fused heterocyclic compounds that can be useful for inhibiting protein kinase, including Bruton's tyrosine kinase (Btk), and for treating disorders mediated thereby.

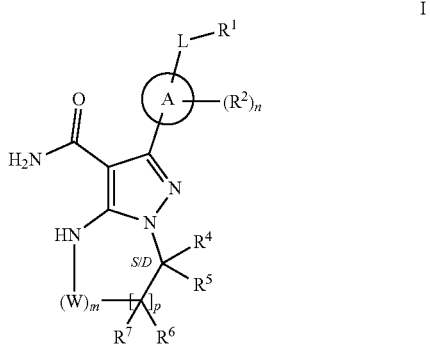

19 Claims, No Drawings

(56) References Cited

U.S. PATENT DOCUMENTS

| | | |
|---|---|---|
| 8,084,620 B2 | 12/2011 | Liu et al. |
| 9,447,106 B2 | 9/2016 | Wang et al. |
| 9,556,188 B2 | 1/2017 | Wang et al. |
| 10,005,782 B2 | 6/2018 | Wang et al. |
| 10,570,139 B2 | 2/2020 | Wang et al. |
| 2006/0178367 A1 | 8/2006 | Currie et al. |
| 2006/0183746 A1 | 8/2006 | Currie et al. |
| 2008/0076921 A1 | 3/2008 | Honigberg et al. |
| 2008/0139582 A1 | 6/2008 | Honigberg et al. |
| 2009/0105209 A1 | 4/2009 | Dewdney et al. |
| 2009/0318441 A1 | 12/2009 | Brain et al. |
| 2010/0004231 A1 | 1/2010 | Dewdney et al. |
| 2010/0016296 A1 | 1/2010 | Singh et al. |
| 2010/0016301 A1 | 1/2010 | Dewdney et al. |
| 2010/0029610 A1 | 2/2010 | Singh et al. |
| 2010/0035841 A1 | 2/2010 | Jankowski et al. |
| 2010/0087464 A1 | 4/2010 | Mi et al. |
| 2010/0105676 A1 | 4/2010 | Liu et al. |
| 2010/0144705 A1 | 6/2010 | Miller |
| 2010/0160292 A1 | 6/2010 | Whitney et al. |
| 2010/0160303 A1 | 6/2010 | Liu et al. |
| 2010/0222325 A1 | 9/2010 | Berthel et al. |
| 2010/0249092 A1 | 9/2010 | Singh et al. |
| 2010/0254905 A1 | 10/2010 | Honigberg et al. |
| 2011/0118233 A1 | 5/2011 | Blomgren et al. |
| 2011/0124640 A1 | 5/2011 | Liu et al. |
| 2011/0224235 A1 | 9/2011 | Honigberg et al. |
| 2011/0301145 A1 | 12/2011 | Barbosa, Jr. et al. |
| 2012/0028981 A1 | 2/2012 | Miller |
| 2012/0040961 A1 | 2/2012 | Gray et al. |
| 2012/0053189 A1 | 3/2012 | Loury |
| 2012/0058996 A1 | 3/2012 | Liu et al. |
| 2012/0077832 A1 | 3/2012 | Witowski et al. |
| 2012/0082702 A1 | 4/2012 | DeLucca et al. |
| 2012/0129852 A1 | 5/2012 | Duan et al. |
| 2012/0157442 A1 | 6/2012 | Bui et al. |
| 2012/0157443 A1 | 6/2012 | Bui et al. |
| 2012/0232054 A1 | 9/2012 | Moriarty et al. |
| 2013/0079327 A1 | 3/2013 | Yamamoto et al. |
| 2013/0096118 A1 | 4/2013 | Liu et al. |
| 2013/0116213 A1 | 5/2013 | Cha et al. |
| 2013/0261103 A1 | 10/2013 | Currie et al. |
| 2013/0281432 A1 | 10/2013 | Currie et al. |
| 2014/0045833 A1 | 2/2014 | Laurent et al. |
| 2014/0094459 A1 | 4/2014 | Goldstein et al. |
| 2014/0107151 A1 | 4/2014 | Goldstein et al. |
| 2014/0162983 A1 | 6/2014 | Hodous et al. |
| 2014/0221398 A1 | 8/2014 | Goldstein et al. |
| 2014/0243306 A1 | 8/2014 | Heng et al. |
| 2015/0079109 A1 | 3/2015 | Li et al. |
| 2015/0259354 A1 | 9/2015 | Wang et al. |
| 2016/0083392 A1 | 3/2016 | Wang et al. |
| 2017/0073349 A1 | 3/2017 | Wang et al. |
| 2018/0251466 A1 | 9/2018 | Wang et al. |
| 2019/0169201 A1 | 6/2019 | Wang et al. |

FOREIGN PATENT DOCUMENTS

| | | |
|---|---|---|
| WO | WO 2001/016138 A1 | 3/2001 |
| WO | WO 2001/019829 A2 | 3/2001 |
| WO | WO 2002/050071 A1 | 6/2002 |
| WO | WO 2002/072576 A1 | 9/2002 |
| WO | WO 2003/004497 A1 | 1/2003 |
| WO | WO 2004/017908 A2 | 3/2004 |
| WO | WO 2005/005429 A1 | 1/2005 |
| WO | WO 2005/011597 A2 | 2/2005 |
| WO | WO 2005/014599 A1 | 2/2005 |
| WO | WO 2005/047290 A2 | 5/2005 |
| WO | WO 2006/053121 A2 | 5/2006 |
| WO | WO 2006/065946 A1 | 6/2006 |
| WO | WO 2006/099075 A2 | 9/2006 |
| WO | WO 2007/026720 A1 | 3/2007 |
| WO | WO 2007/026950 A1 | 3/2007 |
| WO | WO 2007/027594 A1 | 3/2007 |
| WO | WO 2007/027729 A1 | 3/2007 |
| WO | WO 2007/087068 A2 | 8/2007 |
| WO | WO 2007/136790 A2 | 11/2007 |
| WO | WO 2008/033834 A1 | 3/2008 |
| WO | WO 2008/033854 A1 | 3/2008 |
| WO | WO 2008/033857 A2 | 3/2008 |
| WO | WO 2008/039218 A2 | 4/2008 |
| WO | WO 2008/054827 A2 | 5/2008 |
| WO | WO 2008/144253 A1 | 11/2008 |
| WO | WO 2009/039397 A2 | 3/2009 |
| WO | WO 2009/051822 A1 | 4/2009 |
| WO | WO 2009/077334 A1 | 6/2009 |
| WO | WO 2009/098144 A1 | 8/2009 |
| WO | WO 2009/158571 A1 | 12/2009 |
| WO | WO 2010/000633 A1 | 1/2010 |
| WO | WO 2010/006947 A1 | 1/2010 |
| WO | WO 2010/006970 A1 | 1/2010 |
| WO | WO 2010/028236 A1 | 3/2010 |
| WO | WO 2010/051549 A1 | 5/2010 |
| WO | WO 2010/065898 A2 | 6/2010 |
| WO | WO 2010/068788 A1 | 6/2010 |
| WO | WO 2010/068806 A1 | 6/2010 |
| WO | WO 2010/068810 A2 | 6/2010 |
| WO | WO 2010/122038 A1 | 10/2010 |
| WO | WO 2011/006074 A1 | 1/2011 |
| WO | WO 2011/140488 A1 | 11/2011 |
| WO | WO 2011/153514 A2 | 12/2011 |
| WO | WO 2012/020008 A1 | 2/2012 |
| WO | WO 2012/135801 A1 | 10/2012 |
| WO | WO 2012/143522 A1 | 10/2012 |
| WO | WO 2012/156334 A1 | 11/2012 |
| WO | WO 2012/158795 A1 | 11/2012 |
| WO | WO 2014/173289 A1 | 10/2014 |
| WO | WO 2015/061752 A1 | 4/2015 |
| WO | WO 2016/087994 A1 | 6/2016 |
| WO | WO 2016/100914 A1 | 6/2016 |
| WO | WO 2016/105582 A1 | 6/2016 |
| WO | WO 2017/046746 A1 | 3/2017 |
| WO | WO 2017/059224 A2 | 4/2017 |
| WO | WO 2018/033135 A1 | 2/2018 |
| WO | WO 2018/137681 A1 | 8/2018 |
| WO | WO 2018/193105 A1 | 10/2018 |
| WO | WO 2019/034009 A1 | 2/2019 |
| WO | WO 2019/108795 | 6/2019 |

OTHER PUBLICATIONS

International Search Report and Written Opinion for International Application No. PCT/CN2014/075943, dated Jul. 18, 2014, 10 pages.

International Search Report and Written Opinion for International Application No. PCT/IB2017/054955, dated Sep. 10, 2018, 16 pages.

International Search Report and Written Opinion for International Application No. PCT/CN2017/098023, dated Nov. 16, 2017, 10 pages.

International Search Report and Written Opinion for International Application No. PCT/US2018/063068, dated Feb. 27, 2019, 8 pages.

Bradshaw, J. M., "The Src, Syk, and Tec family kinases: Distinct types of molecular switches," Cell Signalling, 22:1175-1184 (2010).

Conley, M. E. et al., "Primary B Cell Immunodeficiencies: Comparisons and Contrasts," Annu. Rev. Immunol., 27:199-227 (2009).

Davis, R. E. et al., "Chronic active B-cell-receptor signalling in diffuse large B-cell lymphoma," Nature, 463:88-92 (2010).

Gurcan, H. M. et al., "A review of the current use of rituximab in autoimmune diseases," Int. Immunopharmacol., 9:10-25 (2009).

Hackam, D. G. et al., "Translation of research evidence from animals to humans," JAMA, 296(14):1731-1732 (2006).

Humphries, L. A. et al., "Tec Kinases Mediate Sustained Calcium Influx via Site-specific Tyrosine Phosphorylation of the Phospholipase Cγ Src Homology 2-Src Homology 3 Linker," J. Biol.Chem. 279(36):37651-37661 (2004).

Jenkins, S. M. et al., "Substituent variation in azabicyclic triazole- and tetrazole-based muscarinic receptor ligands," J. Med. Chem., 35(13):2392-2406 (1992).

Jordan, V. C., "Tamoxifen: A most unlikely pioneering medicine," Nature Reviews: Drug Discovery, 2:205-213(2003).

(56) References Cited

OTHER PUBLICATIONS

Khan, W. N., "Regulation of B lymphocyte development and activation by Bruton's tyrosine kinase," Immunol. Res., 23(2/3):147-156 (2001).
Kim, K.-H. et al., "Imidazo[1,5-a]quinoxalines as irreversible BTK inhibitors for the treatment of rheumatoid arthritis," Bioorg. Med. Chem. Lett, 21:6258-6263 (2011).
Lou, Y. et al., "Bruton's tyrosine kinase inhibitors: Approaches to potent and selective inhibition, preclinical and clinical evaluation for inflammatory diseases and B cell malignancies," J. Med. Chem., 55(10):4539-4550 (2012).
Mohamed, A. J. et al., "Bruton's tyrosine kinase (Btk): function, regulation, and transformation with special emphasis on the PH domain," Immunol. Rev., 228:58-73 (2009).
Pan, Z, "Bruton's tyrosine kinase as a drug discovery target," Drug News Perspect, 21(7):357-362 (2008).
Rokosz, L. L. et al., "Kinase inhibitors as drugs for chronic inflammatory and immunological diseases: progress and challenges," Expert Opin. Ther. Targets, 12(7):883-903 (2008).
Smith, C. I. E. et al., "Expression of Bruton's Agammaglobulinemia Tyrosine Kinase Gene, BTK, Is Selectively Down-Regulated in T Lymphocytes and Plasma Cells," J. Immunol., 152:557-565 (1994).
Takayama, T. et al., "Ring-fused pyrazole derivatives as potent inhibitors of lymphocyte-specific kinase (Lck): Structure, synthesis, and SAR," Bioorganic & Medicinal Chemistry Letters, 20(1):112-116 (Jan. 2010).
Takayama, T. et al., "Effects of the novel and potent lymphocyte-specific protein tyrosine kinase inhibitor TKM0150 on mixed lymphocyte reaction and contact hypersensitivity in mice," Arzneimittelforschung, 60(5):282-285 (2010).
Uckun, F. M. et al., "Bruton's tyrosine kinase as a new therapeutic target," Anti-Cancer Agents in Medicinal Chemistry, 7(6):624-632 (2007).
Vetrie, D. et al., "The gene involved in X-linked agammaglobulinaemia is a member of the src family of protein-tyrosine kinases," Nature, 361:226-233 (1993).
Wilson, W. H. et al., "686—The Bruton's Tyrosine Kinase (Btk) Inhibitor, Ibrutinib (PCI-32765), Has Preferential Activity in the ABC Subtype of Relapsed/Refractory De Novo Diffuse Large B-Cell Lymphoma (DLBCL): Interim Results of a Multicenter, Open-Label, Phase2 Study," Poster #686, 54th American Society of Hematology (ASH) annual meeting abstract (Dec. 10, 2012).
Extended European Search Report for European Application No. 17841172.4, dated Mar. 5, 2020, 6 pages.
Extended European Search Report for European Application No. 17841107.0, dated Feb. 21, 2020, 12 pages.
International Search Report and Written Opinion for International Application No. PCT/CN2018/074108, dated Apr. 23, 2018, 12 pages.
International Search Report and Written Opinion for International Application No. PCT/CN2018/100145, dated Nov. 14, 2018, 8 pages.
Caira, E. D. et al., "Crystalline polymorphism of organic compounds," Topics in Current Chemistry, vol. 198, 1998, pp. 163-208.
Luo, J. et al., "Modern Physical Pharmaceutics Theory and Practice," Shang Hai Science and Technology Literature Publishing House, Apr. 2005, pp. 293-295.

SUBSTITUTED PYRAZOLO[1,5-A]PYRIMIDINES AS BRUTON'S TYROSINE KINASE MODULATORS

CROSS-REFERENCE TO RELATED APPLICATIONS

This application is a continuation of U.S. patent application Ser. No. 15/969,864, filed on May 3, 2018, which is a continuation of U.S. patent application Ser. No. 15/359,871, now U.S. Pat. No. 10,005,782, filed on Nov. 23, 2016, which is a continuation of U.S. patent application Ser. No. 14/951,494, now U.S. Pat. No. 9,556,188, filed on Nov. 25, 2015, which is a continuation of U.S. patent application Ser. No. 14/723,417, now U.S. Pat. No. 9,447,106, filed on May 27, 2015, which is a continuation of International Application No. PCT/CN2014/075943, filed on Apr. 22, 2014, which claims the benefit of International Application No. PCT/CN2013/074728, filed on Apr. 25, 2013, the disclosures of which are hereby incorporated by reference in their entirety for all purposes.

INTRODUCTION

Bruton's tyrosine kinase (Btk) belongs to the Tec tyrosine kinase family (Vetrie et al., *Nature* 361: 226-233, 1993; Bradshaw, *Cell Signal.* 22: 1175-84, 2010). Btk is primarily expressed in most hematopoietic cells such as B cells, mast cells and macrophages (Smith et al., *J. Immunol.* 152: 557-565, 1994) and is localized in bone marrow, spleen and lymph node tissue. Btk plays important roles in B-cell receptor (BCR) and FcR signaling pathways, which involve in B-cell development, differentiation (Khan, *Immunol. Res.* 23: 147, 2001). Btk is activated by upstream Src-family kinases. Once activated, Btk in turn phosphorylates PLC gamma, leading to effects on B-cell function and survival (Humphries et al., *J. Biol. Chem.* 279: 37651, 2004). These signaling pathways must be precisely regulated. Mutations in the gene encoding Btk cause an inherited B-cell specific immunodeficiency disease in humans, known as X-linked agammaglobulinemia (XLA) (Conley et al., *Annu. Rev. Immunol.* 27: 199-227, 2009). Aberrant BCR-mediated signaling may result in dysregulated B-cell activation leading to a number of autoimmune and inflammatory diseases. Preclinical studies show that Btk deficient mice are resistant to developing collagen-induced arthritis. Moreover, clinical studies of Rituxan, a CD20 antibody to deplete mature B-cells, reveal the key role of B-cells in a number of inflammatory diseases such as rheumatoid arthritis, systemic lupus erythematosus and multiple sclerosis (Gurcan et al., *Int. Immunopharmacol.* 9: 10-25, 2009). Therefore, Btk inhibitors can be used to treat autoimmune and/or inflammatory diseases.

In addition, aberrant activating of Btk plays important role in pathogenesis of B-cell lymphomas indicating that inhibition of Btk is useful in the treatment of hematological malignancies (Davis et al., *Nature* 463: 88-92, 2010). Preliminary clinical trial results showed that the Bruton's tyrosine kinase (Btk) inhibitor PCI-32765 was effective in treatment of several types of B-cell lymphoma (for example, 54th American Society of Hematology (ASH) annual meeting abstract, December 2012: 686 *The Bruton's Tyrosine Kinase (Btk) Inhibitor, Ibrutinib (PCI-32765), Has Preferential Activity in the ABC Subtype of Relapsed/Refractory De Novo Diffuse Large B-Cell Lymphoma (DLBCL): Interim Results of a Multicenter, Open-Label, Phase2 Study*).

Because Btk plays a central role as a mediator in multiple signal transduction pathways, inhibitors of Btk are of great interest as anti-inflammatory and/or anti-cancer agents (Mohamed et al., *Immunol. Rev.* 228: 58-73, 2009; Pan, *Drug News perspect* 21: 357-362, 2008; Rokosz et al., *Expert Opin. Ther. Targets* 12: 883-903, 2008; Uckun et al., *Anticancer Agents Med. Chem.* 7: 624-632, 2007; Lou et al., *J. Med. Chem.* 55(10): 4539-4550, 2012).

Small molecule inhibitors of Btk are being developed for anti-inflammatory and anticancer therapy. Ibrutinib (PCI-32765, See: U.S. Pat. No. 7,514,444B2 and related documents, for examples, US2012053189A1; WO 2011153514; WO 2011046964; US2010254905A1; WO2010009342; WO2008121742; WO2008054827; US20080139582; US20080076921; U.S. Pat. No. 7,718,662B1; WO2007087068; US20100035841) is a first-in class of Btk inhibitor, currently undergoing multiple clinical trials in relapsed or refractory mantle cell lymphoma (MCL) and chronic lymphocytic leukaemia (CLL). Another Btk inhibitor entered clinical trials is AVL-292 (See, for example, US 20100249092; US20100029610; US2010016296; US20120077832; WO 2011090760; WO 2010028236; WO 2009158571; WO2009051822; WO2010123870). Ono pharmaceuticals and Mannkind Corporation have been doing clinical trials with their small molecular Btk inhibitors, respectively (See, for example, ONO-4059. WO2011152351; WO2007136790A2).

Other Btk inhibitors are also known. See, for example, US2012/0232054 (LOCUS PHARMACEUTICALS, INC.), WO2010126960 (LOCUS PHARMACEUTICALS, INC.), WO 2011/162515 (HANMI HOLDINGS CO. LTD). WO2012135801 (UNIVERSITY OF UTAH RESEARCH FOUNDATION), Kim et al., *Bioorg. Med. Chem. Lett.* 21: 6258-6263, 2011(Pfizer), U.S. Pat. No. 8,084,620B2 (BMS), WO2002050071; WO2008116064; WO2010011837; WO 2011159857(BMS), US2012058996A1; US2012082702A1; US20100160303 (BMS), US2012129852A1 (BMS), WO 2011019780 (BMS). WO2011029043; WO2011029046 (Biogen Idec), U.S. Pat. No. 7,393,848 (CGI), US20060178367; US20060183746 (CGI), EP2068849 (CGI), WO 2005005429; WO 2005014599; WO 2005047290; WO 2006053121; WO2008033834; WO 2008033858; WO 2006099075; WO 2008033854; WO 2008033857; WO 2009039397 (CGI), WO 2009137596: WO 2010056875; WO 2010068788; WO 2010088806; WO 2010068810 (CGI, GENENTECH), WO 2011140488; WO 2012030990; WO 2012031004 (GILEAD & GENENTECH), US2012040961A1 (DANA-FARBER CANCER INSTITUTE), WO 2005011597; WO 2008045627; WO 2008144253 (IRM LLC), WO 2007140222; WO 2013008095 (NOVARTIS), WO 2012170976A2 (Merck), WO2012135944A1 (PHARMASCIENCE), US2010144705A1; US20120028981A1 (PRINCIPIA BIOPHARMA), WO 2010065898A2; WO 2012158795A1; WO 2012158764A1; WO 2012158810A1 (PRINCIPIA BIOPHARMA), US20090318448A1; US20100016301; US2009105209A1; US20100222325; US20100004231 (ROCHE), WO 2012156334A1; WO 2012020008; WO 2010122038; WO 2010006970; WO 2010006947; WO 2010000633; WO 2009077334; WO 2009098144 (ROCHE), WO 2006065946; WO 2007027594; WO 2007027729 (VERTEX).

WO 2007/026720 A1 discloses that a ring-fused pyrazole compound of formula (A), wherein n represents 2 or 3; A represents the formula: —O— or the like; B represents a $C_{1-10}$ alkylene group or the like; C represents a single bond or the formula: —O—; $R^1$— represents a hydrogen atom, a pyrrolidinyl group or the like; R⁴, R⁵ and R⁶ independently represents a hydrogen atom, a halogen atom or the like; D₁=D₂ represents the formula: —CH=CH— or the like; E represents the formula: —O— or —NH— or the like; G represents a C1-10 alkylene group or the like; and R⁷ represents a hydrogen atom, a phenyl group or the like, is useful as an Lck kinase inhibitor:

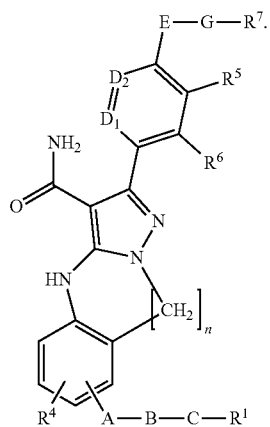

(A)

SUMMARY OF THE INVENTION

The invention provides methods and compositions for inhibiting Btk and treating disease associated with undesirable Btk activity (Btk-related diseases).

In one embodiment the invention provides Btk inhibitors or compounds of formula:

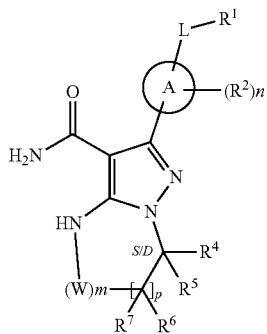

I stereoisomers thereof, and pharmaceutically acceptable salts thereof, wherein:

A is a 5- or 6-membered aromatic ring comprising 0-3 heteroatoms of N, S or O;

each W is independently —(CH₂)— or —C(O)—;

L is a bond, CH₂, NR¹², O, or S;

S/D is a single or double bond, and when a double bond. R⁵ and R⁷ are absent;

m is 0, or an integer of 1-4;

n is 0, or an integer of 1-4, wherein when n is more than 1, each R² may be different;

p is 0, or an integer of 1-2, wherein when p is 0, m is non-zero, and when p is more than 1, each R⁶ and each R⁷ may be different;

R¹, R⁴, R⁵, R⁶, and R⁷ are each independently H, halogen, heteroalkyl, alkyl, alkenyl, cycloalkyl, aryl, saturated or unsaturated heterocyclyl, heteroaryl, alkynyl, —CN, —NR¹³R¹⁴, —OR¹³, —COR¹³, —CO₂R¹³, —CONR¹³R¹⁴, —C(=NR¹³)NR¹⁴R¹⁵, —NR¹³COR¹⁴, —NR¹³CONR¹⁴R¹⁵, —NR¹³CO₂R¹⁴, —SO₂R¹³, —NR¹³SO₂NR¹⁴R¹⁵, or —NR¹³SO₂R¹⁴, wherein the alkyl, alkenyl, alkynyl, cycloalkyl, heteroaryl, aryl, and saturated or unsaturated heterocyclyl are optionally substituted with at least one substituent R¹⁶, wherein (R⁴ and R⁵), or (R⁴ and R⁶), or (R⁶ and R⁷), or (R⁶ and R⁶ when p is 2), together with the atoms to which they are attached, can form a ring selected from cycloalkyl, saturated or unsaturated heterocycle, aryl, and heteroaryl rings optionally substituted with at least one substituent R¹⁶;

R² is halogen, alkyl, —S-alkyl, —CN, —NR¹³R¹⁴, —OR¹³, —COR¹³, —CO₂R¹³, —CONR¹³R¹⁴, —C(=NR¹³)NR¹⁴R¹⁵, —NR¹³COR¹⁴, —NR¹³CONR¹⁴R¹⁵, —NR¹³CO₂R¹⁴, —SO₂R¹³, —NR¹³SO₂NR¹⁴R¹⁵, or —NR¹³SO₂R¹⁴;

R¹² is H or lower alkyl;

R¹³, R¹⁴ and R¹⁵ are each independently H, heteroalkyl, alkyl, alkenyl, alkynyl, cycloalkyl, saturated or unsaturated heterocyclyl, aryl, or heteroaryl; wherein (R¹³ and R¹⁴), and/or (R¹⁴ and R¹⁵) together with the atom(s) to which they are attached, each can form a ring selected from cycloalkyl, saturated or unsaturated heterocycle, aryl, and heteroaryl rings optionally substituted with at least one substituent R¹⁶;

R¹⁶ is halogen, substituted or unsubstituted alkyl, substituted or unsubstituted alkenyl, substituted or unsubstituted alkynyl, substituted or unsubstituted cycloalkyl, substituted or unsubstituted aryl, substituted or unsubstituted heteroaryl, substituted or unsubstituted heterocyclyl, oxo, —CN, —OR', —NR'R", —COR', —CO₂R', —CONR'R", —C(=NR')NR"R''', —NR'COR", —NR'CONR'R", —NR'CO₂R", —SO₂R', —SO₂aryl, —NR'SO₂NR"R''', or —NR'SO₂R", wherein R', R", and R''' are independently hydrogen, halogen, substituted or unsubstituted alkyl, substituted or unsubstituted alkenyl, substituted or unsubstituted alkynyl, substituted or unsubstituted cycloalkyl, substituted or unsubstituted aryl, substituted or unsubstituted heteroaryl, substituted or unsubstituted heterocyclyl, wherein (R' and R"), and/or (R" and R''') together with the atoms to which they are attached, can form a ring selected from cycloalkyl, saturated or unsaturated heterocycle, aryl, and heteroaryl rings.

In exemplary particular embodiments:

(a) S/D is a double bond and R⁵ and R⁷ are absent;

(b) R¹ is H, halogen, alkoxy, heteroalkyl, alkyl, alkenyl, cycloalkyl, aryl, saturated or unsaturated heterocyclyl, heteroaryl, wherein the alkyl, alkenyl, alkynyl, cycloalkyl, heteroaryl, aryl, and saturated or unsaturated heterocyclyl are optionally substituted with at least one substituent R¹⁶;

(c) p is 1 and m is 0, 1 or 2, preferably 0 or 1;

(d) A is phenyl;

(e) each R² is independently halogen, lower alkyl, or lower alkoxy (f) R⁴ and R⁶, together with the atoms to which they are attached, form a ring selected from cycloalkyl, saturated or unsaturated heterocycle, aryl, and heteroaryl rings optionally substituted with at least one substituent R¹⁶.

(g) R⁴ and R⁶, together with the atoms to which they are attached, form a ring of formula:

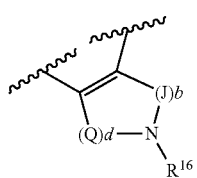

wherein:

Q is —CH$_2$—; J is —CH$_2$—; and d and b are each independently 0, or an integer of 1-4;

(h) S/D is a single bond.

(i) p is 0 and R$^6$ and R$^7$ are absent.

The invention includes all combinations of the recited particular embodiments, such as (a)-(i), supra, as if each combination had been laboriously separately recited.

In exemplary combinations of particular embodiments:

(i) S/D is a double bond and R$^5$ and R$^7$ are absent, R$^1$ is H, halogen, alkoxy, heteroalkyl, alkyl, alkenyl, cycloalkyl, aryl, saturated or unsaturated heterocyclyl, heteroaryl, wherein the alkyl, alkenyl, alkynyl, cycloalkyl, heteroaryl, aryl, and saturated or unsaturated heterocyclyl are optionally substituted with at least one substituent R$^{16}$; and R$^{16}$ is halogen, lower alkyl, or lower alkoxy;

(ii) S/D is a double bond and R$^5$ and R$^7$ are absent; p is 1 and m is 0 or 1 (or 2);

(iii) S/D is a double bond and R$^5$ and R$^7$ are absent; p is 1 and m is 0 or 1 (or 2); A is phenyl; and each R$^2$ is independently halogen, lower alkyl, or lower alkoxy (see, formula II);

(iv) S/D is a double bond and R$^5$ and R$^7$ are absent; and R$^4$ and R$^6$, together with the atoms to which they are attached, form a ring selected from cycloalkyl, saturated or unsaturated heterocycle, aryl, and heteroaryl rings optionally substituted with at least one substituent R$^{16}$.

(v) S/D is a double bond and R$^5$ and R$^7$ are absent; R$^4$ and R$^6$, together with the atoms to which they are attached, form a ring selected from cycloalkyl, saturated or unsaturated heterocycle, aryl, and heteroaryl rings optionally substituted with at least one substituent R$^{16}$; A is phenyl; and each R$^2$ is independently halogen, lower alkyl, or lower alkoxy.

(vi) S/D is a double bond and R$^5$ and R$^7$ are absent; R$^4$ and R$^6$, together with the atoms to which they are attached, form a ring selected from cycloalkyl, saturated or unsaturated heterocycle, aryl, and heteroaryl rings optionally substituted with at least one substituent R$^6$; p is 1 and m 0 or 1 (or 2); A is phenyl; each R$^2$ is independently halogen, lower alkyl, or lower alkoxy; and the R$^4$-R$^6$ ring is of formula:

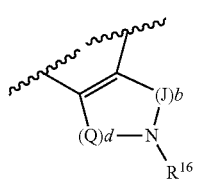

wherein Q is —CH$_2$—; J is —CH$_2$—; and d and b are each independently 0, or an integer of 1-4 (see, formula III);

(vii) S/D is a double bond and R$^5$ and R$^7$ are absent; R$^4$ and R$^6$, together with the atoms to which they are attached, form a ring selected from cycloalkyl, saturated or unsaturated heterocycle, aryl, and heteroaryl rings optionally substituted with at least one substituent R$^{16}$; p is 1 and m is 0 or 1 (or 2); A is phenyl; each R$^2$ is independently halogen, lower alkyl, or lower alkoxy; and the R$^4$-R$^6$ ring is of formula:

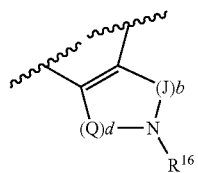

wherein Q is —CH$_2$—; J is —CH$_2$—; and d and b are each independently 0, or an integer of 1-4; and R$^1$ is H, halogen, alkoxy, heteroalkyl, alkyl, alkenyl, cycloalkyl, aryl, saturated or unsaturated heterocyclyl, heteroaryl, wherein the alkyl, alkenyl, alkynyl, cycloalkyl, heteroaryl, aryl, and saturated or unsaturated heterocyclyl are optionally substituted with at least one substituent R$^{16}$;

(viii) S/D is a single bond; p is 1 and m is 0, 1 or 2; A is phenyl; each R$^2$ is independently halogen, lower alkyl, or lower alkoxy (see, formula IV);

(ix) S/D is a single bond; p is 1 and m is 0, 1 or 2; A is phenyl; each R$^2$ is independently halogen, lower alkyl, or lower alkoxy, and R$^1$ is H, halogen, alkoxy, heteroalkyl, alkyl, alkenyl, cycloalkyl, aryl, saturated or unsaturated heterocyclyl, heteroaryl, wherein the alkyl, alkenyl, alkynyl, cycloalkyl, heteroaryl, aryl, and saturated or unsaturated heterocyclyl are optionally substituted with at least one substituent R$^6$; and R$^{16}$ is halogen, lower alkyl, or lower alkoxy;

(x) S/D is a single bond; p is 0 and R$^6$ and R$^7$ are absent; A is phenyl; and each R$^2$ is independently halogen, lower alkyl, or lower alkoxy (see, formula V);

(xi) S/D is a single bond; p is 0 and R$^6$ and R$^7$ are absent; A is phenyl; and each R$^2$ is independently halogen, lower alkyl, or lower alkoxy, and R$^1$ is H, halogen, alkoxy, heteroalkyl, alkyl, alkenyl, cycloalkyl, aryl, saturated or unsaturated heterocyclyl, heteroaryl, wherein the alkyl, alkenyl, alkynyl, cycloalkyl, heteroaryl, aryl, and saturated or unsaturated heterocyclyl are optionally substituted with at least one substituent R$^{16}$; and R$^{16}$ is halogen, lower alkyl, or lower alkoxy.

In particular embodiments the invention provides compounds of formula II, III, IV and V, stereoisomers thereof, and pharmaceutically acceptable salts thereof, wherein substituents are as defined herein:

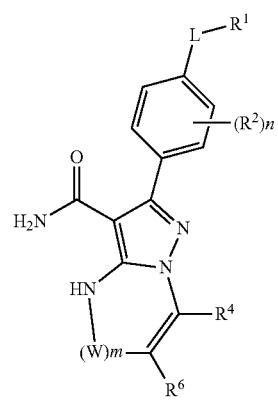

II

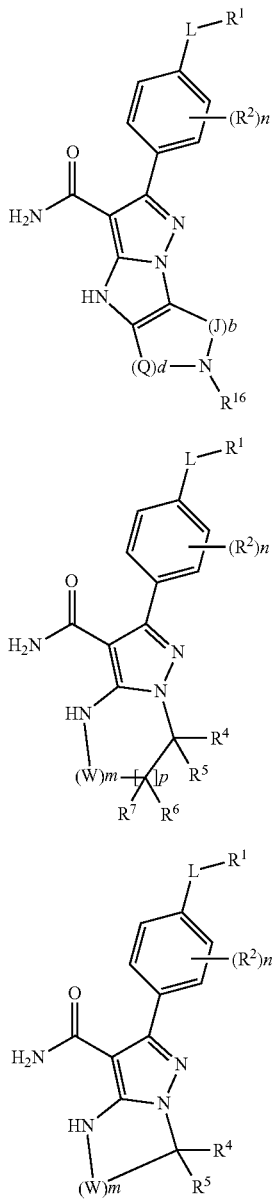

The invention also provides compounds of the examples herein, or of Table I, II or III, (below), stereoisomers thereof, and pharmaceutically acceptable salts thereof.

The invention also provides subject compounds having a Btk-inhibiting activity corresponding to a IC50 of 10 uM or less in the BTK KINASE ASSAY.

The invention also provides pharmaceutical compositions comprising a therapeutically effective amount of a subject compound in unit dosage form and one or more pharmaceutically acceptable carriers.

The invention also provides combinations comprising a therapeutically effective amount of a subject compound and a different agent therapeutically active against an autoimmune and/or inflammatory disease.

The invention also provides methods treating a Btk related disease, or disease associated with undesirable Btk activity, particularly an allergic disease, an autoimmune disease (e.g. rheumatoid arthritis), an inflammatory disease, or cancer (e.g. a B-cell proliferative disorder, such as chronic lymphocytic lymphoma, non-Hodgkin's lymphoma, diffuse large B cell lymphoma, mantle cell lymphoma, follicular lymphoma or chronic lymphocytic leukemia), which methods generally comprise administering to a mammal in need thereof an effective amount of a subject compound, an N-oxide thereof or a prodrug thereof, and optionally detecting a resultant amelioration of disease or symptom thereof, or Bkt-inhibition.

The invention also provides pharmaceutical compositions comprising a subject compound in unit dosage, administrable form, and methods of inducing autophagy, comprising administering to a person in need thereof an effective amount of a subject compound or composition.

The invention also provides the subject compounds for use as a medicament, and use of the subject compounds in the manufacture of a medicament for the treatment of a Btk related disease.

DESCRIPTION OF PARTICULAR EMBODIMENTS OF THE INVENTION

Disclosed herein are compounds that can inhibit tyrosine kinases, such as Btk, Blk, Bmx, EGFR, ERBB2, ERBB4, Itk Jak3, Tec and Txk kinases.

The following words, phrases and symbols are generally intended to have the meanings as set forth below, except to the extent that the context in which they are used indicates otherwise. The following abbreviations and terms have the indicated meanings throughout.

The term "alkyl" refers to a hydrocarbon group selected from linear and branched saturated hydrocarbon groups of 1-18, or 1-12, or 1-6 carbon atoms. Examples of the alkyl group include methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), and 1,1-dimethylethyl or t-butyl ("t-Bu"). Other examples of the alkyl group include 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl groups.

Lower alkyl means 1-8, preferably 1-6, more preferably 1-4 carbon atoms; lower alkenyl or alkynyl means 2-8, 2-6 or 2-4 carbon atoms.

The term "alkenyl" refers to a hydrocarbon group selected from linear and branched hydrocarbon groups comprising at least one C=C double bond and of 2-18, or 2-12, or 2-6 carbon atoms. Examples of the alkenyl group may be selected from ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl, and hexa-1,3-dienyl groups.

The term "alkynyl" refers to a hydrocarbon group selected from linear and branched hydrocarbon group, comprising at least one C≡C triple bond and of 2-18, or 2-12, or 2-6 carbon atoms. Examples of the alkynyl group include ethynyl, 1-propynyl, 2-propynyl (propargyl), 1-butynyl, 2-butynyl, and 3-butynyl groups.

The term "cycloalkyl" refers to a hydrocarbon group selected from saturated and partially unsaturated cyclic hydrocarbon groups, comprising monocyclic and polycyclic (e.g., bicyclic and tricyclic) groups. For example, the cycloalkyl group may be of 3-12, or 3-8, or 3-6 carbon atoms. Even further for example, the cycloalkyl group may be a monocyclic group of 3-12, or 3-8, or 3-6 carbon atoms.

Examples of the monocyclic cycloalkyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl groups. Examples of the bicyclic cycloalkyl groups include those having 7-12 ring atoms arranged as a bicycle ring selected from [4,4], [4,5], [5,5], [5,6] and [6,6] ring systems, or as a bridged bicyclic ring selected from bicyclo[2.2.1]heptane, bicyclo[2.2.2]octane, and bicyclo[3.2.2]nonane. The ring may be saturated or have at least one double bond (i.e. partially unsaturated), but is not fully conjugated, and is not aromatic, as aromatic is defined herein.

The term "Aryl" herein refers to a group selected from: 5- and 6-membered carbocyclic aromatic rings, for example, phenyl; bicyclic ring systems such as 7-12 membered bicyclic ring systems wherein at least one ring is carbocyclic and aromatic, selected, for example, from naphthalene, indane, and 1,2,3,4-tetrahydroquinoline; and tricyclic ring systems such as 10-15 membered tricyclic ring systems wherein at least one ring is carbocyclic and aromatic, for example, fluorene.

For example, the aryl group is selected from 5- and 6-membered carbocyclic aromatic rings fused to a 5- to 7-membered cycloalkyl or heterocyclic ring optionally comprising at least one heteroatom selected from N, O, and S, provided that the point of attachment is at the carbocyclic aromatic ring when the carbocyclic aromatic ring is fused with a heterocyclic ring, and the point of attachment can be at the carbocyclic aromatic ring or at the cycloalkyl group when the carbocyclic aromatic ring is fused with a cycloalkyl group. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap with heteroaryl, separately defined below. Hence, if one or more carbocyclic aromatic rings are fused with a heterocyclic aromatic ring, the resulting ring system is heteroaryl, not aryl, as defined herein.

The term "halogen" or "halo" refers to F, Cl, Br or I.

The term "heteroalkyl" refers to alkyl comprising at least one heteroatom.

The term "heteroaryl" refers to a group selected from:

5- to 7-membered aromatic, monocyclic rings comprising 1, 2, 3 or 4 heteroatoms selected from N, O, and S, with the remaining ring atoms being carbon;

8- to 12-membered bicyclic rings comprising 1, 2, 3 or 4 heteroatoms, selected from N, O, and S, with the remaining ring atoms being carbon and wherein at least one ring is aromatic and at least one heteroatom is present in the aromatic ring; and 11- to 14-membered tricyclic rings comprising 1, 2, 3 or 4 heteroatoms, selected from N, O, and S, with the remaining ring atoms being carbon and wherein at least one ring is aromatic and at least one heteroatom is present in an aromatic ring.

For example, the heteroaryl group includes a 5- to 7-membered heterocyclic aromatic ring fused to a 5- to 7-membered cycloalkyl ring. For such fused, bicyclic heteroaryl ring systems wherein only one of the rings comprises at least one heteroatom, the point of attachment may be at the heteroaromatic ring or at the cycloalkyl ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of the heteroaryl group include, but are not limited to, (as numbered from the linkage position assigned priority 1) pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl, tetrazolyl, thienyl, triazinyl, benzothienyl, furyl, benzofuryl, benzoimidazolyl, indolyl, isoindolyl, indolinyl, phthalazinyl, pyrazinyl, pyridazinyl, pyrrolyl, triazolyl, quinolinyl, isoquinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl, benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

The term "heterocyclic" or "heterocycle" or "heterocyclyl" refers to a ring selected from 4- to 12-membered monocyclic, bicyclic and tricyclic, saturated and partially unsaturated rings comprising at least one carbon atoms in addition to 1, 2, 3 or 4 heteroatoms, selected from oxygen, sulfur, and nitrogen. "Heterocycle" also refers to a 5- to 7-membered heterocyclic ring comprising at least one heteroatom selected from N, O, and S fused with 5-, 6-, and/or 7-membered cycloalkyl, carbocyclic aromatic or heteroaromatic ring, provided that the point of attachment is at the heterocyclic ring when the heterocyclic ring is fused with a carbocyclic aromatic or a heteroaromatic ring, and that the point of attachment can be at the cycloalkyl or heterocyclic ring when the heterocyclic ring is fused with cycloalkyl.

"Heterocycle" also refers to an aliphatic spirocyclic ring comprising at least one heteroatom selected from N, O, and S, provided that the point of attachment is at the heterocyclic ring. The rings may be saturated or have at least one double bond (i.e. partially unsaturated). The heterocycle may be substituted with oxo. The point of the attachment may be carbon or heteroatom in the heterocyclic ring. A heterocyle is not a heteroaryl as defined herein.

Examples of the heterocycle include, but not limited to, (as numbered from the linkage position assigned priority 1) 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl, pyranyl, 2-morpholinyl, 3-morpholinyl, oxiranyl, aziridinyl, thiiranyl, azetidinyl, oxetanyl, thietanyl, 1,2-dithietanyl, 1,3-dithietanyl, dihydropyridinyl, tetrahydropyridinyl, thiomorpholinyl, thioxanyl, piperazinyl, homopiperazinyl, homopiperidinyl, azepanyl, oxepanyl, thiepanyl, 1,4-oxathianyl, 1,4-dioxepanyl, 1,4-oxathiepanyl, 1,4-oxazepanyl, 1,4-dithiepanyl, 1,4-thiazepanyl and 1,4-diazepane 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinylimidazolinyl, pyrimidinonyl, 1,1-dioxo-thiomorpholinyl, 3-azabicyclo[3.1.0]hexanyl, 3-azabicyclo[4.1.0]heptanyl and azabicyclo[2.2.2]hexanyl, Substituted heterocycle also includes ring systems substituted with one or more oxo moieties, such as piperidinyl N-oxide, morpholinyl-N-oxide, 1-oxo-1-thiomorpholinyl and 1,1-dioxo-1-thiomorpholinyl.

Substituents are selected from: halogen, —R', —OR', =O, =NR', =N—OR', —NR'R", —SR', —SiR'R"R'", —OC(O)R', —C(O)R', —CO$_2$R', —CONR'R", —OC(O)NR'R", —NR"C(O)R', —NR'—C(O)NR"R'", —NR'—SO$_2$NR'", —NR"CO$_2$R', —NH—C(NH$_2$)=NH, —NR'C(NH$_2$)=NH, —NH—C(NH$_2$)=NR', —S(O)R', —SO$_2$R', —SO$_2$NR'R", —NR"SO$_2$R, —CN and —NO$_2$, —N$_3$, —CH(Ph)$_2$, perfluoro(C1-C4)alkoxy and perfluoro(C1-C4)alkyl, in a number ranging from zero to three, with those groups having zero, one or two substituents being particularly preferred. R', R" and R'" each independently refer to hydrogen, unsubstituted (C1-C8)alkyl and heteroalkyl, unsubstituted aryl, aryl substituted with one to three halogens, unsubstituted alkyl, alkoxy or thioalkoxy groups, or aryl-(C1-C4)alkyl groups. When R' and R" are attached to the same nitrogen atom, they can be combined with the nitrogen atom to form a 5-, 6- or 7-membered ring. Hence, —NR'R" includes 1-pyrrolidinyl and 4-morpholinyl, "alkyl" includes groups such as trihaloalkyl (e.g., —CF$_3$ and —CH$_2$CF$_3$), and when the aryl group is 1,2,3,4-tetrahydronaphthalene, it may be substituted with a substituted or unsubstituted (C3-C7)spirocycloalkyl group. The (C3-C7)spirocycloalkyl group may be substituted in the same manner as defined herein for "cycloalkyl".

Preferred substituents are selected from: halogen, —R', —OR', =O, —NR'R", —SR', —SiR'R"R'", —OC(O)R', —C(O)R', —CO$_2$R', —CONR'R", —OC(O)NR'R", —NR"C(O)R', —NR"CO$_2$R', —NR'—SO$_2$NR"R'", —S(O)R', —SO$_2$R', —SO$_2$NR'R", —NR"SO$_2$R, —CN and —NO$_2$, perfluoro(C1-C4)alkoxy and perfluoro(C1-C4)alkyl, where R' and R" are as defined above.

The term "fused ring" herein refers to a polycyclic ring system, e.g., a bicyclic or tricyclic ring system, in which two rings share only two ring atoms and one bond in common. Examples of fused rings may comprise a fused bicyclic cycloalkyl ring such as those having from 7 to 12 ring atoms arranged as a bicyclic ring selected from [4,4], [4,5], [5,5], [5,6] and [6,6] ring systems as mentioned above; a fused bicylclic aryl ring such as 7 to 12 membered bicyclic aryl ring systems as mentioned above, a fused tricyclic aryl ring such as 10 to 15 membered tricyclic aryl ring systems mentioned above; a fused bicyclic heteroaryl ring such as 8- to 12-membered bicyclic heteroaryl rings as mentioned above, a fused tricyclic heteroaryl ring such as 11- to 14-membered tricyclic heteroaryl rings as mentioned above; and a fused bicyclic or tricyclic heterocyclyl ring as mentioned above.

The compounds may contain an asymmetric center and may thus exist as enantiomers. Where the compounds possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds and/or pharmaceutically acceptable salts thereof are intended to be included. Unless specifically mentioned otherwise, reference to one isomer applies to any of the possible isomers. Whenever the isomeric composition is unspecified, all possible isomers are included.

The term "substantially pure" means that the target stereoisomer contains no more than 35%, such as no more than 30%, further such as no more than 25%, even further such as no more than 20%, by weight of any other stereoisomer(s). In some embodiments, the term "substantially pure" means that the target stereoisomer contains no more than 10%, for example, no more than 5%, such as no more than 1%, by weight of any other stereoisomer(s).

When compounds contain olefin double bonds, unless specified otherwise, such double bonds are meant to include both E and Z geometric isomers.

Some of the compounds may exist with different points of attachment of hydrogen, referred to as tautomers. For example, compounds including carbonyl —CH$_2$C(O)— groups (keto forms) may undergo tautomerism to form hydroxyl —CH=C(OH)— groups (enol forms). Both keto and enol forms, individually as well as mixtures thereof, are also intended to be included where applicable.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents (Eliel, E. and Wilen, S. Stereochemistry of Organic Compounds. New York: John Wiley & Sons, Inc., 1994; Lochmuller, C. H., et al. "Chromatographic resolution of enantiomers: Selective review." J. Chromatogr, 113(3) (1975): pp. 283-302). Racemic mixtures of chiral compounds of the invention can be separated and isolated by any suitable method, including: (1) formation of ionic, diastereomeric salts with chiral compounds and separation by fractional crystallization or other methods. (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W., Ed. Drug Stereochemistry: Analytical Methods and Pharmacology. New York: Marcel Dekker, Inc., 1993.

"Pharmaceutically acceptable salts" include, but are not limited to salts with inorganic acids, selected, for example, from hydrochlorates, phosphates, diphosphates, hydrobromates, sulfates, sulfinates, and nitrates: as well as salts with organic acids, selected, for example, from malates, maleates, fumarates, tartrates, succinates, citrates, lactates, methanesulfonates, p-toluenesulfonates, 2-hydroxyethylsulfonates, benzoates, salicylates, stearates, alkanoates such as acetate, and salts with HOOC—(CH$_2$)n-COOH, wherein n is selected from 0 to 4. Similarly, examples of pharmaceutically acceptable cations include, but are not limited to, sodium, potassium, calcium, aluminum, lithium, and ammonium.

In addition, if a compound is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

"Treating," "treat," or "treatment" refers to administering at least one compound and/or at least one stereoisomer thereof, and/or at least one pharmaceutically acceptable salt thereof to a subject in recognized need thereof that has, for example, cancer.

An "effective amount" refers to an amount of at least one compound and/or at least one stereoisomer thereof, and/or at least one pharmaceutically acceptable salt thereof effective to "treat" a disease or disorder in a subject, and that will elicit, to some significant extent, the biological or medical response of a tissue, system, animal or human that is being sought, such as when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

The term "at least one substituent" includes, for example, from 1 to 4, such as from 1 to 3, further as 1 or 2, substituents. For example, "at least one substituent $R^{16}$" herein includes from 1 to 4, such as from 1 to 3, further as 1 or 2, substituents selected from the list of $R^{16}$ as described herein.

The invention provides compounds of formula:

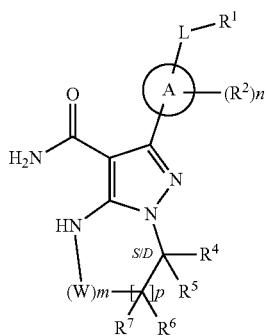

I stereoisomers thereof, and pharmaceutically acceptable salts thereof.

$R^1$ (and $R^4$, $R^5$, $R^6$, and $R^7$) are each independently H, halogen, heteroalkyl, alkyl, alkenyl, cycloalkyl, aryl, saturated or unsaturated heterocyclyl, heteroaryl, alkynyl, —CN, —NR$^{13}$R$^{14}$, —OR$^{13}$, —COR$^{13}$, —CO$_2$R$^{13}$, —CONR$^{13}$R$^{14}$, —C(=NR$^{13}$)NR$^{14}$R$^{15}$, —NR$^{13}$COR$^{14}$, —NR$^{13}$CONR$^{14}$R$^{15}$, —NR$^{13}$CO$_2$R$^{14}$, —SO$_2$R$^{13}$, —NR$^{13}$SO$_2$NR$^{14}$R$^{15}$, or —NR$^{13}$SO$_2$R$^{14}$, wherein the alkyl, alkenyl, alkynyl, cycloalkyl, heteroaryl, aryl, and saturated or unsaturated heterocyclyl are optionally substituted with at least one substituent $R^{16}$.

$R^{13}$, $R^{14}$ and $R^{15}$ are each independently H, heteroalkyl, alkyl, alkenyl, alkynyl, cycloalkyl, saturated or unsaturated heterocyclyl, aryl, or heteroaryl; wherein ($R^{13}$ and $R^{14}$), and/or ($R^{14}$ and $R^{15}$) together with the atom(s) to which they are attached, each can form a ring selected from cycloalkyl, saturated or unsaturated heterocycle, aryl, and heteroaryl rings optionally substituted with at least one substituent $R^{16}$. In particular embodiments $R^{13}$, $R^{14}$ and $R^{15}$ are each independently H, lower alkyl, or lower alkoxy.

$R^{16}$ is halogen, substituted or unsubstituted alkyl, substituted or unsubstituted alkenyl, substituted or unsubstituted alkynyl, substituted or unsubstituted cycloalkyl, substituted or unsubstituted aryl, substituted or unsubstituted heteroaryl, substituted or unsubstituted heterocyclyl, oxo, —CN, —OR', —NR'R", —COR', —CO$_2$R', —CONR'R", —C(=NR')NR"R'", —NR'COR", —NR'CONR'R", —NR'CO$_2$R", —SO$_2$R', —SO$_2$aryl, —NR'SO$_2$NR'''R''', or —NR'SO$_2$R", wherein R', R", and R'" are independently hydrogen, halogen, substituted or unsubstituted alkyl, substituted or unsubstituted alkenyl, substituted or unsubstituted alkynyl, substituted or unsubstituted cycloalkyl, substituted or unsubstituted aryl, substituted or unsubstituted heteroaryl, substituted or unsubstituted heterocyclyl, wherein (R' and R"), and/or (R" and R'") together with the atoms to which they are attached, can form a ring selected from cycloalkyl, saturated or unsaturated heterocycle, aryl, and heteroaryl rings.

$R^{16}$ of $R^1$ in particular embodiments is halogen, lower alkyl, or lower alkoxy.

$R^1$ in particular embodiments is an optionally hetero-, optionally substituted hydrocarbon selected from heteroalkyl, alkyl, alkenyl, cycloalkyl, aryl, saturated or unsaturated heterocyclyl, heteroaryl, wherein the alkyl, alkenyl, alkynyl, cycloalkyl, heteroaryl, aryl, and saturated or unsaturated heterocyclyl are optionally substituted with at least one substituent $R^{16}$, wherein cyclic structures are preferably 3-8 membered ring structures comprising 0-3 heteroatoms of N, S or O, and the aryl is preferably a 5- or 6-membered aromatic ring comprising 0-3 heteroatoms of N, S or O, wherein the hydrocarbon is preferably a C1-C12 or C1-C8 hydrocarbon.

$R^1$ in particular embodiments is heteroalkyl, alkyl, alkenyl, cycloalkyl, aryl, saturated or unsaturated heterocyclyl, heteroaryl, wherein the alkyl, alkenyl, alkynyl, cycloalkyl, heteroaryl, aryl, and saturated or unsaturated heterocyclyl are optionally substituted with at least one substituent $R^{16}$.

$R^1$ in particular embodiments is lower alkyl or alkenyl, optionally cyclic and optionally substituted, particularly with halogen, lower alkyl, or lower alkoxy, and comprising 0-3 heteroatoms of N, S or O. Examples include methylcyclopropyl, cyclohexyl, cyclopentyl, methoxyethyl, halide, methyl, ethyl, propyl and butyl. Other exemplary $R^1$ moieties include 5-membered aromatic rings like pyrrole, pyrazole, imidazole, furan and hydrogenations thereof (e.g. pyrrolidine, pyrazolidine, imidazolidine, tetrahydrofuran), and 6-membered rings like benzene (phenyl), pyridine, pyran, diazines, triazines and tetrazines, and hydrogenations thereof (e.g. cyclohexane, di- and tetra-hydropyridine, piperidine, tetrahydropyran, etc.), each of which may be substituted, particularly with halogen, lower alkyl, or lower alkoxy.

L is a bond, $CH_2$, $NR^{12}$, O, or S, wherein $R^{12}$ is H or lower alkyl, e.g. methyl.

A is a 5- or 6-membered aromatic ring comprising 0-3 heteroatoms of N, S or O. Preferred 5-membered aromatic rings include pyrrole, pyrazole, imidazole, furan and 6-membered rings include benzene (phenyl), pyridine, pyran, diazines, triazines and tetrazines.

n is 0, 1, 2, 3 or 4, wherein when n is more than 1, each $R^2$ may be different. In particular embodiments n is 0 (i.e. A is unsubstituted).

$R^2$ is halogen, alkyl, —S-alkyl, —CN, —$NR^{13}R^{14}$, —$OR^{13}$, —$COR^{13}$, —$CO_2R^{13}$, —$CONR^{13}R^{14}$, —$C(=NR^{13})NR^{14}R^{15}$, —$NR^{13}COR^{14}$, —$NR^{13}CONR^{14}R^{15}$, —$NR^{13}CO_2R^{14}$, —$SO_2R^{13}$, —$NR^{13}SO_2NR^{14}R^{15}$, or —$NR^{13}SO_2R^{14}$; wherein $R^{13}$, $R^{14}$ and $R^{15}$ are each independently H, heteroalkyl, alkyl, alkenyl, alkynyl, cycloalkyl, saturated or unsaturated heterocyclyl, aryl, or heteroaryl; wherein ($R^{13}$ and $R^{14}$), and/or ($R^{14}$ and $R^{15}$) together with the atom(s) to which they are attached, each can form a ring selected from cycloalkyl, saturated or unsaturated heterocycle, aryl, and heteroaryl rings optionally substituted with at least one substituent $R^{16}$.

$R^2$ in particular embodiments is halogen, alkyl, —S-alkyl, —CN, —$NR^{13}R^{14}$, —$OR^{13}$, —$COR^{13}$, —$CO_2R^{13}$, —$CONR^{13}R^{14}$, —$C(=NR^{13})NR^{14}R^{15}$, —$NR^{13}COR^{14}$, —$NR^{13}CONR^{14}R^{15}$, —$NR^{13}CO_2R^{14}$, —$SO_2R^{13}$, —$NR^{13}SO_2NR^{14}R^{15}$, or —$NR^{13}SO_2R^{14}$, preferably wherein the alkyl (including —S-alkyl) is lower alkyl, and $R^{13}$, $R^{14}$ and $R^{15}$ are each independently H, lower alkyl, or lower alkoxy.

$R^2$ in particular embodiments is halogen, lower alkyl, or lower alkoxy.

each W is independently —($CH_2$)— or —C(O)—, wherein if m is 2, 3 or 4, preferably no more than one W is carbonyl;

S/D is a single or double bond, and when a double bond, $R^5$ and $R^7$ are absent;

m is 0, 1, 2, 3 or 4, preferably 0, 1, 2 or 3, and in particular embodiments 0, 1 or 2, or 0 or 1.

p is 0 (and $R^6$ and $R^7$ are absent), or an integer of 1-2, wherein when p is 0, m is non-zero, and when p is more than 1, each $R^6$ and each $R^7$ may be different; generally p+m is 1, 2, 3 or 4, preferably 1, 2 or 3, and in particular embodiments 1.

In particular embodiments p is 2 and m is 0 or 1; p is 1 and m is 0 or 1 (or 0, 1 or 2); or p is 0 and m is 1 or 2 (or 1, 2 or 3).

$R^4$ and $R^5$, or $R^4$ and $R^6$, or $R^6$ and $R^7$, or $R^6$ and $R^6$ (when p is 2), together with the atoms to which they are attached, can form a ring selected from cycloalkyl, saturated or unsaturated heterocycle, aryl, and heteroaryl rings optionally substituted with at least one substituent $R^{16}$. These rings are generally 4-8-membered and include 5-membered aromatic rings like pyrrole, pyrazole, imidazole, furan and hydrogenations thereof (e.g. pyrrolidine, pyrazolidine, imidazolidine, tetrahydrofuran), and 6-membered rings like benzene (phenyl), pyridine, pyran, diazines, triazines and tetrazines, and hydrogenations thereof (e.g. cyclohexane, di- and tetra-hydropyridine, piperidine, tetrahydropyran, etc.), each of which may be unsubstituted or substituted, particularly with halogen, lower alkyl, lower alkoxy, —COR', or NR'COR", wherein R', R" are substituted or unsubstituted alkenyl.

$R^4$ and $R^5$ (or $R^6$ and $R^7$, or $R^6$ and $R^6$, when p is 2), in particular embodiments form piperidine, azacycloheptanyl, or azetidine, optionally substituted, particularly N-substituted with moieties such as benzyl, acyl, acryloyl, etc.

$R^4$ and $R^6$, in particular embodiments, together with the atoms to which they are attached, form a ring of formula:

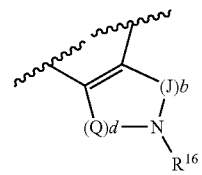

wherein:

Q is —$CH_2$—; J is —$CH_2$—; and d and b are each independently 0, or an integer of 1-4.

$R^4$ and $R^6$ in particular embodiments form phenyl, piperidine, azacycloheptanyl, pyrrolidine, optionally substituted, particularly N-substituted with moieties such as benzyl, acyl, acryloyl, methylamine-acryloyl, etc.

The invention includes all combinations of the recited particular and preferred embodiments as if each combination had been laboriously separately recited. For example, in particular embodiments, supra, A is phenyl; W is —($CH_2$)—; L is O; S/D is a single bond; m is 1; n is 0; p is 1; $R^1$ is phenyl; $R^2$ is absent; $R^5$ is H; and $R^6$ and $R^7$ are H; yielding the combination:

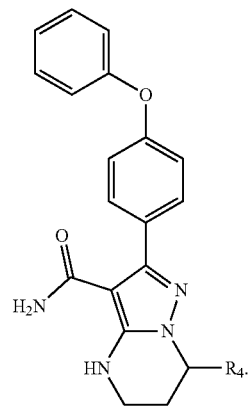

$R^4$, supra, includes N-containing C1-C8 alkyl, N-containing C3-C8 cycloalkyl and phenyl, for example, methylamine, aniline, azetidine, pyrrolidine, piperidine, azacycloheptenyl, each optionally substituted, particularly N-substituted with moieties such as benzyl, acyl, acryloyl, substituted-acryloyl, propiolyl, substituted-propiolyl, etc., such as structure combinations:

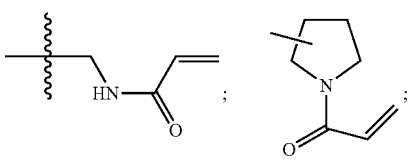

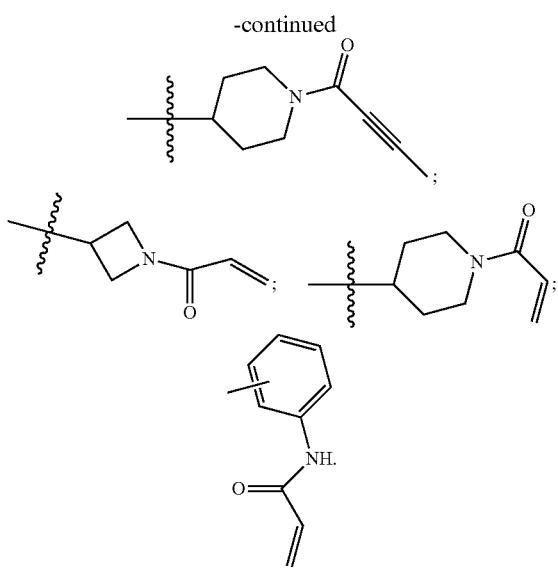

In particular examples, $R^4$ is 1-acryloylpiperidin-4-yl (e.g. compound 27) or 1-(but-2-ynoyl)piperidin-4-yl (e.g. compound 176).

The invention also provides all the compounds of the examples herein, and of Table I, II and III, stereoisomers thereof, and pharmaceutically acceptable salts thereof.

The subject compounds and stereoisomers thereof, and pharmaceutically acceptable salts thereof may be employed alone or in combination with at least one other therapeutic agent for treatment. In some embodiments, the compounds, stereoisomers thereof, and pharmaceutically acceptable salts thereof can be used in combination with at least one additional therapeutic agent. The at least one additional therapeutic agent can be, for example, selected from anti-hyperproliferative, anti-cancer, and chemotherapeutic agents. The compound and/or one pharmaceutically acceptable salt disclosed herein may be administered with the at least one other therapeutic agent in a single dosage form or as a separate dosage form. When administered as a separate dosage form, the at least one other therapeutic agent may be administered prior to, at the same time as, or following administration of the compound and/or one pharmaceutically acceptable salt disclosed herein.

A "chemotherapeutic agent" is a chemical compound useful in the treatment of cancer, regardless of mechanism of action. Chemotherapeutic agents include compounds used in "targeted therapy" and conventional chemotherapy. Suitable chemotherapeutic agents can be, for example, selected from: agents that induce apoptosis; polynucleotides (e.g., ribozymes); polypeptides (e.g., enzymes); drugs; biological mimetics; alkaloids; alkylating agents; antitumor antibiotics; antimetabolites; hormones; platinum compounds; monoclonal antibodies conjugated with anticancer drugs, toxins, and/or radionuclides; biological response modifiers (e.g., interferons, such as IFN-a and interleukins, such as IL-2); adoptive immunotherapy agents; hematopoietic growth factors; agents that induce tumor cell differentiation (e.g., all-trans-retinoic acid); gene therapy reagents; antisense therapy reagents and nucleotides; tumor vaccines; and inhibitors of angiogenesis.

Examples of chemotherapeutic agents include Erlotinib (TARCEVA®, Genentech/OSI Pharm.); Bortezomib (VELCADE®, Millennium Pharm.); Fulvestrant (FASLODEX®, AstraZeneca); Sunitinib (SUTENT®, Pfizer): Letrozole (FEMARA®, Novartis): Imatinib mesylate (GLEEVEC®, Novartis); PTK787/ZK 222584 (Novartis); Oxaliplatin (Eloxatin®, Sanofi); 5-FU (5-fluorouracil); Leucovorin; Rapamycin (Sirolimus, RAPAMUNE®, Wyeth); Lapatinib (TYKERB®, GSK572016, Glaxo Smith Kline); Lonafarnib (SCH 66336); Sorafenib (NEXAVAR®, Bayer); Irinotecan (CAMPTOSAR®, Pfizer) and Gefitinib (IRESSA®, AstraZeneca); AG1478, AG1571 (SU 5271, Sugen); alkylating agents such as thiotepa and CYTOXAN® cyclophosphamide; alkyl sulfonates such as busulfan, improsulfan and piposulfan; aziridines such as benzodepa, carboquone, meturedepa, and uredepa; ethylenimines and methylamelamines such as altretamine, triethylenemelamine, trietylenephosphoramide, triethiylenethiophosphoramide and trimethylmelamine; acetogenins (such as bullatacin and bullatacinone); a camptothecin (such as the synthetic analog topotecan); bryostatin; callystatin; CC-1065 and its adozelesin, carzelesin and bizelesin synthetic analogs; cryptophycins (such as cryptophycin 1 and cryptophycin 8); dolastatin; duocarmycin and the synthetic analogs thereof, such as KW-2189 and CB1-TM1; eleutherobin; pancratistatin; a sarcodyctin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimustine; antibiotics such as the enediyne antibiotics (e.g., calicheamicin, such as calicheamicin gamma1I and calicheamicin omega1I (Angew Chem. Intl. Ed. Engl. (1994) 33:183-186); dynemicin, such as dynemicin A; bisphosphonates, such as clodronate; an esperamicin; as well as neocarzinostatin chromophore and related chromoprotein enediyne antibiotic chromophores, aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminol evulinic acid; eniluracil: amsacrine; bestrabucil: bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products. Eugene, Oreg.); razoxane; rhizoxin; sizofuran; spirogermanium; tenuazonic acid; triaziquone; 2,2',2"-trichlorotriethylamine; trichothecenes (such as T-2 toxin, verracurin A, roridin A and anguidine);

urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chlorambucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone: teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

The "chemotherapeutic agent" can also be selected, for example, from: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifene citrate): (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, such as those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above.

The "chemotherapeutic agent" can also be selected, for example, from therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with a subject compound and stereoisomers thereof, and pharmaceutically acceptable salt thereof may, for example, be selected from: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

Also provided is a composition comprising a subject compound and stereoisomers thereof, and pharmaceutically acceptable salts thereof, and at least one pharmaceutically acceptable carrier.

The composition comprising a subject compound and stereoisomers thereof, and pharmaceutically acceptable salts thereof can be administered in various known manners, such as orally, topically, rectally, parenterally, by inhalation spray, or via an implanted reservoir, although the most suitable route in any given case will depend on the particular host, and nature and severity of the conditions for which the active ingredient is being administered. The term "parenteral" as used herein includes subcutaneous, intracutaneous, intravenous, intramuscular, intraarticular, intraarterial, intrasynovial, intrasternal, intrathecal, intralesional and intracranial injection or infusion techniques. The compositions disclosed herein may be conveniently presented in unit dosage form and prepared by any of the methods well known in the art.

The subject compounds and stereoisomers thereof, and pharmaceutically acceptable salts thereof can be administered orally in solid dosage forms, such as capsules, tablets, troches, dragées, granules and powders, or in liquid dosage forms, such as elixirs, syrups, emulsions, dispersions, and suspensions. The subject compounds and stereoisomers thereof, and pharmaceutically acceptable salts thereof disclosed herein can also be administered parenterally, in sterile liquid dosage forms, such as dispersions, suspensions or solutions. Other dosages forms that can also be used to administer the subject compounds and stereoisomers thereof, and pharmaceutically acceptable salts thereof disclosed herein as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules containing the compound and/or the at least one pharmaceutically acceptable salt thereof disclosed herein and powdered carriers, such as lactose, starch, cellulose derivatives, magnesium stearate, stearic acid, and the like, can also be used. Similar diluents can be used to make compressed tablets. Both tablets and capsules can be manufactured as sustained release products to provide for continuous release of medication over a period of time. Compressed tablets can be sugar coated or film coated to mask any unpleasant taste and protect the tablet from the atmosphere, or enteric coated for selective disintegration in the gastrointestinal tract.

Liquid dosage forms for oral administration can further comprise at least one agent selected from coloring and flavoring agents to increase patient acceptance.

In general, water, a suitable oil, saline, aqueous dextrose (glucose), and related sugar solutions and glycols such as propylene glycol or polyethylene glycols can be examples of suitable carriers for parenteral solutions. Solutions for parenteral administration may comprise a water soluble salt of the at least one compound describe herein, at least one suitable stabilizing agent, and if necessary, at least one buffer substance. Antioxidizing agents such as sodium bisulfite, sodium sulfite, or ascorbic acid, either alone or combined, can be examples of suitable stabilizing agents. Citric acid and its salts and sodium EDTA can also be used as examples of suitable stabilizing agents. In addition, parenteral solutions can further comprise at least one preservative, selected, for example, from benzalkonium chloride, methyl- and propylparaben, and chlorobutanol.

A pharmaceutically acceptable carrier is, for example, selected from carriers that are compatible with active ingredients of the composition (and in some embodiments, capable of stabilizing the active ingredients) and not deleterious to the subject to be treated. For example, solubilizing agents, such as cyclodextrins (which can form specific, more soluble complexes with the at least one compound and/or at least one pharmaceutically acceptable salt disclosed herein), can be utilized as pharmaceutical excipients for delivery of the active ingredients. Examples of other carriers include colloidal silicon dioxide, magnesium stearate, cellulose, sodium lauryl sulfate, and pigments such as D&C Yellow #10. Suitable pharmaceutically acceptable carriers are described in *Remington's Pharmaceutical Sciences*, A. Osol, a standard reference text in the art.

The subject compounds and stereoisomers thereof, and pharmaceutically acceptable salts thereof disclosed herein can further be examined for efficacy in treating Btk related diseases by in vivo assays. For example, the compound and/or the at least one pharmaceutically acceptable salts thereof disclosed herein can be administered to an animal (e.g., a mouse model) having Btk related diseases and its therapeutic effects can be accessed. Positive results in one or more of such tests are sufficient to increase the scientific storehouse of knowledge and hence sufficient to demonstrate practical utility of the compounds and/or salts tested. Based on the results, an appropriate dosage range and administration route for animals, such as humans, can also be determined.

For administration by inhalation, the subject compounds and stereoisomers thereof, and pharmaceutically acceptable salts thereof may be conveniently delivered in the form of an aerosol spray presentation from pressurized packs or nebulisers. The subject compounds and stereoisomers thereof, and pharmaceutically acceptable salts thereof may also be delivered as powders, which may be formulated and the powder composition may be inhaled with the aid of an insufflation powder inhaler device. One exemplary delivery system for inhalation can be metered dose inhalation (MDI) aerosol, which may be formulated as a suspension or solution of a subject compound and stereoisomers thereof, and pharmaceutically acceptable salts thereof disclosed herein in at least one suitable propellant, selected, for example, from fluorocarbons and hydrocarbons.

For ocular administration, an ophthalmic preparation may be formulated with an appropriate weight percentage of a solution or suspension of the subject compound and stereoisomers thereof, and pharmaceutically acceptable salts thereof in an appropriate ophthalmic vehicle, such that the subject compound and stereoisomers thereof, and at least one pharmaceutically acceptable salts thereof is maintained in contact with the ocular surface for a sufficient time period to allow the compound to penetrate the corneal and internal regions of the eye.

Useful pharmaceutical dosage-forms for administration of the subject compounds and stereoisomers thereof, and pharmaceutically acceptable salts thereof disclosed herein include, but are not limited to, hard and soft gelatin capsules, tablets, parenteral injectables, and oral suspensions.

The dosage administered will be dependent on factors, such as the age, health and weight of the recipient, the extent of disease, type of concurrent treatment, if any, frequency of treatment, and the nature of the effect desired. In general, a daily dosage of the active ingredient can vary, for example, from 0.1 to 2000 milligrams per day. For example, 10-500 milligrams once or multiple times per day may be effective to obtain the desired results.

In some embodiments, a large number of unit capsules can be prepared by filling standard two-piece hard gelatin capsules each with, for example, 100 milligrams of the subject compound and stereoisomers thereof, and pharmaceutically acceptable salt thereof disclosed herein in powder, 150 milligrams of lactose, 50 milligrams of cellulose, and 6 milligrams magnesium stearate.

In some embodiments, a mixture of the compound, stereoisomers thereof, and pharmaceutically acceptable salts thereof a digestible oil such as soybean oil, cottonseed oil or olive oil can be prepared and injected by means of a positive displacement pump into gelatin to form soft gelatin capsules containing 100 milligrams of the active ingredient. The capsules are washed and dried.

In some embodiments, a large number of tablets can be prepared by conventional procedures so that the dosage unit comprises, for example, 100 milligrams of the compound, stereoisomers thereof, and pharmaceutically acceptable salts thereof, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

In some embodiments, a parenteral composition suitable for administration by injection can be prepared by stirring 1.5% by weight of the compound and/or at least an enantiomer, a diastereomer, or pharmaceutically acceptable salt thereof disclosed herein in 10% by volume propylene glycol. The solution is made to the expected volume with water for injection and sterilized.

In some embodiment, an aqueous suspension can be prepared for oral administration. For example, each 5 milliliters of an aqueous suspension comprising 100 milligrams of finely divided compound, stereoisomers thereof, and pharmaceutically acceptable salts thereof, 100 milligrams of sodium carboxymethyl cellulose, 5 milligrams of sodium benzoate, 1.0 grams of sorbitol solution, U.S.P., and 0.025 milliliters of vanillin can be used.

The same dosage forms can generally be used when the compound, stereoisomers thereof, and pharmaceutically acceptable salts thereof are administered stepwise or in conjunction with at least one other therapeutic agent. When drugs are administered in physical combination, the dosage form and administration route should be selected depending on the compatibility of the combined drugs. Thus the term coadministration is understood to include the administration of at least two agents concomitantly or sequentially, or alternatively as a fixed dose combination of the at least two active components.

The compounds, stereoisomers thereof, and pharmaceutically acceptable salt thereof disclosed herein can be administered as the sole active ingredient or in combination with at least one second active ingredient, selected, for example, from other active ingredients known to be useful for treating Btk related diseases in a patient.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

General Reaction Scheme for Compound Preparation

The subject compounds and pharmaceutically acceptable salts thereof, can be prepared from (a) commercially available starting materials (b) known starting materials which may be prepared as described in literature procedures (c) new intermediates described in the schemes and experimental procedures herein. In making the compounds of the invention, the order of synthetic steps may be varied to increase the yield of desired product. Some of compounds in this invention may be generated by the methods as shown in the following reaction schemes and the description thereof.

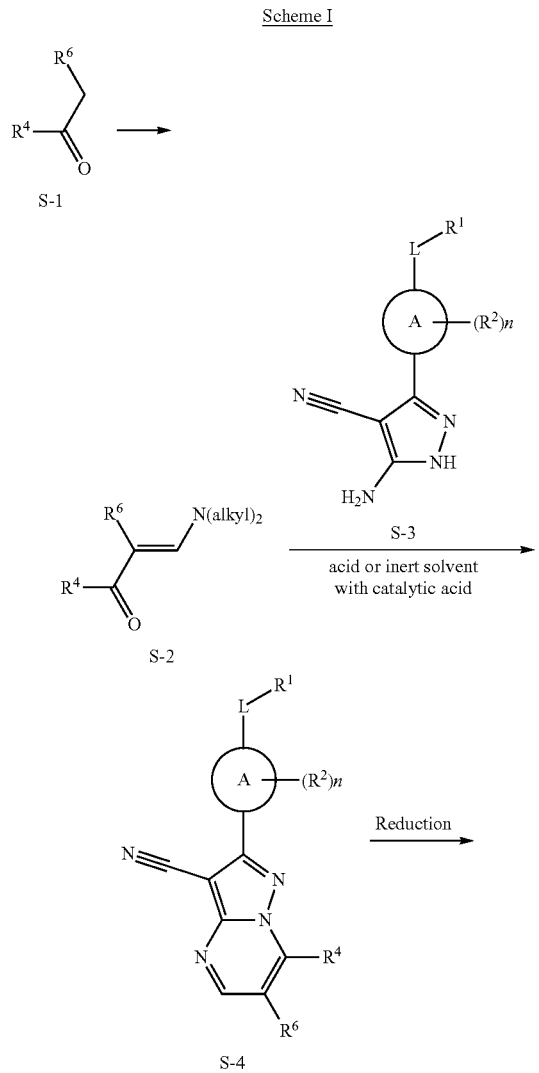

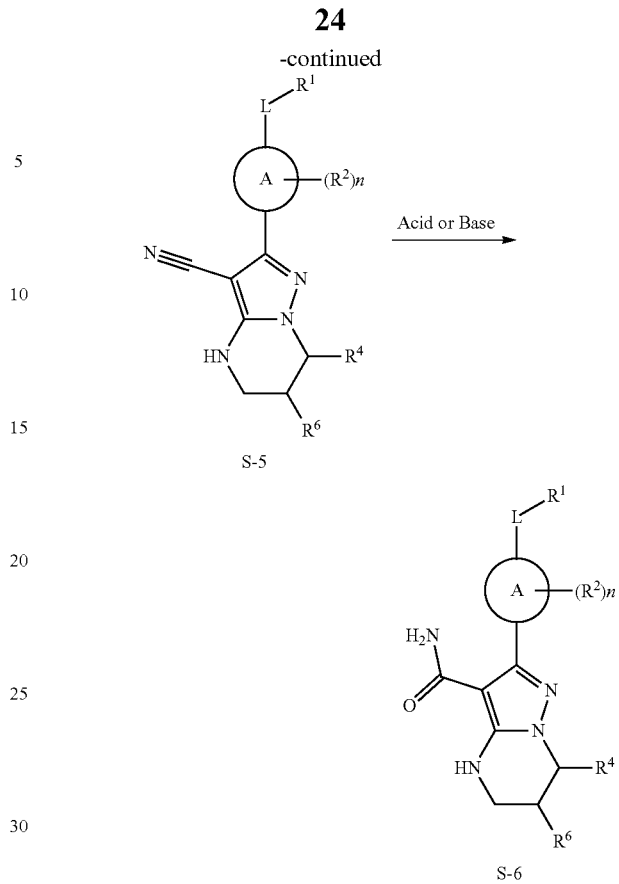

Scheme I above shows a general synthetic route that is used for preparing the compound S-6 of this invention, where A, $R_1$, $R_2$, $R_4$, $R_6$, L and n are as described herein. Reaction of methyl ketone S-1 in acetals of N,N-dialkylformamides or acetals of N,N-dialkylacetamide at reflux temperature for several hours afforded 3-dialkylamino-1-(aryl, heteroaryl or alkyl)-2-propen-1-one S-2. Intermediate S-3 may be prepared by methods substantially similar to those described in International Patent Publication No. WO 2001/019829 and No. WO 2011/046964. The reaction of intermediate S-3 and an appropriately substituted 3-dialkylamino-1-(aryl, heteroaryl or alkyl)-2-propen-1-one S-2 in weak acid such as acetic acid or in an inert solvent such as toluene, acetonitrile or dimethoxyethane with catalytic acid, at 80° C. to reflux temperature for several hours afforded the nitrile compound S-4. Reduction of the pyrimidine ring with reducing agents such as sodium borohydride (NaBH$_4$), Pd/C or NaBH$_4$ followed with Pd/C gave tetrahydropyrazolopyrimidine S-5, and subsequent hydrolysis of nitrile under alkaline condition such as NaOH or KOH plus H$_2$O$_2$ in alcohol, or under acid condition such as H$_3$PO$_4$, H$_2$SO$_4$, or BF$_3$·HOAc, yielded the carboxamide S-6.

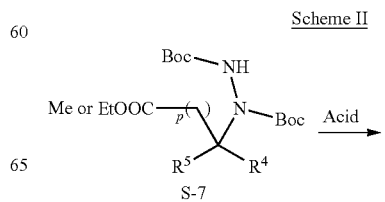

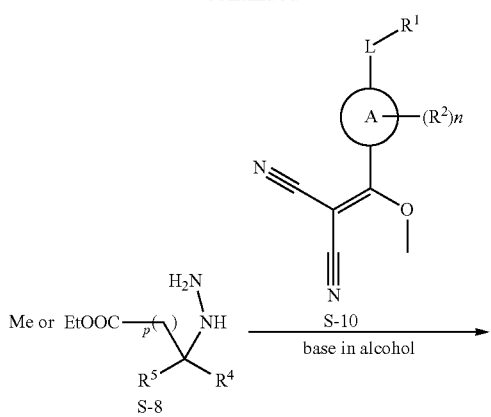

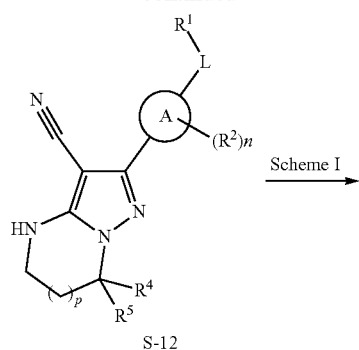

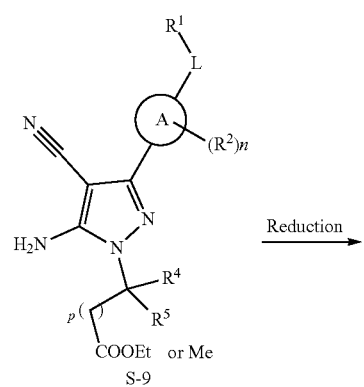

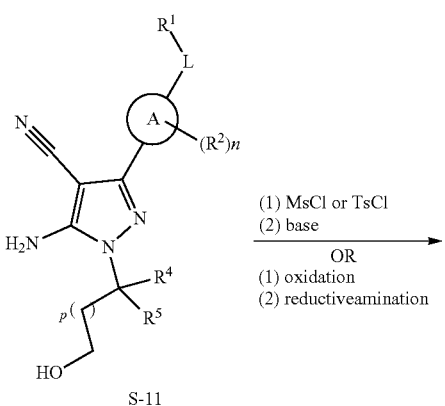

Scheme II describes a general synthetic route to prepare carboxamide S-13, where A, $R_1$, $R_2$, $R_4$, $R_5$, L, n and p are as described herein. The protected hydrazine S-7 known can be conveniently prepared by the methods as described in the literature (J. Med. Chem. 1992, 35, 2392). Deprotection with acid, followed by condensation of this building block with intermediate S-10 (also described in International Patent Publication No. WO 2001/019829 and No. WO 2011/046964) in alkaline solvent such as TEA/ethanol afforded pyrazole ester S-9. The pyrazole alcohol S-11 can be prepared from an ester S-9 through a reductive process. The reducing agents which may be used for this process include, but are not limited to $LiBH_4$, $NaBH_4$ and Super Hydride. Intramolecular N-alkylation or reductive amination gave the nitriles S-12, which was converted to carboxamide S-13 by the same methods as described in Scheme I.

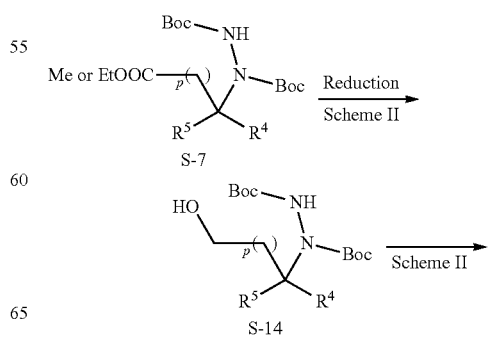

27
-continued
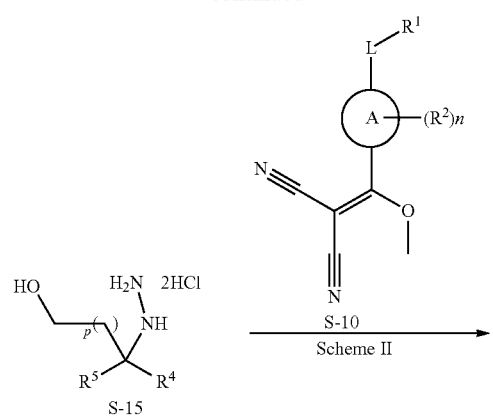
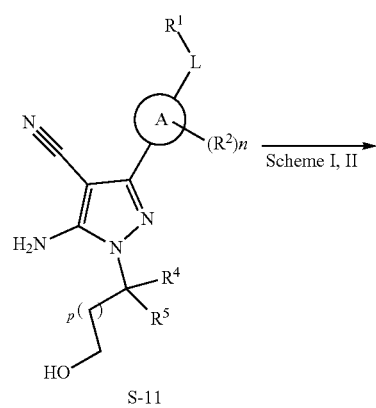
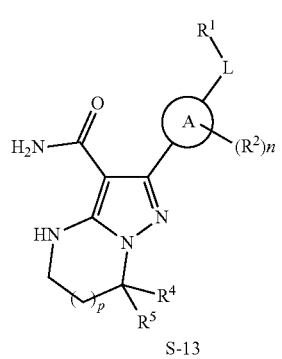
28
-continued
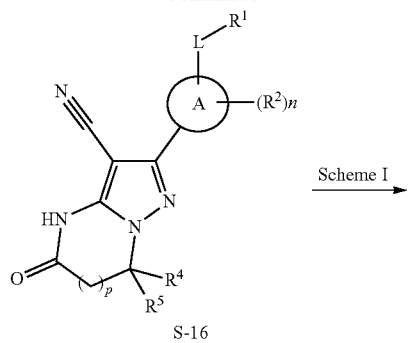
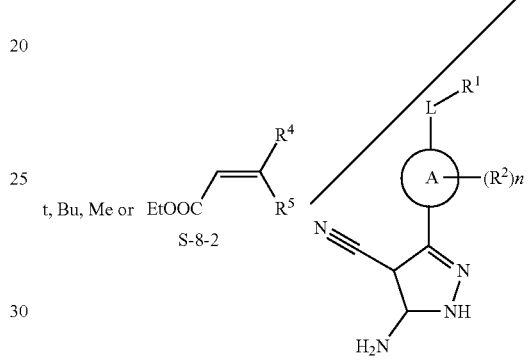
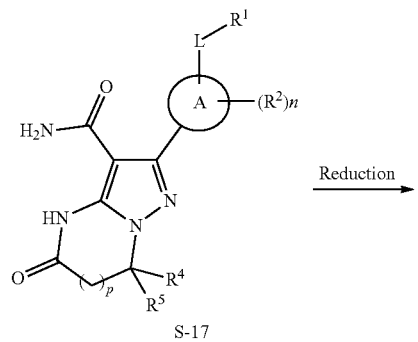
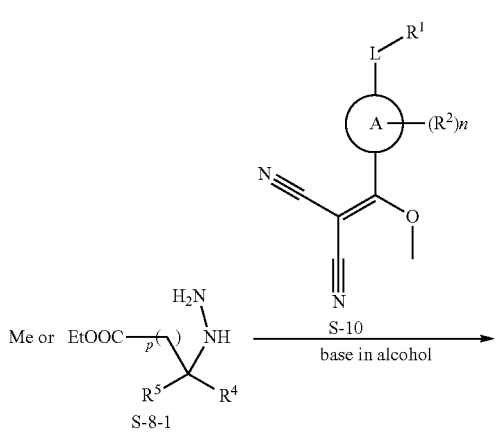
Scheme III describes alternative routes to prepare carboxamide S-13.

Scheme IV

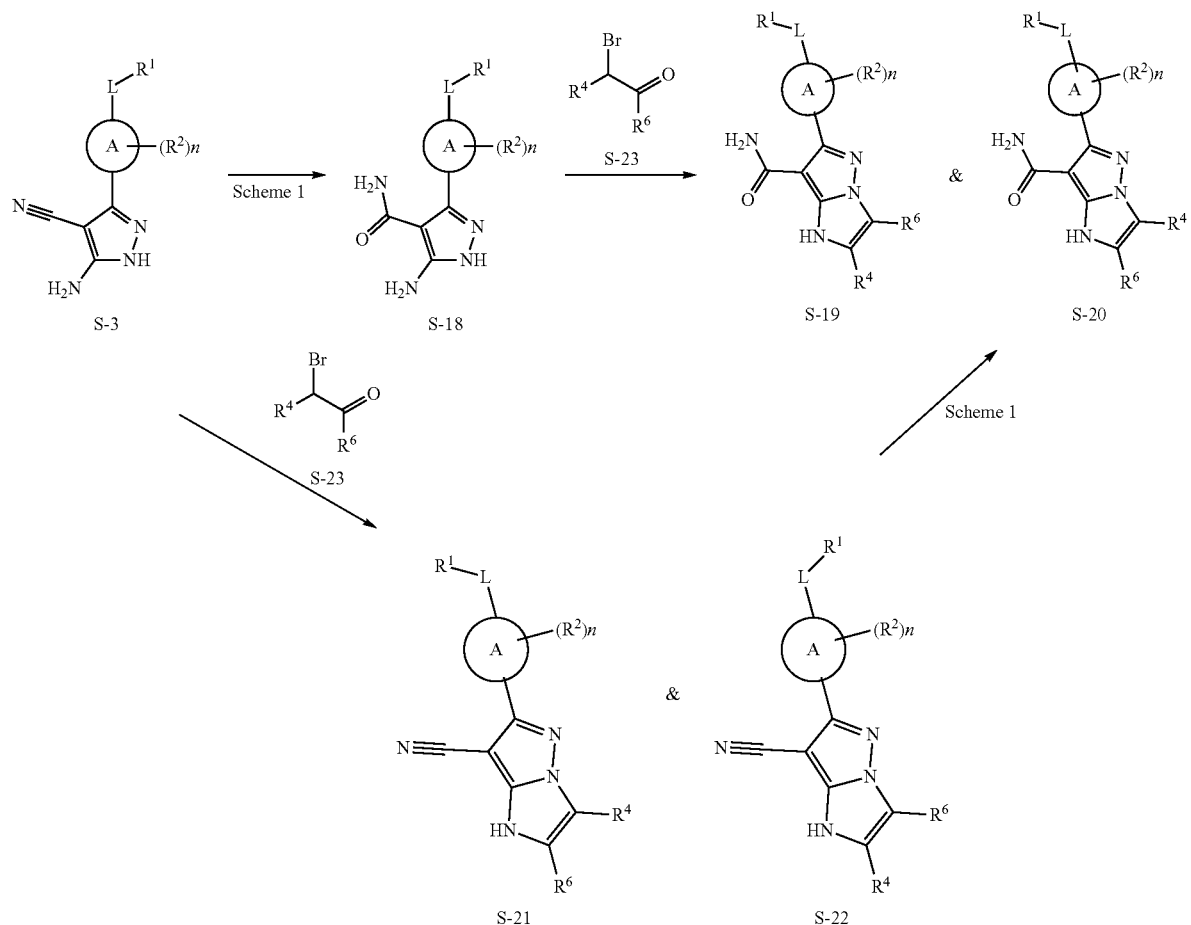

Scheme IV above shows general synthetic routes that have been used for preparing compounds S-19 and S-20 of this invention, where A, $R_1$, $R_2$, $R_4$, $R_6$, L and n are as described herein. Hydrolysis of nitrile S-3 afforded carboxamide S-18 by the same methods as described in Scheme I. The cyclization of pyrazole carboxamide S-18 or pyrazole nitrile S-3 with the commercially available or prepared haloketone S-23 gave regioisomers S-19 and S-20, or S-21 and S-22. The nitriles S-21 and S-22 were hydrolyzed to afford carboxamides S-19 and S-20 according to Scheme I.

Scheme V

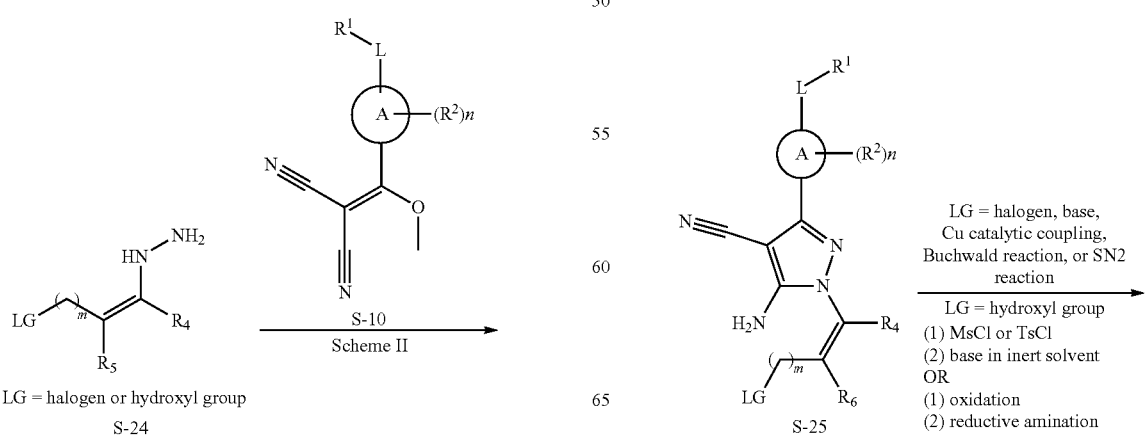

-continued

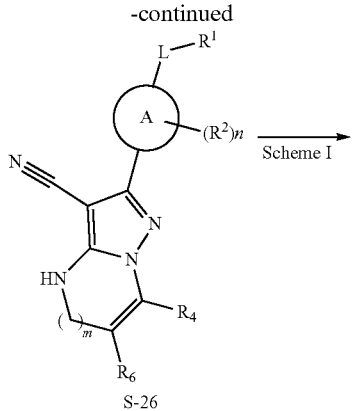

S-26

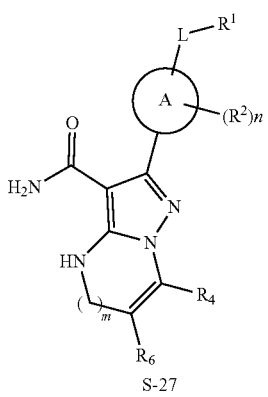

S-27

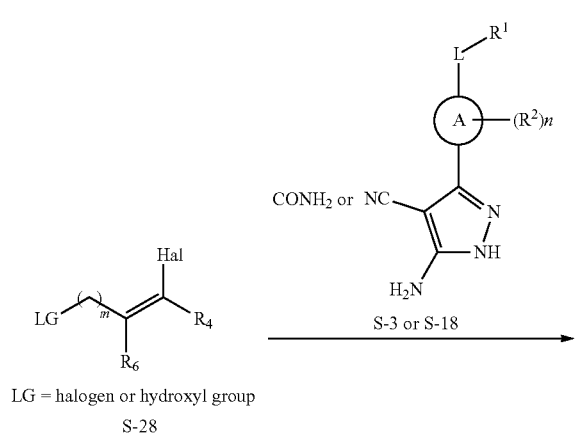

LG = halogen or hydroxyl group
S-28

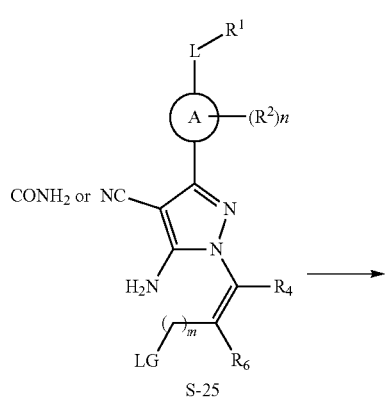

S-25

-continued

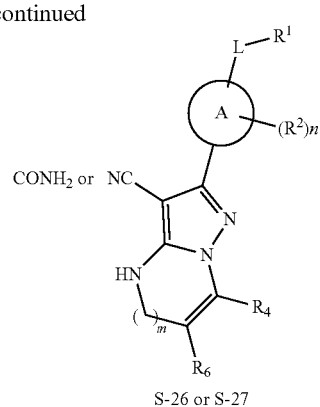

S-26 or S-27

Scheme V above shows general synthetic routes that have been used for preparing compound S-27 of this invention, where A, $R_1$, $R_2$, $R_4$, $R_6$, L, m and n are as described herein. The pyrazole S-25 was prepared by cyclization of intermediate S-10 with the commercially available or prepared hydrazine S-24 in alcohol according to one of steps in Scheme II. The intramolecular cyclization of intermediate S-25 was performed with the process included, but not limited to Cu catalytic coupling, Buchwald reaction, SN2 reaction or reductive amination. Finally, nitrile S-26 was hydrolyzed to afford carboxamide S-27 according to Scheme I. Alternatively, nucleophilic substitution, followed by intramolecular cyclization afforded carboxamide S-27.

Scheme VI

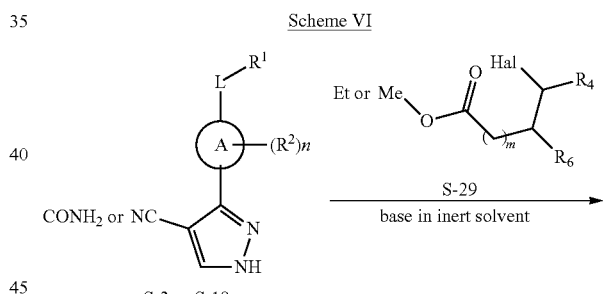

S-3 or S-18

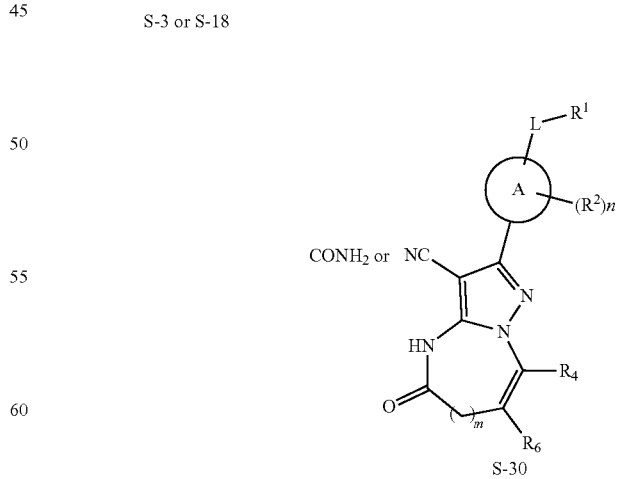

S-30

Scheme VI above shows a general synthetic route that has been used for preparing compound S-30 of this invention, where A. $R_1$, $R_2$, $R_4$, $R_6$, L, m and n are as described herein.

The intramolecular amide S-30 was prepared by heating the mixture of nitrile S-3 or carboxamide S-18 and ester S-29 in inert solvent such as DMF with presence of base such as K$_2$CO$_3$ and TEA.

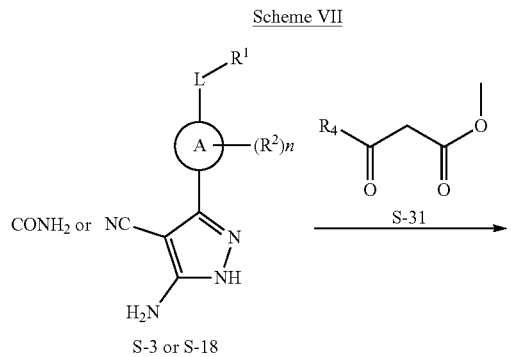

Scheme VII

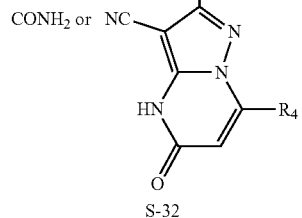

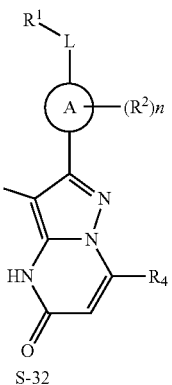

S-32

Scheme VII above shows a general synthetic route that has been used for preparing compound S-32 of this invention, where A, R$_1$, R$_2$, R$_4$, L and n are as described herein. The amide S-32 was prepared by heating the mixture of nitrile S-3 or carboxamide S-18 and β-ketoester S-31 in weak acid such as acetic acid or in an inert solvent such as toluene, acetonitrile or dimethoxyethane with catalytic acid.

Scheme VIII

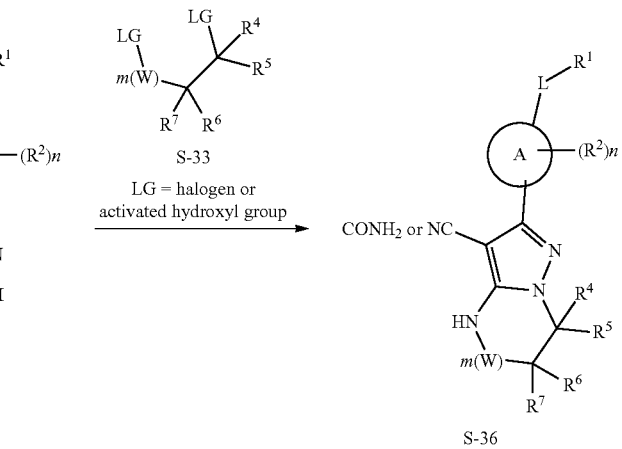

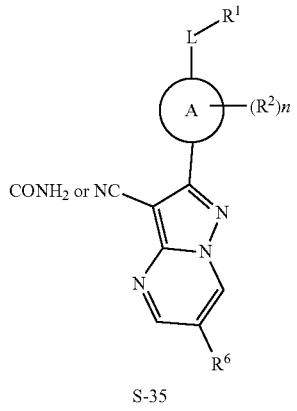

Scheme VIII above shows a general synthetic route that has been used for preparing compound S-36 of this invention, when A, $R_1$, $R_2$, $R_6$, $R_7$, L, W, m and n are as described herein. The intermolecular cyclization of nitrile S-3 or carboxamide S-18 and commercially available or prepared intermediate S-33 was performed in inert solvent such as DMF with presence of base such as $K_2CO_3$ and TEA to afford compound S-36. Alternatively, condensation of nitrile S-3 or carboxamide S-18 with dialdehyde S-34, followed by reduction yielded compound S-36.

EXAMPLES

The examples below are intended to be purely exemplary and should not be considered to be limiting in any way. Efforts have been made to ensure accuracy with respect to numbers used (for example, amounts, temperature, etc.), but some experimental errors and deviations should be accounted for. Unless indicated otherwise, temperature is in degrees Centigrade. Reagents were purchased from commercial suppliers such as Sigma-Aldrich, Alfa Aesar, or TCI, and were used without further purification unless indicated otherwise.

Unless indicated otherwise, the reactions set forth below were performed under a positive pressure of nitrogen or argon or with a drying tube in anhydrous solvents; the reaction flasks were fitted with rubber septa for the introduction of substrates and reagents via syringe; and glassware was oven dried and/or heat dried.

$^1$H NMR spectra were recorded on a Agilent instrument operating at 400 MHz. $^1$HNMR spectra were obtained using $CDCl_3$, $CD_2Cl_2$, $CD_3OD$, $D_2O$, $d_6$-DMSO, $d_6$-acetone or $(CD_3)_2CO$ as solvent and tetramethylsilane (0.00 ppm) or residual solvent ($CDCl_3$: 7.25 ppm; $CD_3OD$: 3.31 ppm; $D_2O$: 4.79 ppm; $d_6$-DMSO: 2.50 ppm; d6-acetone: 2.05; $(CD_3)_2CO$: 2.05) as the reference standard. When peak multiplicities are reported, the following abbreviations are used: s (singlet), d (doublet), t (triplet), q (quartet), qn (quintuplet), sx (sextuplet), m (multiplet), br (broadened), dd (doublet of doublets), dt (doublet of triplets). Coupling constants, when given, are reported in Hertz (Hz).

LC-MS spectrometer (Agilent 1260) Detector: MWD (190-400 nm), Mass detector: 6120 SQ
Mobile phase: A: acetonitrile with 0.1% Formic acid, B: water with 0.1% Formic acid
Column: Poroshell 120 EC-C18, 4.6×50 mm, 2.7 μm
Gradient method: Flow: 1.8 mL/min

| Time (min) | A (%) | B (%) |
| --- | --- | --- |
| 0.00 | 5 | 95 |
| 1.5 | 95 | 5 |
| 2.0 | 95 | 5 |
| 2.1 | 5 | 95 |
| 3.0 | 5 | 95 |

Preparative HPLC was conducted on a column (150×21.2 mm ID, 5 μm, Gemini NX-C18) at a flow rate of 20 ml/min. injection volume 2 ml, at room temperature and UV Detection at 214 nm and 254 nm.

In the following examples, the abbreviations below are used:
Brine Saturated aqueous sodium chloride solution
$BnNH_2$ Benzyl amine
CbzCl Benzyl chloroformate
DCM Dichloromethane
DCE 1,2-Dichlorethane
DIEA N,N-diisopropylethylamine
DMF N,N-Dimethylformamide
DMF-DMA N,N-dimethylformamide dimethylacetal
DMAP N,N-dimethylpyridin-4-amine
DCC N,N-dicyclohexylcarbodiimide
DHP 3,4-Dihydro-2H-pyrane
EA Ethyl acetate
HATU O-(7-Azabenzotriazol-1-yl)-N,N,N',N'-tetramethyluronium hexafluorophosphate
HOAc Acetic acid
$H_2O_2$ Hydrogen peroxide solution 30% (w/w) in $H_2O$
IPA Isopropanol
MTBE Methyl tert-butyl ether
MsCl Methanesulfuryl chloride
NBS N-Bromosuccinimide
Pd/C Palladium on carbon powder
$Pd(OH)_2$/C Palladium hydroxide on carbon powder
PE Petroleum ether
$PPh_3$ Triphenylphosphine
Pre-TLC Prepared thin layer chromatography
sat Saturated
$Tf_2O$ Trifluoromethanesulfonic anhydride
THF Tetrahydrofuran
TEA Triethylamine
$TMSCHN_2$ (Trimethylsilyl)diazomethane
TMSCl Chlorotrimethylsilane Example 1: Synthesis of Compounds 1-4

Compound 1: 7-(3-Aminophenyl)-2-(4-phenoxyphenyl) pyrazolo[1,5-a]pyrimidine-3-carbonitrile

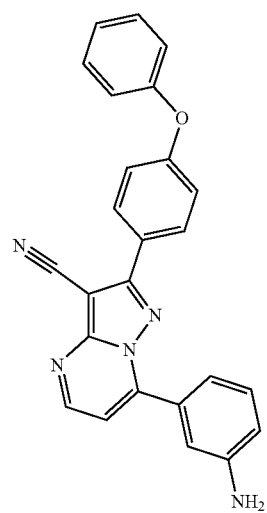 [SMILES: N#Cc1c(-c2ccc(Oc3ccccc3)cc2)nn2c(-c3cccc(N)c3)ccnc12]

Step 1: 2-(Hydroxy(4-phenoxyphenyl)methylene)malononitrile

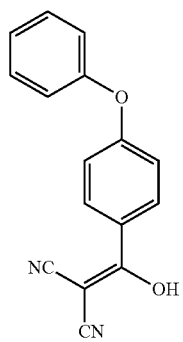

A solution of 4-phenoxybenzoic acid (300 g, 1.4 mol) in $SOCl_2$ (1.2 L) was stirred at 80° C. under $N_2$ for 3 hr. The mixture was concentrated in vacuum to give the intermediate (315 g) which was used for next step without further purification.

To a solution of propanedinitrile (89.5 g, 1,355 mmol) and DIEA (350 g, 2,710 mmol) in THF (800 mL) was dropwise a solution of the intermediate (315 g) in toluene (800 mL) at 0~5° C. over 2 hr. The resultant mixture was allowed to warm to RT and stirred for 16 hr. The reaction was quenched with water (2.0 L) and extracted with of EA (2.0 L×3). The combined organic layers were washed with 1,000 mL of 3N HCl aqueous solution, brine (2.0 L×3), dried over $Na_2SO_4$ and concentrated to give the crude product (330 g, 93%). $^1$H NMR (DMSO-$d_6$) δ 7.62 (d, J=8.8 Hz, 2H), 7.46-7.38 (m, 2H), 7.18 (t, J=7.6 Hz, 1H), 7.06 (d, J=8.0 Hz, 2H), 6.94 (d, J=8.8 Hz, 2H). MS (ESI) m/e [M+1]$^+$ 262.9.

Step 2: 2-(Methoxy(4-phenoxyphenyl)methylene)malononitrile

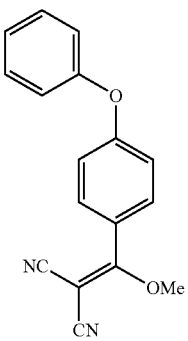 [SMILES: COC(=C(C#N)C#N)c1ccc(Oc2ccccc2)cc1]

A solution of 2-(hydroxy(4-phenoxyphenyl)methylene) malononitrile (50 g, 190.8 mmol) in $CH(OMe)_3$ (500 mL) was heated to 75° C. for 16 hr. Then the mixture was concentrated to a residue and washed with MeOH (50 mL) to give 25 g (47.5%) of 2-(methoxy(4-phenoxyphenyl) methylene)malononitrile as a yellow solid. $^1$H NMR (DMSO-$d_6$) δ 7.70 (d, J=8.4 Hz, 2H), 7.52-7.45 (m, 2H), 7.28 (t, J=7.6 Hz, 1H), 7.22-7.06 (m, 4H), 3.93 (s, 3H). MS (ESI) m/e [M+1]$^+$ 276.9.

Step 3: 5-Amino-3-(4-phenoxyphenyl)-1H-pyrazole-4-carbonitrile

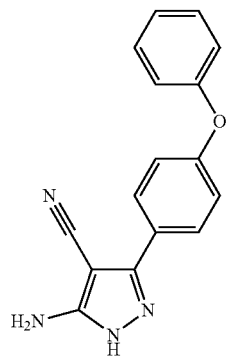

To a solution of 2-(methoxy(4-phenoxyphenyl)methylene)malononitrile (80 g, 290 mmol) in ethanol (200 mL) was added hydrazine hydrate (20 mL). The mixture was stirred at RT for 16 hr then was concentrated to give the crude product and washed with MeOH (30 mL) to afford 55 g (68.8%) of 5-amino-3-(4-phenoxyphenyl)-1H-pyrazole-4-carbonitrile as a off-white solid. $^1$H NMR (DMSO-$d_6$) δ 12.11 (br s, 1H), 7.80 (d, J=8.8 Hz, 2H), 7.46-7.39 (m, 2H), 7.18 (t, J=7.6 Hz, 1H), 7.12-7.04 (m, 4H), 6.43 (br s, 2H).

Step 4: (E)-N-(3-(3-(dimethylamino)acryloyl)phenyl)acetamide

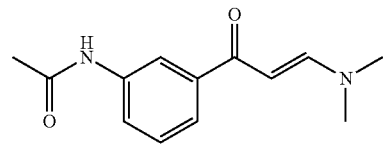 [SMILES: CC(=O)Nc1cccc(C(=O)/C=C/N(C)C)c1]

A solution of N-(3-acetylphenyl)acetamide (1.77 g, 10.0 mmol) in DMF-DMA (6 mL) with molecular sieve (10 portions) was stirred at 100° C. under $N_2$ for 2 hr. the mixture was concentrated and washed with MTBE (30 mL) to afford 2.1 g (90%) of (E)-N-(3-(3-(dimethylamino)acryloyl)phenyl)acetamide as a yellow solid.

Step 5: N-(3-(3-cyano-2-(4-phenoxyphenyl)pyrazolo[1,5-a]pyrimidin-7-yl)phenyl) acetamide

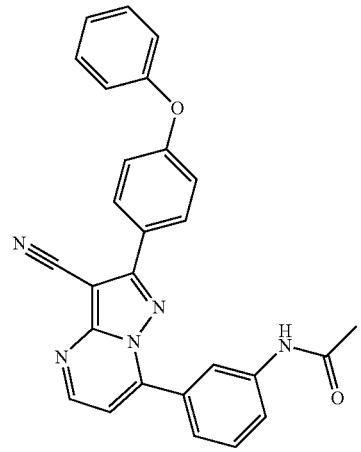 [SMILES: CC(=O)Nc1cccc(-c2ccnc3c(C#N)c(-c4ccc(Oc5ccccc5)cc4)nn23)c1]

To a solution of (E)-N-(3-(3-(dimethylamino)acryloyl)phenyl)acetamide (46 mg, 0.2 mmol) in HOAc (5 mL) was added 5-amino-3-(4-phenoxyphenyl)-1H-pyrazole-4-carbonitrile (55 mg, 0.2 mmol). The mixture was stirred at 118° C. for 4 hr. Then the reaction mixture was concentrated to a residue and partitioned between ethyl acetate (100 mL) and brine (100 mL). Organic layer was separated, washed with brine (2×100 mL), dried over sodium sulfate and concentrated to afford 80 mg (90%) of N-(3-(3-cyano-2-(4-phenoxyphenyl)pyrazolo[1,5-a]pyrimidin-7-yl)phenyl)acetamide as a colorless oil. MS (ESI) m/e [M+1]+ 446.

Step 6: 7-(3-Aminophenyl)-2-(4-phenoxyphenyl)pyrazolo[1,5-a]pyrimidine-3-carbonitrile

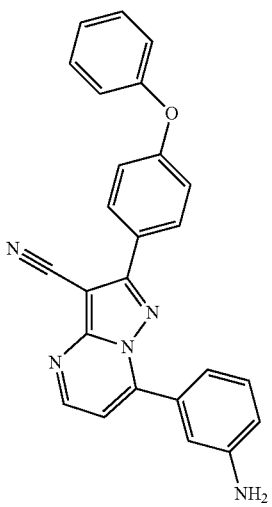 [SMILES: N#Cc1c(-c2ccc(Oc3ccccc3)cc2)nn2c(-c3cccc(N)c3)ccnc12]

To a solution of N-(3-(3-cyano-2-(4-phenoxyphenyl)pyrazolo[1,5-a]pyrimidin-7-yl) phenyl)acetamide (285 mg, 0.64 mmol) in ethanol (6 mL) was added HCl (3 mL). The mixture stirred at 75° C. for 3 hr. Concentrated to afford 250 mg (97%) of 7-(3-aminophenyl)-2-(4-phenoxyphenyl)pyrazolo[1,5-a]pyrimidine-3-carbonitrile as a yellow solid. $^1$H NMR (400 MHz, DMSO-$d_6$) δ 8.90 (d, J=4.4 Hz, 1H), 8.67 (br s, 2H), 8.15 (d, J=8.8 Hz, 2H), 8.06 (s, 1H), 7.87 (d, J=8.0 Hz, 1H), 7.64 (t, J=8.0 Hz, 1H), 7.57 (d, J=4.4 Hz, 1H), 7.48-7.44 (m, 3H), 7.25-7.18 (m, 3H), 7.13 (d, J=8.0 Hz, 2H). MS (ESI) m/e [M+1]+ 404.

Compound 2: 7-(3-Aminophenyl)-2-(4-phenoxyphenyl)-4,5,6,7-tetrahydropyrazolo [1,5-a]pyrimidine-3-carboxamide

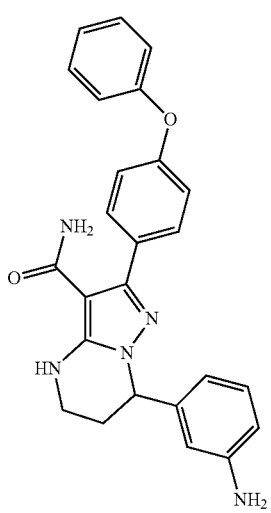

Step 1: 7-(3-Aminophenyl)-2-(4-phenoxyphenyl)-4,5,6,7-tetrahydropyrazolo[1,5-a]pyrimidine-3-carbonitrile

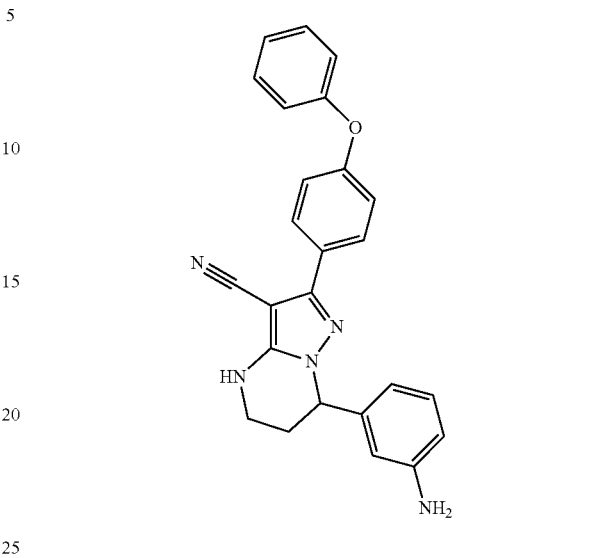

To a solution of 7-(3-aminophenyl)-2-(4-phenoxyphenyl)pyrazolo[1,5-a]pyrimidine-3-carbonitrile (150 mg, 0.372 mmol) in ethanol (10 mL) was added NaBH$_4$ (70 mg, 1.86 mmol). The mixture was stirred at rt for 16 hr and 60° C. for 2 hr. Then the reaction mixture was concentrated to a residue and partitioned between EA (50 mL) and brine (40 mL). Organic layer was separated from aqueous layer, washed with brine (50 mL×2), dried over Na$_2$SO$_4$ and concentrated to afford 135 mg (crude) of 7-(3-aminophenyl)-2-(4-phenoxyphenyl)-4,5,6,7-tetrahydropyrazolo[1,5-a]pyrimidine-3-carbonitrile as a yellow solid. MS (ESI) m/e [M+1]+ 408.

Step 2: 7-(3-Aminophenyl)-2-(4-phenoxyphenyl)-4,5,6,7-tetrahydropyrazolo[1,5-a]pyrimidine-3-carboxamide

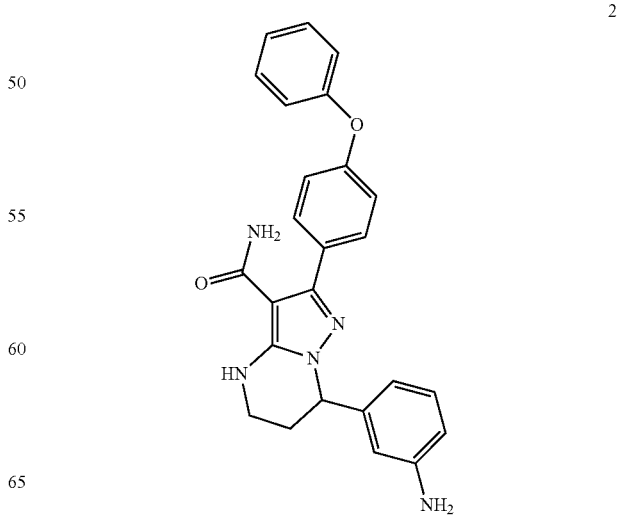

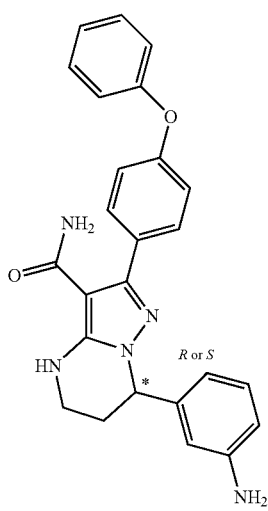 [SMILES: NC(=O)c1c(-c2ccc(Oc3ccccc3)cc2)nn2c1NCCC2c1cccc(N)c1]

2a

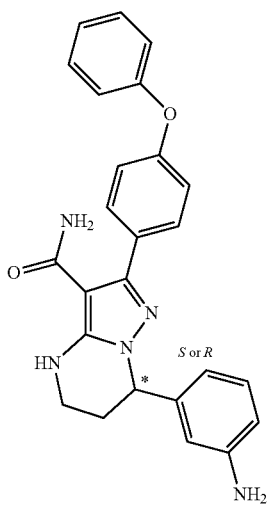

2b

| Column | CHIRALCEL AS-H |
|---|---|
| Column size | 2 cm × 25 cm |
| Injection | 2 mL |
| Mobile phase | CO$_2$/MeOH = 70/30 |
| Flow rate | 45 mL/min |
| Wave length | UV 210 nm |
| Temperature | 35° C. |
| Sample solution | 6 mg/mL in mobile phase |
| Prep-SFC equipment | DAICEL-SFC |

The chiral analysis conditions are shown below.

| Column | CHIRALPAK AD-H |
|---|---|
| Column size | 0.46 cm I.D. × 15 cm L, 5 um |
| Injection | 2 uL |
| Mobile phase | n-Hexane/EtOH (0.1% triethyl amine) = 50/50 (v/v) |
| Flow rate | 1.0 mL/min |
| Wave length | UV 214, 254 nm |

Compound 3 and 4: 7-(3-Acrylamidophenyl)-2-(4-phenoxyphenyl)-4,5,6,7-tetra hydropyrazolo[1,5-a] pyrimidine-3-carboxamide and 7-(3-(3-chloropropanamido)phenyl)-2-(4-phenoxyphenyl)-4,5,6,7-tetrahydropyrazolo[1,5-a] pyrimidine-3-carboxamide

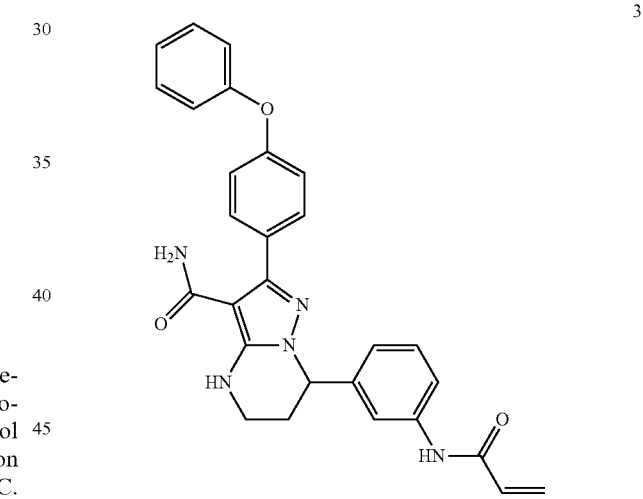

3

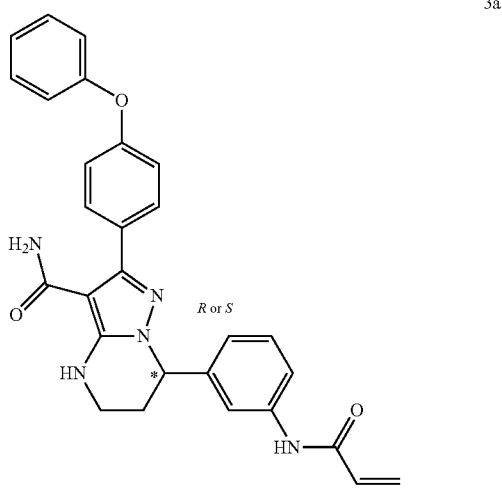

3a

To a solution of 7-(3-aminophenyl)-2-(4-phenoxyphenyl)-4,5,6,7-tetrahydro pyrazolo[1,5-a]pyrimidine-3-carbonitrile (130 mg, 0.32 mmol) in DMSO (2 mL) and ethanol (2 mL) was added a solution of 5N NaOH aqueous solution (1 mL) and H$_2$O$_2$ (1 mL). The mixture was stirred at 60° C. for 30 minutes, concentrated and partitioned between EA (100 mL) and brine (100 mL). Organic layer was separated, washed with brine (3×100 mL), dried over Na$_2$SO$_4$ and purified by chromatography column on silica gel eluting with PE/EA to afford 35 mg (26%) of 7-(3-aminophenyl)-2-(4-phenoxyphenyl)-4,5,6,7-tetrahydropyrazolo[1,5-a]pyrimidine-3-carboxamide as a yellow solid. $^1$H NMR (400 MHz, DMSO-d$_6$) δ 7.50 (d, J=8.4 Hz, 2H), 7.40-7.33 (m, 2H), 7.16 (t, J=7.6 Hz, 1H), 7.06 (d, J=8.0 Hz, 2H), 7.03 (d, J=8.4 Hz, 2H), 6.97 (t, J=7.6 Hz, 1H), 6.76 (s, 1H), 6.44 (d, J=8.4 Hz, 1H), 6.23-6.21 (m, 2H), 5.30-5.25 (m, 1H), 5.09 (s, 2H), 3.30-3.28 (m, 1H), 3.12-3.02 (m, 1H), 2.34-2.26 (m, 1H), 2.05-2.01 (m, 1H). MS (ESI) m/e [M+1]$^+$ 426.

Compound 2 was separated into two enantiomeric stereoisomers compound 2a (peak 1, R or S, retention time at 8.94 min in chiral analysis), and compound 2b (peak 2, S or R, retention time at 10.11 min in chiral analysis) by chiral prep-HPLC. The chiral separation conditions are shown below.

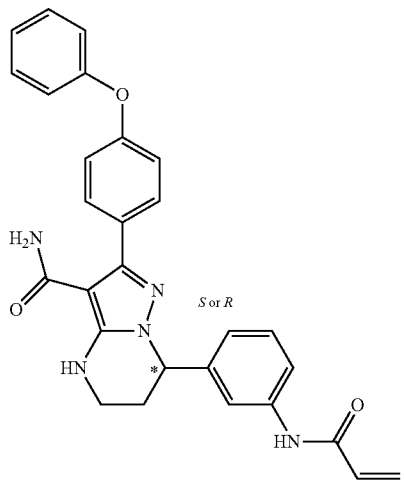

3b

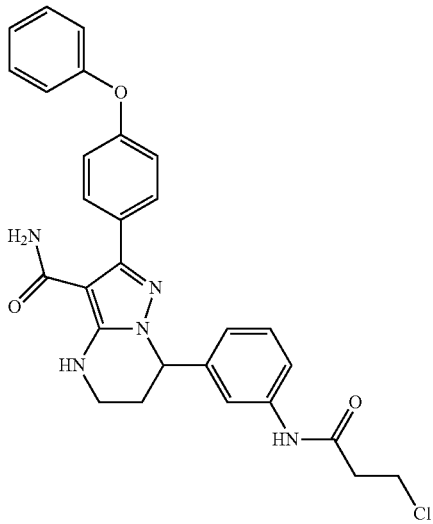

4

To a solution of 7-(3-aminophenyl)-2-(4-phenoxyphenyl)-4,5,6,7-tetrahydro pyrazolo[1,5-a]pyrimidine-3-carboxamide (30 mg, 0.071 mmol) in DCM (2 mL) was added pyridine (0.2 mL). Then acryloyl chloride (6 mg, 0.084 mmol) was added dropwise. The mixture was stirred at RT for 0.5 hr and partitioned between DCM (20 mL) and brine (20 mL). Organic layer was separated from aqueous layer, washed with brine (2×20 mL), dried over $Na_2SO_4$ and purified by Pre-TLC (DCM/$CH_3OH$=10/1) to afford 1.82 mg (5.38%) of 7-(3-acrylamidophenyl)-2-(4-phenoxyphenyl)-4,5,6,7-tetrahydropyrazolo[1,5-a]pyrimidine-3-carboxamide as a white solid. $^1$H NMR (400 MHz, $CD_3OD$) δ 7.58 (d, J=8.8 Hz, 1H), 7.46 (d, J=8.8 Hz, 2H), 7.34-7.26 (m, 4H), 7.10 (t, J=7.6 Hz, 1H), 7.04-6.95 (m, 4H), 6.84 (d, J=7.6 Hz, 1H), 6.39-6.25 (m, 2H), 5.69 (dd, J=2.4, 9.6 Hz, 1H), 5.47-5.44 (m, 1H), 3.38-3.31 (m, 1H), 3.22-3.12 (m, 1H), 2.52-2.42 (m, 1H), 2.23-2.17 (m, 1H). MS (ESI) m/e [M+1]$^+$ 480.

2.21 mg of byproduct 7-(3-(3-chloropropanamido)phenyl)-2-(4-phenoxyphenyl)-4,5,6,7-tetrahydropyrazolo[1,5-a]pyrimidine-3-carboxamide as a white solid. $^1$H NMR (400 MHz, $CD_3OD$) δ 7.57 (d, J=8.0 Hz, 1H), 7.52 (d, J=8.8 Hz, 2H), 7.42-7.30 (m, 4H), 7.16 (t, J=7.6 Hz, 1H), 7.09-7.01 (m, 4H), 6.89 (d, J=8.0 Hz, 1H), 5.53-5.48 (m, 1H), 3.85 (t, J=6.4 Hz, 2H), 3.44-3.37 (m, 1H), 3.26-3.19 (m, 1H), 2.83 (t, J=6.4 Hz, 2H), 2.60-2.44 (m, 1H), 2.33-2.22 (m, 1H). MS (ESI) m/e [M+1]$^+$ 516.2.

Compound 3a (peak 1, R or S, retention time at 4.45 min) and 3b (peak 2, R or S, retention time at 7.41 min) was prepared from 2a and 2b according to the procedure similar to those for compound 3.

The chiral analysis conditions are shown below.

| Column | CHIRALPAK AD-H |
|---|---|
| Column size | 0.46 cm I.D. × 15 cm L, 5 um |
| Injection | 2 uL |
| Mobile phase | n-Hexane/EtOH (0.1% triethyl amine) = 50/50 (v/v) |
| Flow rate | 1.0 mL/min |
| Wave length | UV 254 nm |

Compound 5: 7-(2-Aminophenyl)-2-(4-phenoxyphenyl)-4,5,6,7-tetrahydropyrazolo [1,5-a]pyrimidine-3-carboxamide

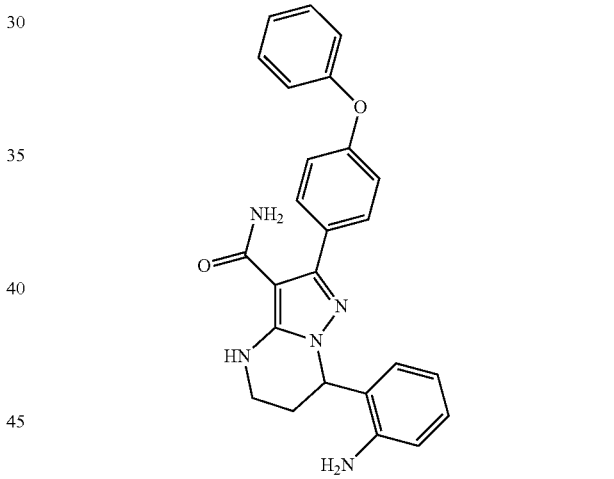

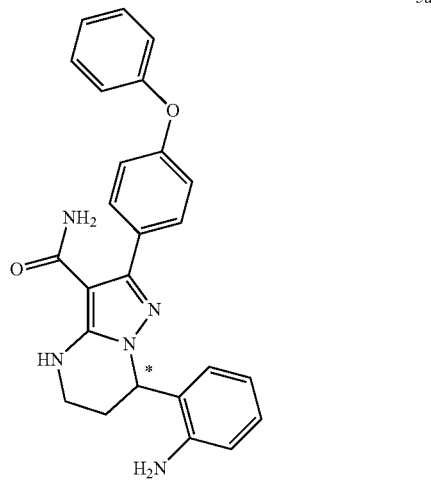

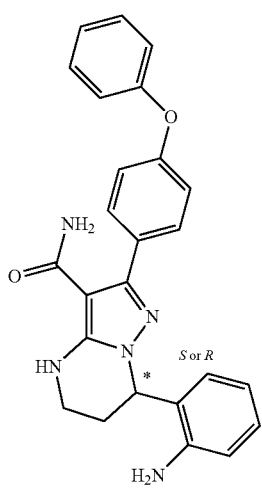

5b

The desired product was prepared from 1-(2-nitrophenyl) ethanone and 5-amino-3-(4-phenoxyphenyl)-1H-pyrazole-4-carbonitrile according to the procedures similar to those for 7-(3-aminophenyl)-2-(4-phenoxyphenyl)pyrazolo[1,5-a]pyrimidine-3-carbonitrile (step 4 to step 5), compound 2 (step 1 and 2) and compound 68 (step 8) under appropriate conditions recognized by one of ordinary skill in the art. $^1$H NMR (DMSO-d$_6$) δ 7.48-7.44 (m, 2H), 7.40-7.33 (m, 2H), 7.15-7.09 (m, 1H), 7.05-6.97 (m, 4H), 6.92 (td, J=8.0, 1.2 Hz, 1H), 6.75 (br s, 1H), 6.64 (dd, J=8.0, 1.2 Hz, 1H), 6.46 (td, J=7.6, 1.2 Hz, 1H), 6.23 (dd, J=7.6, 1.2 Hz, 1H), 5.57-5.52 (m, 1H), 5.19 (br s, 2H), 3.27-3.17 (m, 1H), 2.93 (td, J=2.8, 12.0 Hz, 1H), 2.21-2.11 (m, 1H), 2.10-2.05 (m, 1H). MS (ESI) m/e [M+1]$^+$ 426.0.

Compound 5 was separated into two enantiomeric stereoisomers compound 5a (peak 1, R or S, retention time at 7.30 min in chiral analysis), and compound 5b (peak 2, S or R, retention time at 9.68 min in chiral analysis) by chiral prep-HPLC. The chiral separation conditions are shown below.

| Column | CHIRALCEL OD-H |
|---|---|
| Column size | 3 cm × 25 cm |
| Injection | 8 mL |
| Mobile phase | Hexane/IPA = 50/50 |
| Flow rate | 20 mL/min |
| Wave length | UV 254 nm |
| Temperature | 35 |
| Sample solution | 4 mg/mL in mobile phase |
| Prep-SFC equipment | DAICEL-YMC |

The chiral analysis conditions are shown below.

| Column | CHIRALPAK IC |
|---|---|
| Column size | 0.46 cm I.D. × 15 cm L |
| Injection | 2 uL |
| Mobile phase | MeOH = 100 (v/v) |
| Flow rate | 1.0 mL/min |
| Wave length | UV 254 nm |

Compound 6: 7-(2-Acrylamidophenyl)-2-(4-phenoxyphenyl)-4,5,6,7-tetrahydro pyrazolo[1,5-a]pyrimidine-3-carboxamide

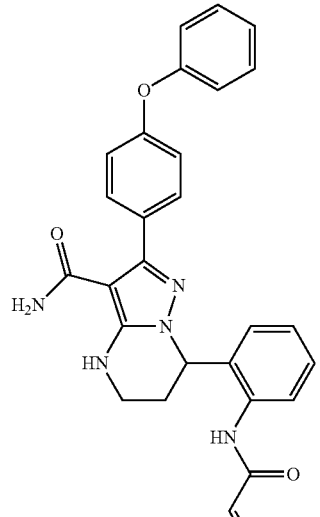

6

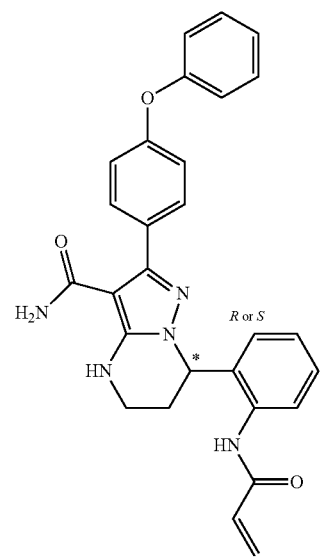

6a

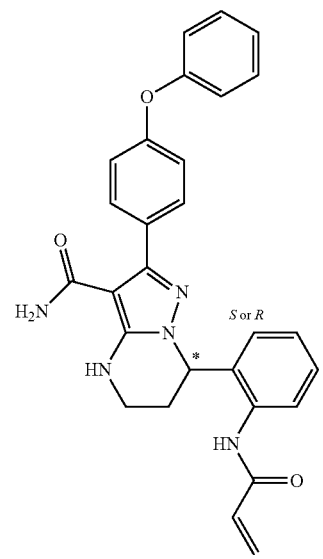

6b

The desired compound was prepared from compound 5 and acryloyl chloride according to the procedure similar to that for compound 3. $^1$H NMR (DMSO-d$_6$) δ 9.81 (s, 1H), 7.50-7.32 (m, 5H), 7.26 (td, J=7.6, 1.2 Hz, 1H), 7.21-7.08 (m, 2H), 7.04-6.98 (m, 4H), 6.79 (s, 1H), 6.60 (dd, J=7.6, 1.2 Hz, 1H), 6.50 (dd, J=17.0, 10.2 Hz, 1H), 6.24 (dd, J=17.0, 1.9 Hz, 1H), 5.77-5.74 (m, 2H), 3.26-3.22 (m, 1H), 2.98-2.92 (m, 1H), 2.32-2.25 (m, 1H), 1.96-1.93 (m, 1H). MS (ESI) m/e [M+1]$^+$ 480.

Compound 6a (peak 1, R or S, retention time at 4.02 min) and 6b (peak 2, R or S, retention time at 6.68 min) was prepared from 5a and 5b according to the procedure similar to that for compound 3.

The chiral analysis conditions are shown below.

| | |
|---|---|
| Column | CHIRALPAK AD-H |
| Column size | 0.46 cm I.D. × 15 cm L, 5 um |
| Injection | 2 uL |
| Mobile phase | n-Hexane/EtOH (0.1% triethyl amine) = 70/30 (v/v) |
| Flow rate | 1.0 mL/min |
| Wave length | UV 214, 254 nm |

Example 2: Synthesis of Compounds 7 and 8

Compound 7: 7-(3-Aminophenyl)-2-(4-phenoxyphenyl) pyrazolo[1,5-a] pyrimidine-3-carboxamide

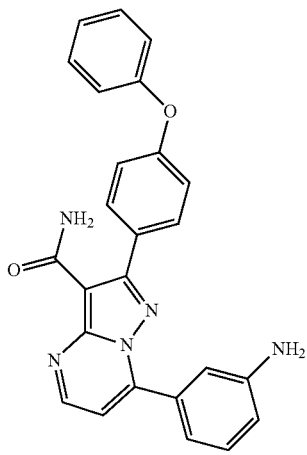 [SMILES: NC(=O)c1c(-c2ccc(Oc3ccccc3)cc2)nn2c(-c3cccc(N)c3)ccnc12]

To a solution of 7-(3-aminophenyl)-2-(4-phenoxyphenyl)-4,5,6,7-tetrahydro pyrazolo[1,5-a]pyrimidine-3-carboxamide (4 mg, 0.01 mmol) in DCE (2 mL) was added active MnO$_2$ (100 mg, 1.15 mmol). The mixture was stirred at 75° C. for 2 hr and filtered. The filtrate was purified by Pre-TLC (DCM/CH$_3$OH=10/1) to afford 2 mg (50%) of 7-(3-aminophenyl)-2-(4-phenoxyphenyl)pyrazolo[1,5-a]pyrimidine-3-carboxamide as a yellow solid. $^1$H NMR (400 MHz, CD$_3$OD-d$_4$ and CDCl$_3$-d$_1$) δ 8.62 (d. J=4.4 Hz, 1H), 7.88 (d, J=8.8 Hz, 2H), 7.41-7.39 (m, 2H), 7.31-7.26 (m, 3H), 7.11 (d, J=4.4 Hz, 1H), 7.10-7.04 (m, 2H), 7.01-6.97 (m, 4H), 6.90-6.86 (m, 1H).

Compound 8: 7-(3-Acrylamidophenyl)-2-(4-phenoxyphenyl)pyrazolo[1,5-a] pyrimidine-3-carboxamide

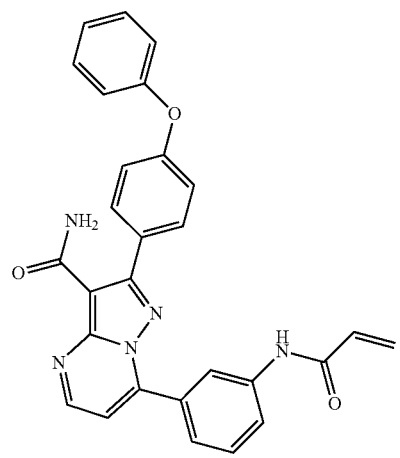 [SMILES: C=CC(=O)Nc1cccc(-c2ccnc3c(C(N)=O)c(-c4ccc(Oc5ccccc5)cc4)nn23)c1]

To a solution of 7-(3-aminophenyl)-2-(4-phenoxyphenyl) pyrazolo[1,5-a] pyrimidine-3-carboxamide (100 mg, 0.24 mmol) in DCM (10 mL) was added TEA (3 drops), followed by acryloyl chloride (32 mg, 0.36 mmol). The mixture was stirred at RT for 1 min and partitioned between DCM (50 mL) and brine (50 mL). Organic layer was separated from aqueous layer, dried over Na$_2$SO$_4$, concentrated and purified by Pre-TLC (DCM/CH$_3$OH=10/1) to afford 12 mg (11%) of 7-(3-acrylamido phenyl)-2-(4-phenoxyphenyl)pyrazolo[1,5-a]pyrimidine-3-carboxamide as a white solid. $^1$H NMR (400 MHz, DMSO-d$_6$) δ 10.42 (s, 1H), 8.80 (d, J=4.4 Hz, 1H), 8.47 (s, 1H), 8.07 (s, 1H), 7.95 (d, J=8.8 Hz, 2H), 7.89 (d, J=8.4 Hz, 1H), 7.81 (d, J=8.0 Hz, 1H), 7.56 (t, J=8.0 Hz, 1H), 7.47 (br s, 1H), 7.42-7.37 (m, 3H), 7.15 (t, J=7.6 Hz, 1H), 7.06 (d, J=8.0 Hz, 2H), 7.01 (d, J=8.8 Hz, 2H), 6.44 (dd, J=10.1, 16.9 Hz, 1H), 6.26 (dd, J=1.6, 16.9 Hz, 1H), 5.76 (dd, J=1.6, 10.1 Hz, 1H). MS (ESI) m/e [M+1]$^+$ 476.

Example 3: Synthesis of Compounds 9-10

Compound 9: 7-(2-Aminophenyl)-2-(4-(benzyloxy)phenyl)-4,5,6,7-tetrahydro pyrazolo[1,5-a]pyrimidine-3-carboxamide

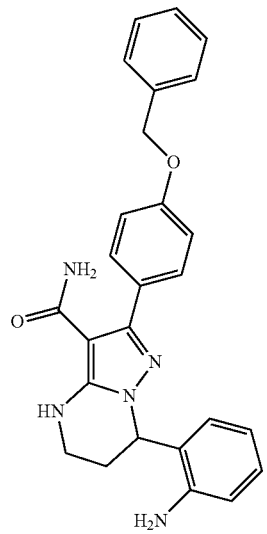 [SMILES: NC(=O)c1c(-c2ccc(OCc3ccccc3)cc2)nn2c1NCCC2c1ccccc1N]

Step 1, 2, 3: 5-Amino-3-(4-(benzyloxy)phenyl)-1H-pyrazole-4-carbonitrile

Step 6: 7-(2-Aminophenyl)-2-(4-hydroxyphenyl)-4,5,6,7-tetrahydropyrazolo [1,5-a]pyrimidine-3-carbonitrile

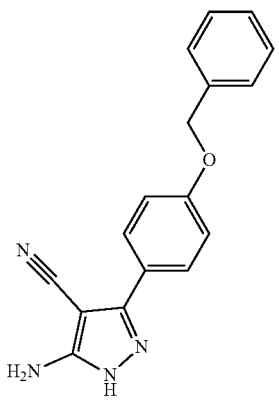 [SMILES: N#Cc1c(-c2ccc(OCc3ccccc3)cc2)n[nH]c1N]

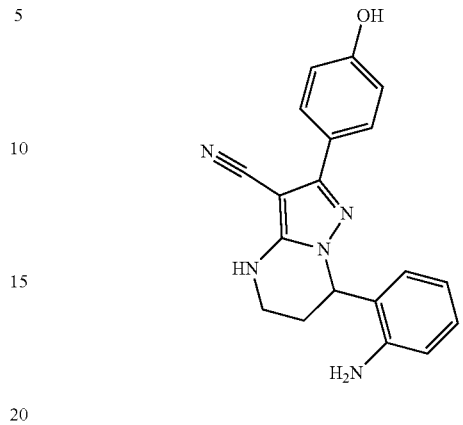

The desired product was prepared from 4-(benzyloxy) benzoic acid according to the procedures similar to those (step 1 to 3) for 5-amino-3-(4-phenoxyphenyl)-1H-pyrazole-4-carbonitrile under appropriate conditions recognized by one of ordinary skill in the art. $^1$H NMR (400 MHz, DMSO-$d_6$) δ 12.01 (s, 1H), 7.72 (d, J=8.8 Hz, 2H), 7.50-7.44 (m, 2H), 7.44-7.37 (m, 2H), 7.36-7.32 (m, 1H), 7.11 (d, J=7.2 Hz, 2H), 6.39 (br s, 2H) and 5.16 (s, 2H).

To a solution of 2-(4-(benzyloxy)phenyl)-7-(2-nitrophenyl)pyrazolo[1,5-a] pyrimidine-3-carbonitrile (2 g, 4.47 mmol) in CH$_3$OH (20 mL) and DCM (20 mL) was added 10% w/w Pd/C (300 mg). The mixture was stirred at RT under H$_2$ for 16 hr. Filtered and purified by chromatography column on silica gel (elution with DCM/CH$_3$OH) to afford 0.92 g (62%) of 7-(2-aminophenyl)-2-(4-hydroxyphenyl)-4,5,6,7-tetrahydropyrazolo[1,5-a]pyrimidine-3-carbonitrile as a yellow solid. MS (ESI, m/e) [M+1]$^+$ 331.9.

Step 7: 7-(2-Aminophenyl)-2-(4-(benzyloxy)phenyl)-4,5,6,7-tetrahydropyrazolo [1,5-a]pyrimidine-3-carbonitrile Step 4, 5: 2-(4-(Benzyloxy)phenyl)-7-(2-nitrophenyl)pyrazolo[1,5-a]pyrimidine-3-carbonitrile

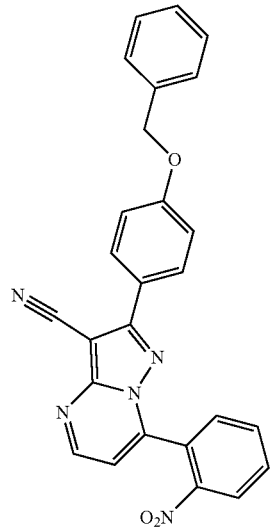 [SMILES: N#Cc1c(-c2ccc(OCc3ccccc3)cc2)nn2c(-c3ccccc3[N+](=O)[O-])ccnc12]

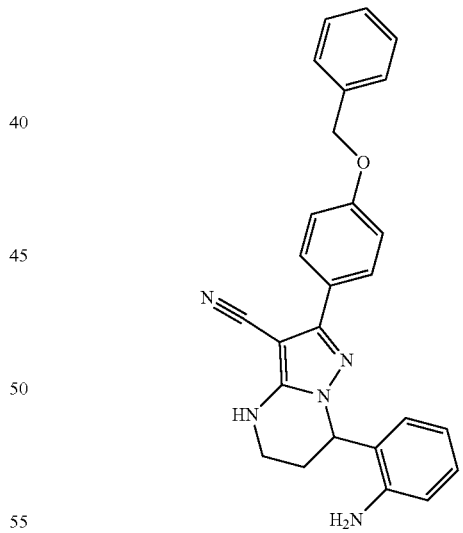

The desired product was prepared from 1-(2-nitrophenyl) ethanone and 5-amino-3-(4-(benzyloxy)phenyl)-1H-pyrazole-4-carbonitrile according to the procedures similar to those (step 4 and step 5) for N-(3-(3-cyano-2-(4-phenoxyphenyl) pyrazolo[1,5-a]pyrimidin-7-yl)phenyl)acetamide under appropriate conditions recognized by one of ordinary skill in the art.

To a solution of 7-(2-aminophenyl)-2-(4-hydroxyphenyl)-4,5,6,7-tetrahydro pyrazolo[1,5-a]pyrimidine-3-carbonitrile (331 mg, 1.0 mmol) in acetone (10 mL) was added (bromomethyl)benzene (204 mg, 1.2 mmol) and K$_2$CO$_3$ (276 mg, 2.0 mmol). The mixture was stirred at RT for 16 hr, 50 mL of acetone was added and filtered. The filtrate was concentrated to afford 400 mg (95%) of 7-(2-aminophenyl)-2-(4-(benzyloxy)phenyl)-4,5,6,7-tetrahydropyrazolo[1,5-a] pyrimidine-3-carbonitrile as a yellow solid. MS (ESI) m/e [M+1]$^+$421.9.

Step 8: 7-(2-Aminophenyl)-2-(4-(benzyloxy)phenyl)-4,5,6,7-tetrahydropyrazolo [1,5-a]pyrimidine-3-carboxamide

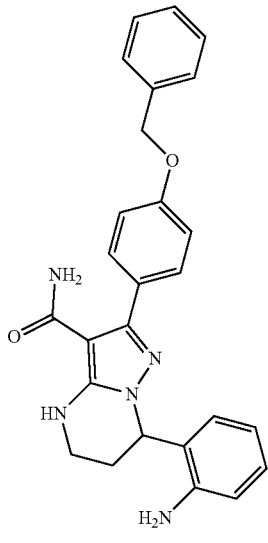 [SMILES: NC(=O)c1c(-c2ccc(OCc3ccccc3)cc2)nn2c1NCCC2c1ccccc1N]

The desired product was prepared from 7-(2-aminophenyl)-2-(4-(benzyloxy)phenyl)-4,5,6,7-tetrahydropyrazolo[1,5-a]pyrimidine-3-carbonitrile using the procedure similar to step 2 for compound 2. $^1$H NMR (400 MHz, DMSO-d$_6$) δ 7.47-7.33 (m, 7H), 7.06 (d, J=8.4 Hz, 2H), 6.96 (t, J=7.6 Hz, 1H), 6.75 (br s, 1H), 6.68 (d, J=7.6 Hz, 1H), 6.50 (t, J=7.6 Hz, 1H), 6.28 (d, J=7.6 Hz, 1H), 5.59-5.54 (m, 1H), 5.19 (br s, 2H), 5.12 (s, 2H), 3.30-3.20 (m, 1H), 3.02-2.92 (m, 1H), 2.25-2.14 (m, 1H) and 2.13-2.03 (m, 1H). MS (ESI) m/e [M+1]$^+$ 439.9.

Compound 10: 7-(2-Acrylamidophenyl)-2-(4-(benzyloxy)phenyl)-4,5,6,7-tetrahydro pyrazolo[1,5-a]pyrimidine-3-carboxamide

10

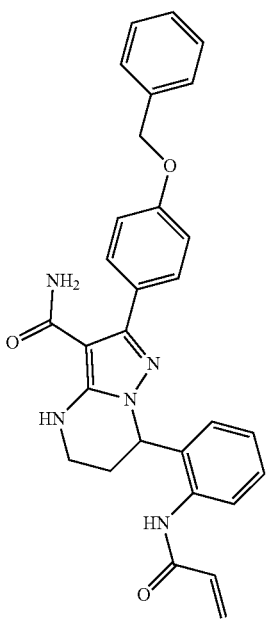

10a

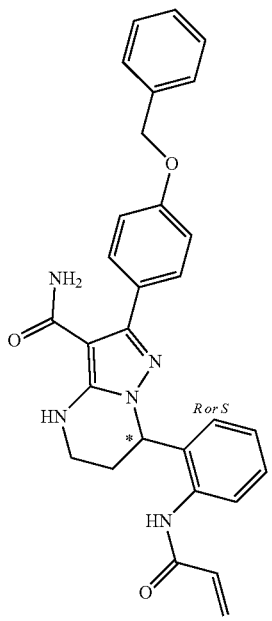

10b

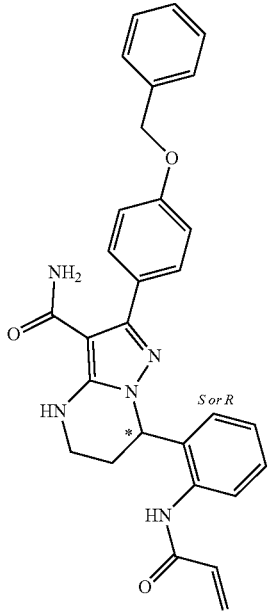

The desired product was prepared from 7-(2-aminophenyl)-2-(4-(benzyloxy)phenyl)-4,5,6,7-tetrahydropyrazolo[1,5-a]pyrimidine-3-carboxamide and acryloyl chloride using the procedure similar to that for compound 8. $^1$H NMR (400 MHz, DMSO-d$_6$) δ 9.84 (s, 1H), 7.46-7.37 (m, 7H), 7.33-7.28 (m, 2H), 7.21 (t, J=7.6 Hz, 1H), 7.06 (d, J=8.8 Hz, 2H), 6.81 (br s, 1H), 6.64 (d, J=7.6 Hz, 1H), 6.53 (dd, J=10.3, 16.8 Hz, 1H), 6.27 (d, J=1.8, 16.8 Hz, 1H), 5.59-5.57 (m, 2H), 5.12 (s, 2H), 3.30-3.26 (m, 1H), 3.04-2.92 (m, 1H), 2.35-2.27 (m, 1H) and 1.95-1.97 (m, 1H). MS (ESI) m/e [M+1]$^+$ 493.9.

Compound 10 was separated into two enantiomeric stereoisomers compound 10a (peak 1, R or S, retention time at 3.15 min in chiral analysis), and compound 10b (peak 2, S or R, retention time at 3.91 min in chiral analysis) by chiral prep-HPLC. The chiral separation conditions are shown below.

| Column | CHIRALPAK IC-3 |
| --- | --- |
| Column size | 2 cm × 25 cm |
| Injection | 3 mL |
| Mobile phase | MeOH/ACN = 50/50 |
| Flow rate | 10 mL/min |
| Wave length | UV 220 nm |
| Temperature | 35 |
| Sample solution | 2.5 mg/mL in mobile phase |
| Prep-SFC equipment | DAICEL-YMC |

The chiral analysis conditions are shown below.

| Column | CHIRALPAK IC |
| --- | --- |
| Column size | 0.46 cm I.D. × 15 cm L, 5 um |
| Injection | 3 uL |
| Mobile phase | MeOH/ACN = 50/50 (v/v) |
| Flow rate | 1.0 mL/min |
| Wave length | UV 214, 254 nm |

Example 4: Synthesis of Compounds 11-12

Compound 11: 7-(2-Aminophenyl)-2-(4-(4-fluorophenoxy)phenyl)-4,5,6,7-tetrahydro pyrazolo[1,5-a]pyrimidine-3-carboxamide

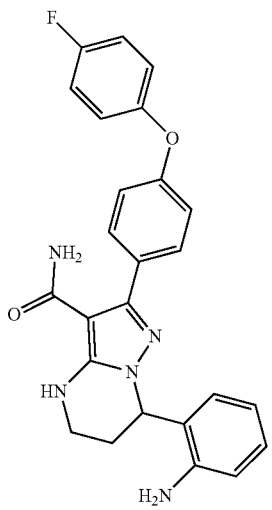 [SMILES: NC(=O)c1c(-c2ccc(Oc3ccc(F)cc3)cc2)nn2c1NCCC2c1ccccc1N]

Step 1: Benzyl 2-(3-cyano-2-(4-hydroxyphenyl)-4,5,6,7-tetrahydropyrazolo[1,5-a]pyrimidin-7-yl)phenylcarbamate

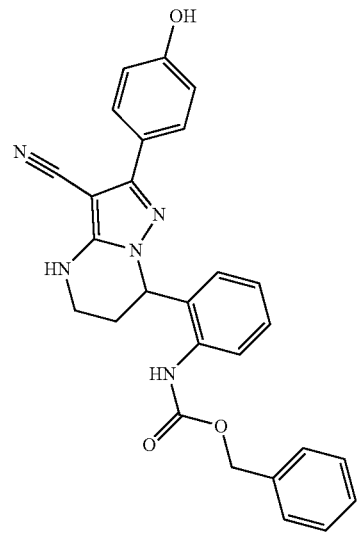 [SMILES: N#Cc1c(-c2ccc(O)cc2)nn2c1NCCC2c1ccccc1NC(=O)OCc1ccccc1]

To a solution of 7-(2-aminophenyl)-2-(4-hydroxyphenyl)-4,5,6,7-tetrahydro pyrazolo[1,5-a]pyrimidine-3-carbonitrile (730 mg, 2.21 mmol) in THF (30 mL) was added $K_2CO_3$ (610 mg, 4.42 mmol), CbzCl (564 mg, 3.32 mmol). After stirring at 65° C. for 16 hr, the mixture was concentrated in vacuum. The residue was partitioned between 150 mL of DCM and 150 mL of brine. Organic layers were separated from aqueous layers, dried over $Na_2SO_4$ and purified by chromatography column on silica gel eluting with DCM/$CH_3OH$ to afford 370 mg (62%) of benzyl 2-(3-cyano-2-(4-hydroxyphenyl)-4,5,6,7-tetrahydropyrazolo[1,5-a]pyrimidin-7-yl)phenylcarbamate as a white solid. $^1$H NMR (400 MHz, DMSO-$d_6$) δ 9.71 (s, 1H), 9.33 (s, 1H), 7.66 (s, 1H), 7.58 (d, J=8.4 Hz, 2H), 7.44-7.28 (m, 7H), 7.17 (t, J=7.6 Hz, 1H), 6.79 (d, J=8.4 Hz, 2H), 6.59 (d, J=7.6 Hz, 1H), 5.82-5.77 (m, 1H), 5.17 (s, 2H), 3.25-3.18 (m, 1H), 2.97-2.87 (m, 1H), 2.36-2.24 (m, 1H), 2.08-2.00 (m, 1H).

Step 2: Benzyl 2-(3-cyano-2-(4-(4-fluorophenoxy)phenyl)-4,5,6,7-tetrahydropyrazolo [1,5-a]pyrimidin-7-yl)phenylcarbamate

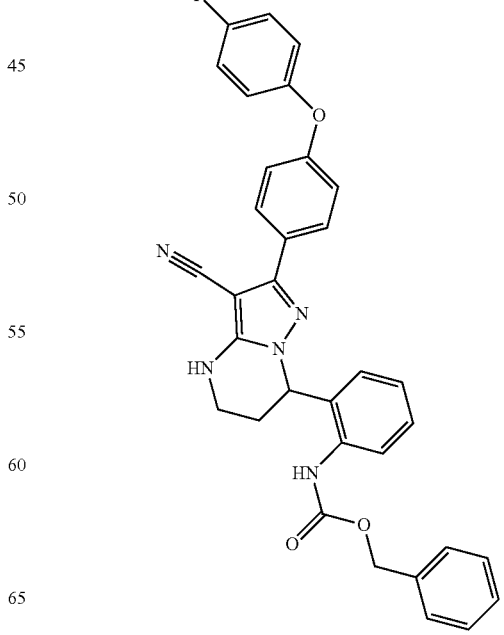

To a solution of benzyl 2-(3-cyano-2-(4-hydroxyphenyl)-4,5,6,7-tetrahydro pyrazolo[1,5-a]pyrimidin-7-yl)phenylcarbamate (370 mg, 0.8 mmol) in 20 mL of DCM was added 4-fluorophenylboronic acid (167 mg, 1.2 mmol), TEA (162 mg, 1.6 mmol) and Cu(OAc)$_2$ (216 mg, 1.2 mmol). After stirring at RT for 16 hr, 100 mL of DCM, 10 mL of CH$_3$OH and 100 mL of brine were added to the mixture. Organic layers were separated from aqueous layers, washed with brine (100 mL×2), dried over Na$_2$SO$_4$ and purified by chromatography column on silica gel eluting with DCM/CH$_3$OH to afford 334 mg (75%) of benzyl 2-(3-cyano-2-(4-(4-fluorophenoxy)phenyl)-4,5,6,7-tetrahydro pyrazolo[1,5-a]pyrimidin-7-yl)phenylcarbamate as a white solid. $^1$H NMR (400 MHz, DMSO-d$_6$) δ 9.34 (s, 1H), 7.76-7.74 (m, 3H), 7.45-7.10 (m, 12H), 7.02 (d, J=8.4 Hz, 2H), 6.59 (d, J=8.0 Hz, 1H), 5.85-5.80 (m, 1H), 5.17 (s, 2H), 3.25-3.18 (m, 1H), 2.97-2.87 (m, 1H), 2.36-2.24 (m, 1H), 2.08-2.00 (m, 1H).

Step 3: Benzyl 2-(3-carbamoyl-2-(4-(4-fluorophenoxy)phenyl)-4,5,6,7-tetrahydro pyrazolo[1,5-a]pyrimidin-7-yl)phenylcarbamate

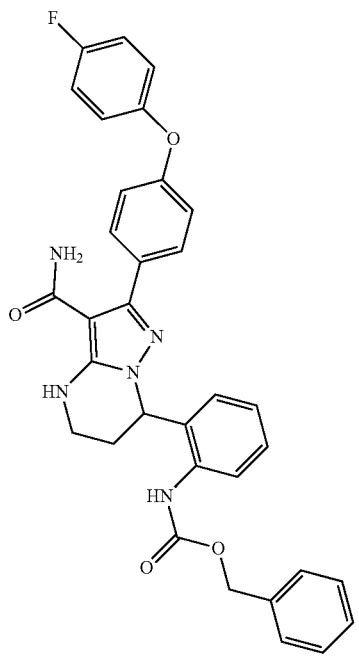 [SMILES: NC(=O)c1c(-c2ccc(Oc3ccc(F)cc3)cc2)nn2c1NCCC2c1ccccc1NC(=O)OCc1ccccc1]

The desired product was prepared from benzyl 2-(3-cyano-2-(4-(4-fluorophenoxy)phenyl)-4,5,6,7-tetrahydropyrazolo [1,5-a]pyrimidin-7-yl)phenylcarbamate using the procedure similar to step 2 for compound 2. MS (ESI) m/e [M+1]$^+$ 577.9.

Step 4: 7-(2-Aminophenyl)-2-(4-(4-fluorophenoxy)phenyl)-4,5,6,7-tetrahydro pyrazolo[1,5-a]pyrimidine-3-carboxamide

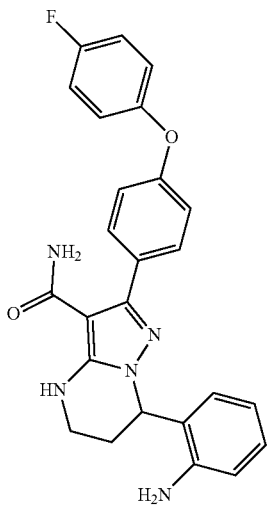 [SMILES: NC(=O)c1c(-c2ccc(Oc3ccc(F)cc3)cc2)nn2c1NCCC2c1ccccc1N]

To a solution of benzyl 2-(3-carbamoyl-2-(4-(4-fluorophenoxy)phenyl)-4,5,6,7-tetrahydropyrazolo[1,5-a]pyrimidin-7-yl)phenylcarbamate (100 mg, 0.17 mmol) in 5 mL of DCM and 5 mL of CH$_3$OH was added 10% w/w Pd/C (50 mg). After stirring at RT under H$_2$ for 16 hr, the mixture was filtered and the cake was washed with DCM/CH$_3$OH (¼, 50 mL). The filtrate was concentrated and purified by chromatography column on silica gel eluting with DCM/CH$_3$OH to afford 10 mg (13%) of 7-(2-aminophenyl)-2-(4-(4-fluorophenoxy)phenyl)-4,5,6,7-tetrahydro pyrazolo[1,5-a]pyrimidine-3-carboxamide as a white solid. $^1$H NMR (400 MHz, CD$_3$OD-d) δ 7.39 (d, J=8.8 Hz, 2H), 7.02-6.91 (m, 7H), 6.66 (d, J=7.6 Hz, 1H), 6.53 (t, J=7.6 Hz, 1H), 6.33 (d, J=7.6 Hz, 1H), 5.54-5.50 (m, 1H), 3.30-3.24 (m, 1H), 3.12-3.06 (m, 1H) and 2.31-2.20 (m, 2H). MS (ESI) m/e [M+1]$^+$ 443.9.

Compound 12: 7-(2-Acrylamidophenyl)-2-(4-(4-fluorophenoxy)phenyl)-4,5,6,7-tetrahydropyrazolo[1,5-a]pyrimidine-3-carboxamide

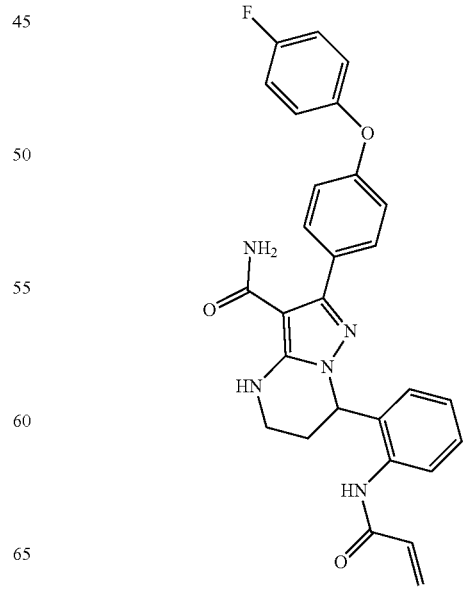

The desired product was prepared from 7-(2-aminophenyl)-2-(4-(4-fluorophenoxy) phenyl)-4,5,6,7-tetrahydro pyrazolo[1,5-a]pyrimidine-3-carboxamide and acryloyl chloride using the procedure similar to that for compound 8. $^1$H NMR (400 MHz, CD$_3$OD-d$_4$) δ 7.47 (d, J=8.4 Hz, 2H), 7.39 (t, J=7.6 Hz, 1H), 7.33 (t, J=7.6 Hz, 1H), 7.26 (t, J=7.6 Hz, 1H), 7.12-7.00 (m, 6H), 6.81 (d, J=8.0 Hz, 1H), 6.53-6.46 (m, 1H), 6.39-6.35 (m, 1H), 5.87-5.76 (m, 1H), 5.73-5.69 (m, 1H), 3.36-3.30 (m, 1H), 3.22-3.17 (m, 1H), 2.45-2.39 (m, 1H) and 2.17-2.14 (m, 1H). MS (ESI) m/e [M+1]$^+$ 497.9.

Example 5: Synthesis of Compounds 13-14

Compound 13: 7-(2-(Methylamino)phenyl)-2-(4-phenoxyphenyl)-4,5,6,7-tetrahydropyrazolo[1,5-a]pyrimidine-3-carboxamide

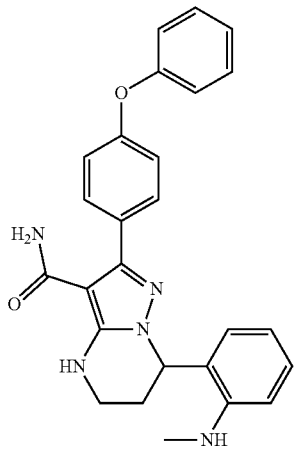 [SMILES: CNc1ccccc1C1CCNc2c(C(N)=O)c(-c3ccc(Oc4ccccc4)cc3)nn21]

Step 1: N-(2-(3-cyano-2-(4-phenoxyphenyl)pyrazolo[1,5-a]pyrimidin-7-yl)phenyl)-2,2,2-trifluoroacetamide

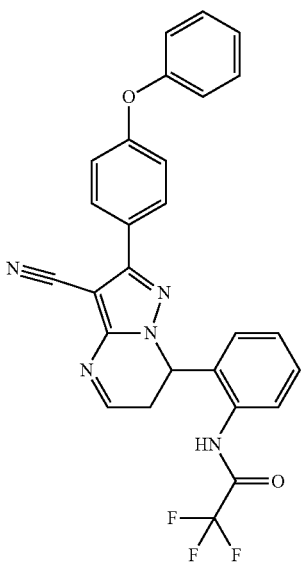 [SMILES: N#Cc1c(-c2ccc(Oc3ccccc3)cc2)nn2c1N=CCC2c1ccccc1NC(=O)C(F)(F)F]

To a solution of 7-(2-aminophenyl)-2-(4-phenoxyphenyl)pyrazolo[1,5-a]pyrimidine-3-carbonitrile (60 mg, 0.15 mmol) in 5 mL of DCM was added three drops of DIEA and three drops of trifluoroacetic anhydride. The reaction mixture was stirred at rt for 2 hr, then partitioned between water (20 mL) and DCM (20 mL). The organic layer was concentrated to give the product as a yellow solid (50 mg, yield: 67%), which was used in the next step without further purification.

Step 2: 7-(2-(Methylamino)phenyl)-2-(4-phenoxyphenyl)pyrazolo[1,5-a]pyrimidine-3-carbonitrile

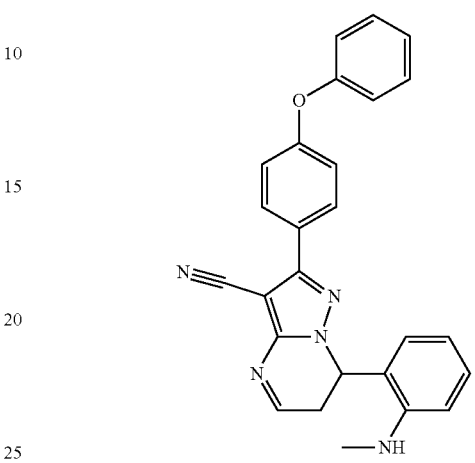

To a solution of N-(2-(3-cyano-2-(4-phenoxyphenyl)pyrazolo[1,5-a]pyrimidin-7-yl) phenyl)-2,2,2-trifluoroacetamide (50 mg, 0.1 mmol) in 5 mL of acetone was added KOH (11.2 mg, 0.2 mmol) and CH$_3$I (0.5 mL). The reaction mixture was stirred at rt for 15 hr, then concentrated to remove acetone. The residue was partitioned between 20 mL of water and 20 mL of EA. The organic layer was concentrated and purified by pre-TLC (PE/EA=2/1) to give the product as a white solid (15 mg, yield: 37%). $^1$H NMR (DMSO-d$_6$) δ 8.82 (d. J=4.4 Hz, 1H), 7.97 (d. J=8.8 Hz, 2H), 7.47-7.38 (m, 4H), 7.31 (dd, J=1.6, 7.2 Hz, 1H), 7.23-7.17 (m, 3H), 7.11 (d, J=8.8 Hz, 2H), 6.77-6.69 (m, 2H), 5.35-5.31 (m, 1H), 2.68 (d, J=4.8 Hz, 3H). MS (ESI) m/e [M+1]$^+$ 417.9.

Step 3: 7-(2-(Methylamino)phenyl)-2-(4-phenoxyphenyl)-4,5,6,7-tetrahydropyrazolo [1,5-a]pyrimidine-3-carbonitrile

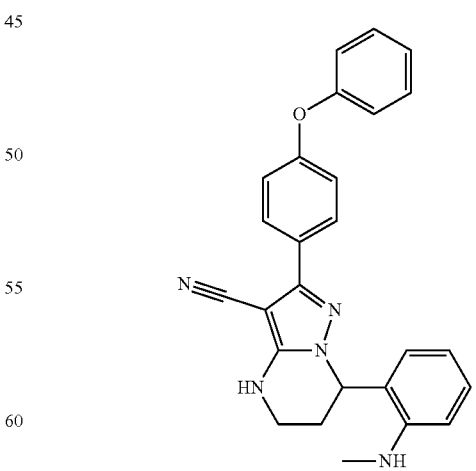

To a solution of 7-(2-(methylamino)phenyl)-2-(4-phenoxyphenyl)pyrazolo[1,5-a]pyrimidine-3-carbonitrile (250 mg, 0.6 mmol) in 10 mL EtOH was added NaBH$_4$ (100 mg). The reaction mixture was stirred at rt for 15 hr, and then concentrated to remove EtOH. The residue was partitioned between 30 mL of water and 30 mL of EA. The organic layer was concentrated. The residue was dissolved in 10 mL of MeOH, followed by 10% w/w Pd/C (50 mg). The reaction mixture was stirred at it under 1 atm. of $H_2$ for 15 hr. Then, the mixture was filtered. The filtrate was concentrated and purified by the flash chromatography (PE/EA=1/1) to give the product as a white solid (144 mg, yield: 56.5%). MS (ESI) m/e [M+1]$^+$ 421.9.

Step 4: 7-(2-(Methylamino)phenyl)-2-(4-phenoxyphenyl)-4,5,6,7-tetrahydropyrazolo [1,5-a]pyrimidine-3-carboxamide

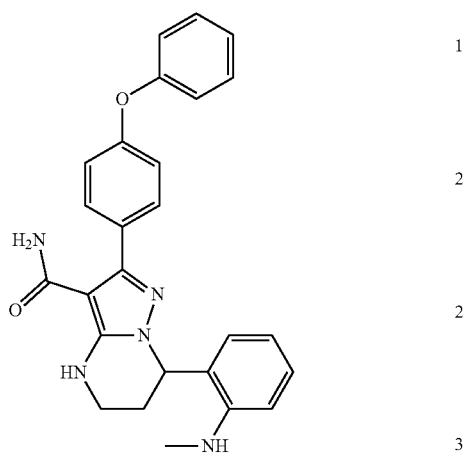

The desired product was prepared from 7-(2-(methylamino)phenyl)-2-(4-phenoxy phenyl)-4,5,6,7-tetrahydropyrazolo[1,5-a]pyrimidine-3-carbonitrile using the procedure similar to step 2 for compound 2. $^1$H NMR (DMSO-d$_6$) δ 7.49 (d, J=8.8 Hz, 2H), 7.44-7.35 (m, 2H), 7.18-7.01 (m, 6H), 6.76 (s, 1H), 6.58 (d, J=7.6 Hz, 2H), 6.54 (t, J=7.6 Hz, 1H), 6.28 (dd, J=1.2, 7.6 Hz, 1H), 5.60-5.57 (m, 1H), 5.50-5.49 (m, 1H), 3.29-3.24 (m, 1H), 2.98-2.93 (m, 1H), 2.76 (d, J=4.8 Hz, 3H), 2.24-2.18 (m, 1H), 2.06-2.03 (m, 1H). MS (ESI) m/e [M+1]$^+$ 439.8.

Compound 14: 7-(2-(N-methylacrylamido)phenyl)-2-(4-phenoxyphenyl)-4,5,6,7-tetrahydropyrazolo[1,5-a]pyrimidine-3-carboxamide

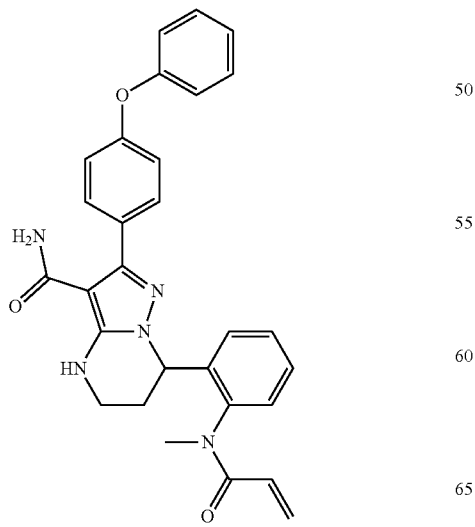

The desired product was prepared from 7-(2-(methylamino)phenyl)-2-(4-phenoxy phenyl)-4,5,6,7-tetrahydropyrazolo [1,5-a]pyrimidine-3-carboxamide and acryloyl chloride using the procedure similar to that for compound 8. $^1$H NMR (DMSO-d$_6$) δ 7.45-7.37 (m, 6H), 7.29-7.24 (m, 1H), 7.15 (t, J=7.6 Hz, 1H), 7.06-7.00 (m, 5H), 6.81 (d, J=7.6 Hz, 1H), 6.25-6.16 (m, 2H), 5.94-5.87 (m, 1H), 5.63-5.51 (m, 1H), 5.41-5.35 (m, 1H), 3.41-3.22 (m, 5H), 2.41-1.97 (m, 2H). MS (ESI) m/e [M+1]$^+$ 493.9.

Example 6: Synthesis of Compounds 15-16

Compound 15: 2-(4-(4-Fluorophenoxy)phenyl)-7-(2-(methylamino)phenyl)-4,5,6,7-tetrahydropyrazolo[1,5-a]pyrimidine-3-carboxamide

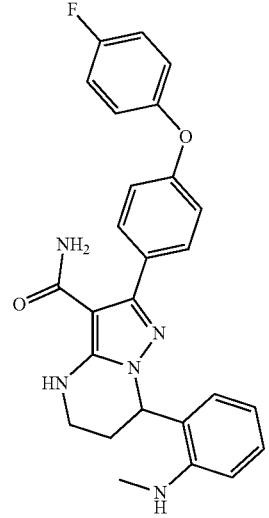 [SMILES: CNc1ccccc1C1CCNc2c(C(N)=O)c(-c3ccc(Oc4ccc(F)cc4)cc3)nn21]

Step 1: N-(2-(3-cyano-2-(4-hydroxyphenyl)-4,5,6,7-tetrahydropyrazolo[1,5-a] pyrimidin-7-yl)phenyl)-2,2,2-trifluoroacetamide

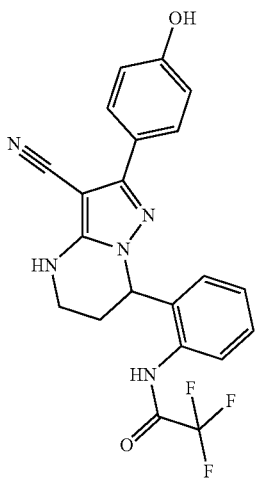 [SMILES: N#Cc1c(-c2ccc(O)cc2)nn2c1NCCC2c1ccccc1NC(=O)C(F)(F)F]

To a solution of 7-(2-aminophenyl)-2-(4-hydroxyphenyl)-4,5,6,7-tetrahydro pyrazolo[1,5-a]pyrimidine-3-carbonitrile (33.1 mg, 0.1 mmol) in DCM (10 mL) was added trifluoroacetic anhydride (1 drop) and DIEA (1 drop). After stirring at RT for 1 hr, the mixture was partitioned between 10 mL of DCM and 10 mL of brine. Organic layer was separated from aqueous layers, dried over Na$_2$SO$_4$ and concentrated to afford 40 mg (93%) of N-(2-(3-cyano-2-(4-hydroxyphenyl)-4,5,6,7-tetrahydropyrazolo[1,5-a] pyrimidin-7-yl)phenyl)-2,2,2-trifluoroacetamide as a yellow solid. MS (ESI) m/e [M+1]$^+$ 427.8.

Step 2: N-(2-(3-cyano-2-(4-(4-fluorophenoxy)phenyl)-4,5,6,7-tetrahydropyrazolo [1,5-a]pyrimidin-7-yl)phenyl)-2,2,2-trifluoroacetamide

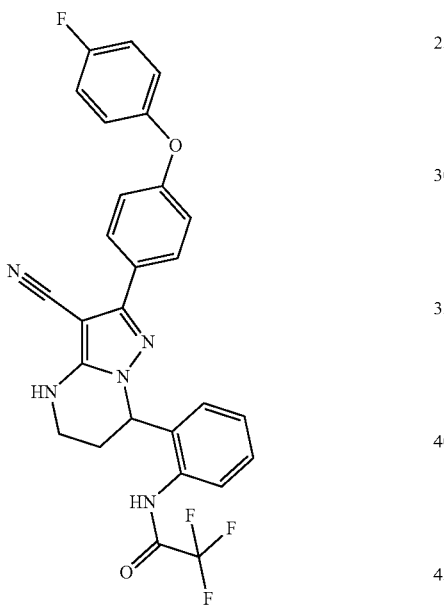

To a solution of N-(2-(3-cyano-2-(4-hydroxyphenyl)-4,5,6,7-tetrahydropyrazolo [1,5-a]pyrimidin-7-yl)phenyl)-2,2,2-trifluoroacetamide (42.7 mg, 0.10 mmol) in DCM (3 mL) was added 4-fluorophenylboronic acid (17 mg, 0.12 mmol), TEA (21 mg, 0.2 mmol) and Cu(OAc)$_2$ (22 mg, 0.12 mmol). After stirring at RT for 16 hr, the mixture was purified by Pre-TLC (DCM/CH$_3$OH=20/1) to afford 30 mg (57%) of N-(2-(3-cyano-2-(4-(4-fluorophenoxy)phenyl)-4,5,6,7-tetrahydropyrazolo[1,5-a]pyrimidin-7-yl)phenyl)-2,2,2-trifluoroacetamide as a colorless oil. $^1$H NMR (400 MHz, DMSO-d$_6$) δ 11.33 (s, 1H), 7.90-7.77 (m, 3H), 7.52-7.37 (m, 3H), 7.34-7.27 (m, 2H), 7.22-7.14 (m, 2H), 7.10 (d, J=8.8 Hz, 2H), 6.80 (d, J=6.4 Hz, 1H), 5.80-5.75 (m, 1H), 3.37-3.28 (m, 1H), 3.09-2.95 (m, 1H), 2.50-2.37 (m, 1H), 2.10-1.95 (m, 1H). MS (ESI) m/e [M+1]$^+$ 521.8.

Step 3: N-(2-(3-cyano-2-(4-(4-fluorophenoxy)phenyl)-4,5,6,7-tetrahydropyrazolo [1,5-a]pyrimidin-7-yl)phenyl)-2,2,2-trifluoro-N-methylacetamide

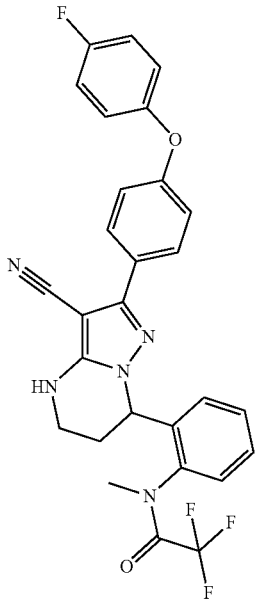 [SMILES: CN(C(=O)C(F)(F)F)c1ccccc1C1CCNc2c(C#N)c(-c3ccc(Oc4ccc(F)cc4)cc3)nn21]

To a solution of N-(2-(3-cyano-2-(4-(4-fluorophenoxy)phenyl)-4,5,6,7-tetrahydro pyrazolo[1,5-a]pyrimidin-7-yl)phenyl)-2,2,2-trifluoroacetamide (187 mg, 0.36 mmol) in acetone (10 mL) was added K$_2$CO$_3$ (100 mg, 0.72 mmol) and CH$_3$I (15 drops). After stirring at RT for 2 hr, the mixture was filtered. The filtrate was concentrated to afford 192 mg (100%) of N-(2-(3-cyano-2-(4-(4-fluorophenoxy)phenyl)-4,5,6,7-tetrahydropyrazolo[1,5-a]pyrimidin-7-yl)phenyl)-2,2,2-trifluoro-N-methylacetamide as yellow solid. MS (ESI) m/e [M+1]$^+$ 535.8.

Step 4: 2-(4-(4-Fluorophenoxy)phenyl)-7-(2-(methylamino)phenyl)-4,5,6,7-tetrahydro pyrazolo[1,5-a]pyrimidine-3-carboxamide

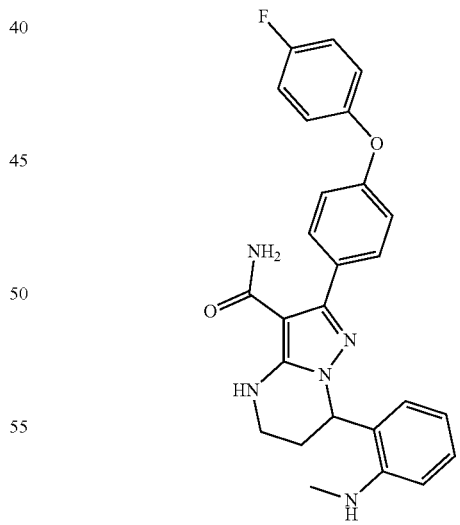

The desired product was prepared form N-(2-(3-cyano-2-(4-(4-fluorophenoxy)phenyl)-4,5,6,7-tetrahydropyrazolo [1,5-a]pyrimidin-7-yl)phenyl)-2,2,2-trifluoro-N-methylacetamide using the procedure similar to step 2 for compound 2. $^1$H NMR (400 MHz, CD$_3$OD-d$_4$) δ 7.39 (d, J=8.8 Hz, 2H), 7.09-6.90 (m, 7H), 6.58 (d, J=8.0 Hz, 1H), 6.51 (t, J=7.2 Hz, 1H), 6.30 (d, J=7.2 Hz, 1H), 5.52-5.48 (m, 1H), 3.27-3.24 (m, 1H), 3.11-3.02 (m, 1H), 2.76 (s, 3H), 2.32-2.10 (m, 2H). MS (ESI) m/e [M+1]$^+$ 457.9.

Compound 16: 2-(4-(4-Fluorophenoxy)phenyl)-7-(2-(N-methylacrylamido)phenyl)-4,5,6,7-tetrahydropyrazolo[1,5-a]pyrimidine-3-carboxamide

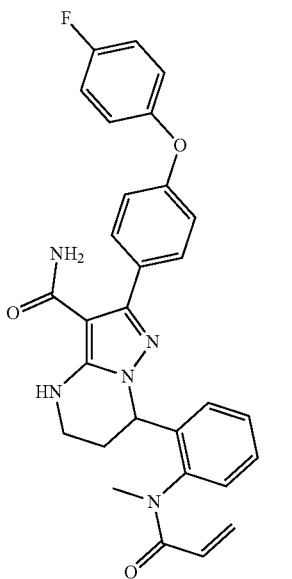 [SMILES: C=CC(=O)N(C)c1ccccc1C1CCNc2c(C(N)=O)c(-c3ccc(Oc4ccc(F)cc4)cc3)nn21]

The desired product was prepared from 2-(4-(4-fluorophenoxy)phenyl)-7-(2-(methylamino)phenyl)-4,5,6,7-tetrahydro pyrazolo[1,5-a]pyrimidine-3-carboxamide and acryloyl chloride using the procedure similar to that for compound 8. $^1$H NMR (400 MHz, DMSO-$d_6$) δ 7.47-7.37 (m, 4H), 7.30-7.15 (m, 3H), 7.12-7.08 (m, 2H), 6.99 (d, J=8.4 Hz, 2H), 6.81 (d, J=7.2 Hz, 1H), 6.25-5.85 (m, 2H), 5.63-5.49 (m, 1H), 5.42-5.32 (m, 1H), 3.40-3.20 (m, 6H), 2.45-2.20 (m, 1H), 2.15-1.90 (m, 1H). MS (ESI) m/e [M+1]$^+$ 511.9.

Example 7: Synthesis of Compounds 17-18

Compound 17: 7-(2-Aminophenyl)-2-(4-(cyclopentyloxy)phenyl)-4,5,6,7-tetrahydro pyrazolo[1,5-a]pyrimidine-3-carboxamide

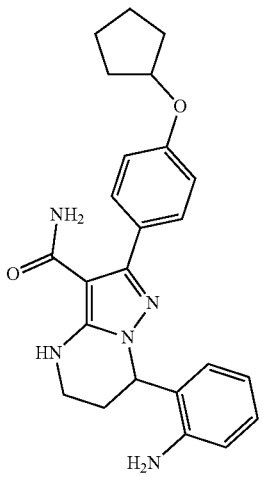 [SMILES: NC(=O)c1c(-c2ccc(OC3CCCC3)cc2)nn2c1NCCC2c1ccccc1N]

The desired product was prepared from 7-(2-aminophenyl)-2-(4-hydroxyphenyl)-4,5,6,7-tetrahydropyrazolo[1,5-a]pyrimidine-3-carbonitrile and bromocyclopentane using the procedures similar to those (step 7 and step 8) for compound 9, under appropriate conditions recognized by one of ordinary skill in the art. $^1$H NMR (400 MHz, DMSO-$d_6$) δ 7.37 (d, J=8.8 Hz, 2H), 6.97-6.92 (m, 3H), 6.74 (br s, 1H), 6.67 (d, J=7.6 Hz, 1H), 6.49 (t, J=7.6 Hz, 1H), 6.27 (d, J=7.6 Hz, 1H), 5.58-5.53 (m, 1H), 5.15 (s, 2H), 4.86-4.80 (m, 1H), 3.24-3.27 (m, 1H), 3.02-2.93 (m, 1H), 2.22-2.16 (m, 1H), 2.14-2.08 (m, 1H), 1.98-1.85 (m, 2H), 1.91-1.70 (m, 4H), 1.64-1.54 (m, 2H). MS (ESI) m/e [M+1]$^+$ 418.0.

Compound 18: 7-(2-Acrylamidophenyl)-2-(4-(cyclopentyloxy)phenyl)-4,5,6,7-tetra hydropyrazolo[1,5-a]pyrimidine-3-carboxamide

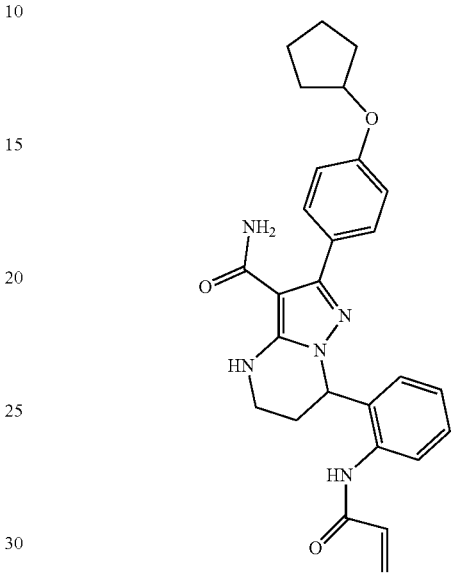

The desired product was prepared from compound 17 and acryloyl chloride using the procedure similar to that for compound 8. $^1$H NMR (400 MHz, DMSO-$d_6$) δ 9.83 (s, 1H), 7.45 (d, J=7.6 Hz, 1H), 7.37 (d, J=8.8 Hz, 2H) 7.29 (t, J=7.6 Hz, 1H), 7.21 (t, J=7.6 Hz, 1H), 6.93 (d, J=8.8 Hz, 2H), 6.81 (s, 1H), 6.64 (d. J=7.6 Hz, 1H), 6.53 (dd. J=10.2, 17.0 Hz, 1H), 6.27 (d, J=17.0 Hz, 1H), 5.80-5.77 (m, 2H), 4.86-4.79 (m, 1H), 3.27-3.23 (m, 1H), 3.03-2.94 (m, 1H), 2.36-2.25 (m, 1H), 1.99-1.91 (m, 3H) and 1.75-1.53 (m, 6H). MS (ESI) m/e [M+1]$^+$ 471.9.

Example 8: Synthesis of Compounds 19-20

Compound 19: 7-(2-Aminophenyl)-2-(4-(cyclopropylmethoxy)phenyl)-4,5,6,7-tetrahydropyrazolo[1,5-a]pyrimidine-3-carboxamide

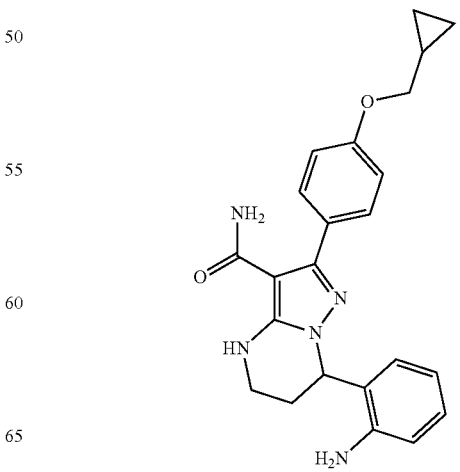

Step 1: 7-(2-Aminophenyl)-2-(4-(cyclopropylmethoxy)phenyl)-4,5,6,7-tetrahydropyrazolo[1,5-a]pyrimidine-3-carbonitrile

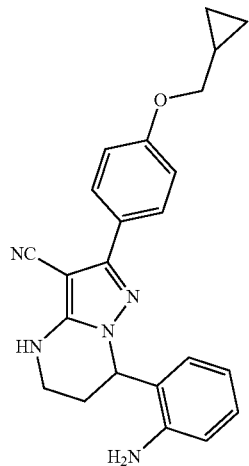 [SMILES: N#Cc1c(-c2ccc(OCC3CC3)cc2)nn2c1NCCC2c1ccccc1N]

To a solution of 7-(2-aminophenyl)-2-(4-hydroxyphenyl)-4,5,6,7-tetrahydropyrazolo[1,5-a]pyrimidine-3-carbonitrile (331 mg, 1.0 mmol) in acetone (15 mL) was added (bromomethyl)cyclopropane (135 mg, 1.0 mmol) and $K_2CO_3$ (276 mg, 2.0 mmol). After stirring at 56° C. for 16 hr, the mixture was filtered. The cake was washed with acetone (20 mL×2). The filtrate was concentrated to afford 300 mg of desired product (78%) as a yellow solid. MS (ESI) m/e $[M+1]^+$ 386.0.

Step 2: 7-(2-Aminophenyl)-2-(4-(cyclopropylmethoxy)phenyl)-4,5,6,7-tetrahydropyrazolo[1,5-a]pyrimidine-3-carboxamide

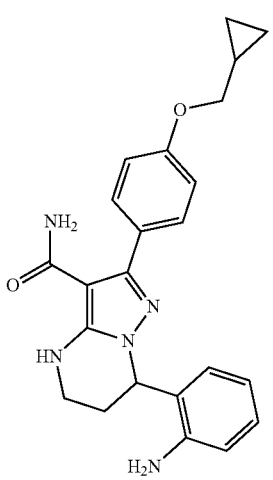 [SMILES: NC(=O)c1c(-c2ccc(OCC3CC3)cc2)nn2c1NCCC2c1ccccc1N]

To a solution of 7-(2-aminophenyl)-2-(4-(cyclopropylmethoxy)phenyl)-4,5,6,7-tetrahydropyrazolo[1,5-a]pyrimidine-3-carbonitrile (350 mg, 0.91 mmol) in EtOH (4 mL) and DMSO (4 mL) was added NaOH aqueous solution (5N, 2 mL) and $H_2O_2$ (2 mL). After stirring at 60° C. for 3 hr, the mixture was partitioned between 100 mL of $H_2O$ and 100 mL of EA. The organic layer was separated from aqueous layers, washed with saturated brines (100 mL×2), dried over $Na_2SO_4$ and concentrated. The residue was purified by chromatography column on silica gel (elution with DCM/MeOH) to afford 150 mg (41%) of desired product as a white solid. $^1$H NMR (400 MHz, DMSO-$d_6$) δ 7.37 (d, J=8.8 Hz, 2H), 6.97-6.92 (m, 3H), 6.75 (br s, 1H), 6.67 (d, J=8.0 Hz, 1H), 6.49 (t, J=7.6 Hz, 1H), 6.27 (d, J=7.6 Hz, 1H), 5.58-5.54 (m, 1H), 5.16 (s, 2H), 3.83 (d, J=7.2 Hz, 2H), 3.27-3.24 (m, 1H), 3.01-2.92 (m, 1H), 2.23-2.13 (m, 1H), 2.13-2.07 (m, 1H), 1.24-1.18 (m, 1H), 0.59-0.54 (m, 2H) and 0.34-0.30 (m, 2H). MS (ESI) m/e $[M+1]^+$ 404.0.

Compound 20: 7-(2-Acrylamidophenyl)-2-(4-(cyclopropylmethoxy)phenyl)-4,5,6,7-tetrahydropyrazolo[1,5-a]pyrimidine-3-carboxamide

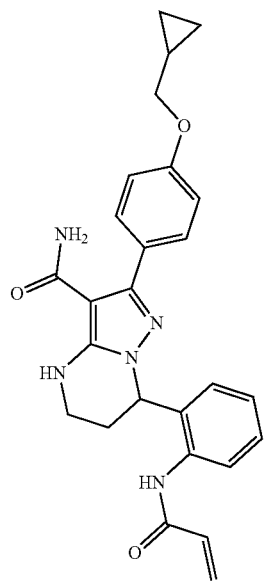

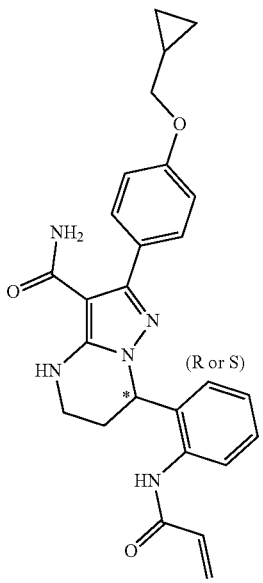

-continued

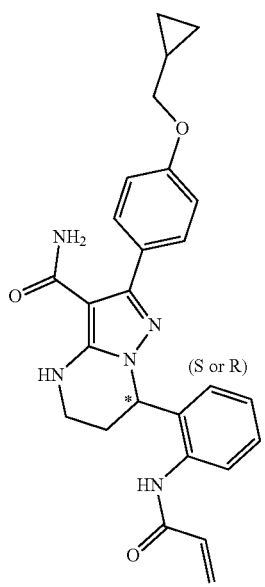

20b

The desired product was prepared from compound 19 and acryloyl chloride according to the procedure similar to that for compound 8. ¹H NMR (400 MHz, DMSO-$d_6$) δ 9.83 (s, 1H), 7.45 (d, J=8.0 Hz, 1H), 7.37 (d, J=8.4 Hz, 2H), 7.30 (t, J=7.6 Hz, 1H), 7.21 (t, J=7.6 Hz, 1H), 6.96 (d, J=8.4 Hz, 2H), 6.81 (s, 1H), 6.64 (d, J=8.0 Hz, 1H), 6.53 (dd, J=10.2, 16.7 Hz, 1H), 6.27 (d, J=16.7 Hz, 1H), 5.80-5.77 (m, 2H), 3.83 (d, J=7.2 Hz, 2H), 3.27-3.23 (m, 1H), 3.03-2.93 (m, 1H), 2.36-2.25 (m, 1H), 2.02-1.91 (m, 1H), 1.23-1.14 (m, 1H), 0.59-0.53 (m, 2H) and 0.34-0.29 (m, 2H). MS (ESI) m/e [M+1]⁺ 457.9.

Compound 20 was separated into two enantiomeric stereoisomers compound 20a (peak 1, R or S, retention time at 3.03 min in chiral analysis), and compound 20b (peak 2, S or R, retention time at 3.82 min in chiral analysis) by chiral prep-HPLC. The chiral separation conditions are shown below.

| Column | CHIRALPAK IC-3 |
| --- | --- |
| Column size | 2 cm × 25 cm |
| Injection | 3 mL |
| Mobile phase | MeOH/ACN = 50/50 |
| Flow rate | 10 mL/min |
| Wave length | UV 254 nm |
| Temperature | 35° C. |
| Sample solution | 2.5 mg/mL in mobile phase |
| Prep-SFC equipment | DAICEL-YMC |

The chiral analysis conditions are shown below.

| Column | CHIRALPAK IC |
| --- | --- |
| Column size | 0.46 cm I.D. × 15 cm L, 5 um |
| Injection | 3 uL |
| Mobile phase | MeOH/ACN = 50/50 (v/v) |
| Flow rate | 1.0 mL/min |
| Wave length | UV 214, 254 nm |

Example 9: Synthesis of Compounds 21-22

Compound 21: 7-(2-Aminophenyl)-2-(4-(2-methoxyethoxy)phenyl)-4,5,6,7-tetrahydropyrazolo[1,5-a]pyrimidine-3-carboxamide

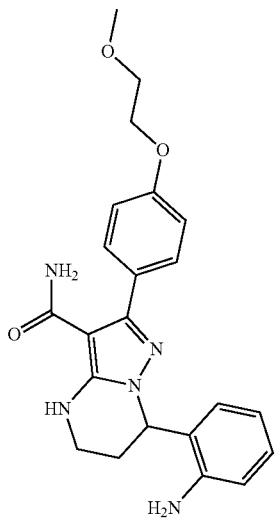 [SMILES: COCCOc1ccc(-c2nn3c(c2C(N)=O)NCCC3c2ccccc2N)cc1]

The desired product was prepared from 7-(2-aminophenyl)-2-(4-hydroxyphenyl)-4,5,6,7-tetrahydropyrazolo[1,5-a]pyrimidine-3-carbonitrile and 1-bromo-2-methoxyethane using the procedures similar to those (step 7 and step 8) for compound 9, under appropriate conditions recognized by one of ordinary skill in the art. ¹H NMR (400 MHz, DMSO-$d_6$) δ 7.38 (d, J=8.6 Hz, 2H), 7.00-6.94 (m, 3H), 6.75 (br s, 1H), 6.69 (d, J=7.6 Hz, 1H), 6.51 (t, J=7.6 Hz, 1H), 6.28 (d, J=7.6 Hz, 1H), 5.59-5.54 (m, 1H), 5.21 (br s, 1H), 4.11 (t. J=4.0 Hz, 2H), 3.66 (t, J=4.0 Hz, 2H), 3.30 (s, 3H), 3.28-3.25 (m, 1H), 3.02-2.92 (m, 1H), 2.24-2.16 (m, 1H) and 2.13-2.05 (m, 1H). MS (ESI) m/e [M+1]⁺ 407.9.

Compound 22: 7-(2-Acrylamidophenyl)-2-(4-(2-methoxyethoxy)phenyl)-4,5,6,7-tetrahydropyrazolo[1,5-a]pyrimidine-3-carboxamide

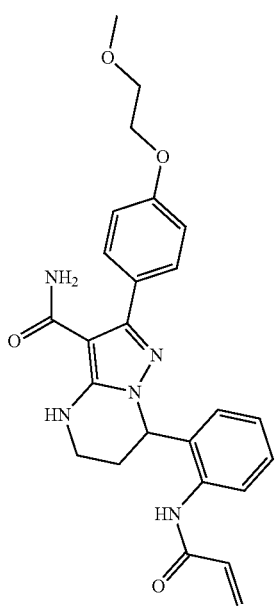 [SMILES: C=CC(=O)Nc1ccccc1C1CCNc2c(C(N)=O)c(-c3ccc(OCCOC)cc3)nn21]

The desired product was prepared from compound 21 and acryloyl chloride according to procedure similar to that for compound 8. ¹H NMR (400 MHz, DMSO-$d_6$) δ 9.84 (s, 1H), 7.45 (d, J=8.0 Hz, 1H), 7.37 (d, J=8.6, 2H), 7.30 (t, J=7.6 Hz, 1H), 7.21 (t, J=7.6 Hz, 1H), 6.93 (d, J=8.6 Hz, 2H), 6.81 (s, 1H), 6.64 (d, J=8.0 Hz, 1H), 6.53 (dd, J=10.5, 17.0 Hz, 1H), 6.27 (dd, J=1.7, 17.0 Hz, 1H), 5.80-5.77 (m, 2H), 4.11 (t, J=4.4 Hz, 2H), 3.66 (t. J=4.4 Hz, 2H), 3.30 (s, 3H), 3.27-3.23 (m, 1H), 3.03-2.94 (m, 1H), 2.36-2.25 (m, 1H), 2.01-1.95 (m, 1H). MS (ESI) m/e [M+1]+ 462.0.

Example 10: Synthesis of Compounds 23-24

Compound 23: 7-(2-Aminophenyl)-2-(4-(tetrahydro-2H-pyran-4-yloxy)phenyl)-4,5,6,7-tetrahydropyrazolo[1,5-a]pyrimidine-3-carboxamide

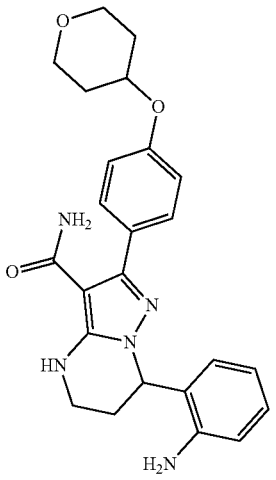 [SMILES: NC(=O)c1c(-c2ccc(OC3CCOCC3)cc2)nn2c1NCCC2c1ccccc1N]

Step 1: 7-(2-Aminophenyl)-2-(4-(tetrahydro-2H-pyran-4-yloxy)phenyl)-4,5,6,7-tetrahydropyrazolo[1,5-a]pyrimidine-3-carbonitrile

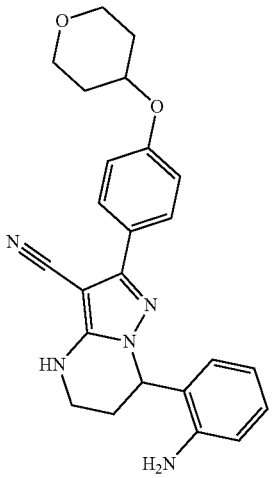 [SMILES: N#Cc1c(-c2ccc(OC3CCOCC3)cc2)nn2c1NCCC2c1ccccc1N]

To a solution of 7-(2-aminophenyl)-2-(4-hydroxyphenyl)-4,5,6,7-tetrahydro pyrazolo[1,5-a]pyrimidine-3-carbonitrile (33 mg, 0.1 mmol) in THF (5 mL) was added PPh$_3$ (78.6 mg, 0.25 mmol) and tetrahydro-2H-pyran-4-ol (10 mg, 0.1 mmol). DIAD (51 mg, 0.25 mmol) was added dropwise to the mixture at 0° C. and stirred at 0° C. for 10 min under N$_2$. The mixture was allowed to warm to rt and stirred at RT for 16 hr. The mixture was concentrated in vacuum and partitioned between DCM (20 mL) and brine (20 mL). Organic layer was separated from aqueous layers, dried over sodium sulfate and purified by Pre-TLC (DCM/CH$_3$OH=10/1) to afford 5 mg (12%) of 7-(2-aminophenyl)-2-(4-(tetrahydro-2H-pyran-4-yloxy)phenyl)-4,5,6,7-tetrahydropyrazolo[1,5-a]pyrimidine-3-carbonitrile as a colorless oil. $^1$H NMR (400 MHz, DMSO-d$_6$) δ 7.70 (d, J=8.4 Hz, 2H), 7.66-7.58 (m, 2H), 7.58-7.52 (m, 1H), 7.03 (d, J=8.4 Hz, 2H), 6.97 (t, J=7.6 Hz, 1H), 6.69 (d, J=8.0 Hz, 1H), 6.49 (t, J=7.6 Hz, 1H), 6.23 (d, J=8.0 Hz, 1H), 5.63 (s, 1H), 5.21 (s, 2H), 4.66-4.56 (m, 1H), 3.90-3.79 (m, 2H), 3.54-3.43 (m, 2H), 3.25-3.18 (m, 1H), 2.97-2.86 (m, 1H), 2.21-2.07 (m, 2H), 2.02-1.92 (m, 2H), 1.65-1.50 (m, 2H). MS (ESI) m/e [M+1]+ 415.9.

Step 2: 7-(2-Aminophenyl)-2-(4-(tetrahydr-2H-pyran-4-yloxy)phenyl)-4,5,6,7-tetrahydropyrazolo[1,5-a]pyrimidine-3-carboxamide

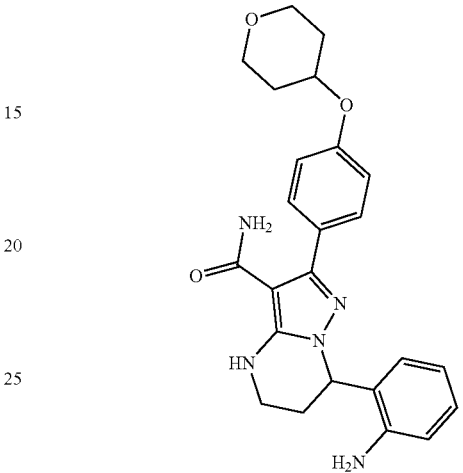

The desired product was prepared from 7-(2-aminophenyl)-2-(4-(tetrahydro-2H-pyran-4-yloxy)phenyl)-4,5,6,7-tetrahydropyrazolo[1,5-a]pyrimidine-3-carbonitrile using the procedure similar to step 2 for compound 2. $^1$H NMR (400 MHz, DMSO-d$_6$) δ 7.38 (d, J=8.8 Hz, 2H), 7.02 (d, J=8.8 Hz, 2H), 6.95 (t, J=7.6 Hz, 1H), 6.75 (s, 1H), 6.67 (d, J=7.8 Hz, 1H), 6.49 (t, J=7.6 Hz, 1H), 6.26 (d, J=7.8 Hz, 1H), 5.56 (s, 1H), 5.16 (s, 2H), 4.64-4.54 (m, 1H), 3.91-3.79 (m, 2H), 3.53-3.42 (m, 2H), 3.29-3.19 (m, 1H), 3.01-2.92 (m, 1H), 2.25-2.05 (m, 2H), 2.02-1.91 (m, 2H) and 1.64-1.52 (m, 2H). MS (ESI) m/e [M+1]+ 433.9.

Compound 24: 7-(2-Acrylamidophenyl)-2-(4-(tetrahydro-2H-pyran-4-yloxy)phenyl)-4,5,6,7-tetrahydropyrazolo[1,5-a]pyrimidine-3-carboxamide

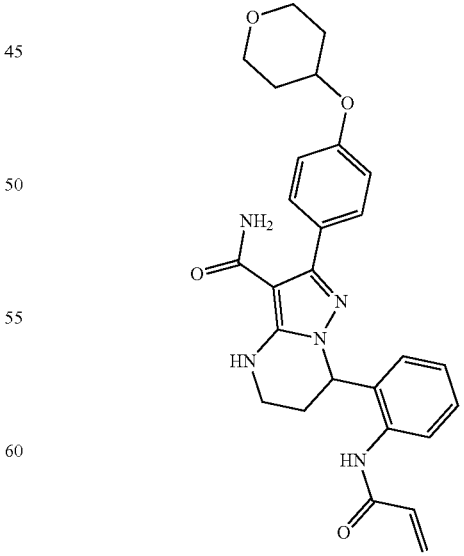

The desired product was prepared from compound 23 and acryloyl chloride using the procedure similar to that for compound 8. $^1$H NMR (400 MHz, DMSO-d$_6$) δ 9.83 (s, 1H), 7.45 (d, J=8.0 Hz, 1H), 7.38 (d, J=8.6 Hz, 2H), 7.30 (t, J=7.6 Hz, 1H), 7.21 (t, J=7.6 Hz, 1H), 7.02 (d, J=8.6 Hz, 2H), 6.81 (s, 1H), 6.63 (d. J=8.0 Hz, 1H), 6.53 (dd. J=17.0, 10.3 Hz, 1H), 6.27 (dd, J=17.0, 1.6 Hz, 1H), 5.82-5.74 (m, 2H), 4.66-4.51 (m, 1H), 3.90-3.78 (m, 2H), 3.54-3.40 (m, 2H), 3.31-3.18 (m, 1H), 3.03-2.93 (m, 1H), 2.37-2.24 (m, 1H), 2.04-1.92 (m, 3H) and 1.64-1.51 (m, 2H). MS (ESI) m/e [M+1]⁺ 487.9.

Example 11: Synthesis of Compounds 25-27

Compound 25: 7-(1-(Tert-butoxycarbonyl)piperidin-4-yl)-2-(4-phenoxyphenyl)-4,5,6,7-tetrahydropyrazolo[1,5-a]pyrimidine-3-carboxamide

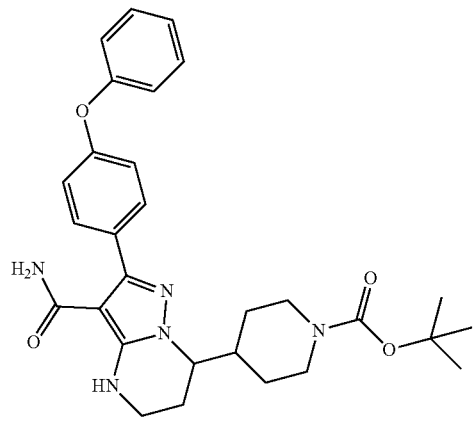 [SMILES: CC(C)(C)OC(=O)N1CCC(C2CCNc3c(C(N)=O)c(-c4ccc(Oc5ccccc5)cc4)nn32)CC1]

The desired product was prepared from tert-butyl 4-acetylpiperidine-1-carboxylate and 5-amino-3-(4-phenoxyphenyl)-1H-pyrazole-4-carbonitrile according to the procedures for 7-(3-aminophenyl)-2-(4-phenoxyphenyl) pyrazolo[1,5-a]pyrimidine-3-carbonitrile (step 4 to 5) and compound 2 (step 1 and 2) under appropriate conditions recognized by one of ordinary skill in the art. ¹H NMR (CD₃OD-d₄) δ 7.40 (d, J=8.4 Hz, 2H), 7.32-7.25 (m, 2H), 7.06 (t, J=7.6 Hz, 1H), 7.01-6.94 (m, 4H), 4.10-4.00 (m, 2H), 3.98-3.91 (m, 1H), 3.35-3.30 (m, 2H), 2.70-2.58 (m, 2H), 2.18-2.02 (m, 2H), 2.02-1.84 (m, 1H), 1.65-1.45 (m, 2H), 1.39-1.12 (m, 2H), 1.35 (s, 9H). MS (ESI) m/e [M+1]⁺ 518.0.

Compound 26: 7-(Piperidin-4-yl)-2-(4-phenoxyphenyl)-4,5,6,7-tetrahydropyrazolo [1,5-a]pyrimidine-3-carboxamide trifluoroacetate

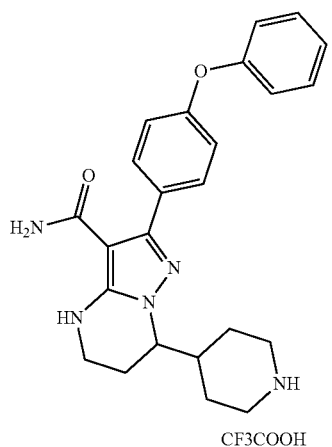

The desired product was prepared from compound 25 according to the procedure similar to step 2 for compound 38. ¹H NMR (DMSO-d₆) δ 8.47 (br s, 1H), 8.16 (br s, 1H), 7.50 (d, J=8.4 Hz, 2H), 7.46-7.38 (m, 2H), 7.18 (t, J=7.6 Hz, 1H), 7.10-7.04 (m, 4H), 6.72 (br s, 1H), 4.08-4.01 (m, 1H), 3.34-3.26 (m, 4H), 2.94-2.75 (m, 2H), 2.28-2.14 (m, 1H), 2.07-1.88 (m, 2H), 1.87-1.80 (m, 1H), 1.75-1.66 (m, 1H), 1.60-1.43 (m, 2H). MS (ESI) m/e [M+1]⁺ 418.0.

Compound 27: 7-(1-Acryloylpiperidin-4-yl)-2-(4-phenoxyphenyl)-4,5,6,7-tetrahydropyrazolo[1,5-a]pyrimidine-3-carboxamide

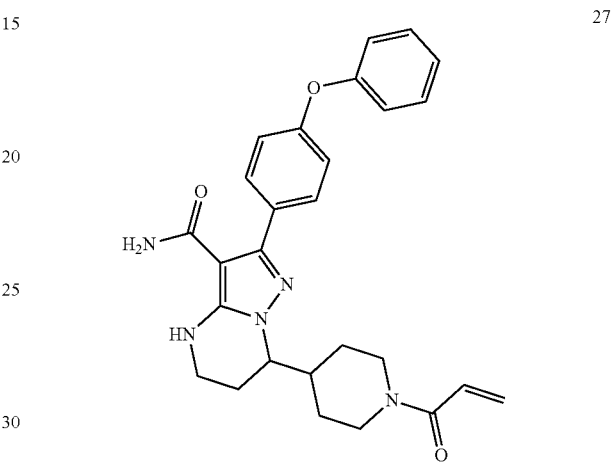

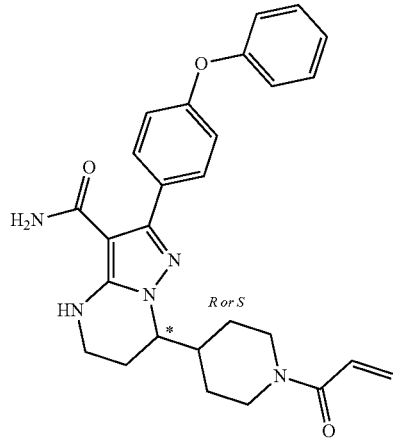

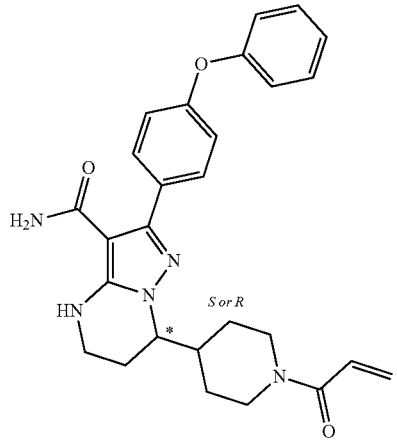

The desired product was prepared from compound 26 and acryloyl chloride according to the procedure similar to that for compound 8. $^1$H NMR (DMSO-$d_6$) δ 7.50 (d, J=8.8 Hz, 2H), 7.46-7.38 (m, 2H), 7.17 (t. J=7.6 Hz, 1H), 7.08 (d, J=7.6 Hz, 2H), 7.05 (d, J=8.8 Hz, 2H), 6.83-6.76 (m, 1H), 6.68 (br s, 1H), 6.07 (d, J=18.4 Hz, 1H), 5.64 (d, J=10.4 Hz, 1H), 4.52-4.42 (m, 1H), 4.11-3.98 (m, 2H), 3.33-3.24 (m, 2H), 3.04-2.94 (m, 1H), 2.67-2.55 (m, 1H), 2.33-2.25 (m, 1H), 2.01-1.93 (m, 2H), 1.78-1.66 (m, 1H), 1.61-1.50 (m, 1H), 1.30-1.18 (m, 2H). MS (ESI) m/e [M+1]$^+$ 471.9.

Compound 27 was separated into two enantiomeric stereoisomers compound 27a (peak 1, R or S, retention time at 6.49 min in chiral analysis), and compound 27b (peak 2, S or R, retention time at 8.03 min in chiral analysis) by chiral prep-HPLC. The chiral separation conditions are shown below.

| Column | CHIRALPAK IC |
|---|---|
| Column size | 2 cm × 25 cm |
| Injection | 2 mL |
| Mobile phase | MeOH/ACN = 60/40 |
| Flow rate | 15 mL/min |
| Wave length | UV 254 nm |
| Temperature | 35° C. |
| Sample solution | 0.5 mg/mL in mobile phase |
| Prep-SFC equipment | DAICEL-YMC |

The chiral analysis conditions are shown below.

| Column | CHIRALPAK IC |
|---|---|
| Column size | 0.46 cm I.D. × 15 cm L, 5 um |
| Injection | 2 uL |
| Mobile phase | MeOH/ACN = 60/40 (v/v) |
| Flow rate | 1.0 mL/min |
| Wave length | UV 214, 254 nm |

Example 12: Synthesis of Compounds 28-29

Compound 28: 7-(Azetidin-3-yl)-2-(4-phenoxyphenyl)-4,5,6,7-tetrahydropyrazolo [1,5-a]pyrimidine-3-carboxamide

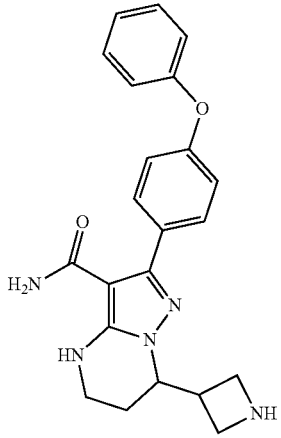 [SMILES: NC(=O)c1c(-c2ccc(Oc3ccccc3)cc2)nn2c1NCCC2C1CNC1]

Step 1: Tert-butyl 3-(methoxy(methyl)carbamoyl)azetidine-1-carboxylate

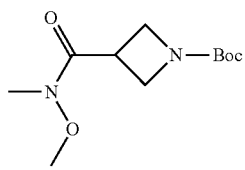

To a solution of 1-(tert-butoxycarbonyl)azetidine-3-carboxylic acid (5.15 g, 25.6 mmol) in THF (100 mL) was added DCC (7.11 g, 34.5 mmol), Et$_3$N (5.18 g, 51.2 mmol) and N,O-dimethylhydroxylamine hydrochloride (3.44 g, 35.3 mmol), the reaction was stirred at RT for about 16 hr. Concentrated under reduced pressure to remove solvent, the residue was portioned between EA (100 mL) and water (50 mL), the aqueous was further extracted with EA (50 mL×3). The combined organic phases were washed with brine (20 mL), concentrated under reduced pressure to remove solvent, then purified by column chromatography on silica gel (200-300 mesh, CH$_2$Cl$_2$/MeOH=20/1) to give the crude product (~8.0 g) as a colorless oil. MS (ESI) m/e [M+23]$^+$ 266.9, [M-55] 189.0.

Step 2: Tert-butyl 3-acetylazetidine-1-carboxylate

To a solution of tert-butyl 3-(methoxy(methyl)carbamoyl)azetidine-1-carboxylate (7.0 g, 28.7 mmol) in THF (150 mL) was added CH$_3$MgBr (43 mL, 43 mmol) at 0° C., then slowly warmed to RT for about 2 hr, 10% aqueous of citric acid (30 mL) was added to the mixture, and extracted with EA (50 mL×3), the combined organic phases were washed with brine (20 mL), dried over Na$_2$SO$_4$, filtered, concentrated and purified by column chromatography on silica gel (200-300 mesh, PE/EA=2/1), to give the crude product (4.0 g, 70%) as a colorless oil. MS (ESI) m/e [M-55]$^+$ 144.0.

Compound 28: 7-(Azetidin-3-yl)-2-(4-phenoxyphenyl)-4,5,6,7-tetrahydropyrazolo [1,5-a]pyrimidine-3-carboxamide

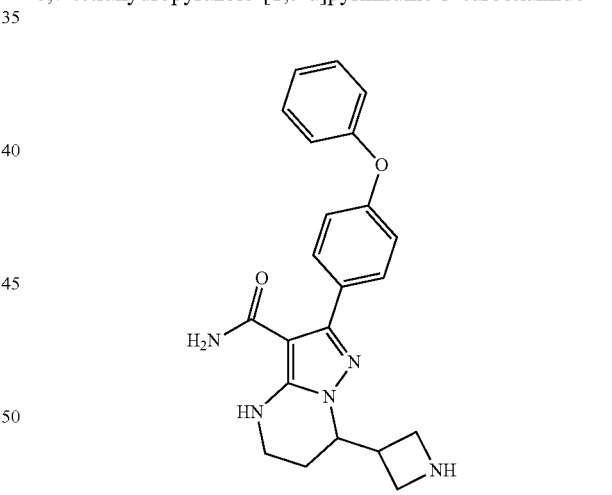

The desired product was prepared from tert-butyl 3-acetylazetidine-1-carboxylate and 5-amino-3-(4-phenoxyphenyl)-1H-pyrazole-4-carbonitrile according to the procedures for 7-(3-aminophenyl)-2-(4-phenoxyphenyl)pyrazolo[1,5-a]pyrimidine-3-carbonitrile (step 4 to 5), compound 2 (step 1 and 2) and compound 38 (step 2), under appropriate conditions recognized by one of ordinary skill in the art. $^1$H NMR (DMSO-$d_6$) δ 8.70 (br s, 1H), 8.44 (br s, 1H), 7.50 (d, J=8.6 Hz, 2H), 7.45-7.40 (m, 2H), 7.18 (t, J=7.6 Hz, 1H), 7.08 (d, J=7.4 Hz, 2H), 7.06 (d, J=8.6 Hz, 2H), 6.72 (br s, 1H), 4.46-4.38 (m, 1H), 4.24-4.15 (m, 1H), 4.07-3.94 (m, 3H), 3.29-3.24 (m, 2H), 3.19-3.10 (m, 1H), 2.13-2.04 (m, 1H), 1.78-1.69 (m, 1H). MS (ESI) m/e [M+1]$^+$ 390.0.

Compound 29: 7-(1-Acryloylazetidin-3-yl)-2-(4-phenoxyphenyl)-4,5,6,7-tetrahydropyrazolo[1,5-a]pyrimidine-3-carboxamide

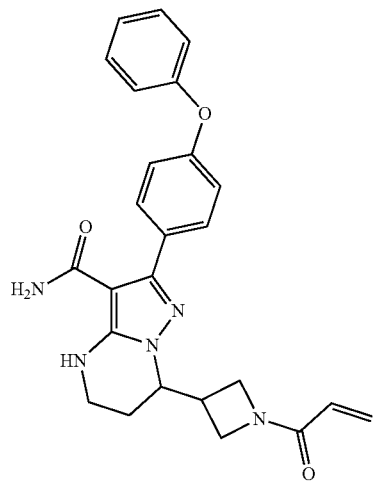

29

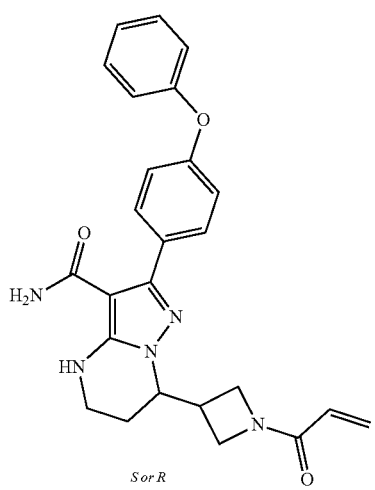

29a

R or S

29b

The desired product was prepared from compound 28 and acryloyl chloride according to the procedure similar to that for compound 8. ¹H NMR (DMSO-d₆) δ 7.50 (d, J=8.4 Hz, 2H), 7.44-7.40 (m, 2H), 7.20-7.15 (m, 1H), 7.10-7.04 (m, 4H), 6.69 (br s, 1H), 6.37-6.26 (m, 1H), 6.12-6.04 (m, 1H), 5.68-560 (m, 1H), 4.43-4.25 (m, 2H), 4.18-4.08 (m, 1H), 4.04-3.96 (m, 1H), 3.86-3.80 (m, 1H), 3.32-3.26 (m, 2H), 3.02-2.92 (m, 1H), 2.14-2.06 (m, 1H), 1.79-1.70 (m, 1H). MS (ESI) m/e [M+1]⁺ 444.0.

Compound 29 was separated into two enantiomeric stereoisomers compound 29a (peak 1, R or S, retention Lime at 10.54 min in chiral analysis), and compound 29b (peak 2, S or R, retention time at 13.98 min in chiral analysis) by chiral prep-HPLC. The chiral separation conditions are shown below.

| Column | CHIRALCEL OJ-H |
|---|---|
| Column size | 2 cm × 25 cm |
| Injection | 3 ml |
| Mobile phase | CO₂/(MeOH70%ACN30%) = 75/25 |
| Flow rate | 45 ml/min |
| Wave length | UV 220 nm |
| Temperature | 35 |
| Sample solution | 3 mg/ml in mobile phase |
| Prep-SFC equipment | DAICEL-SFC |

The chiral analysis conditions are shown below.

| Column | CHIRALPAK AD |
|---|---|
| Column size | 0.46 cm I.D. × 15 cm L, 5 um |
| Injection | 3 uL |
| Mobile phase | n-Hexane/EtOH (0.1% triethyl amine) = 70/30 (v/v) |
| Flow rate | 1.0 mL/min |
| Wave length | UV 214, 254 nm |

Example 13: Synthesis of Compounds 30-31

Compound 30: Cis-7-Acryloyl-2-(4-phenoxyphenyl)-4,5,5a,6,7,8,9,9a-octahydro pyrazolo[1,5-a]pyrido[3,4-e]pyrimidine-3-carboxamide and Cis-7-acryloyl-2-(4-phenoxyphenyl)-4,4a,5,6,7,8,8a,9-octahydropyrazolo[1,5-a]pyrido[4,3-d]pyrimidine-3-carboxamide

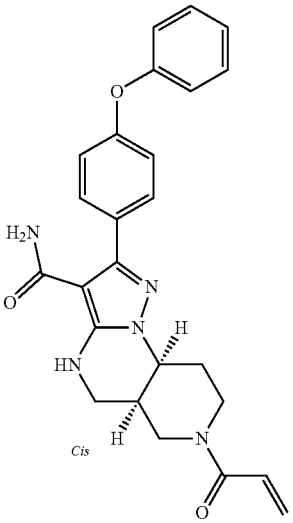

30

30a

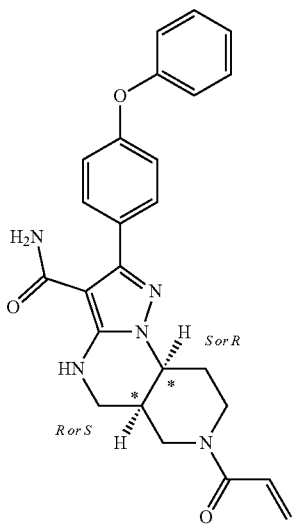

30b

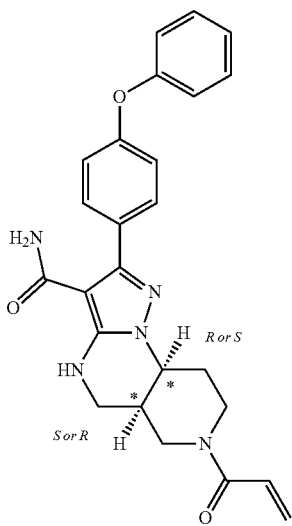

31

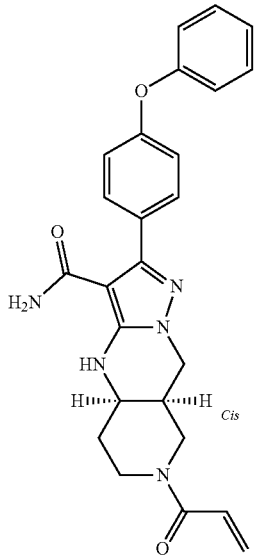

The desired product was prepared from tert-butyl 4-oxopiperidine-1-carboxylate and 5-amino-3-(4-phenoxy-phenyl)-1H-pyrazole-4-carbonitrile according to the procedures for compound 27, under appropriate conditions recognized by one of ordinary skill in the art. $^1$H NMR (DMSO-d$_6$) δ 7.51 (d, J=8.4 Hz, 2H), 7.46-7.38 (m, 2H), 7.17 (t, J=7.6 Hz, 1H), 7.11-7.01 (m, 4H), 6.90-6.78 (m, 1H), 6.65 (s, 1H), 6.18-6.06 (m, 1H), 5.73-5.63 (m, 1H), 4.45-4.33 (m, 1H), 3.84-3.34 (m, 5H), 3.22-3.16 (m, 1H), 2.40-2.32 (m, 1H), 2.21-2.10 (m, 1H), 2.00-1.90 (m, 1H). MS (ESI) m/e [M+1]$^+$ 443.9.

Compound 30 was separated into two enantiomeric stereoisomers compound 30a (peak 1, R or S, retention time at 10.64 min in chiral analysis), and compound 30b (peak 2, S or R, retention time at 15.18 min in chiral analysis) by chiral prep-HPLC. The chiral separation conditions are shown below.

| | |
|---|---|
| Column | CHIRALCEL ID |
| Column size | 3 cm × 25 cm |
| Injection | 7 mL |
| Mobile phase | MeOH/EA = 30/70 |
| Flow rate | 25 ml/min |
| Wave length | UV 254 nm |
| Temperature | 35° C. |
| Sample solution | 2 mg/ml in mobile phase |
| Prep-SFC equipment | DAICEL-YMC |

The chiral analysis conditions are shown below.

| | |
|---|---|
| Column | CHIRALPAK AD-H |
| Column size | 0.46 cm I.D. × 15 cm L, 5 um |
| Injection | 3 uL |
| Mobile phase | n-Hexane/EtOH (0.1% triethyl amine) = 50/50 (v/v) |
| Flow rate | 1.0 mL/min |
| Wave length | UV 214, 254 nm |

The compound 31 was obtained as one byproduct in the preparation of compound 30. $^1$H NMR (DMSO-d$_6$ at 80° C.) δ 7.53 (d, J=8.4 Hz, 2H), 7.46-7.38 (m, 2H), 7.17 (t, J=7.6 Hz, 1H), 7.11-7.02 (m, 4H), 6.82 (dd, J=16.8, 10.6 Hz, 1H), 6.42 (br s, 1H), 6.10 (dd. J=16.8, 2.3 Hz, 1H), 6.01 (br s, 2H), 5.68 (dd. J=10.6, 2.3 Hz, 1H), 4.17 (dd, J=5.4, 12.2 Hz, 1H), 3.67 (t, J=12.2 Hz, 1H), 3.28 (td, J=4.0, 10.4 Hz, 1H), 2.24-2.17 (m, 1H), 1.93-1.81 (m, 1H), 1.47-1.33 (m, 1H). MS (ESI) m/e [M+1]$^+$ 443.9.

Example 14: Synthesis of Compounds 32-33

Compound 32: 7-(Aminomethyl)-2-(4-phenoxyphenyl)-4,5,6,7-tetrahydropyrazolo [1,5-a]pyrimidine-3-carboxamide

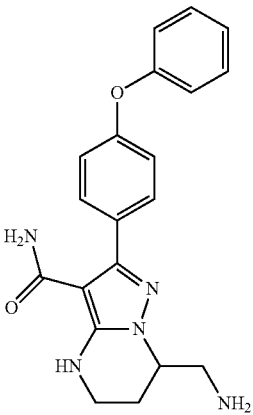 [SMILES: NCC1CCNc2c(C(N)=O)c(-c3ccc(Oc4ccccc4)cc3)nn21]

Step 1: (E)-2-(4-(Dimethylamino)-2-oxobut-3-enyl)isoindoline-1,3-dione

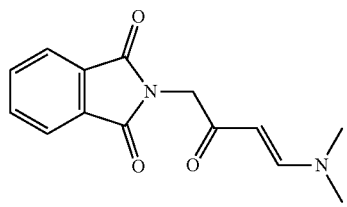 [SMILES: CN(C)/C=C/C(=O)CN1C(=O)c2ccccc2C1=O]

To a solution of 2-(2-oxopropyl)isoindoline-1,3-dione (1 g, 4.9 mmol) in 20 mL of DMF-DMA was added some of 4A molecular sieve. The reaction mixture was stirred at 100° C. under N₂ for 15 hr. After cooling down to RT, the mixture was filtered and collected 600 mg (47.5%) of crude (E)-2-(4-(dimethylamino)-2-oxobut-3-enyl) isoindoline-1,3-dione as a solid. MS (ESI) m/e [M+1]$^+$ 259.1.

Step 2: 7-((1,3-Dioxoisoindolin-2-yl)methyl)-2-(4-phenoxyphenyl)pyrazolo[1,5-a]pyrimidine-3-carbonitrile

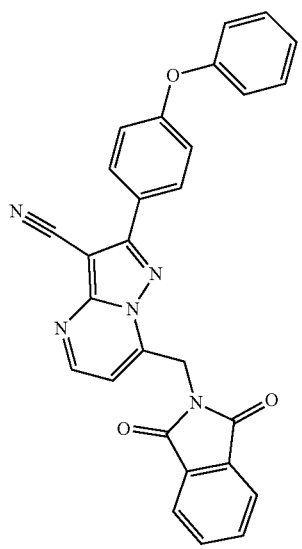 [SMILES: N#Cc1c(-c2ccc(Oc3ccccc3)cc2)nn2c(CN3C(=O)c4ccccc4C3=O)ccnc12]

A mixture of (E)-2-(4-(dimethylamino)-2-oxobut-3-enyl) isoindoline-1,3-dione (600 mg, 2.33 mmol) and 5-amino-3-(4-phenoxy phenyl)-1H-pyrazole-4-carbonitrile (642 mg, 2.33 mmol) in 20 mL of HOAc was stirred and heated to 120° C. for 15 hr. The mixture was concentrated and suspended in 30 mL of solvent (PE/EA=4/1). The mixture was filtered and the solid was purified by pre-TLC (DCM/EA=50/1) to give 430 mg (40%) of 7-((1,3-dioxoisoindolin-2-yl)methyl)-2-(4-phenoxyphenyl)pyrazolo [1,5-a]pyrimidine-3-carbonitrile as a solid. $^1$H NMR (400 MHz, DMSO-d₆) δ 8.74 (d, J=4.4 Hz, 1H), 8.05 (d, J=8.8 Hz, 2H), 7.96-7.90 (m, 1H), 7.88-7.85 (m, 2H), 7.50 (d, J=4.4 Hz, 1H), 7.46-7.37 (m, 2H), 7.21-7.09 (m, 5H), 5.32 (s, 2H). MS (ESI) m/e [M+1]$^+$ 472.1.

Step 3: 7-(Aminomethyl)-2-(4-phenoxyphenyl)pyrazolo[1,5-a]pyrimidine-3-carbonitrile

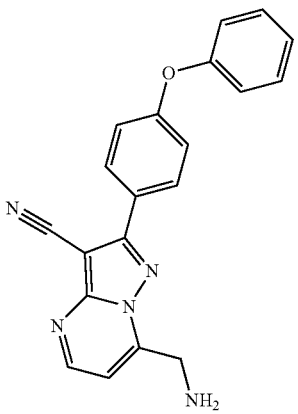 [SMILES: N#Cc1c(-c2ccc(Oc3ccccc3)cc2)nn2c(CN)ccnc12]

To a solution of 7-((1,3-dioxoisoindolin-2-yl)methyl)-2-(4-phenoxyphenyl) pyrazolo[1,5-a]pyrimidine-3-carbonitrile (290 mg, 0.62 mmol) in 5 mL of MeOH and 5 mL of dioxane was added 12 drops of hydrazine hydrate. The reaction mixture was stirred and heated to 60° C. for 3 hr. The mixture was concentrated and suspended in 20 mL of solvent (DCM/MeOH=10/1). The mixture was filtered and the filtrate was concentrated and purified by the flash chromatography eluting with EA followed by DCM/MeOH (10/1) to give 150 mg (71%) of 7-(aminomethyl)-2-(4-phenoxyphenyl) pyrazolo[1,5-a]pyrimidine-3-carbonitrile as a solid. MS (ESI) m/e [M+1]$^+$ 342.1.

Step 4: 7-(Aminomethyl)-2-(4-phenoxyphenyl)-4,5,6,7-tetrahydropyrazolo[1,5-a]pyrimidine-3-carbonitrile

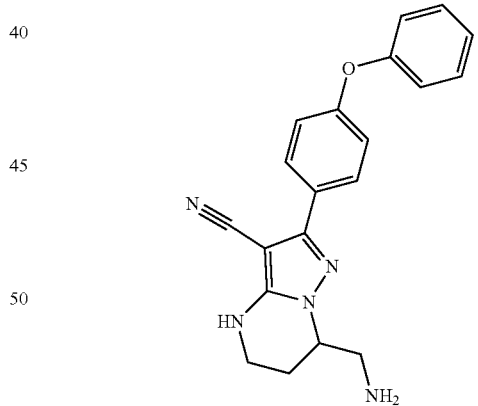

To a solution of 7-(aminomethyl)-2-(4-phenoxyphenyl) pyrazolo[1,5-a]pyrimidine-3-carbonitrile (150 mg, 0.44 mmol) in 20 mL of EtOH was added NaBH₄ (200 mg). The reaction mixture was stirred at rt for 15 hr. The mixture was concentrated to remove the solvent. The residue was partitioned between EA (20 mL) and water (20 mL). The organic layers were concentrated to give 150 mg (100%) of crude 7-(aminomethyl)-2-(4-phenoxyphenyl)-4,5,6,7-tetrahydropyrazolo[1,5-a]pyrimidine-3-carbonitrile as a solid, which was used in the next step without further purification. MS (ESI) m/e [M+1]$^+$ 346.0.

Step 5: 7-(Aminomethyl)-2-(4-phenoxyphenyl)-4,5,6,7-tetrahydropyrazolo[1,5-a]pyrimidine-3-carboxamide

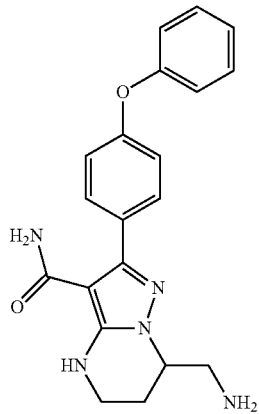 [SMILES: NCC1CCNc2c(C(N)=O)c(-c3ccc(Oc4ccccc4)cc3)nn21]

To a solution of 7-(aminomethyl)-2-(4-phenoxyphenyl)-4,5,6,7-tetrahydropyrazolo [1,5-a]pyrimidine-3-carbonitrile (15 mg, 0.043 mmol) in 2 mL of EtOH was added 1 mL of DMSO, 0.5 mL of NaOH (5N) and 0.5 mL of $H_2O_2$ (30% aqueous solution). After stirring at 60° C. for 2 hr, the mixture was concentrated to remove EtOH. The residue was partitioned between water (30 mL) and EA (20 mL). The organic phase was concentrated and purified by pre-HPLC eluting from 20% to 40% $CH_3CN$ in 0.1% TFA in $H_2O$. Fractions containing the desired product were combined and lyophilized overnight to give the product as a TFA salt (10 mg, 64%). $^1H$ NMR (400 MHz, DMSO-$d_6$) δ 8.07 (br s, 3H), 7.62 (d, J=8.8 Hz, 2H), 7.43-7.35 (m, 2H), 7.25 (t, J=7.6 Hz, 1H), 7.15-7.12 (m, 4H), 6.77 (br s, 1H), 4.38-4.30 (m, 1H), 3.40-3.20 (m, 4H), 2.16-2.06 (m, 1H), 2.00-1.80 (m, 1H). MS (ESI) m/e [M+1]$^+$ 364.0.

Compound 33: 7-(Acrylamidomethyl)-2-(4-phenoxyphenyl)-4,5,6,7-tetrahydro pyrazolo[1,5-a]pyrimidine-3-carboxamide

33

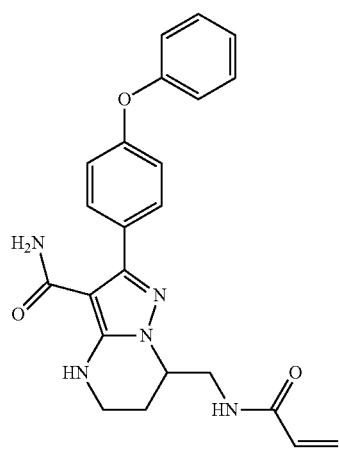

33a

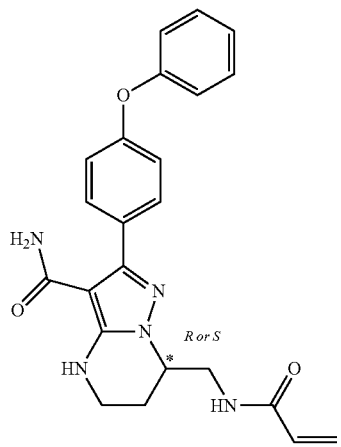

33b

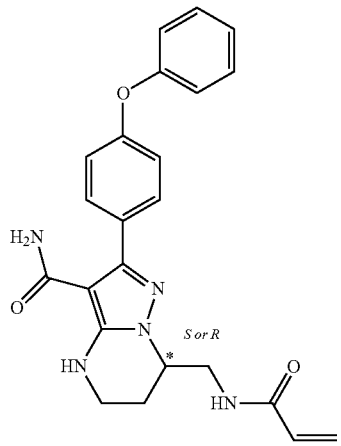

To a solution of 7-(aminomethyl)-2-(4-phenoxyphenyl)-4,5,6,7-tetrahydropyrazolo [1,5-a]pyrimidine-3-carboxamide (125 mg, 0.344 mmol) in 5 mL of DCM was added $Et_3N$ (four drops) and acryloyl chloride (46.5 mg, 0.52 mmol). After stirring at rt for 30 mins. The mixture was partitioned between water (10 mL) and DCM (5 mL). The organic layer was concentrated and purified by pre-TLC (DCM/MeOH=20/1) to give 40 mg (28%) of product. $^1H$ NMR (400 MHz, DMSO-$d_6$) δ 8.37 (t, J=6.0 Hz, 1H), 7.59 (d, J=8.8 Hz, 2H), 7.54-7.43 (m, 2H), 7.25 (t, J=7.6 Hz, 1H), 7.16-7.11 (m, 4H), 6.76 (s, 1H), 6.33 (dd, J=10.1, 17.0 Hz, 1H), 6.18 (dd, J=1.9, 17.0 Hz, 1H), 5.69 (dd, J=1.9, 10.1 Hz, 1H), 4.28-4.22 (m, 1H), 3.92-3.80 (m, 1H), 3.50-3.30 (m, 3H), 2.14-1.94 (m, 2H). MS (ESI) m/e [M+1]$^+$ 417.9.

Compound 33 was separated into two enantiomeric stereoisomers compound 33a (peak 1. R or S, retention time at 6.04 min in chiral analysis), and compound 33b (peak 2, S or R, retention time at 8.87 min in chiral analysis) by chiral prep-HPLC. The chiral separation conditions are shown below.

| | |
|---|---|
| Column | CHIRALCEL AD-H |
| Column size | 3 cm × 25 cm |
| Injection | 5 mL |
| Mobile phase | $CO_2$/MeOH = 75/25 |
| Flow rate | 65 mL/min |
| Wave length | UV 220 nm |

| | |
|---|---|
| Temperature | 35 |
| Sample solution | 4.5 mg/mL in mobile phase |
| Prep-SFC equipment | DAICEL-SFC |

The chiral analysis conditions are shown below.

| | |
|---|---|
| Column | CHIRALPAK AD-H |
| Column size | 0.46 cm I.D. × 15 cm L, 5 um |
| Injection | 1 uL |
| Mobile phase | n-Hexane/EtOH (0.1% triethyl amine) = 70/30 (v/v) |
| Flow rate | 1.0 mL/min |
| Wave length | UV 214, 254 nm |

Example 15: Synthesis of Compounds 34-35

Compound 34: 7-((Methylamino)methyl)-2-(4-phenoxyphenyl)-4,5,6,7-tetrahydro pyrazolo[1,5-a]pyrimidine-3-carboxamide

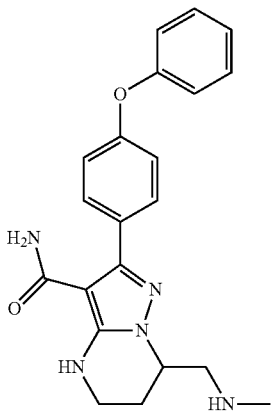 [SMILES: CNCC1CCNc2c(C(N)=O)c(-c3ccc(Oc4ccccc4)cc3)nn21]

Step 1: N-((3-cyano-2-(4-phenoxyphenyl)pyrazolo[1,5-a]pyrimidin-7-yl)methyl)-2,2,2-trifluoroacetamide

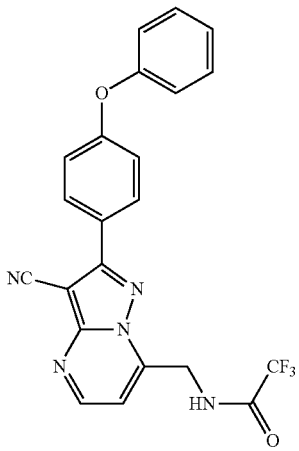 [SMILES: N#Cc1c(-c2ccc(Oc3ccccc3)cc2)nn2c(CNC(=O)C(F)(F)F)ccnc12]

To a solution of 7-(aminomethyl)-2-(4-phenoxyphenyl)pyrazolo[1,5-a]pyrimidine-3-carbonitrile (50 mg, 0.147 mmol) in 5 mL of DCM was added three drops of DIEA and two drops of trifluoroacetic anhydride. After stirring at it for 2 hr, 10 mL water was added to the mixture and extracted with DCM (5 mL×2). The DCM layers were concentrated to give a yellow solid (50 mg, 78%), which was used in the next step without further purification.

Step 2: N-((3-cyano-2-(4-phenoxyphenyl)pyrazolo[1,5-a]pyrimidin-7-yl)methyl)-2,2,2-trifluoro-N-methylacetamide

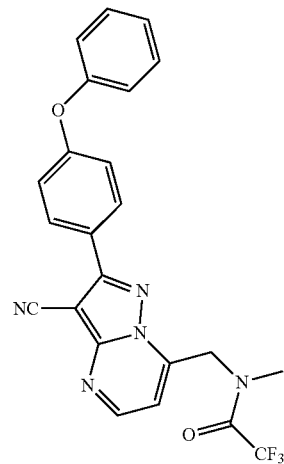 [SMILES: CN(Cc1ccnc2c(C#N)c(-c3ccc(Oc4ccccc4)cc3)nn12)C(=O)C(F)(F)F]

To a solution of N-((3-cyano-2-(4-phenoxyphenyl)pyrazolo[1,5-a]pyrimidin-7-yl) methyl)-2,2,2-trifluoroacetamide (40 mg, 0.091 mmol) in 5 mL of acetone was added $K_2CO_3$ (50 mg) and $CH_3I$ (0.5 mL). After stirring at rt for 4 hr, the mixture was concentrated. The residue was partitioned between 10 mL of water and 10 mL of DCM. The organic layer was concentrated and purified by Pre-TLC (DCM/MeOH=20/1) to give a yellow solid (30 mg, 73%). MS (ESI) m/e [M+1]$^+$ 451.9.

Step 3: 7-((Methylamino)methyl)-2-(4-phenoxyphenyl)-4,5,6,7-tetrahydropyrazolo [1,5-a]pyrimidine-3-carbonitrile

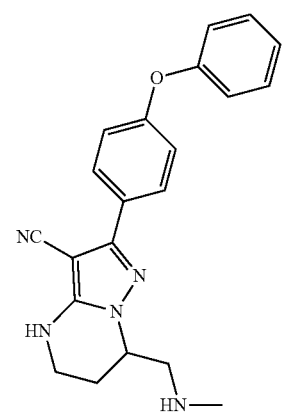 [SMILES: CNCC1CCNc2c(C#N)c(-c3ccc(Oc4ccccc4)cc3)nn21]

To a solution of N-((3-cyano-2-(4-phenoxyphenyl)pyrazolo[1,5-a]pyrimidin-7-yl) methyl)-2,2,2-trifluoro-N-methylacetamide (40 mg, 0.089 mmol) in 15 mL of EtOH was added $NaBH_4$ (50 mg). After stirring at rt for 30 mins, the mixture was concentrated. The residue was partitioned between 20 mL of water and 20 mL of EA. The EA layer was concentrated and purified by Pre-TLC (DCM/MeOH=5/1) to give a white solid (20 mg, 63%). MS (ESI) m/e [M+1]$^+$ 359.9.

Step 4: 7-((Methylamino)methyl)-2-(4-phenoxyphenyl)-4,5,6,7-tetrahydropyrazolo [1,5-a]pyrimidine-3-carboxamide

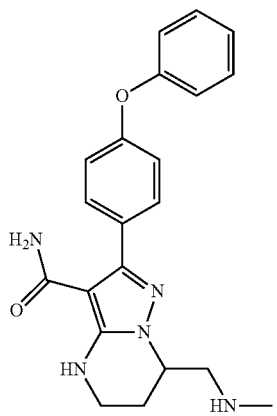 [SMILES: CNCC1CCNc2c(C(N)=O)c(-c3ccc(Oc4ccccc4)cc3)nn21]

To a solution of 7-((methylamino)methyl)-2-(4-phenoxyphenyl)-4,5,6,7-tetrahydro pyrazolo[1,5-a]pyrimidine-3-carbonitrile (20 mg, 0.0557 mmol) in 2 mL of EtOH was added 1 mL of DMSO, 0.5 mL of NaOH (5N) and 0.5 mL of $H_2O_2$ (30% solution). The reaction mixture was stirred at 60° C. for 1 hr. Then the mixture was concentrated to remove EtOH. The residue was partitioned between water (20 mL) and EA (20 mL). The EA layer was concentrated to give the product as a white solid (10 mg, yield: 48%). $^1H$ NMR (400 MHz, DMSO-$d_6$) δ 7.51 (d, J=8 Hz, 2H), 7.47-7.40 (m, 2H), 7.19 (t, J=7.6 Hz, 1H), 7.11-7.04 (m, 4H), 6.61 (s, 1H), 4.26-4.16 (m, 1H), 3.34-3.27 (m, 2H), 2.97-2.95 (m, 1H), 2.83-2.77 (m, 1H), 2.33 (s, 3H), 2.08-2.02 (m, 2H). MS (ESI) m/e [M+1]$^+$ 378.0.

Compound 35: 7-((N-Methyl(acrylamido)methyl)-2-(4-phenoxyphenyl)-4,5,6,7-tetrahydro pyrzolo[1,5-a]pyrimidine-3-carboxamide

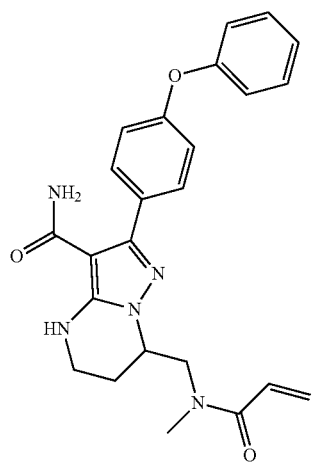 [SMILES: C=CC(=O)N(C)CC1CCNc2c(C(N)=O)c(-c3ccc(Oc4ccccc4)cc3)nn21]

To a solution of 7-((methylamino)methyl)-2-(4-phenoxyphenyl)-4,5,6,7-tetrahydro pyrazolo[1,5-a]pyrimidine-3-carboxamide (92 mg, 0.244 mmol) in 5 mL of DCM was added Et$_3$N (three drops) and acryloyl chloride (33 mg, 0.366 mmol). The reaction mixture was stirred at rt for 30 min. Then the mixture was partitioned between water (30 mL) and DCM (20 mL). The organic layer was concentrated and purified by pre-TLC (DCM/MeOH=15/1) to give the product as a white solid (25 mg, yield: 24%). $^1H$ NMR (400 MHz. DMSO-$d_6$ and $D_2O$ at 80° C.) δ 7.51 (d, J=8.4 Hz, 2H), 7.44-7.39 (m, 2H), 7.20-7.14 (m, 1H), 7.10-7.04 (m, 4H), 6.75-6.57 (m, 2H), 6.10-5.85 (m, 1H), 5.67-5.50 (m, 1H), 4.45-4.38 (m, 1H), 4.00-3.70 (m, 2H), 3.40-3.30 (m, 2H), 3.00 (s, 3H), 2.14-1.90 (m, 2H). MS (ESI) m/e [M+1]$^+$ 432.0.

Example 16: Synthesis of Compounds 36-37

Compound 36: 7-(Aminomethyl)-2-(1-benzyl-1H-pyrazol-4-yl)-4,5,6,7-tetrahydro pyrazolo[1,5-a]pyrimidine-3-carboxamide trifluoroacetate

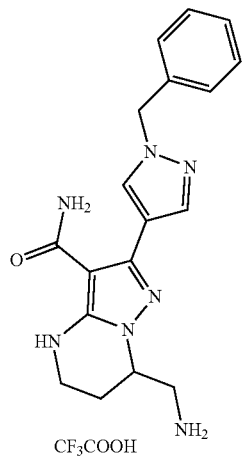 [SMILES: "CF3COOH" ; NCC1CCNc2c(C(N)=O)c(-c3cnn(Cc4ccccc4)c3)nn21]

Step 1: Ethyl 1-benzyl-1H-pyrazole-4-carboxylate

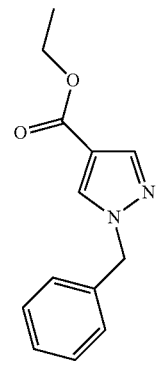 [SMILES: CCOC(=O)c1cnn(Cc2ccccc2)c1]

To a mixture of ethyl 1H-pyrazole-4-carboxylate (35.0 g, 250 mmol) and K$_2$CO$_3$ (69.0 g, 500 mmol) in CH$_3$CN (250 mL) was added BnBr (42.7 g, 250 mmol). The mixture was stirred at RT for 18 h and concentrated. The residue was suspended in EA (500 mL), washed with water (200 mL×2), dried over Na$_2$SO$_4$ and concentrated to give the desired compound as a white solid (53.0 g, 91.2%). $^1H$ NMR (DMSO-$d_6$) δ 8.46 (s, 1H), 7.88 (s, 1H), 7.41-7.19 (m, 5H), 5.37 (s, 2H), 4.21 (q, 2H, J=5.4 Hz), 1.25 (t, 3H, J=5.4 Hz). MS (ESI) m/e [M+1]$^+$ 231.0.

Step 2: 1-Benzyl-1H-pyrazole-4-carboxylic acid

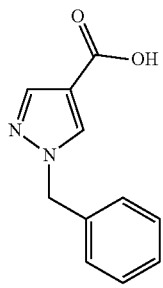 [SMILES: O=C(O)c1cnn(Cc2ccccc2)c1]

A mixture of ethyl 1-benzyl-1H-pyrazole-4-carboxylate (53.0 g, 0.23 mol) and LiOH (19.4 g, 0.46 mol) in THF (100 mL) and H$_2$O (100 mL) was stirred at reflux for 6 h. Then, THF was removed, the residue was acidify by 6N HCl, precipitation was formed, filtered and dried to give the desired compound as a white solid (44.0 g, 92.8%). $^1$H NMR (DMSO-d$_6$) δ 12.36 (s, 1H), 8.39 (s, 1H), 7.85 (s, 1H), 7.38-7.27 (m, 5H), 5.37 (s, 2H). MS (ESI) m/e [M+1]$^+$ 202.9.

Step 3: 2-((1-Benzyl-1H-pyrazol-4-yl)(hydroxy)methylene)malononitrile

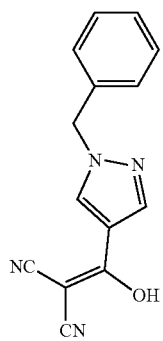 [SMILES: N#CC(C#N)=C(O)c1cnn(Cc2ccccc2)c1]

A solution of 1-benzyl-1H-pyrazole-4-carboxylic acid (25.0 g, 123.8 mmol) in SOCl$_2$ (250 mL) was heated to reflux for 3 hr. The mixture was concentrated in vacuum to give the intermediate, which was used in the next step without further purification. To a solution of propanedinitrile (8.2 g, 12.8 mmol), DIEA (32.0 g, 247.6 mmol) in THF (250 mL) was added dropwise a solution of intermediate in toluene (250 mL) at 0-5° C. over 1 hr. The resultant mixture was allowed to warm to RT and stirred for 16 hr. The reaction was quenched with water (500 mL) and extracted with EA (500 mL×3), The organic layers were washed with 3N HCl (500 mL), brine (500 mL×3), dried over Na$_2$SO$_4$ and concentrated to give the crude product (26.5 g, 85.0%) as a yellow solid. MS (ESI) m/e [M+1]$^+$ 250.9.

Step 4: 2-((1-Benzyl-1H-pyrazol-4-yl)(methoxy)methylene)malononitrile

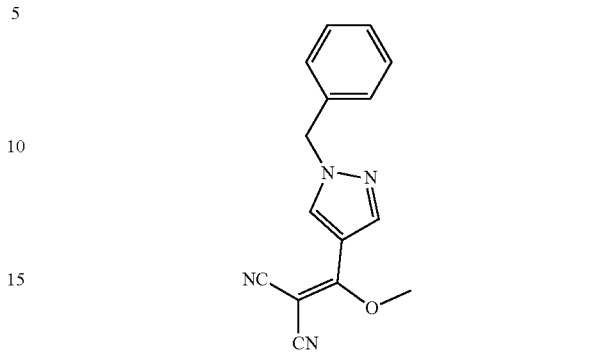

A solution of 2-((1-benzyl-1H-pyrazol-4-yl)(hydroxy)methylene)malononitrile (26.5 g, 106 mmol) in CH(OMe)$_3$ (250 mL) was heated to 75° C. for 16 hr. Then the solution was concentrated. The residue was washed with MeOH (50 mL) to give 14.5 g (51.8%) of 2-((1-benzyl-1H-pyrazol-4-yl)(methoxy)methylene)malononitrile as an off-white solid. $^1$H NMR (DMSO-d$_6$) δ 8.71 (s, 1H), 8.08 (s, 1H), 7.42-7.24 (m, 5H), 5.46 (s, 2H), 4.12 (s, 3H). MS (ESI) m/e [M+1]$^+$ 264.9.

Step 5: 5-Amino-2'-benzyl-3,4'-bi(1H-pyrazole)-4-carbonitrile

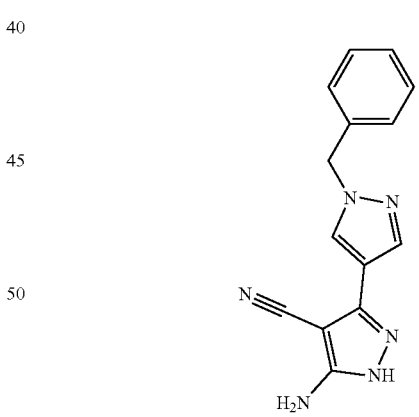

A mixture of 2-((1-benzyl-1H-pyrazol-4-yl)(methoxy)methylene)malononitrile (14.5 g, 54.9 mmol) and hydrazine hydrate (10 mL) in EtOH (500 mL) was stirred at RT for 4 hr. Then the mixture was concentrated to give the crude product, washed with MeOH to afford 10 g (69.0%) of 5-amino-2'-benzyl-3,4'-bi(1H-pyrazole)-4-carbonitrile as an off-white solid. $^1$H NMR (DMSO-d$_6$) δ 11.76 (br s, 1H), 8.18 (s, 1H), 7.82 (s, 1H), 7.34-7.26 (m, 5H), 6.11 (br s, 2H), 5.40 (s, 2H). MS (ESI) m/e [M+1]$^+$ 264.9.

Compound 36: 7-(Aminomethyl)-2-(1-benzyl-1H-pyrazol-4-yl)-4,5,6,7-tetrahydro pyrazolo[1,5-a]pyrimidine-3-carboxamide trifluoroacetate

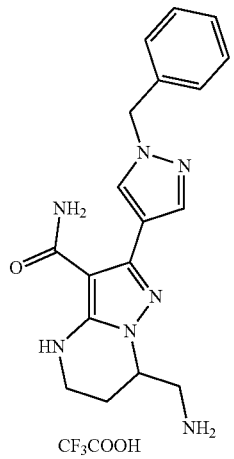 [SMILES: "CF3COOH" ; NCC1CCNc2c(C(N)=O)c(-c3cnn(Cc4ccccc4)c3)nn21]

CF₃COOH

The desired product was prepared from 5-amino-2'-benzyl-3,4'-bi(1H-pyrazole)-4-carbonitrile and (E)-2-(4-(dimethylamino)-2-oxobut-3-enyl)isoindoline-1,3-dione according to the procedures (step 2 to 5) for compound 32, under appropriate conditions recognized by one of ordinary skill in the art. $^1$H NMR (400 MHz, DMSO-$d_6$) δ 8.14 (s, 1H), 7.97 (br s, 3H), 7.74 (s, 1H), 739-7.24 (m, 5H), 5.37 (s, 2H), 4.40-4.25 (m, 1H), 3.37-3.16 (m, 4H), 2.16-2.08 (m, 1H), 1.99-1.89 (m, 1H). MS (ESI) m/e $[M+1]^+$ 352.0.

Compound 37: 7-(Acrylamidomethyl)-2-(1-benzyl-1H-pyrazol-4-yl)-4,5,6,7-tetrahydropyrazolo[1,5-a]pyrimidine-3-carboxamide

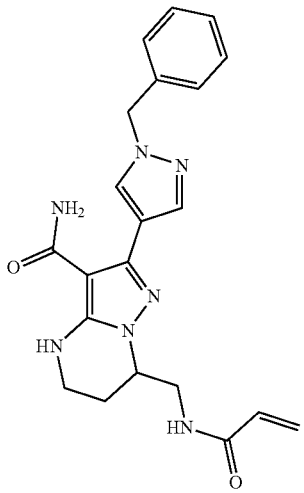 [SMILES: C=CC(=O)NCC1CCNc2c(C(N)=O)c(-c3cnn(Cc4ccccc4)c3)nn21]

The desired product was prepared from compound 36 and acryloyl chloride using the procedure similar to that for compound 8. $^1$H NMR (400 MHz, DMSO-$d_6$) δ 8.27 (t, J=6.1 Hz, 1H), 8.11 (s, 1H), 7.67 (s, 1H), 7.41-7.21 (m, 5H), 6.58 (s, 1H), 6.25 (br s, 2H), 6.25 (dd, J=17.1, 10.1 Hz, 1H), 6.10 (dd, J=17.1, 2.1 Hz, 1H), 5.62 (dd. J=10.1, 2.1 Hz, 1H), 5.36 (s, 2H), 4.16-4.10 (m, 1H), 3.83-3.72 (m, 1H), 3.42-3.30 (m, 1H), 3.30-3.22 (m, 2H), 2.00-1.96 (m, 1H), 1.95-1.86 (m, 1H). MS (ESI) m/e $[M+1]^+$ 405.9.

Example 17: Synthesis of Compounds 38-40

Compound 38 1'-Benzyl-6-(4-phenoxyphenyl)-1,2-dihydrospiro[imidazo[1,2-b]pyrazole-3,4'-piperidine]-7-carboxamide

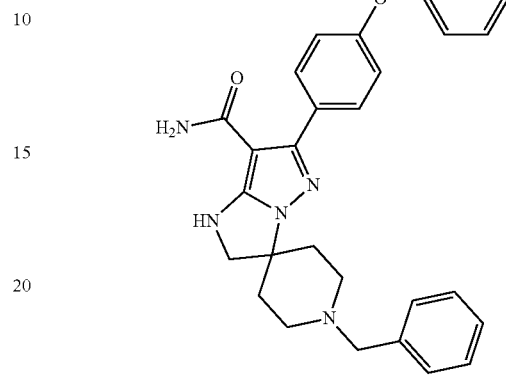

Step 1: di-tert-Butyl 1-(1-benzyl-4-(ethoxycarbonyl)piperidin-4-yl)hydrazine-1,2-dicarboxylate

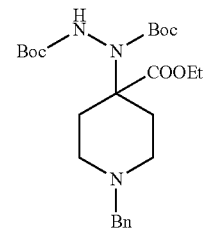 [SMILES: CCOC(=O)C1(N(NC(=O)OC(C)(C)C)C(=O)OC(C)(C)C)CCN(Cc2ccccc2)CC1]

To a solution of diisopropylamine (153 mg, 1.5 mmol) in THF (20 mL) was added n-BuLi (2.5 M, 0.6 mL) at −75° C. under N₂. After 5 min, ethyl 1-benzylpiperidine-4-carboxylate (247 mg, 1.0 mmol) was added and the resulting mixture then stirred at −70° C. for 10 min, before adding di-tert-butyl azodicarboxylate (345 mg, 1.5 mmol). The reaction was stirred for 30 min, then quenched with aqueous NH₄Cl (10 mL) and extracted with EA (10 mL×3). The combined organic layers were dried over Na₂SO₄ and concentrated to give the crude product (350 mg, 72%) as an off-white solid. MS (ESI, m/e) $[M+1]^+$ 478.3.

Step 2: Ethyl 1-benzyl-4-hydrazinylpiperidine-4-carboxylate hydrochloride

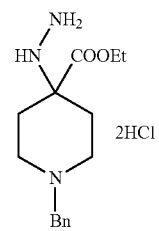

A mixture of di-tert-butyl 1-(1-benzyl-4-(ethoxycarbonyl)piperidin-4-yl)hydrazine-1,2-dicarboxylate (1.0 g, 2.09 mmol) and con. HCl (1.0 mL) in MeOH (10 mL) was heated to reflux for 2 hr. The mixture was then concentrated to give the crude product (650 mg, 88.9%) as a yellow solid. MS (ESI, m/e) [M+1]⁺ 278.0.

Step 3: Ethyl 4-(5-amino-4-cyano-3-(4-phenoxyphenyl)-1H-pyrazol-1-yl)-1-benzyl piperidine-4-carboxylate

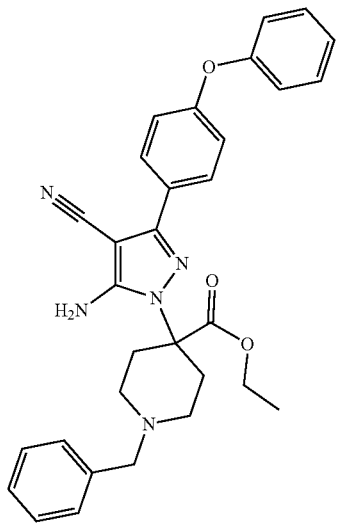 [SMILES: CCOC(=O)C1(n2nc(-c3ccc(Oc4ccccc4)cc3)c(C#N)c2N)CCN(Cc2ccccc2)CC1]

A mixture of ethyl 1-benzyl-4-hydrazinylpiperidine-4-carboxylate hydrochloride (580 mg, 1.57 mmol), 2-(methoxy(4-phenoxyphenyl)methylene)malononitrile (433 mg, 1.57 mmol) and TEA (475 mg, 4.71 mmol) in CHCl₃ (20 mL) was heated to reflux for 16 hr under N₂. The mixture was concentrated and purified by chromatography column on silica gel using 50% of EA in PE as eluant to give the product (280 mg 34.2%) as a yellow solid. MS (ESI, m/e) [M+1]⁺521.9.

Step 4: 5-Amino-1-(1-benzyl-4-(hydroxymethyl)piperidin-4-yl)-3-(4-phenoxyphenyl)-1H-pyrazole-4-carbonitrile

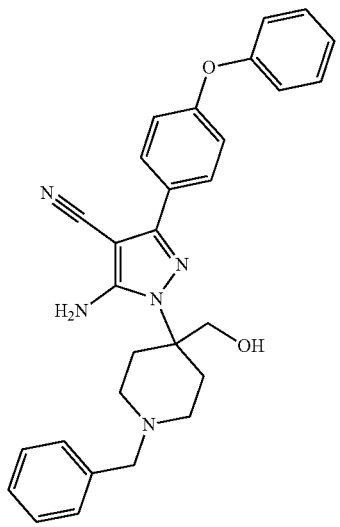 [SMILES: N#Cc1c(-c2ccc(Oc3ccccc3)cc2)nn(C2(CO)CCN(Cc3ccccc3)CC2)c1N]

To a solution of ethyl 4-(5-amino-4-cyano-3-(4-phenoxyphenyl)-1H-pyrazol-1-yl)-1-benzylpiperidine-4-carboxylate (52 mg, 0.1 mmol) in MeOH (5 mL) was added NaBH₄ (8 mg, 0.2 mmol). After 10 min. the reaction was quenched with water (5 mL) and extracted with EA (10 mL×3). The organic combined layers was dried over Na₂SO₄ and concentrated to give the crude product (34 mg, 70.9%) as an off-white solid. MS (ESI, m/e) [M+1]⁺ 480.0.

Step 5: (4-(5-Amino-4-cyano-3-(4-phenoxyphenyl)-1H-pyrazol-1-yl)-1-benzyl piperidin-4-yl) methyl methanesulfonate

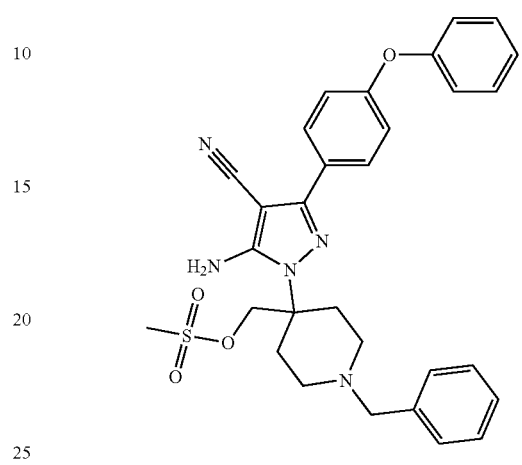

To a solution of 5-amino-1-(1-benzyl-4-(hydroxymethyl)piperidin-4-yl)-3-(4-phenoxyphenyl)-1H-pyrazole-4-carbonitrile (50 mg, 0.1 mmol) and TEA (20 mg, 0.20 mmol) in DCM (5 mL) was added MsCl (14 mg, 0.12 mmol) at 0° C. After 5 min, the reaction was quenched with water (5 mL) and extracted with DCM (5 mL×3). The combined organic layers were dried over Na₂SO₄ and concentrated and purified by Prep-TLC (10% of MeOH in DCM) to give the product (35 mg, 62.8%) as a yellow solid. ¹H NMR (400 MHz, DMSO-d₆) δ 7.80 (d, J=8.8 Hz, 2H), 7.45-7.36 (m, 2H), 7.37-7.22 (m, 5H), 7.17 (t, J=7.6 Hz, 1H), 7.11 (d, J=8.8 Hz, 2H), 7.06 (d, J=8.0 Hz, 2H), 6.49 (br s, 2H), 4.48 (s, 2H), 3.40 (s, 2H), 3.10 (s, 3H), 2.88-2.55 (m, 4H), 2.19-2.16 (m, 2H), 1.92-1.86 (m, 2H). MS (ESI, m/e) [M+1]⁺ 557.9.

Step 6: 1'-Benzyl-6-(4-phenoxyphenyl)-1,2-dihydrospiro[imidazo[1,2-b]pyrazole-3,4'-piperidine]-7-carbonitrile

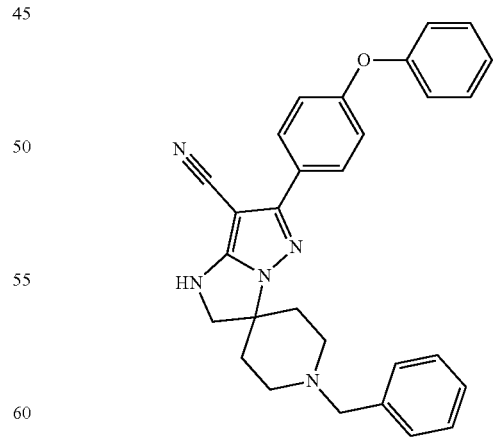

A mixture of (4-(5-amino-4-cyano-3-(1-phenoxyphenyl)-1H-pyrazol-1-yl)-1-benzylpiperidin-4-yl)methyl methanesulfonate (35 mg, 0.06 mmol) and Cs₂CO₃ (31 mg, 0.09 mmol) in DMF (2 mL) was heated to 50° C. for 16 hr. The reaction was quenched with water (5 mL) and extracted with EA (5 mL×3). The combined organic layers were dried over Na₂SO₄, concentrated and purified by Prep-TLC (10% of MeOH in DCM) to give the product (12 mg, 43.2%) as a yellow solid. $^1$H NMR (400 MHz, DMSO-d$_6$) δ 7.79 (d, J=8.4 Hz, 2H), 7.43-7.40 (m, 3H), 7.38-7.29 (m, 4H), 7.26 (br s, 1H), 7.19 (t, J=7.6 Hz, 1H), 7.12-7.05 (m, 4H), 3.85 (s, 2H), 3.53 (s, 2H), 2.89-2.80 (m, 2H), 2.22-2.12 (m, 2H), 2.10-1.96 (m, 2H), 1.85-1.75 (m, 2H). MS (ESI, m/e) [M+1]⁺ 462.0.

Step 7: 1'-Benzyl-6-(4-phenoxyphenyl)-1,2-dihydrospiro[imidazo[1,2-b]pyrazole-3,4'-piperidine]-7-carboxamide

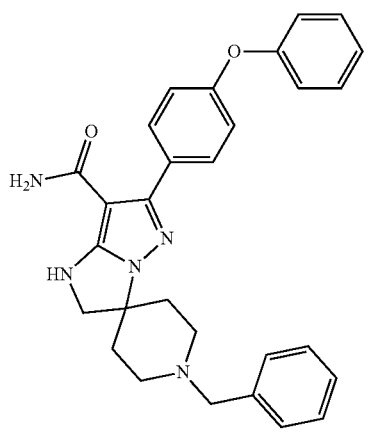 [SMILES: NC(=O)c1c(-c2ccc(Oc3ccccc3)cc2)nn2c1NCC21CCN(Cc2ccccc2)CC1]

The desired product was prepared from 1'-benzyl-6-(4-phenoxyphenyl)-1,2-dihydrospiro[imidazo[1,2-b]pyrazole-3,4'-piperidine]-7-carbonitrile according to the procedure similar to step 2 for compound 2. $^1$H NMR (400 MHz, DMSO-d$_6$) δ 7.63 (d, J=8.4 Hz, 2H), 7.45-7.39 (m, 3H), 7.37-7.31 (m, 4H), 7.16 (t, J=7.6 Hz, 1H), 7.12-6.94 (m, 4H), 6.43 (s, 1H), 3.78 (s, 2H), 3.55 (br s, 2H), 2.89-2.82 (m, 2H), 2.15-2.11 (m, 2H), 1.84-1.72 (m, 2H). MS (ESI, m/e) [M+1]⁺ 479.9.

Compound 39: 6-(4-Phenoxyphenyl)-1,2-dihydrospiro[imidazo[1,2-b]pyrazole-3,4'-piperidine]-7-carboxamide

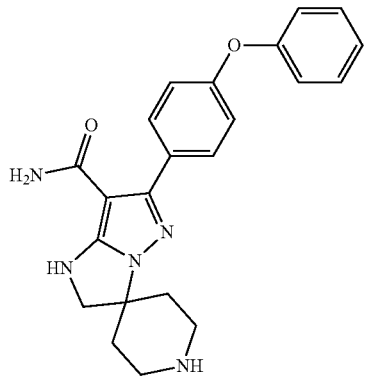 [SMILES: NC(=O)c1c(-c2ccc(Oc3ccccc3)cc2)nn2c1NCC21CCNCC1]

A mixture of 1'-benzyl-6-(4-phenoxyphenyl)-1,2-dihydrospiro[imidazo[1,2-b] pyrazole-3,4'-piperidine]-7-carboxamide (50 mg, 0.10 mmol), 10% w/w Pd(OH)₂/C (5 mg) in MeOH (10 mL) and HOAc (1 drop) was stirred for 16 hr under H₂. The mixture was filtrated and the filtrate was concentrated to give the crude product (20 mg 51.4%) as a yellow solid. MS (ESI, m/e) [M+1]⁺ 390.0.

Compound 40: 1'-Acryloyl-6-(4-phenoxyphenyl)-1,2-dihydrospiro[imidazo[1,2-b]pyrazole-3,4'-piperidine]-7-carboxamide

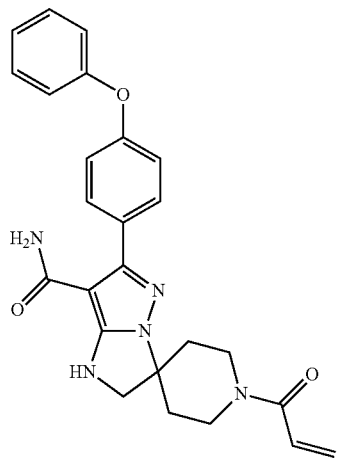 [SMILES: C=CC(=O)N1CCC2(CC1)CNc1c(C(N)=O)c(-c3ccc(Oc4ccccc4)cc3)nn12]

Compound 40 was prepared from compound 39 and acryloyl chloride according to the procedure similar to that for compound 8. $^1$H NMR (400 MHz, DMSO-d$_6$) δ 7.64 (d, J=8.8 Hz, 2H), 7.44-7.37 (m, 2H), 7.16 (t, J=7.6 Hz, 1H), 7.05 (d, J=7.6 Hz, 2H), 6.97 (d, J=8.8 Hz, 2H), 6.86 (dd, J=10.5, 16.7 Hz, 1H), 6.51 (br s, 1H), 6.12 (dd, J=2.3, 16.7 Hz, 1H), 5.69 (dd, J=2.3, 10.5 Hz, 1H), 4.13-3.95 (m, 2H), 3.83 (s, 2H), 3.60-3.38 (m, 2H), 1.99-1.76 (m, 4H). MS (ESI, m/e) [M+1]⁺ 443.9.

Example 18: Synthesis of Compounds 41-43

Compound 41: 1-Benzyl-2'-(4-phenoxyphenyl)-5',6'-dihydro-4'H-spiro[piperidine-4,7'-pyrazolo[1,5-a]pyrimidine]-3'-carboxamide

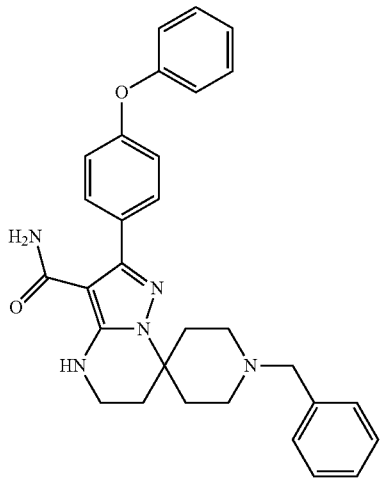 [SMILES: NC(=O)c1c(-c2ccc(Oc3ccccc3)cc2)nn2c1NCCC21CCN(Cc2ccccc2)CC1]

Step 1: Ethyl 2-(1-benzylpiperidin-4-ylidene)acetate

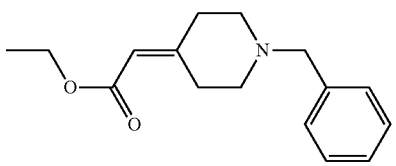 [SMILES: CCOC(=O)C=C1CCN(Cc2ccccc2)CC1]

To a suspension of NaH (318 mg, 7.94 mmol) in THF (20 mL) was added a solution of ethyl 2-(diethoxyphosphoryl)acetate (1.78 g, 7.94 mmol) in THF (5 mL) dropwise over 30 min at 0° C. After stirring for 10 min, a solution of 1-benzylpiperidin-4-one (1.0 g, 5.29 mmol) in THF (5 mL) was added dropwise at 0° C. over 20 min. The mixture was allowed to stir for 60 min. Then, the reaction was quenched with water (10 mL). The mixture was extracted with EA (10 mL×3). The combined organic layers were dried over $Na_2SO_4$, concentrated and purified by chromatography column on silica gel using 25% of EA in PE as eluant to give the product (1.2 g, 87.3%) as a yellow oil. MS (ESI, m/e) [M+1]$^+$ 260.0.

Step 2: 1-Benzyl-5'-oxo-2'-(4-phenoxyphenyl)-5',6'-dihydro-4'H-spiro[piperidine-4,7'-pyrazolo[1,5-a]pyrimidine]-3'-carbonitrile

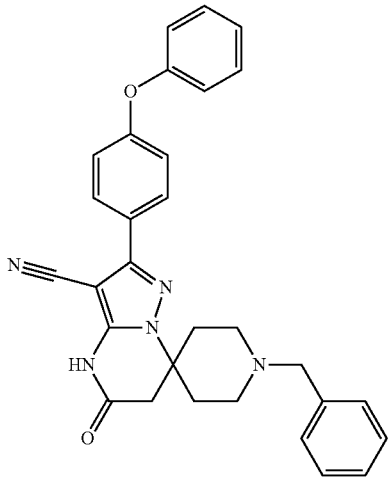 [SMILES: N#Cc1c(-c2ccc(Oc3ccccc3)cc2)nn2c1NC(=O)CC21CCN(Cc2ccccc2)CC1]

A mixture of 5-amino-3-(4-phenoxyphenyl)-1H-pyrazole-4-carbonitrile (1.0 g, 3.6 mmol), ethyl 2-(1-benzylpiperidin-4-ylidene)acetate (1.1 g, 4.3 mmol) and $K_2CO_3$ (745 mg, 5.4 mmol) in DMF (20 mL) was heated to 80° C. for 16 hr under $N_2$. The reaction was quenched with water (20 mL) and extracted with EA (20 mL×3). The combined organic layers were dried over $Na_2SO_4$, concentrated and purified by chromatography column on silica gel using 30% of EA in PE as eluant to give the product (950 mg, 54.9%) as a yellow solid. $^1$H NMR (400 MHz, DMSO-$d_6$) δ 11.92 (s, 1H), 7.84 (d, J=8.8 Hz, 2H), 7.48-7.40 (m, 2H), 7.36-7.29 (m, 4H), 7.27-7.23 (m, 1H), 7.20 (t, J=7.6 Hz, 1H), 7.15-7.07 (m, 4H), 3.55 (s, 2H), 3.01 (s, 2H), 2.81-2.73 (m, 2H), 2.39-2.27 (m, 2H), 2.26-2.16 (m, 2H), 1.83-1.74 (m, 2H). MS (ESI, m/e) [M+1]$^+$ 489.9.

Step 3: 1-Benzyl-5'-oxo-2'-(4-phenoxyphenyl)-5',6'-dihydro-4'H-spiro[piperidine-4,7'-pyrazolo[1,5-a]pyrimidine]-3'-carboxamide

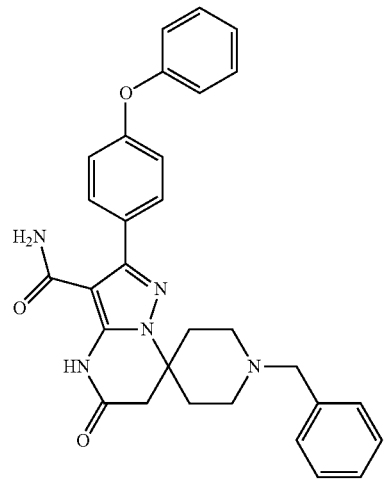 [SMILES: NC(=O)c1c(-c2ccc(Oc3ccccc3)cc2)nn2c1NC(=O)CC21CCN(Cc2ccccc2)CC1]

A solution of 1-benzyl-5'-oxo-2'-(4-phenoxyphenyl)-5',6'-dihydro-4'H-spiro [piperidine-4,7'-pyrazolo[1,5-a]pyrimidine]-3'-carbonitrile (500 mg, 1.02 mmol) in $H_3PO_4$ (5 mL) was heated to 130° C. for 1 hr. The mixture was poured to water (20 mL) and extracted with EA (20 mL×3). The combined organic layers were dried over $Na_2SO_4$, concentrated and purified by chromatography column on silica gel using 5% of MeOH in DCM as eluant to afford the product (180 mg, 34.8%) as a yellow solid. MS (ESI, m/e) [M+1]$^+$ 507.9.

Step 4: 1-Benzyl-2'-(4-phenoxyphenyl)-5',6'-dihydro-4'H-spiro[piperidine-4,7'-pyrazolo[1,5-a]pyrimidine]-3'-carboxamide

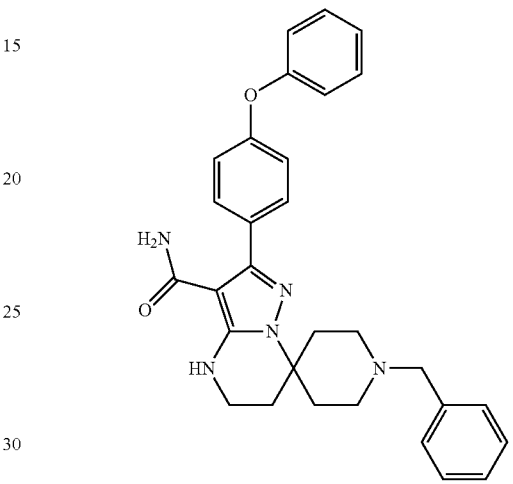

A solution of 1-benzyl-5'-oxo-2'-(4-phenoxyphenyl)-5',6'-dihydro-4'H-spiro [piperidine-4,7'-pyrazolo[1,5-a]pyrimidine]-3'-carboxamide (180 mg, 0.36 mmol) in BH$_3$/THF (1N, 20 mL) was heated to reflux for 3 hr. The reaction was quenched with MeOH (20 mL) and con. HCl (2 mL). The mixture was stirred at 60° C. for 1 hr, then was basified with NaHCO$_3$ and extracted with EA (20 mL×3). The combined organic layers were dried over Na$_2$SO$_4$, concentrated and purified by chromatography column on silica gel eluting with 5% of MeOH in DCM to give the product (120 mg, 67.6%) as a yellow solid. $^1$H NMR (400 MHz, CD$_3$OD-$d_4$) δ 7.39-7.22 (m, 9H), 7.09-7.04 (m, 1H), 6.99-6.94 (m, 4H), 3.86 (s, 2H), 3.35 (t, J=5.6 Hz, 2H), 3.19-3.11 (m, 2H), 2.80-2.66 (m, 2H), 2.50-2.40 (m, 2H), 2.10 (t, J=5.6 Hz, 2H), 1.87-1.78 (m, 2H). MS (ESI, m/e) [M+1]$^+$ 493.9.

Compound 42: 2'-(4-Phenoxyphenyl)-5',6'-dihydro-4'H-spiro[piperidine-4,7'-pyrazolo [1,5-a]pyrimidine]-3'-carboxamide trifluoroacetate

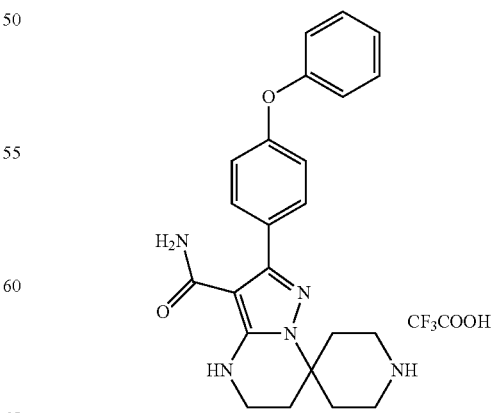

Compound 42 was prepared from 1-benzyl-2'-(4-phenoxyphenyl)-5',6'-dihydro-4'H-spiro[piperidine-4,7'-pyrazolo[1,5-a]pyrimidine]-3'-carboxamide according to the procedure similar to that for compound 39. ¹H NMR (400 MHz, DMSO-d₆) δ 8.66 (br s, 2H), 7.51 (d, J=8.6 Hz, 2H), 7.46-7.37 (m, 2H), 7.18 (t, J=7.6 Hz, 1H), 7.11-7.04 (m, 4H), 6.79 (s, 1H), 3.40-3.33 (m, 4H), 3.17-3.06 (m, 2H), 2.46-2.35 (m, 2H), 2.17-2.10 (m, 2H), 1.96-1.87 (m, 2H). MS (ESI, m/e) [M+1]⁺ 403.9.

Compound 43: 1-Acryloyl-2'-(4-phenoxyphenyl)-5,6'-dihydro-4'H-spiro[piperidine-4,7'-pyrazolo[1,5-a]pyrimidine]-3'-carboxamide

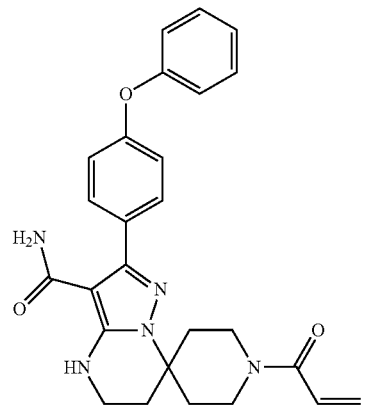 [SMILES: C=CC(=O)N1CCC2(CCNc3c(C(N)=O)c(-c4ccc(Oc5ccccc5)cc4)nn32)CC1]

Compound 43 was prepared from compound 42 and acryloyl chloride according to the procedure similar to that for compound 8. ¹HNMR (400 MHz, DMSO-d₆) δ 7.50 (d, J=8.8 Hz, 2H), 7.45-7.37 (m, 2H), 7.17 (t, J=7.2 Hz, 1H), 7.12-7.01 (m, 4H), 6.85 (dd, J=10.4, 16.7 Hz, 1H), 6.73 (s, 1H), 6.11 (dd, J=2.4, 16.7 Hz, 1H), 5.68 (dd, J=2.4, 10.4 Hz, 1H), 4.23 (d, J=13.2 Hz, 1H), 4.03 (d. J=13.2 Hz, 1H), 3.43 (t, J=12.0, 1H), 3.37-3.33 (m, 2H), 3.16 (t, J=12.0 Hz, 1H), 2.24-2.08 (m, 4H), 1.82-1.73 (m, 2H). MS (ESI, m/e) [M+1]⁺ 457.9.

Example 19: Synthesis of Compounds 44-46

Compound 44: 1-Benzyl-6'-(4-phenoxyphenyl)-1',2'-dihydrospiro[azetidine-3,3'-imidazo[1,2-b]pyrazole]-7'-carboxamide

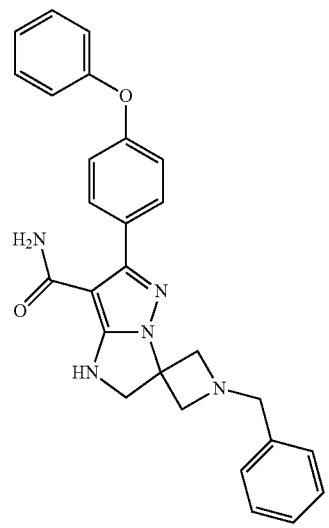 [SMILES: NC(=O)c1c(-c2ccc(Oc3ccccc3)cc2)nn2c1NCC21CN(Cc2ccccc2)C1]

Step 1: Methyl 1-benzylazetidine-3-carboxylate

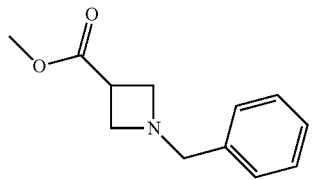

To a solution of methyl azetidine-3-carboxylate (5.0 g, 33.1 mmol) and DIEA (10.7 g, 82.8 mmol) in DMF (50 mL) was added dropwise bromomethyl benzene (5.7 g, 33.1 mmol) at 0° C. over 10 min. After stirring for 2 hr at rt, the mixture was poured to water (50 mL) and extracted with EA (50 mL×3). The combined organic layers were dried over Na₂SO₄ and concentrated and purified by chromatography column on silica (EA/PE=1/4) to give the product (3.5 g, 51.6%) as a light yellow oil. ¹H NMR (DMSO-d₆) δ 7.34-7.20 (m, 5H), 3.62 (s, 3H), 3.53 (s, 2H), 3.41-3.35 (m, 1H), 3.29-3.31 (m, 2H), 3.19-3.22 (m, 2H). MS (ESI, m/e) [M+1]⁺ 206.0.

Step 2: Di-tert-butyl 1-(1-benzyl-3-(methoxycarbonyl)azetidin-3-yl)hydrazine-1,2-dicarboxylate

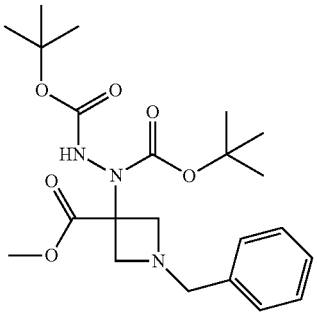 [SMILES: COC(=O)C1(N(NC(=O)OC(C)(C)C)C(=O)OC(C)(C)C)CN(Cc2ccccc2)C1]

The desired product was prepared from methyl 1-benzylazetidine-3-carboxylate and ditert-butyl azodicarboxylate using the procedure similar to step 1 for compound 38. MS (ESI, m/e) [M+1]⁺ 435.9.

Step 3 to 5: 5-Amino-1-(1-benzyl-3-(hydroxymethyl)azetidin-3-yl)-3-(4-phenoxy phenyl)-1H-pyrazole-4-carbonitrile

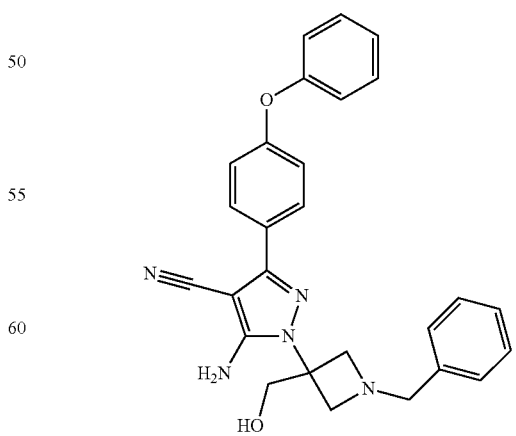

The desired product was prepared from di-tert-butyl 1-(1-benzyl-3-(methoxycarbonyl)azetidin-3-yl)hydrazine-1,2-dicarboxylate using the procedures similar to those (step 2 to 4) for compound 38. $^1$H NMR (DMSO-d$_6$) δ 7.78 (d, J=8.8 Hz, 2H), 7.46-7.38 (m, 2H), 7.36-7.21 (m, 5H), 7.18 (t, J=7.6 Hz, 1H), 7.11-7.04 (m, 4H), 6.17 (s, 2H), 5.50 (t, J=5.2 Hz, 1H), 3.89 (d, J=5.2 Hz, 2H), 3.61-3.63 (m, 4H), 3.38 (d, J=6.4 Hz, 2H). MS (ESI, m/e) [M+1]$^+$ 451.9.

Step 6: (3-(5-Amino-4-cyano-3-(4-phenoxyphenyl)-1H-pyrazol-1-yl)-1-benzyl azetidin-3-yl)methyl methanesulfonate

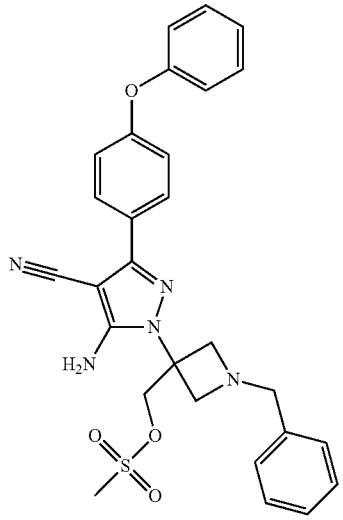 [SMILES: CS(=O)(=O)OCC1(n2nc(-c3ccc(Oc4ccccc4)cc3)c(C#N)c2N)CN(Cc2ccccc2)C1]

The desired product was prepared from 5-amino-1-(1-benzyl-3-(hydroxymethyl)azetidin-3-yl)-3-(4-phenoxy phenyl)-1H-pyrazole-4-carbonitrile using the procedure similar to step 5 for compound 38. $^1$H NMR (DMSO-d$_6$) δ 7.82-7.74 (m, 2H), 7.46-7.38 (m, 2H), 7.36-7.23 (m, 5H), 7.21-7.15 (m, 1H), 7.13-7.04 (m, 4H), 6.52 (s, 2H), 4.69 (s, 2H), 3.70 (d, J=8.4 Hz, 2H), 3.66 (s, 2H), 3.49 (d, J=8.4 Hz, 2H), 3.13 (s, 3H). MS (ESI, m/e) [M+1]$^+$ 529.9.

Step 7, 8: 1-Benzyl-6'-(4-phenoxyphenyl)-1',2'-dihydrospiro[azetidine-3,3'-imidazo [1,2-b]pyrazole]-7'-carboxamide

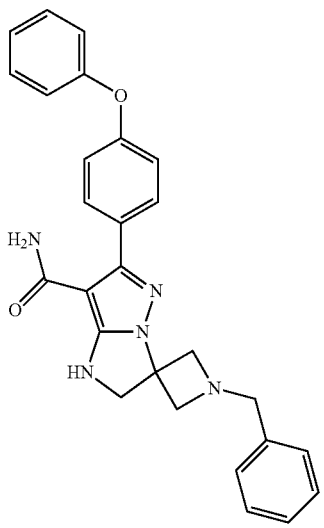 [SMILES: NC(=O)c1c(-c2ccc(Oc3ccccc3)cc2)nn2c1NCC21CN(Cc2ccccc2)C1]

The desired product was prepared from (3-(5-amino-4-cyano-3-(4-phenoxyphenyl)-1H-pyrazol-1-yl)-1-benzyl azetidin-3-yl)methyl methanesulfonate using the procedures similar to those (step 6 and 7) for compound 38. $^1$H NMR (DMSO-d$_6$) δ 7.66 (d, J=8.8 Hz, 2H), 7.46-7.38 (m, 2H), 7.35-7.28 (m, 4H), 7.28-7.21 (m, 1H), 7.16 (t, J=7.6 Hz, 1H), 7.06 (d, J=8.0 Hz, 2H), 7.01 (d, J=8.8 Hz, 2H), 6.52 (s, 1H), 4.19 (s, 2H), 3.67 (s, 2H), 3.54 (s, 4H). MS (ESI, m/e) [M+1]$^+$ 451.9.

Compound 45: 6'-(4-Phenoxyphenyl)-1',2'-dihydrospiro[azetidine-3,3'-imidazo[1,2-b]pyrazole]-7'-carboxamide

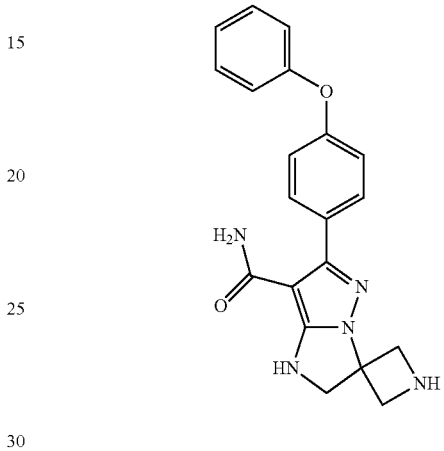

The desired product was prepared from compound 44 using the procedure similar to that for compound 39. $^1$H NMR (DMSO-d$_6$) δ 7.67 (d, J=8.4 Hz, 2H), 7.46-7.36 (m, 2H), 7.16 (t, J=7.6 Hz, 1H), 7.06 (d, J=7.6 Hz, 2H), 7.00 (d, J=8.4 Hz, 2H), 6.62 (s, 1H), 4.19-4.20 (m, 4H), 3.78 (d. J=9.6 Hz, 2H). MS (ESI, m/e) [M+1]$^+$ 361.9.

Compound 46: 1-Acryloyl-6'-(4-phenoxyphenyl)-1',2'-dihydrospiro[azetidine-3,3'-imidazo[1,2-b]pyrazole]-7'-carboxamide

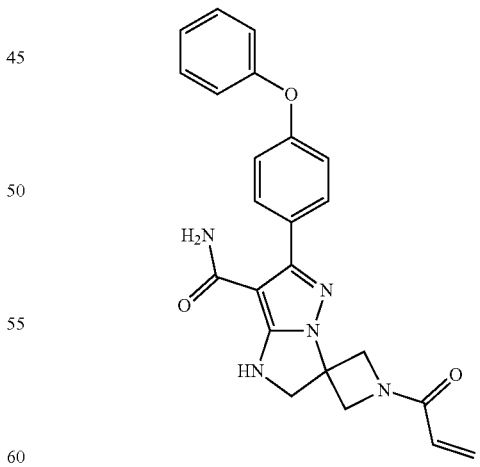

The desired product was prepared from compound 45 and acryloyl chloride using the procedure similar to that for compound 8. $^1$H NMR (DMSO-d$_6$) δ 7.66 (d, J=8.8 Hz, 2H), 7.45-7.37 (m, 2H), 7.16 (t, J=7.6 Hz, 1H), 7.06 (d, J=7.6 Hz, 2H), 7.00 (d, J=8.8 Hz, 2H), 6.62 (s, 1H), 6.36 (dd, J=17.0, 10.3 Hz, 1H), 6.15 (dd, J=17.0, 2.1 Hz, 1H), 5.72 (dd. J=10.3, 2.1 Hz, 1H), 4.62 (d, J=9.6 Hz, 1H), 4.56 (d, J=9.6 Hz, 1H), 4.32 (d, J=11.2 Hz, 1H), 4.27 (d, J=11.2 Hz, 1H), 4.22 (s, 2H). MS (ESI, m/e) [M+1]+ 415.9.

Example 20: Synthesis of Compounds 47-50

Compound 47: 2-(3-Aminophenyl)-6-(4-phenoxyphenyl)-1H-imidazo[1,2-b] pyrazole-7-carboxamide

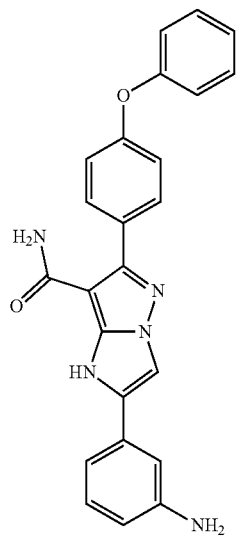

Step 1: 5-Amino-3-(4-phenoxyphenyl)-1H-pyrazole-4-carboxamide

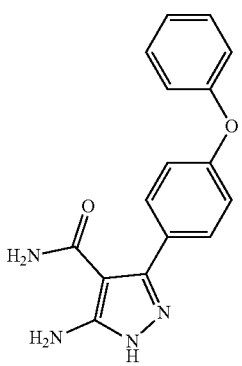 [SMILES: NC(=O)c1c(-c2ccc(Oc3ccccc3)cc2)n[nH]c1N]

A solution of 5-amino-3-(4-phenoxyphenyl)-1H-pyrazole-4-carbonitrile (1.0 g, 3.6 mmol) in H₃PO₄ (20 mL) was heated to 120° C. for 4 hr. The mixture was then poured into water (100 mL), extracted with EA (100 mL×3). The combined organic layers were dried over Na₂SO₄ and concentrated to give the product (850 mg, 77.5%) as yellow solid. MS (ESI, m/e) [M+1]+ 295.1.

Step 2: 2-(3-Nitrophenyl)-6-(4-phenoxyphenyl)-1H-imidazo[1,2-b]pyrazole-7-carboxamide

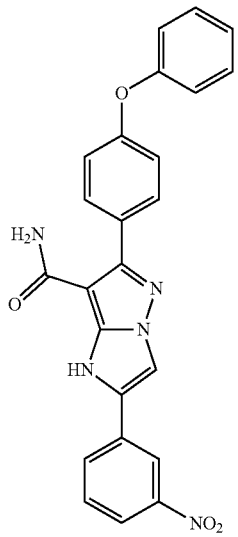

A mixture of 5-amino-3-(4-phenoxyphenyl)-1H-pyrazole-4-carboxamide (29.4 mg, 0.1 mmol) and 2-bromo-1-(3-nitrophenyl)ethanone (24.4 mg, 0.1 mmol) in EtOH (2 mL) was stirred at 80° C. for 16 hr. The mixture was filtered to afford 5 mg of crude 2-(3-nitrophenyl)-6-(4-phenoxyphenyl)-1H-imidazo[1,2-b]pyrazole-7-carboxamide as a yellow solid. MS (ESI) m/e [M+1]+ 440.0.

Step 3: 2-(3-Aminophenyl)-6-(4-phenoxyphenyl)-1H-imidazo[1,2-b]pyrazole-7-carboxamide

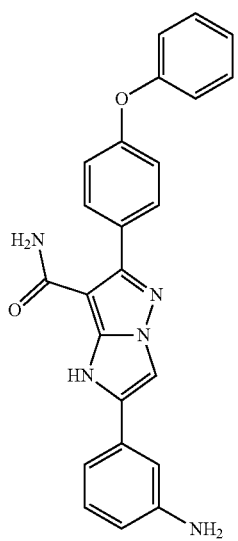

To a solution of 2-(3-nitrophenyl)-6-(4-phenoxyphenyl)-1H-imidazo[1,2-b] pyrazole-7-carboxamide (600 mg, 1.37 mmol) in 10 mL of MeOH and 10 mL of DCM was added 10% w/w Pd/C (100 mg). After stirring at RT under H₂ for 4 hr, the mixture was filtered. The filtrate was concentrated and purified by Pre-HPLC eluting from 30% to 90% CH₃CN in 0.1% TFA in H₂O. Fractions containing the desired product were combined and lyophilized overnight to afford 73 mg (13%) of 2-(3-aminophenyl)-6-(4-phenoxyphenyl)-

1H-imidazo[1,2-b]pyrazole-7-carboxamide as a white solid. ¹H NMR (400 MHz, DMSO-d₆) δ 12.03 (d, J=10.4 Hz, 1H), 8.14 (d, J=8.0 Hz, 1H), 7.73 (d, J=8.4 Hz, 2H), 7.47-7.40 (m, 2H), 7.38-7.26 (m, 3H), 7.18 (t, J=7.6 Hz, 1H), 7.10 (d. J=8.0 Hz, 2H), 7.03 (d, J=8.4 Hz, 2H) and 6.98-6.86 (m, 2H). MS (ESI) m/e [M+1]⁺ 409.9.

Compound 48: 2-(3-Acrylamidophenyl)-6-(4-phenoxyphenyl)-1H-imidazo[1,2-b]pyrazole-7-carboxamide

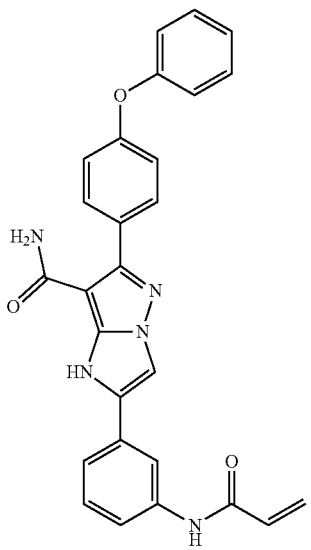 [SMILES: C=CC(=O)Nc1cccc(-c2cn3nc(-c4ccc(Oc5ccccc5)cc4)c(C(N)=O)c3[nH]2)c1]

The desired product was prepared from 2-(3-aminophenyl)-6-(4-phenoxyphenyl)-1H-imidazo[1,2-b]pyrazole-7-carboxamide and acryloyl chloride using the procedure similar to that for compound 8. ¹H NMR (400 MHz, CD₃OD-d₄) δ 8.06 (s, 1H), 7.83 (s, 1H), 7.64 (d, J=8.4 Hz, 1H), 7.52-7.38 (m, 5H), 7.15 (t, J=7.6 Hz, 1H), 7.09-7.05 (m, 4H), 6.49-6.37 (m, 2H) and 5.80 (dd, J=4.0, 8.8 Hz, 1H). MS (EST) m/e [M+1]⁺ 463.9.

Compound 49: 3-(3-Aminophenyl)-6-(4-phenoxyphenyl)-1H-pyrazolo[1,5-a]imidazole-7-carboxamide

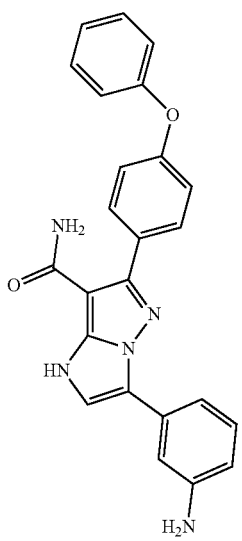 [SMILES: NC(=O)c1c(-c2ccc(Oc3ccccc3)cc2)nn2c(-c3cccc(N)c3)c[nH]c12]

The desired compound was separated as another isomer in the step 2 of compound 48. ¹H NMR (400 MHz, DMSO-d₆) δ 12.22 (d, J=2.4 Hz, 1H), 8.03 (s, 1H), 7.89 (d, J=2.4 Hz, 1H), 7.81-7.68 (m, 3H), 7.46-7.37 (m, 4H), 7.19 (t, J=7.6 Hz, 1H), 7.13-7.08 (m, 5H) and 6.98 (d, J=7.6 Hz, 1H). MS (ESI) m/e [M+1]⁺ 410.1.

Compound 50: 3-(3-Acrylamidophenyl)-6-(4-phenoxyphenyl)-1H-imidazo[1,2-b]pyrazole-7-carboxamide

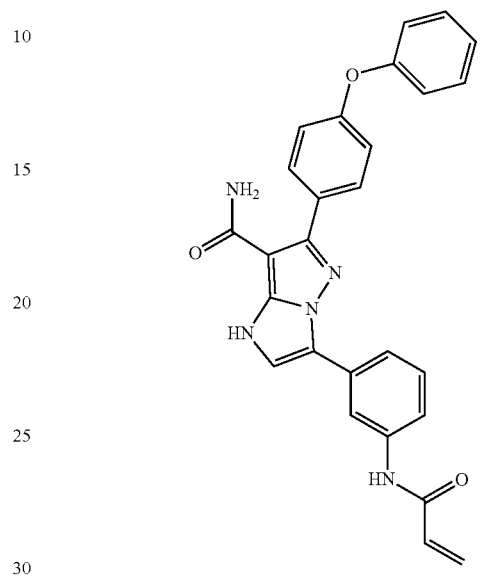

The desired product was prepared from compound 49 and acryloyl chloride using the procedure similar to compound 8. ¹H NMR (400 MHz, DMSO-d₆) δ 12.18 (d, J=2.4 Hz, 1H), 10.31 (s, 1H), 8.38 (s, 1H), 7.85 (d, J=8.0 Hz, 1H), 7.80-7.73 (m, 4H), 7.46-7.40 (m, 3H), 7.19 (t, J=8.0 Hz, 1H), 7.13-7.07 (m, 4H), 6.50 (dd, J=10.2, 17.0 Hz, 1H), 6.27 (d, J=17.0 Hz, 1H), 5.76 (d. J=10.2 Hz, 1H). MS (ESI) m/e [M+1]⁺ 463.9.

Example 21: Synthesis of Compounds 51 to 60

Compound 51: 2-(4-Phenoxyphenyl)-5,6,7,8-tetrahydro-4H-pyrazolo[5',1':2,3] imidazo[4,5-c]pyridine-3-carboxamide trifluoroacetate

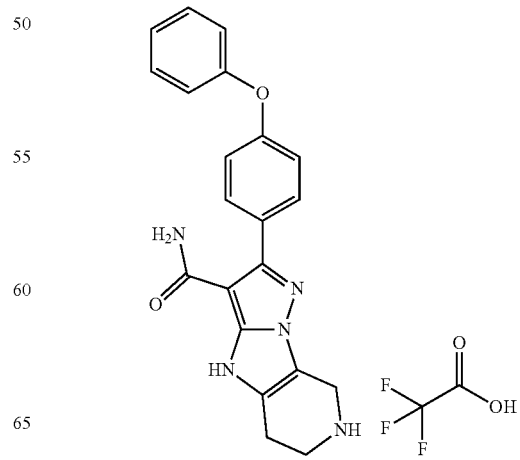

Step 1: tert-Butyl 3-bromo-4-oxopiperidine-1-carboxylate

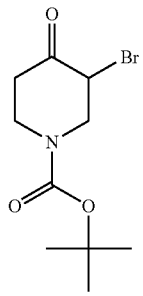

To a solution of tert-butyl 4-oxopiperidine-1-carboxylate (5 g, 25 mmol) in 30 mL of DMF at RT was added TEA (7.7 mL, 55 mmol) followed by TMSCl (3.5 mL, 27.6 mmol), then the mixture was stirred at 75° C. overnight. The reaction was cooled to RT, cold sat. aq. NaHCO$_3$ (200 mL) was added followed by cold hexane (200 mL). The organic layer was washed with brine, dried over Na$_2$SO$_4$, concentrated to get the crude product directly used in the next step. The residue was dissolved in 15 mL of THF and stirred at 0° C. for 15 min. A solution of NBS (4.47 g, 25 mmol) in 80 mL of THF was added slowly. After addition, the reaction was stirred at RT overnight. Water (200 mL) was added to the reaction followed by 200 mL of hexane. The organic layer was washed with brine, dried over Na$_2$SO$_4$ and concentrated to get crude product which was chromatographed on 60 g of silica gel using PE/EA (20/1 to 8/1) as eluant to afford 5.56 g (78%) of tert-butyl 3-bromo-4-oxopiperidine-1-carboxylate as a white solid. $^1$H NMR (400 MHz, DMSO-d$_6$) δ 4.85-4.70 (m, 1H), 4.20-4.00 (m, 1H), 3.90-3.55 (m, 3H), 2.80-2.68 (m, 1H), 2.54-2.44 (m, 1H), 1.43 (s, 9H). MS (ESI) m/e [M-t-Bu]$^+$221.9, 224.0.

Step 2: tert-Butyl 3-cyano-2-(4-phenoxyphenyl)-5,6-dihydro-4H-pyrazolo[5',1':2,3]imidazo[4,5-c]pyridine-7(8H)-carboxylate

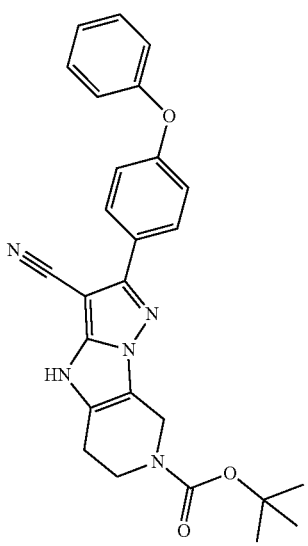 [SMILES: CC(C)(C)OC(=O)N1CCc2[nH]c3c(C#N)c(-c4ccc(Oc5ccccc5)cc4)nn3c2C1]

A mixture of 5-amino-3-(4-phenoxyphenyl)-1H-pyrazole-4-carbonitrile (1.5 g, 5.4 mmol) and K$_2$CO$_3$ (2.24 g, 16.3 mmol) in 50 mL of DMF at 80° C. was stirred under N$_2$ for 45 min before tert-butyl 3-bromo-4-oxopiperidine-1-carboxylate (4.5 g, 16.3 mmol) was added in one portion. Then the mixture was stirred at 80° C. for 1 hr. After cooling down to RT, 150 mL of water and 150 mL of EA was added. Aqueous phase was further extracted with EA (100 mL×3). The combined organic layers were washed with brine, dried over Na$_2$SO$_4$ and concentrated to get crude product which was chromatographed on 15 g of silica gel using DCM/MeOH (400/1 to 200/1) as eluant to afford 850 mg (35%) of tert-butyl 3-cyano-2-(4-phenoxyphenyl)-5,6-dihydro-4H-pyrazolo[5',1':2,3]imidazo[4,5-c]pyridine-7(8H)-carboxylate as an off-white solid. MS (ESI) m/e [M+1]$^+$455.9.

Step 3: 2-(4-Phenoxyphenyl)-5,6,7,8-tetrahydro-4H-pyrazolo[5',1':2,3]imidazo[4,5-c]pyridine-3-carboxamide trifluoroacetate

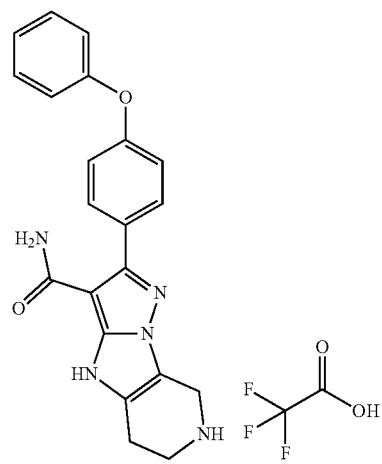

A solution of tert-butyl 3-cyano-2-(4-phenoxyphenyl)-5,6-dihydro-4H-pyrazolo [5',1':2,3]imidazo[4,5-c]pyridine-7 (8H)-carboxylate (130 mg, 0.28 mmol) in H$_3$PO$_4$ (85 wt. % in H$_2$O, 20 mL) was stirred at 100° C. for 1.5 hr, until TLC and LCMS analysis showed that most of starting material was consumed. The mixture was cooled to room temperature and poured into water (100 mL). The mixture was adjust to PH=9-10 with solid K$_2$CO$_3$. The suspension was extracted with EA (100 mL×4). The combined organic layers were washed with brine (200 mL), dried over Na$_2$SO$_4$ and concentrated to get the crude product which was purified with pre-HPLC eluting from 10% to 90% CH$_3$CN in 0.1% TFA in H$_2$O. Fractions containing the desired product were combined and lyophilized overnight to give 15 mg (11%) of 2-(4-phenoxyphenyl)-5,6,7,8-tetrahydro-4H-pyrazolo[5',1': 2,3]imidazo[4,5-c]pyridine-3-carboxamide trifluoroacetate as a white solid. $^1$H NMR (400 MHz, DMSO-d$_6$) δ 11.99 (s, 1H), 9.32 (s, 2H), 7.66 (d, J=8.6 Hz, 2H), 7.43 (d, J=7.6 Hz, 1H), 7.41 (d, J=7.6 Hz, 1H), 7.18 (t, J=7.6 Hz, 1H), 7.10-7.06 (m, 4H), 4.44 (s, 2H), 3.49 (m, 2H), 2.95-2.92 (m, 2H). MS (ESI) m/e [M+1]+373.9.

Compound 52: 7-Acryloyl-2-(4-phenoxyphenyl)-5,6,7,8-tetrahydro-4H-pyrazolo [5',1':2,3]imidazo[4,5-c]pyridine-3-carboxamide

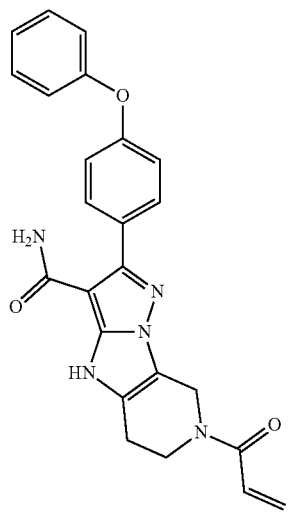 [SMILES: C=CC(=O)N1CCc2[nH]c3c(C(N)=O)c(-c4ccc(Oc5ccccc5)cc4)nn3c2C1]

The desired product was prepared from compound 51 and acryloyl chloride using the procedure similar to that for compound 8. ¹H NMR (400 MHz, DMSO-d₆ at 80° C.) δ 11.55 (s, 1H), 7.71 (d, J=8.6 Hz, 2H), 7.43 (d, J=7.6 Hz, 1H), 7.41 (d, J=7.6 Hz, 1H), 7.18 (t, J=7.6 Hz, 1H), 7.10-7.05 (m, 4H), 6.88 (dd, J=10.6, 17.1 Hz, 1H), 6.24 (s, 2H), 6.15 (d, J=17.1 Hz, 1H), 5.74 (d, J=10.6 Hz, 1H), 4.78 (s, 2H), 3.94-3.91 (m, 2H), 2.80-2.76 (m, 2H). MS (ESI) m/e [M+1]⁺ 427.9.

Compound 53: 7-(3-Chloropropanoyl)-2-(4-phenoxyphenyl)-5,6,7,8-tetrahydro-4H-pyrazolo[5',1':2,3]imidazo[4,5-c]pyridine-3-carboxamide

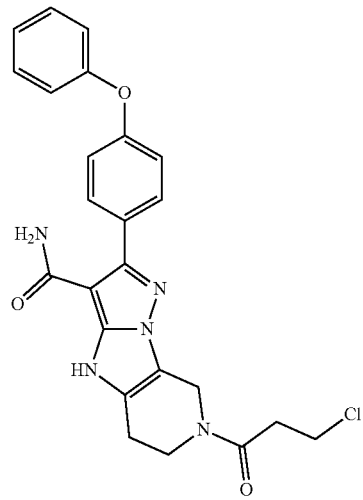 [SMILES: NC(=O)c1c(-c2ccc(Oc3ccccc3)cc2)nn2c3c([nH]c12)CCN(C(=O)CCCl)C3]

7-Acryloyl-2-(4-phenoxyphenyl)-5,6,7,8-tetrahydro-4H-pyrazolo[5',1':2,3]imidazo[4,5-c]pyridine-3-carboxamide (40 mg, 0.09 mmol) was suspended in Sat. HCl (gas)/dioxane (50 mL), then the mixture was stirred RT for about 1.5 hr, and concentrated to dryness. The residue was suspended into 2 mL of MeOH and 2 mL of water. The organic layer was discarded, aqueous layer was lyophilized to get 40 mg (90%) of 7-(3-chloropropanoyl)-2-(4-phenoxyphenyl)-5,6,7,8-tetrahydro-4H-pyrazolo[5',1':2,3]imidazo[4,5-c]pyridine-3-carboxamide as an off-white solid. ¹H NMR (400 MHz, DMSO-d₆) δ 11.79-11.76 (m, 1H), 7.68 (d, J=8.6 Hz, 2H), 7.43 (d, J=7.6 Hz, 1H), 7.41 (d, J=7.6 Hz, 1H), 7.18 (t, J=7.6 Hz, 1H), 7.10-7.04 (m, 4H), 4.71-4.70 (m, 2H), 3.85-3.79 (m, 4H), 3.02 (t, J=6.4 Hz, 2H), 2.79-2.69 (m, 2H). MS (ESI) m/e [M+1]⁺ 463.8, 465.8.

Compound 54 and 55: (E)-7-(4-(Dimethylamino)but-2-enoyl)-2-(4-phenoxyphenyl)-5,6,7,8-tetrahydro-4H-pyrazolo[5',1':2,3]imidazo[4,5-c]pyridine-3-carboxamide and 7-Acetyl-2-(4-phenoxyphenyl)-5,6,7,8-tetrahydro-4H-pyrazolo[5',1':2,3]imidazo [4,5-c]pyridine-3-carboxamide

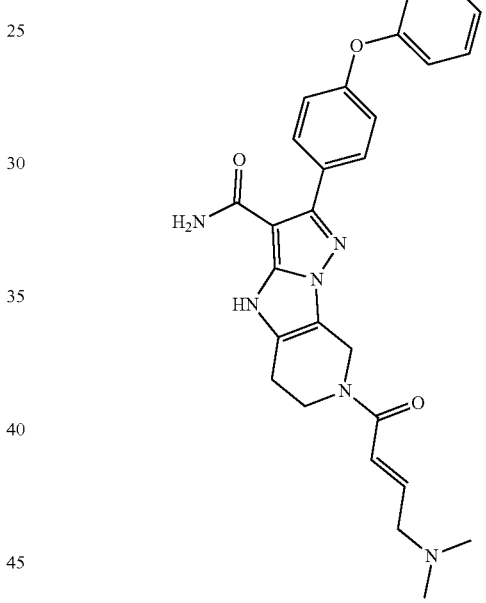

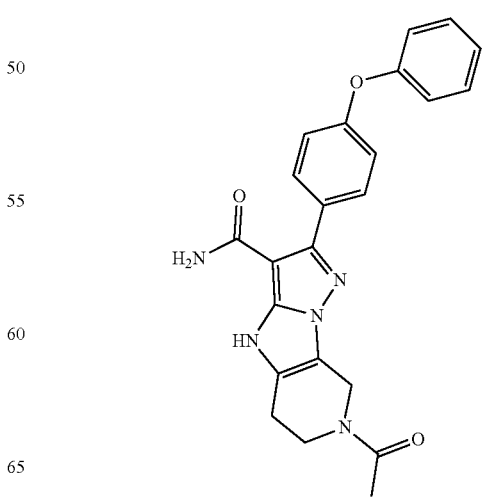

A mixture of (E)-4-(dimethylamino)but-2-enoic acid hydrochloride (147 mg, 0.88 mmol), HATU (611 mg, 1.6 mmol) and TEA (328 mg, 3.2 mmol) in 50 mL of DCM was stirred at RT for about 2 hr before 2-(4-phenoxyphenyl)-5,6,7,8-tetrahydro-4H-pyrazolo[5',1':2,3]imidazo[4,5-c]pyridine-3-carboxamide (300 mg, 0.8 mmol) was added. The mixture was stirred at RT overnight. TLC and LCMS analysis showed that starting material was consumed. To the reaction were added 100 mL of water and 50 mL of DCM. Aqueous phase was further extracted with 50 mL of DCM. The combined organic layers were washed with brine, dried over $Na_2SO_4$, concentrated to get crude product which was chromatographed on 5 g of silica gel using DCM/MeOH (20/1 to 10/1) as eluant to afford 145 mg (37%) of (E)-7-(4-(dimethylamino) but-2-enoyl)-2-(4-phenoxyphenyl)-5,6,7,8-tetrahydro-4H-pyrazolo[5',1':2,3]imidazo[4,5-c]pyridine-3-carboxamide, which was dried by lyophilization. $^1$H NMR (400 MHz, DMSO-d, at 80° C.) δ 11.52 (s, 1H), 7.69 (d, J=8.6 Hz, 2H), 7.42 (d, J=7.6 Hz, 1H), 7.41 (d, J=7.6 Hz, 1H), 7.16 (t, J=7.6 Hz, 1H), 7.12-6.99 (m, 4H), 6.78-6.56 (m, 2H), 6.22 (s, 2H), 4.75 (s, 2H), 3.89 (t, J=5.6 Hz, 2H), 3.12 (d, J=5.6 Hz, 2H), 2.80-2.72 (m, 2H), 2.22 (s, 6H). MS (ESI) m/e [M+1]$^+$ 484.9.

7-Acetyl-2-(4-phenoxyphenyl)-5,6,7,8-tetrahydro-4H-pyrazolo[5',1':2,3]imidazo[4,5-c]pyridine-3-carboxamide was prepared as a byproduct due to some of HOAc residue in the last step. $^1$H NMR (400 MHz, DMSO-d$_6$) δ 11.77-11.73 (m, 1H), 7.70-7.66 (m, 2H), 7.43 (d, J=7.6 Hz, 1H), 7.41 (d, J=7.6 Hz, 1H), 7.18 (t, J=7.6 Hz, 1H), 7.13-6.94 (m, 4H), 4.68 (s, 2H), 3.83-3.76 (m, 2H), 2.82-2.77 (m, 2H), 2.14 (s, 3H). MS (ESI) m/e [M+1]$^+$416.

Compound 56: 7-(2-Cyanoacetyl)-2-(4-phenoxyphenyl)-5,6,7,8-tetrahydro-4H-pyrazolo[5',1':2,3]imidazo[4,5-c]pyridine-3-carboxamide

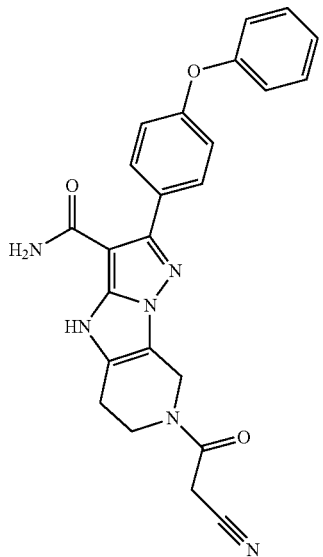 [SMILES: N#CCC(=O)N1CCc2[nH]c3c(C(N)=O)c(-c4ccc(Oc5ccccc5)cc4)nn3c2C1]

The desired compound was prepared from 2-(4-phenoxyphenyl)-5,6,7,8-tetrahydro-4H-pyrazolo[5',1':2,3]imidazo[4,5-c]pyridine-3-carboxamide and 2-cyanoacetic acid according to the procedure similar to that for compound 54. $^1$H NMR (400 MHz, DMSO-d$_6$ at 80° C.) δ 11.55 (s, 1H), 7.68 (d, J=8.6 Hz, 2H), 7.41 (d, J=7.6 Hz, 1H), 7.39 (d, J=7.6 Hz, 1H), 7.16 (t, J=7.6 Hz, 1H), 7.11-6.93 (m, 4H), 6.22 (br s, 2H), 4.68 (s, 2H), 4.14 (s, 2H), 3.86-3.79 (m, 2H), 2.84-2.73 (m, 2H). MS (ESI) m/e [M+1]$^+$ 440.9.

Compound 57: 7-(3-(Dimethylamino)propanoyl)-2-(4-phenoxyphenyl)-5,6,7,8-tetrahydro-4H-pyrazolo[5',1':2,3]imidazo[4,5-c]pyridine-3-carboxamide trifluoroacetate

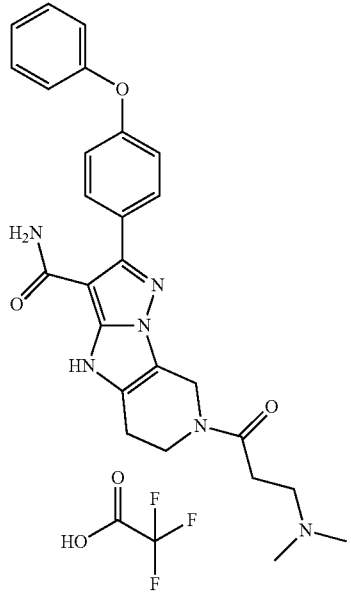

To a solution of 7-acryloyl-2-(4-phenoxyphenyl)-5,6,7,8-tetrahydro-4H-pyrazolo [5',1':2,3]imidazo[4,5-c]pyridine-3-carboxamide (6 mg, 0.014 mmol) in 5 mL of MeOH at RT was added NaOMe (15 mg, 0.28 mmol) followed by dimethylamine hydrochloride (12 mg, 014 mmol), then the mixture was stirred at 50° C. overnight. After cooling down to RT, the mixture was concentrated. The residue was purified by pre-HPLC eluting from 0% to 60% CH$_3$CN in H$_2$O. Fractions containing the desired product were combined and lyophilized overnight to give 2.5 mg (35%) of 6-(3-(dimethylamino)propanoyl)-2-(4-phenoxyphenyl)-5,6,7,8-tetrahydro-4H-pyrazolo[1',5':1,2]imidazo[4,5-c]pyridine-3-carboxamide as a yellow solid. $^1$H NMR (400 MHz, DMSO-d$_6$) 11.84-11.82 (m, 1H), 9.55 (s, 1H), 7.69-7.66 (m, 2H), 7.44 (d, J=7.6 Hz, 1H), 7.42 (d, J=7.6 Hz, 1H), 7.18 (t, J=7.6 Hz, 1H), 7.10-7.04 (m, 4H), 4.75-4.72 (m, 2H), 3.87-3.82 (m, 2H), 3.02-3.00 (m, 2H), 2.84-2.78 (m, 2H), 2.77 (s, 6H), 2.71-2.68 (m, 2H). MS (ESI) m/e [M+]+472.9.

Compound 58: 7-(But-2-enoyl)-2-(4-phenoxyphenyl)-5,6,7,8-tetrahydro-4H-pyrazolo [5',1':2,3]imidazo[4,5-c]pyridine-3-carboxamide

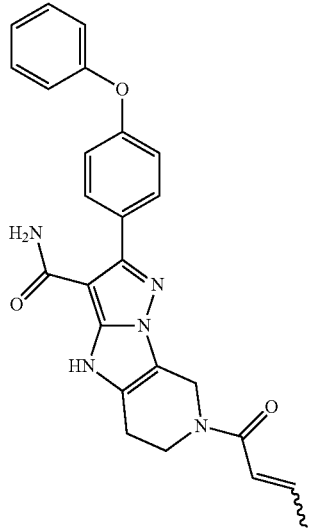

The desired compound was prepared from 2-(4-phenoxyphenyl)-5,6,7,8-tetrahydro-4H-pyrazolo[5',1':2,3]imidazo[4,5-c]pyridine-3-carboxamide and but-2-enoic acid according to the procedure similar to that for compound 54. $^1$H NMR (400 MHz, DMSO-d$_6$) δ 11.78-11.71 (m, 1H), 7.68 (d, J=8.6 Hz, 2H), 7.46-7.39 (m, 2H), 7.18 (t, J=7.6 Hz, 1H), 7.11-7.04 (m, 4H), 6.73-6.63 (m, 2H), 4.80-4.71 (m, 2H), 3.90 (s, 2H), 2.76-2.70 (m, 2H), 1.88-1.86 (m, 3H). MS (ESI) m/e [M+1]$^+$ 441.9.

Compound 59 and 60: (E)-7-(3-Cyanoallyl)-2-(4-phenoxyphenyl)-5,6,7,8-tetrahydro-4H-pyrazolo[5',1':2,3]imidazo[4,5-c]pyridine-3-carboxamide and (Z)-7-(3-Cyanoallyl)-2-(4-phenoxyphenyl)-5,6,7,8-tetrahydro-4H-pyrazolo[5',1':2,3]imidazo[4,5-c]pyridine-3-carboxamide

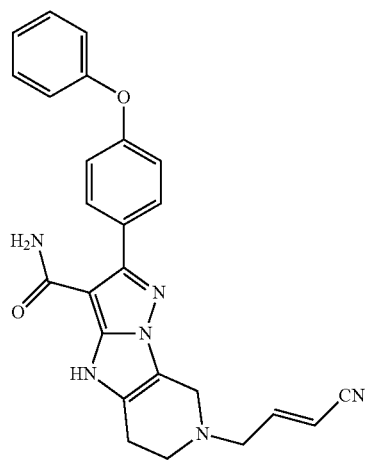

-continued

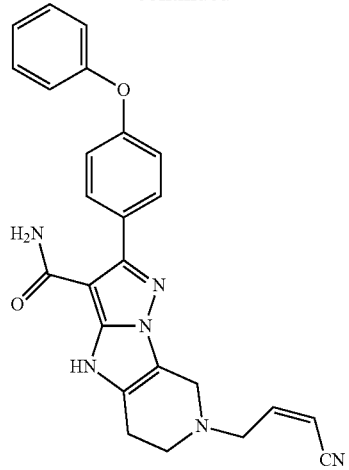

To a solution of 2-(4-phenoxyphenyl)-5,6,7,8-tetrahydro-4H-pyrazolo[5',1':2,3] imidazo[4,5-c]pyridine-3-carboxamide (100 mg, 0.268 mmol) in 10 mL of acetone at RT was added K$_2$CO$_3$ (140 mg, 1.07 mmol). After stirring at RT for 2 hr, 4-bromobut-2-enenitrile (40 mg, 0.268 mmol) in 2 mL of acetone was added and stirred at RT overnight. The mixture was then partitioned between EA (50 mL) and water (100 mL). The aqueous phase was further extracted with 50 mL of EA. The combined organic layers were washed with brine, dried over Na$_2$SO$_4$, concentrated to get crude product which was further purified by pre-TLC (DCM/MeOH=15/1) to afford 7 mg (6%) of (E)-7-(3-cyanoallyl)-2-(4-phenoxyphenyl)-5,6,7,8-tetrahydro-4H-pyrazolo[5',1':2,3]imidazo[4,5-c]pyridine-3-carboxamide as a light yellow solid. $^1$H NMR (400 MHz, CDCl$_3$) δ 10.45 (s, 1H), 7.59 (d, J=8.4 Hz, 2H), 7.42-7.30 (m, 2H), 7.16 (t J=7.6 Hz, 1H), 7.10 (d, J=8.4 Hz, 2H), 7.06 (d, J=7.6 Hz, 2H), 6.76 (dt, J=16.3, 4.6 Hz, 1H), 5.67 (d, J=16.3 Hz, 1H), 5.62 (s, 2H), 3.82 (s, 2H), 3.41 (d, J=4.6 Hz, 2H), 2.95-2.75 (m, 4H). MS (ESI) m/e [M+1]$^+$ 439.9.

4 mg (3.4%) of (Z)-7-(3-cyanoallyl)-2-(4-phenoxyphenyl)-5,6,7,8-tetrahydro-4H-pyrazolol[5',1':2,3]imidazo[4,5-c]pyridine-3-carboxamide as a light yellow solid. $^1$H NMR (400 MHz, CDCl$_3$) δ 10.22 (s, 1H), 7.60 (d, J=8.4 Hz, 2H), 7.41-7.33 (m, 2H), 7.16 (t, J=7.6 Hz, 1H), 7.10 (d, J=8.4 Hz, 2H), 7.06 (d, J=7.6 Hz, 2H), 6.70-6.59 (m, 1H), 5.58 (s, 2H), 5.53 (d, J=11.2 Hz, 1H), 3.85 (s, 2H), 3.64 (d, J=6.4 Hz, 2H), 2.99-2.80 (m, 4H). MS (ESI) m/e [M+1]$^+$ 439.9.

Example 22: Synthesis of Compounds 61 to 64

Compound 61: 2-(4-Phenoxyphenyl)-4H-pyrazolo[1',5':1,2]imidazo[4,5-c]pyridine-3-carboxamide

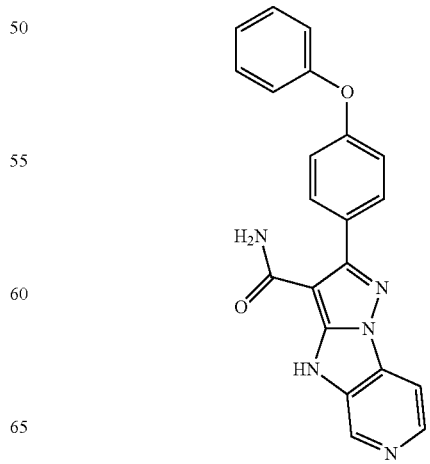

113

Step 1: 3-Bromo-4-hydrazinylpyridine

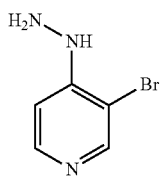

A mixture of 3-bromo-4-chloropyridine (5 g, 0.026 mol) and hydrazine hydrate (80% in water, 80 mL) in dioxane (100 mL) was stirred at 100° C. overnight. After cooling down to RT, the mixture was concentrated. The residue was partitioned between 300 mL of EA and 300 mL of aq. sat. NH$_4$Cl. The organic layer was washed with brine, dried over Na$_2$SO$_4$, filtered and concentrated to get crude product which was suspended in 30 mL of cold isopropyl alcohol and filtered. The collected solid was dried in air to get 4.2 g (87%) of 3-bromo-4-hydrazinylpyridine as a white solid. $^1$H NMR (400 MHz, DMSO-d$_6$) δ 8.18 (s, 1H), 8.07 (d, J=5.6 Hz, 1H), 7.37 (s, 1H), 7.01 (d, J=5.6 Hz, 1H), 4.36 (s, 2H).

Step 2: 5-Amino-1-(3-bromopyridin-4-yl)-3-(4-phenoxyphenyl)-1H-pyrazole-4-carbonitrile

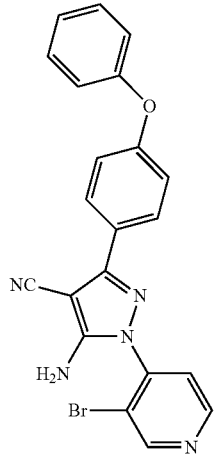 [SMILES: N#Cc1c(-c2ccc(Oc3ccccc3)cc2)nn(-c2ccncc2Br)c1N]

A mixture of 2-(methoxy(4-phenoxyphenyl)methylene)malononitrile (7.3 g, 0.026 mol) and 3-bromo-4-hydrazinylpyridine (4.2 g, 0.022 mol) in ethanol (300 mL) was stirred at reflux under N$_2$ overnight. The reaction was cooled to RT slowly and stirred at RT for about 4 hr till solid precipitated. The solid was filtered, collected and washed with hexane to get 3.38 g (35%) of 5-amino-1-(3-bromopyridin-4-yl)-3-(4-phenoxyphenyl)-1H-pyrazole-4-carbonitrile as a light yellow solid. MS (ESI) m/e [M+1]$^+$ 431.8, 433.8.

114

Step 3: 5-Amino-1-(3-bromopyridin-4-yl)-3-(4-phenoxyphenyl)-1H-pyrazole-4-carboxamide

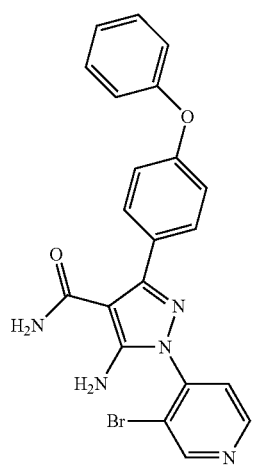 [SMILES: NC(=O)c1c(-c2ccc(Oc3ccccc3)cc2)nn(-c2ccncc2Br)c1N]

The desired compound was prepared from 5-amino-1-(3-bromopyridin-4-yl)-3-(4-phenoxyphenyl)-1H-pyrazole-4-carbonitrile according to the procedure similar to step 3 for compound 51. MS (ESI) m/e [M+1]$^+$ 449.8, 451.8.

Step 4: 2-(4-Phenoxyphenyl)-4H-pyrazolo[1',5':1,2]imidazo[4,5-c]pyridine-3-carboxamide

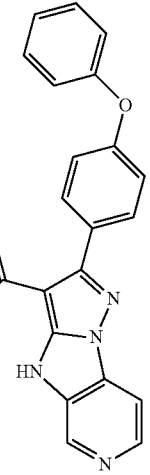

A mixture of 5-amino-1-(3-bromopyridin-4-yl)-3-(4-phenoxyphenyl)-1H-pyrazole-4-carboxamide (3.96 g, 8.8 mmol). CuI (836 mg, 4.4 mmol), N$^1$,N$^2$-dimethylethane-1,2-diamine (77 mg, 0.88 mmol), K$_3$PO$_4$ (5.59 g, 26.4 mmol) in 100 mL of DMF was stirred at 100° C. under N$_2$ for 2 hr, until TLC showed that most of starting material was consumed. After cooling down to RT, the mixture was filtered and concentrated. The residue was chromatographed on 30 g of silica gel using DCM/MeOH (20/1 to 10/1) as eluant to afford 3.2 g (99%) of 2-(4-Phenoxyphenyl)-4H-pyrazolo[1',5':1,2]imidazo[4,5-c]pyridine-3-carboxamide as a tan solid. $^1$H NMR (400 MHz, DMSO-d$_6$) δ 12.63 (br s, 1H), 8.85 (s, 1H), 8.46 (s, 1H), 7.96 (d, J=4.6 Hz, 1H), 7.81 (d, J=8.6 Hz, 2H), 7.45 (d, J=7.6 Hz, 1H), 7.43 (d, J=7.6 Hz, 1H), 7.20 (t, J=7.6 Hz, 1H), 7.14-7.09 (m, 4H). MS (ESI) m/e [M+I]$^+$369.9.

Compound 62: 2-(4-Phenoxyphenyl)-5,6,7,8-tetrahydro-4H-pyrazolo[1',5':1,2]imidazo [4,5-c]pyridine-3-carboxamide

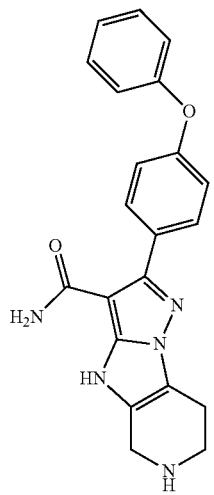 [SMILES: NC(=O)c1c(-c2ccc(Oc3ccccc3)cc2)nn2c3c([nH]c12)CNCC3]

Step 1: 6-Benzyl-2-(4-phenoxyphenyl)-5,6,7,8-tetrahydro-4H-pyrazolol[1',5':1,2]imidazo[4,5-c]pyridine-3-carboxamide

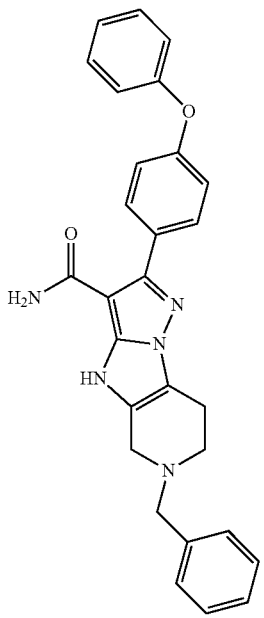 [SMILES: NC(=O)c1c(-c2ccc(Oc3ccccc3)cc2)nn2c3c([nH]c12)CN(Cc1ccccc1)CC3]

To a suspension of 2-(4-phenoxyphenyl)-4H-pyrazolo[1',5':1.2]imidazo[4,5-c] pyridine-3-carbox-amide (2.46 g, 0.0067 mol) in 150 mL of THF was added benzyl bromide (1.14 g, 0.0067 mol) dropwise, then the mixture was stirred at 65° C. overnight. After cooling down to RT, the mixture was concentrated, the residue was suspended in 150 mL of MeOH, NaBH$_4$ (10 g, 0.26 mol) was added portionwise. The mixture was stirred at RT overnight. To the reaction was added 200 mL of water followed by 200 mL of DCM. The aqueous phase was further extracted with 100 mL of DCM. The combined organic layers were washed with brine, dried over Na$_2$SO$_4$ and concentrated to get the crude product which was chromatographed on 10 g of silica gel using DCM/MeOH (200/1 to 80/1) as eluant to afford 0.786 g (26%) of 6-benzyl-2-(4-phenoxyphenyl)-5,6,7,8-tetrahydro-4H-pyrazolo[1',5':1,2]imidazo[4,5-c]pyridine-3-carboxamide as a tan foam. MS (ESI) m/e [M+1]$^+$ 463.9.

Step 2: 2-(4-Phenoxyphenyl)-5,6,7,8-tetrahydro-4H-pyrazolo[1',5':1,2]imidazo[4,5-c]pyridine-3-carboxamide

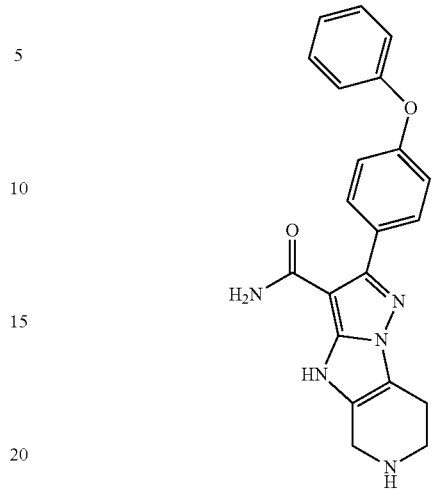

A mixture of 6-benzyl-2-(4-phenoxyphenyl)-5,6,7,8-tetrahydro-4H-pyrazolo [1',5':1,2]imidazo[4,5-c]pyridine-3-carboxamide (640 mg, 0.00138 mol) and 10% w/w Pd/C (700 mg) in 60 mL of MeOH was stirred at RT under 1 atm of H$_2$ overnight. TLC and LCMS analysis showed starting material was consumed. The reaction was filtered, filtrate was concentrated to get 397 mg (77%) of 2-(4-phenoxyphenyl)-5,6,7,8-tetrahydro-4H-pyrazolo[1',5':1,2]imidazo[4,5-c]pyridine-3-carboxamide. $^1$H NMR (400 MHz, CD$_3$OD-d$_4$) δ 7.65-7.55 (m, 2H), 7.43-7.33 (m, 2H), 7.18-7.12 (m, 1H), 7.11-6.99 (m, 4H), 4.18 (s, 2H), 3.44 (t, J=5.8 Hz, 2H), 3.01 (t, J=5.8 Hz, 2H). MS (ESI) m/e [M+1]$^+$ 373.9.

Compound 63: 6-Acryloyl-2-(4-phenoxyphenyl)-5,6,7,8-tetrahydro-4H-pyrazolo [1',5':1,2]imidazo[4,5-c]pyridine-3-carboxamide trifluoroacetate

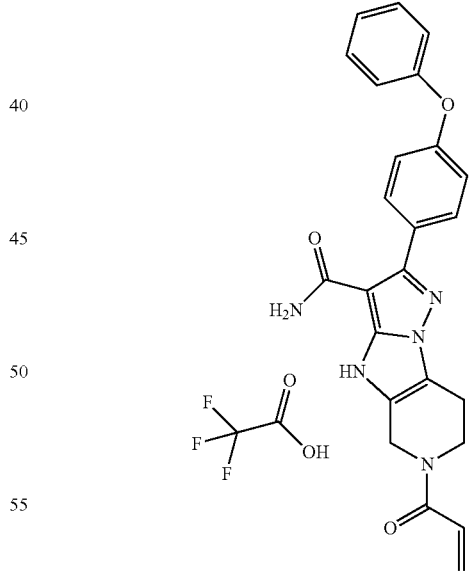

The desired compound was prepared from 2-(4-phenoxyphenyl)-5,6,7,8-tetrahydro-4H-pyrazolo[1',5':1,2]imidazo [4,5-c]pyridine-3-carboxamide and acryloyl chloride according to the procedure similar to that for compound 8. $^1$H NMR (400 MHz, DMSO-d$_6$) δ 11.79 (s, 1H), 7.73 (d, J=8.6 Hz, 2H), 7.50 (d, J=7.6 Hz, 1H), 7.48 (d, J=7.6 Hz, 1H), 7.24 (L, J=7.6 Hz, 1H), 7.17-7.11 (m, 4H), 7.06-6.98 (m, 1H), 7.22-6.26 (m, 1H), 5.84-5.82 (m, 1H), 4.72 (s, 2H), 4.00-3.97 (m, 2H), 2.94-2.90 (m, 2H). MS (ESI) m/e [M+1]$^+$ 427.9.

Compound 64: (E)-6-(4-(Dimethylamino)but-2-enoyl)-2-(4-phenoxyphenyl)-5,6,7,8-tetrahydro-4H-pyrazolo[1',5':1,2]imidazo[4,5-c]pyridine-3-carboxamide trifluoroacetate

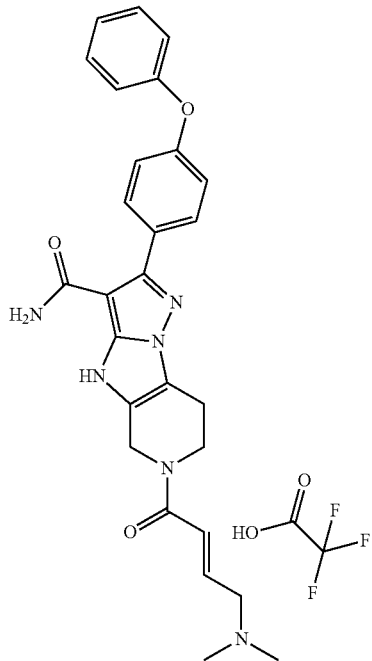

The desired compound was prepared from 2-(4-phenoxyphenyl)-5,6,7,8-tetrahydro-4H-pyrazolo[1',5':1,2]imidazo[4,5-c]pyridine-3-carboxamide and (E)-4-(dimethylamino)but-2-enoic acid hydrochloride according to the procedure similar to that for compound 54. $^1$H NMR (400 MHz, DMSO-$d_6$) δ 11.82-11.74 (m, 1H), 10.06 (br s, 1H), 7.66 (d, J=8.6 Hz, 2H), 7.43 (d, J=7.6 Hz, 1H), 7.42 (d, J=7.6 Hz, 1H), 7.18 (t, J=7.6 Hz, 1H), 7.10-7.05 (m, 4H), 6.74-6.54 (m, 2H), 4.66 (s, 2H), 3.99-3.86 (m, 4H), 2.88-2.76 (m, 2H), 2.78 (s, 6H). MS (ESI) m/e [M+1]$^+$ 484.9.

Example 23: Synthesis of Compounds 65-67

Compound 65: 7-Nitro-2-(4-phenoxyphenyl)-4H-benzo[4,5]imidazo[1,2-b]pyrazole-3-carboxamide

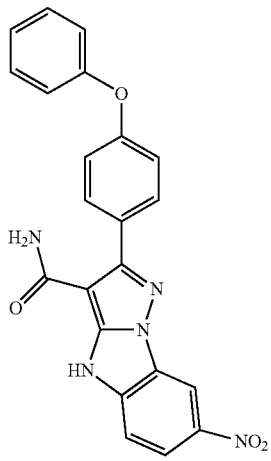 [SMILES: NC(=O)c1c(-c2ccc(Oc3ccccc3)cc2)nn2c1[nH]c1ccc([N+](=O)[O-])cc12]

Step 1: (2-Bromo-5-nitrophenyl)hydrazine

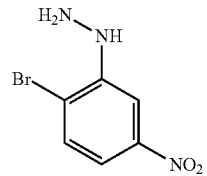

To a suspension of 2-bromo-5-nitroaniline (1 g, 4.6 mmol) in conc. HCl (10 mL) at 0° C. was slowly added a solution of NaNO$_2$ (382 mg, 5.5 mmol) in water (1.5 mL). Then, the mixture was stirred at 0° C. for 3 hr until TLC and LCMS analysis showed that most of 2-bromo-5-nitroaniline was consumed. SnCl$_2$ (1.90 g, 10 mmol) in conc. HCl (3 mL) was slowly added. The mixture was then stirred at RT for 2 hr before re-cooled to 0° C. Then, the PH was adjusted with sat. aq. NaHCO$_3$ to 7-8. The mixture was extracted with ethyl acetate (3×50 mL). The combined organic layers were washed with brine, dried over Na$_2$SO$_4$, filtered and concentrated to get crude product which was further chromatographed on 10 g of silica gel using PE/EA (20/1 to 4/1) as eluant to afford 560 mg (51%) of (2-bromo-5-nitrophenyl)hydrazine as a orange solid. $^1$H NMR (400 MHz, DMSO-$d_6$) δ 7.89 (d, J=2.8 Hz, 1H), 7.60 (d, J=8.6 Hz, 1H), 7.29 (dd, J=2.8, 8.6 Hz, 1H), 7.04 (s, 1H), 4.38 (s, 2H). MS (ESI) m/e [M+1]$^+$ 232, 234.

Step 2: 5-Amino-1-(2-bromo-5-nitrophenyl)-3-(4-phenoxyphenyl)-1H-pyrazole-4-carbonitrile

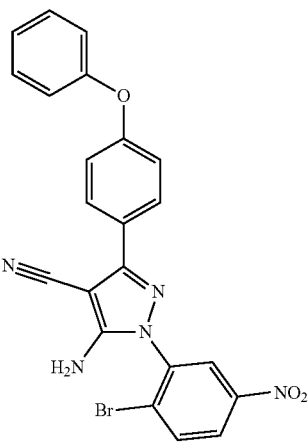 [SMILES: N#Cc1c(-c2ccc(Oc3ccccc3)cc2)nn(-c2cc([N+](=O)[O-])ccc2Br)c1N]

To a solution of 2-(methoxy(4-phenoxyphenyl)methylene)malononitrile (392 mg, 1.42 mmol) in ethanol (30 mL) was added (2-bromo-5-nitrophenyl)hydrazine (300 mg, 1.29 mmol) in one portion, then the mixture was stirred at 70° C. under N$_2$ overnight. The mixture was concentrated to dryness and chromatographed on 5 g of silica gel using PE/EA (10/1 to 211) as eluant to afford 128 mg (21%) of 5-amino-1-(2-bromo-5-nitrophenyl)-3-(4-phenoxyphenyl)-1H-pyrazole-4-carbonitrile as a yellow solid. MS (ESI) m/e [M+1]$^+$ 476, 478.

Step 3: 5-Amino-1-(2-bromo-5-nitrophenyl)-3-(4-phenoxyphenyl)-1H-pyrazole-4-carboxamide

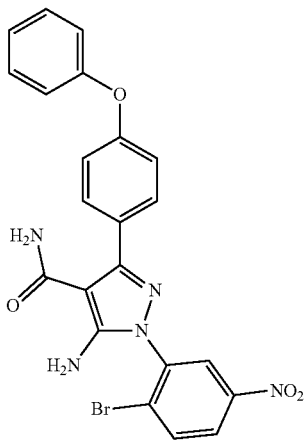 [SMILES: NC(=O)c1c(-c2ccc(Oc3ccccc3)cc2)nn(-c2cc([N+](=O)[O-])ccc2Br)c1N]

A mixture of 5-amino-1-(2-bromo-5-nitrophenyl)-3-(4-phenoxyphenyl)-1H-pyrazole-4-carbonitrile (137 mg, 0.287 mmol) in phosphorous acid (85 wt. % in H₂O, 10 mL) was stirred at 100° C. for 1 hr, until TLC and LCMS analysis showed that most of starting material was consumed. The reaction was cooled to room temperature and partitioned between water (40 mL) and EA (40 mL). Organic layer was separated from aqueous layer. The aqueous phase was then extracted with EA (20 mL). The combined organic layers were washed with brine (50 mL), dried over Na₂SO₄ and concentrated to get the crude product (149 mg) which was used in next step without further purification. MS (ESI) m/e [M+1]⁺ 494, 496.

Step 4: 7-Nitro-2-(4-phenoxyphenyl)-4H-benzo[4.5]imidazo[1,2-b]pyrazole-3-carboxamide

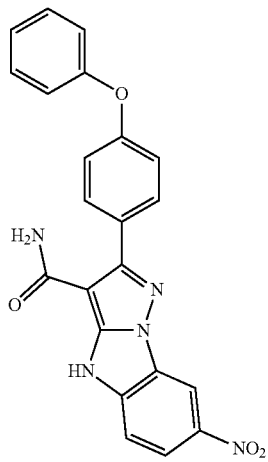 [SMILES: NC(=O)c1c(-c2ccc(Oc3ccccc3)cc2)nn2c1[nH]c1ccc([N+](=O)[O-])cc12]

A mixture of 5-amino-1-(2-bromo-5-nitrophenyl)-3-(4-phenoxyphenyl)-1H-pyrazole-4-carboxamide (149 mg, 0.3 mmol, crude), CuI (5.7 mg, 0.03 mmol), N¹,N²-dimethylethane-1,2-diamine (3 mg, 0.03 mmol), K₃PO₄ (64 mg, 0.3 mol) in 15 mL of DMF was stirred at 60° C. under N₂ for 5 hr, until TLC analysis showed that most of starting material was consumed. The reaction was cooled to RT. The solvent was removed under reduced pressure. The residue was chromatographed on 5 g of silica gel using DCM/MeOH (200/1 to 20/1) to afford 62 mg (52%) of 7-nitro-2-(4-phenoxyphenyl)-4H-benzo[4,5]imidazo[1,2-b]pyrazole-3-carboxamide as a tan solid. MS (ESI) m/e [M+1]⁺ 414.

Compound 66: 7-Amino-2-(4-phenoxyphenyl)-4H-benzo[4,5]imidazo[1,2-b]pyrazole-3-carboxamide

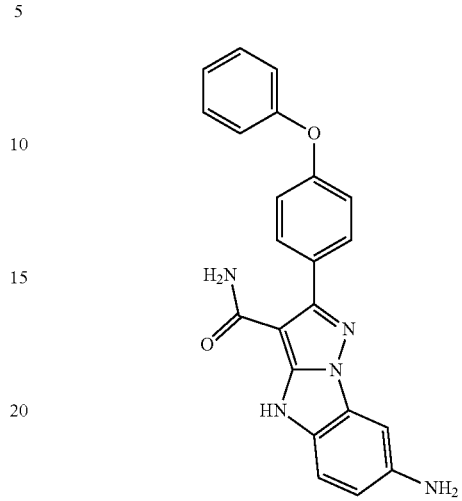

To a solution of 7-nitro-2-(4-phenoxyphenyl)-4H-benzo[4,5]imidazo[1,2-b] pyrazole-3-carboxamide (9 mg, 0.022 mmol) in 3 mL of HOAc was added zinc powder (14 mg, 0.22 mmol). Then the mixture was stirred at RT for 20 min, until TLC and LCMS analysis showed that most of starting material was consumed. The reaction solid was filtered off. The filtrate was concentrated, suspended in 10 mL of EA and filtered. The filtrate was concentrated to get the product as a white solid (4 mg, 50%). ¹H NMR (400 MHz, CD₃OD-d₄) δ 7.60 (d, J=8.6 Hz, 2H), 7.32 (d, J=8.0 Hz, 1H), 7.30 (d, J=8.0 Hz, 1H), 7.23 (d, J=8.4 Hz, 1H), 7.16 (s, 1H), 7.08 (t. J=8.0 Hz, 1H), 7.05-6.95 (m, 4H), 6.79 (dd, J=1.6, 8.4 Hz, 1H). MS (ESI) m/e [M+1]⁺ 384.

Compound 67: 7-Acrylamido-2-(4-phenoxyphenyl)-4H-benzo[4,5]imidazo[1,2-b]pyrazole-3-carboxamide

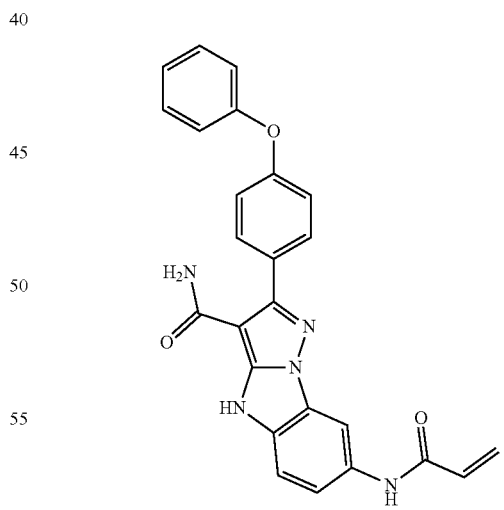

To a solution of 7-amino-2-(4-phenoxyphenyl)-4H-benzo[4,5]imidazo[1,2-b] pyrazole-3-carboxamide (45 mg, 0.11 mmol) in 10 mL of DCM at 0° C. was added TEA (36 mg, 0.35 mmol). Acryloyl chloride (11 mg, 0.12 mmol) in 2 mL of DCM was added dropwise over a period of 20 min. The mixture was stirred until TLC and LCMS analysis showed that most of starting material was consumed. The mixture was then partitioned between water (50 mL) and DCM (20 mL), extracted with additional 20 mL of DCM. The combined organic layer was washed with brine, dried over Na₂SO₄, concentrated and purified by Pre-TLC (DCM/MeOH=20/1) to get 4 mg (7.8%) of 7-acrylamido-2-(4-phenoxyphenyl)-4H-benzo[4,5]imidazo[1,2-b]pyrazole-3-carboxamide as a grey solid. ¹H NMR (400 MHz, CD₃OD-d₄) δ 8.25 (s, 1H), 7.61 (d, J=8.4 Hz, 2H), 7.44 (d, J=8.8 Hz, 1H), 7.39 (d, J=8.8 Hz, 1H), 7.32 (d, J=7.6 Hz, 1H), 7.30 (d, J=7.6 Hz, 1H), 7.08 (t, J=7.6 Hz, 1H), 7.05-6.90 (m, 4H), 6.42-6.25 (m, 2H), 5.69 (dd, J=9.6, 1.9 Hz, 1H). MS (ESI) m/e [M+1]⁺ 438.

Example 24: Synthesis of Compounds 68-69

Compound 68: 8-Amino-2-(4-phenoxyphenyl)-4,5-dihydro-pyrazolo[1,5-a] quinazoline-3-carboxamide

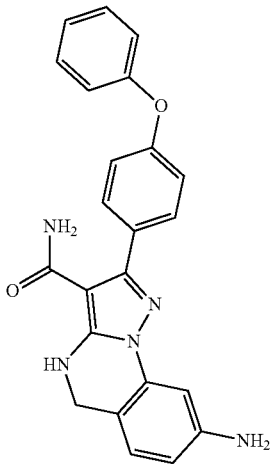 [SMILES: NC(=O)c1c(-c2ccc(Oc3ccccc3)cc2)nn2c1NCc1ccc(N)cc1-2]

Step 1: (2-Fluoro-4-nitrophenyl)methanol

To a solution of 2-fluoro-4-nitrobenzaldehyde (1.0 g, 5.92 mmol) in CH₃OH (10 mL) was added NaBH₄ (814 mg, 22 mmol). After stirring at RT for 15 min, the mixture was concentrated. The residue was partitioned between 100 mL of EA and 100 mL of brine. The combined organic layers were washed with brine (100 mL×2), dried over Na₂SO₄, and concentrated to afford 1.0 g of (2-fluoro-4-nitrophenyl)methanol (99%) as a red solid. MS (ESI) m/e [M+1]⁺ 172.0.

Step 2: 2-(2-Fluoro-4-nitrobenzyloxy)-tetrahydro-2H-pyran

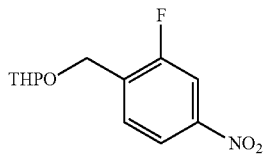

To a solution of (2-fluoro-4-nitrophenyl)methanol (755 mg, 4.42 mmol) in 10 mL of DCM was added TsOH (100 mg, 0.13 mmol) and DHP (408 mg, 4.86 mmol). After stirring at RT for 16 hr, the mixture was concentrated. The residue was partitioned between 100 mL of EA and 100 mL of brine. The combined organic layers were washed with brine (100 mL×2), dried over Na₂SO₄, concentrated and purified by chromatography column on silica gel (elution with PE/EA) to afford 900 mg (80%) of 2-(2-fluoro-4-nitrobenzyloxy)-tetrahydro-2H-pyran as a colorless oil. ¹H NMR (400 MHz, DMSO-d₆) δ 8.34 (dd, J=3.0, 6.2 Hz, 1H), 8.26-8.30 (m, 1H), 7.53 (t, J=9.2 Hz, 1H), 4.82-4.76 (m, 2H), 4.62 (d, J=12.0 Hz, 1H), 3.80-3.74 (m, 1H), 3.52-3.47 (m, 1H), 1.76-1.64 (m, 2H) and 1.58-1.45 (m, 4H).

Step 3: 5-Amino-1-(5-nitro-2-((tetrahydro-2H-pyran-2-yloxy)methyl)phenyl)-3-(4-phenoxyphenyl)-1H-pyrazole-4-carboxamide

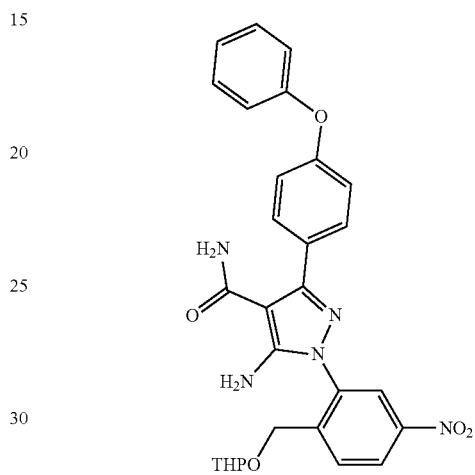

To a solution of 5-amino-3-(4-phenoxyphenyl)-1H-pyrazole-4-carboxamide (27.6 mg, 0.1 mmol) in DMF (3 mL) and CH₃CN (5 mL) was added 2-(2-fluoro-4-nitrobenzyloxy)-tetrahydro-2H-pyran (25.5 mg, 0.1 mmol) and K₂CO₃ (27.6 mg, 0.2 mmol). After stirring at 80° C. under N₂ for 16 hr, the mixture was concentrated and recrystallized with PE/EA to afford 40 mg (80%) of 5-amino-1-(5-nitro-2-((tetrahydro-2H-pyran-2-yloxy)methyl)phenyl)-3-(4-phenoxyphenyl)-1H-pyrazole-4-carboxamide as a yellow solid. MS (ESI) m/e [M+1]⁺ 512.2.

Step 4: 5-Amino-1-(2-(hydroxymethyl)-5-nitrophenyl)-3-(4-phenoxyphenyl)-1H-pyrazole-4-carboxamide

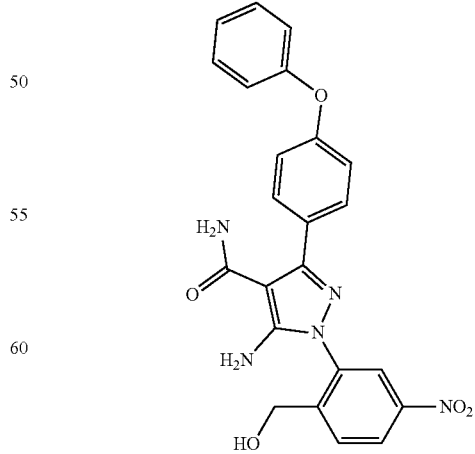

To a solution of 5-amino-1-(5-nitro-2-((tetrahydro-2H-pyran-2-yloxy)methyl) phenyl)-3-(4-phenoxyphenyl)-1H- pyrazole-4-carboxamide (690 mg, 1.3 mmol) in 10 mL of CH₃CN was added hydrochloric acid (3 mL). After stirring at RT for 15 min, the mixture was concentrated to afford 550 mg (95%) of 5-amino-1-(2-(hydroxyl methyl)-5-nitrophenyl)-3-(4-phenoxyphenyl)-1H-pyrazole-4-carboxamide as a yellow solid.

Step 5: 5-Amino-1-(2-formyl-5-nitrophenyl)-3-(4-phenoxyphenyl)-1H-pyrazole-4-carboxamide

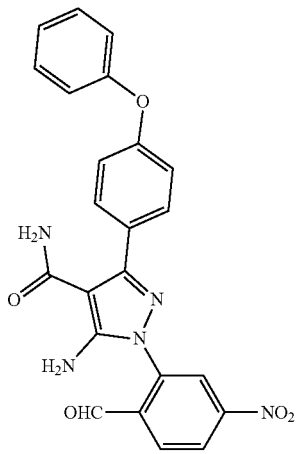 [SMILES: NC(=O)c1c(-c2ccc(Oc3ccccc3)cc2)nn(-c2cc([N+](=O)[O-])ccc2C=O)c1N]

To a solution of 5-amino-1-(2-(hydroxymethyl)-5-nitrophenyl)-3-(4-phenoxy phenyl)-1H-pyrazole-4-carboxamide (550 mg, 1.24 mmol) in 20 mL of DCM was added MnO₂ (500 mg, 5.75 mmol). After stirring at RT for 16 hr, the mixture was filtered. The filtrate was concentrated to afford 400 mg (73%) of 5-amino-1-(2-formyl-5-nitrophenyl)-3-(4-phenoxyphenyl)-1H-pyrazole-4-carboxamide as a yellow solid.

Step 6: 8-Nitro-2-(4-phenoxyphenyl)pyrazolo[1,5-a]quinazoline-3-carboxamide

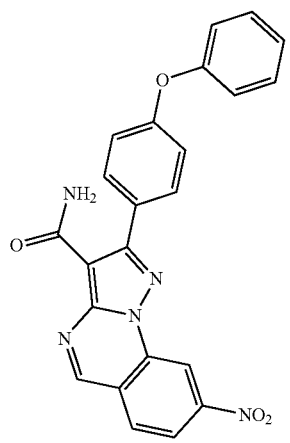 [SMILES: NC(=O)c1c(-c2ccc(Oc3ccccc3)cc2)nn2c1ncc1ccc([N+](=O)[O-])cc12]

To a solution of 5-amino-1-(2-formyl-5-nitrophenyl)-3-(4-phenoxyphenyl)-1H-pyrazole-4-carboxamide (400 mg, 0.9 mmol) in 5 mL of CH₃OH and 5 mL of DCM was added HOAc (1 drops). After stirring at RT for 16 hr, the mixture was concentrated and purified by chromatography column on silica gel eluting with PE/EA to afford 240 mg (63%) of 8-nitro-2-(4-phenoxyphenyl)pyrazolo [1,5-a]quinazoline-3-carboxamide as a yellow solid. MS (ESI) m/e [M+1]⁺ 425.8.

Step 7: 8-Nitro-2-(4-phenoxyphenyl)-4,5-dihydropyrazolo[1,5-a]quinazoline-3-carboxamide

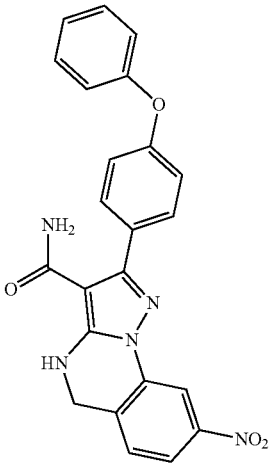 [SMILES: NC(=O)c1c(-c2ccc(Oc3ccccc3)cc2)nn2c1NCc1ccc([N+](=O)[O-])cc1-2]

To a solution of 8-nitro-2-(4-phenoxyphenyl)pyrazolo[1,5-a]quinazoline-3-carboxamide (240 mg, 0.57 mmol) in 10 mL of EtOH and 10 mL of DCM was added NaBH₄ (86 mg, 2.26 mmol) at RT. After stirring at RT for 20 min, 10 mL of water was added. The mixture was concentrated. 5 mL of water was added and filtered. The cake was washed with tert-Butyl methyl ether (30 mL) and dried to afford 200 mg (83%) of 8-nitro-2-(4-phenoxyphenyl)-4,5-dihydropyrazolo[1,5-a]quinazoline-3-carboxamide as a yellow solid. MS (ESI) m/e [M+]⁺ 427.9.

Step 8: 8-Amino-2-(4-phenoxyphenyl)-4,5-dihydropyrazolo[1,5-a]quinazoline-3-carboxamide and 8-amino-2-(4-phenoxyphenyl)pyrazolo[1,5-a]quinazoline-3-carboxamide

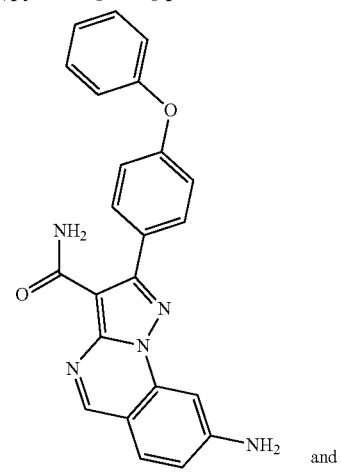 and

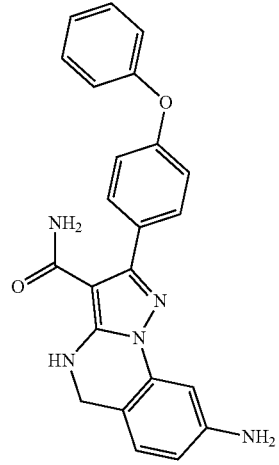

To a solution of 8-nitro-2-(4-phenoxyphenyl)-4,5-dihydropyrazolo[1,5-a] quinazoline-3-carboxamide (200 mg, 0.47 mmol) in 30 mL of CH$_3$OH and 30 mL of DCM was added 10% w/w Pd/C (100 mg). After stirring at RT for 1 hr, the mixture was filtered. The filtrate was concentrated to afford 130 mg (70%) of crude 8-amino-2-(4-phenoxyphenyl)-4,5-dihydropyrazolo[1,5-a]quinazoline-3-carboxamide and 8-amino-2-(4-phenoxyphenyl)pyrazolo[1,5-a]quinazoline-3-carboxamide as a yellow solid. MS (ESI) m/e [M+1]$^+$ 398.0, 395.9.

Step 9: 8-Amino-2-(4-phenoxyphenyl)-4,5-dihydropyrazolo[1,5-a]quinazoline-3-carboxamide

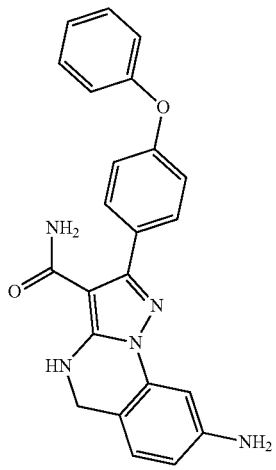 [SMILES: NC(=O)c1c(-c2ccc(Oc3ccccc3)cc2)nn2c1NCc1ccc(N)cc1-2]

To a solution of the mixture of 8-amino-2-(4-phenoxyphenyl)-4,5-dihydro pyrazolo[1,5-a]quinazoline-3-carboxamide and 8-amino-2-(4-phenoxyphenyl) pyrazolo[1,5-a]quinazoline-3-carboxamide (130 mg, 0.33 mmol) in 10 mL of DCM and 10 mL of CH$_3$OH was added NaBH$_4$ (277 mg, 3.3 mmol). After stirring at RT for 15 min, 50 mL of water was added. The mixture was concentrated and filtered. The cake was washed with water (50 mL×2) to afford 60 mg (46%) of 8-amino-2-(4-phenoxyphenyl)-4,5-dihydropyrazolo[1,5-a]quinazoline-3-carboxamide as a yellow solid. $^1$H NMR (400 MHz, DMSO-d$_6$) δ 7.60 (d, J=8.0 Hz, 2H), 7.44 (d, J=7.6 Hz, 1H), 7.42 (d, J=7.6 Hz, 1H), 7.28 (d, J=7.6 Hz, 1H), 7.18 (t, J=7.6 Hz, 1H), 7.14-7.16 (m, 4H), 6.81 (s, 1H), 6.52 (d, J=8.0 Hz, 1H), 6.43 (s, 1H), 5.16 (s, 2H) and 4.37 (s, 2H). MS (ESI) m/e [M+1]$^+$ 397.9.

Compound 69: 8-Acrylamido-2-(4-phenoxyphenyl)-4,5-dihydropyrazolo[1,5-a] quinazoline-3-carboxamide

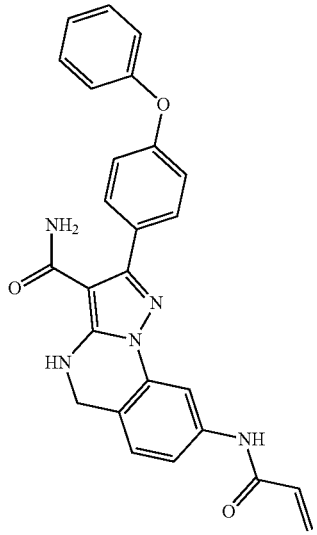 [SMILES: C=CC(=O)Nc1ccc2c(c1)-n1nc(-c3ccc(Oc4ccccc4)cc3)c(C(N)=O)c1NC2]

The desired product was prepared from compound 68 and acryloyl chloride using the procedure similar to that for compound 8. $^1$H NMR (400 MHz, DMSO-d$_6$) δ 10.26 (s, 1H), 7.39-7.63 (m, 4H), 7.52 (d, J=8.8 Hz, 1H), 7.45 (d, J=8.0 Hz, 1H), 7.42 (d, J=8.0 Hz, 1H), 7.19 (t, J=8.0 Hz, 1H), 7.14-7.07 (m, 4H), 7.01 (s, 1H), 6.44 (dd, J=10.4, 17.0 Hz, 1H), 6.26 (dd. J=1.6, 17.0 Hz, 1H), 5.77 (dd, J=1.6, 10.4 Hz, 1H) and 4.51 (s, 2H). MS (ESI) m/e [M+1]$^+$ 451.9.

Example 25: Synthesis of Compounds 70-72

Compound 70: 8-Nitro-2-(4-phenoxyphenyl)-5,6-dihydro-4H-benzo[f]pyrazolo [1,5-a][1,3]diazepine-3-carboxamide

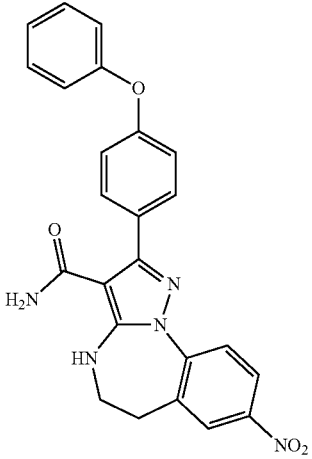 [SMILES: NC(=O)c1c(-c2ccc(Oc3ccccc3)cc2)nn2c1NCCc1cc([N+](=O)[O-])ccc1-2]

Step 1: 2-(2-Fluoro-5-nitrophenyl)ethanol

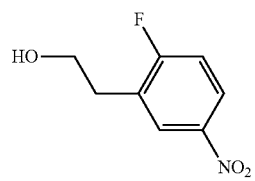

To a solution of 2-(2-fluoro-5-nitrophenyl)acetic acid (2.0 g, 10 mmol) in THF (50 mL) was added borane dimethyl sulfide complex solution (4.0 g, 25 mmol). The reaction was warmed to 60° C. stirred for about 12 hr. After cooling down to RT, CH$_3$OH (20 mL) was slowly added to the reaction, concentrated under reduced pressure to remove solvent. The residue was purified by column chromatography on silica gel (200-300 mesh. PE/EA=2/1) to afford the product as a colorless oil (1.6 g, 86.1%). $^1$H NMR (400 MHz, DMSO-d$_6$) δ 8.27 (t, J=3.2, 6.4 Hz, 1H), 8.19-8.14 (m, 1H), 8.45 (t, J=9.2 Hz, 1H), 4.80 (t, J=5.6 Hz, 1H), 3.66 (dt. J=5.6, 6.4 Hz, 1H), 2.86 (t, J=6.4 Hz, 2H). MS (ESI) m/e [M+1]$^+$ 186.

Step 2: 8-Nitro-2-(4-phenoxyphenyl)-5,6-dihydro-4H-benzo[f]pyrazolo[1,5-a][1,3] diazepine-3-carboxamide

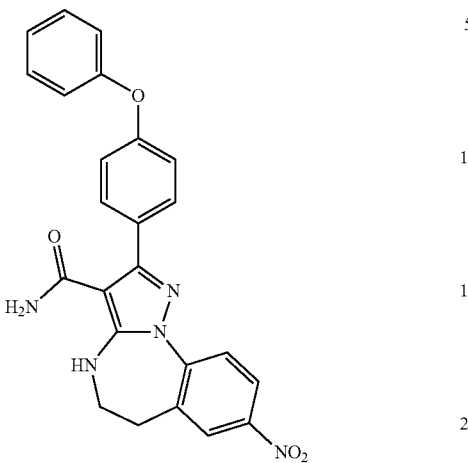

To a solution of 5-amino-3-(4-phenoxyphenyl)-1H-pyrazole-4-carboxamide (30 mg, 0.10 mmol) in DMF (5.0 mL) was added $K_2CO_3$ (28 mg, 0.20 mmol), followed by 2-(2-fluoro-5-nitrophenyl)ethanol (37 mg, 0.20 mmol). The mixture was warmed to 80° C. stirred for about 16 hr. After cooling down to RT, the mixture was concentrated under reduced pressure. The residue was partitioned between ethyl acetate (15 mL) and water (15 mL), the aqueous was extracted with ethyl acetate (3×10 mL). The combined organic phases were washed brine (10 mL), dried over $Na_2SO_4$, filtered, concentrated and purified by Pre-TLC (DCM/$CH_3OH$=20/1) to afford the product about 5.0 mg (11.1%). $^1H$ NMR (400 MHz, DMSO-$d_6$) δ 8.35 (t, J=4.0 Hz, 1H), 8.28 (d, J=2.8 Hz, 1H), 8.22 (dd, J=2.8, 9.2 Hz, 1H), 8.12 (d, J=9.2 Hz, 1H), 7.64-7.60 (m, 2H), 7.45-7.41 (m, 2H), 7.22-7.17 (m, 1H), 7.14-7.09 (m, 4H), 3.72-3.65 (m, 2H), 3.29-3.24 (m, 2H). MS (ESI) m/e [M+1]$^+$ 442.

Compound 71: 8-Amino-2-(4-phenoxyphenyl)-5,6-dihydro-4H-benzo[f]pyrazolo [1,5-a][1,3]diazepine-3-carboxamide

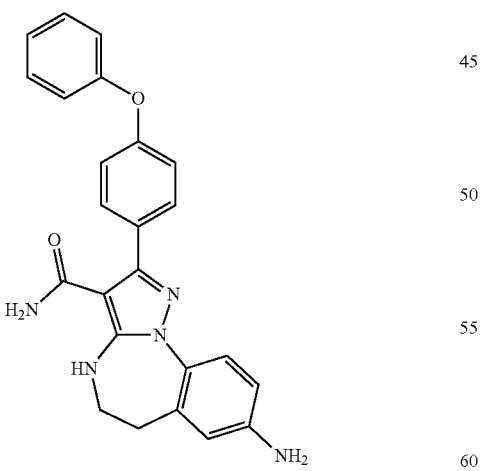

To the solution of 8-nitro-2-(4-phenoxyphenyl)-5,6-dihydro-4H-benzo[f]pyrazolo [1,5-a][1,3]diazepine-3-carboxamide (80 mg, 0.18 mmol) in ethanol (20 mL) was added 10% w/w Pd/C (20 mg), the reaction was stirred at RT under $H_2$ for about 3 hr. Filtered and washed with $CH_3OH$ (20 mL), the filtrate was concentrated under reduced pressure, the residue was purified by Pre-TLC (DCM/$CH_3OH$=20/1) to afford the product as a white solid (20 mg, 26.8%). $^1H$ NMR (400 MHz, DMSO-$d_6$) δ 7.73-7.69 (m, 1H), 7.59-7.55 (m, 2H), 7.45-7.40 (m, 3H), 7.21-7.16 (m, 1H), 7.13-7.07 (m, 4H), 6.59-6.54 (m, 1H), 6.50-6.47 (m, 1H), 5.70-5.40 (br s, 2H), 3.64-3.59 (m, 2H), 2.99-2.94 (m, 2H). MS (ESI) m/e [M+1]$^+$ 412.

Compound 72: 8-Acrylamido-2-(4-phenoxyphenyl)-5,6-dihydro-4H-benzo [f]pyrazolo[1,5-a][1,3]diazepine-3-carboxamide

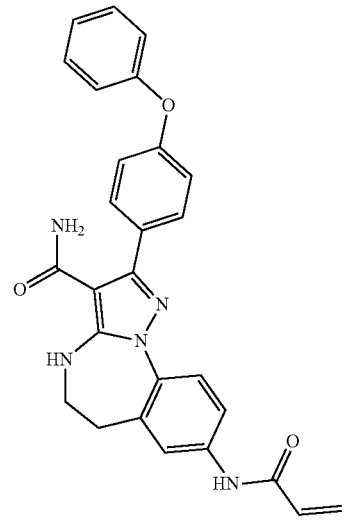 [SMILES: C=CC(=O)Nc1ccc2c(c1)CCNc1c(C(N)=O)c(-c3ccc(Oc4ccccc4)cc3)nn1-2]

The desired compound was prepared from compound 71 and acryloyl chloride according to the procedure similar to that for compound 8. $^1H$ NMR (400 MHz, DMSO-$d_6$) δ 10.25 (s, 1H), 7.95 (t, J=4.0 Hz, 1H), 7.76 (d, J=8.8 Hz, 1H), 7.65-7.58 (m, 4H), 7.46-7.41 (m, 2H), 7.21-7.17 (m, 1H), 7.13-7.08 (m, 4H), 6.44 (dd, J=10.0, 16.8 Hz, 1H), 6.27 (dd, J=2.0, 16.8 Hz, 1H), 5.77 (dd, J=2.0, 10.0 Hz, 1H), 3.68-3.65 (m, 2H), 3.05-3.03 (m, 2H). MS (ESI) m/e [M+1]$^+$ 466.

Example 26: Synthesis of Compounds 73-75

Compound 73: 8-Nitro-5-oxo-2-(4-phenoxyphenyl)-5,6-dihydro-4H-benzo[f]pyrazolo[1,5-a][1,3]diazepine-3-carboxamide

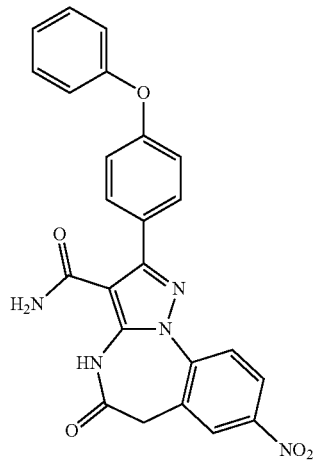

Step 1: Methyl 2-(2-fluoro-5-nitrophenyl)acetate

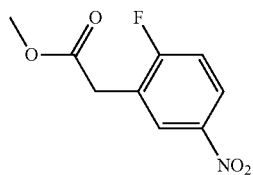

To a solution of 2-(2-fluoro-5-nitrophenyl)acetic acid (1.0 g, 5.0 mmol) in CH₃OH (20 mL) was added con. H₂SO₄ (0.50 mL), the reaction was warmed to 80° C. and stirred for about 3 hr. After cooling down to RT, the reaction was poured into water (20 mL) and concentrated to remove CH₃OH. The aqueous was extracted with ethyl acetate (2×20 mL), the combined organic phases were washed brine (10 mL), dried over Na₂SO₄, filtered and concentrated to afford the product about 1.0 g (93.4%) as a colorless oil. MS (ESI) m/e [M+1]⁺ 214.0.

Step 2: 8-Nitro-5-oxo-2-(4-phenoxyphenyl)-5,6-dihydro-4H-benzo[f]pyrazolo[1,5-a]diazepine-3-carboxamide

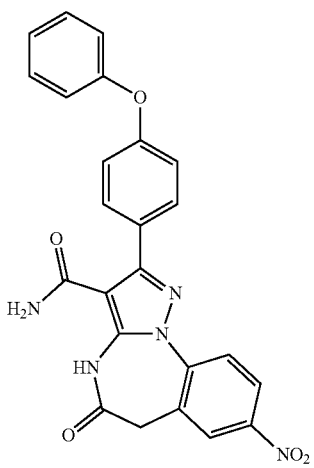 [SMILES: NC(=O)c1c(-c2ccc(Oc3ccccc3)cc2)nn2c1NC(=O)Cc1cc([N+](=O)[O-])ccc1-2]

To a solution of 5-amino-3-(4-phenoxyphenyl)-1H-pyrazole-4-carboxamide (30 mg, 0.10 mmol) in DMF (5 mL) was added K₂CO₃ (28 mg, 0.20 mmol) and methyl 2-(2-fluoro-5-nitrophenyl)acetate (21 mg, 0.10 mmol). The mixture was warmed to 80° C. stirred for about 16 hr. After cooling down to RT, the mixture was concentrated under reduced pressure to remove solvent. The residue was portioned with DCM (10 mL) and water (10 mL), the aqueous was extracted with DCM (2×10 mL), the combined organic phases were washed sat. Sodium chloride (10 mL), dried over anhydrous Sodium sulfate, filtered, concentrated and purified by pre-TLC (DCM/CH₃OH=20/1) got the product about 10 mg (21.9%). ¹H NMR (400 MHz, DMSO-d₆) δ 10.66 (br s, 1H), 8.51 (d, J=2.6 Hz, 1H), 8.37 (dd, J=2.6, 9.2 Hz, 1H), 8.07 (d, J=9.2 Hz, 1H), 7.85 (d, J=8.8 Hz, 2H), 7.65-7.53 (br s, 2H), 7.45-7.40 (m, 2H), 7.22-7.16 (m, 1H), 7.12-7.05 (m, 4H), 3.92 (s, 2H). MS (ESI) m/e [M+1]⁺ 456.1.

Compound 74: 8-Amino-5-oxo-2-(4-phenoxyphenyl)-5,6-dihydro-4H-benzo[f] pyrazolo[1,5-a][1,3]diazepine-3-carboxamide

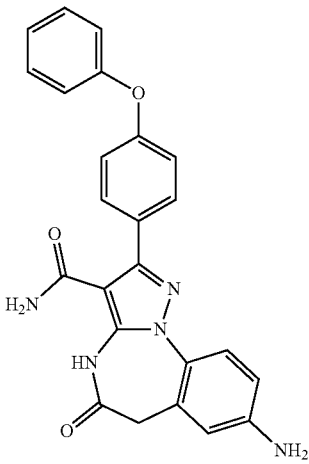

Compound 74 was prepared from 8-nitro-5-oxo-2-(4-phenoxyphenyl)-5,6-dihydro-4H-benzo[f]pyrazolo[1,5-a][1,3]diazepine-3-carboxamide according to the procedure similar to that for compound 71. ¹H NMR (400 MHz, CD₃OD-d₄) δ 7.72-7.67 (m, 2H), 7.52 (d, J=8.8 Hz, 1H), 7.42-7.37 (m, 2H), 7.19-7.14 (m, 1H), 7.11-7.05 (m, 4H), 6.80 (dd. J=2.6, 8.8 Hz, 1H), 6.69 (d, J=2.6 Hz, 1H), 3.59 (s, 2H). MS (ESI) m/e [M+1]⁺ 426.1.

Compound 75: 8-Acrylamido-5-oxo-2-(4-phenoxyphenyl)-5,6-dihydro-4H-benzo[f] pyrazolo[1,5-a][1,3]diazepine-3-carboxamide

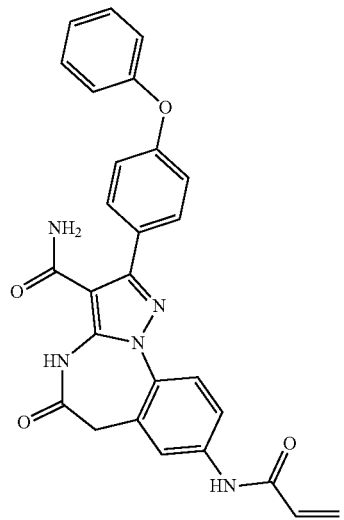 [SMILES: C=CC(=O)Nc1ccc2c(c1)CC(=O)Nc1c(C(N)=O)c(-c3ccc(Oc4ccccc4)cc3)nn1-2]

Compound 75 was prepared from 8-amino-5-oxo-2-(4-phenoxyphenyl)-5,6-dihydro-4H-benzo[f]pyrazolo[1,5-a][1,3]diazepine-3-carboxamide and acryloyl chloride according to the procedure similar to that for compound 8. ¹H NMR (400 MHz, CD₃OD-d₄) δ 7.85-7.79 (m, 3H), 7.75-7.71 (m, 2H), 7.43-7.37 (m, 2H), 7.20-7.14 (m, 1H), 7.12-7.06 (m, 4H), 6.50-6.35 (m, 2H), 5.81 (dd, J=2.6, 9.0 Hz, 1H), 3.75 (s, 2H). MS (ESI) m/e [M+1]⁺ 480.1.

Example 27: Synthesis of Compounds 76-79

Compound 76: 7-Nitro-5-oxo-2-(4-phenoxyphenyl)-4,5-dihydropyrazolo[1,5-a]quinazoline-3-carboxamide

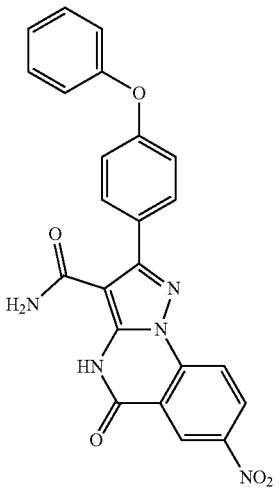 [SMILES: NC(=O)c1c(-c2ccc(Oc3ccccc3)cc2)nn2c1[nH]c(=O)c1cc([N+](=O)[O-])ccc12]

A mixture of 5-amino-3-(4-phenoxyphenyl)-1H-pyrazole-4-carboxamide (220 mg, 0.75 mmol), methyl 2-chloro-5-nitrobenzoate (160 mg, 0.75 mmol) and $K_2CO_3$ (155 mg, 1.13 mmol) in DMF (10 mL) was heated to 80° C. for 16 hr under $N_2$. The reaction was poured into water (30 ml), and extracted with ethyl acetate (20 mL×3). The combined organic layers were dried over $Na_2SO_4$, concentrated under reduced pressure to a residue, which was purified by a silica gel column eluting with 10% to 50% EA in PE to afford 85 mg (27.3%) of 7-nitro-5-oxo-2-(4-phenoxyphenyl)-4,5-dihydropyrazolo[1,5-a]quinazoline-3-carboxamide as a yellow solid. MS (ESI, m/e) [M+1]$^+$ 442.1.

Compound 77: 7-Amino-5-oxo-2-(4-phenoxyphenyl)-4,5-dihydropyrazolo[1,5-a]quinazoline-3-carboxamide

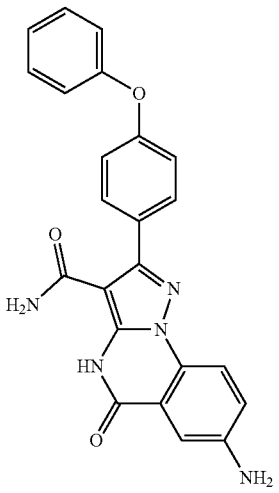

Compound 77 was prepared from 7-nitro-5-oxo-2-(4-phenoxyphenyl)-4,5-dihydro pyrazolo[1,5-a]quinazoline-3-carboxamide according to the procedure similar to that for compound 71. $^1$H NMR (400 MHz, DMSO-d$_6$) δ 10.88 (br s, 1H), 7.80 (d, J=8.4 Hz, 1H), 7.71 (d, J=6.8 Hz, 2H), 7.36-7.42 (m, 2H), 7.27 (s, 1H), 7.02-7.17 (m, 6H), 5.62 (s, 2H). MS (ESI, m/e) [M+1]$^+$ 412.1.

Compound 78: 7-Acrylamido-5-oxo-2-(4-phenoxyphenyl)-4,5-dihydropyrazolo[1,5-a]quinazoline-3-carboxamide

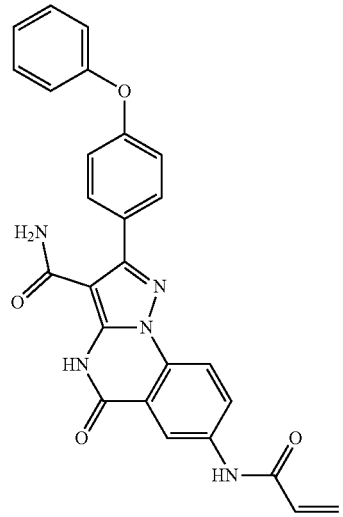 [SMILES: C=CC(=O)Nc1ccc2c(c1)c(=O)[nH]c1c(C(N)=O)c(-c3ccc(Oc4ccccc4)cc3)nn12]

Compound 78 was prepared from 7-amino-5-oxo-2-(4-phenoxyphenyl)-4,5-dihydropyrazolo[1,5-a]quinazoline-3-carboxamide and acryloyl chloride according to the procedure similar to that for compound 8. $^1$H NMR (400 MHz, DMSO-d$_6$) δ 11.37 (s, 1H), 10.77 (s, 1H), 8.65 (s, 1H), 8.24 (d, J=8 Hz, 1H), 8.15 (d, J=8 Hz, 1H), 7.85 (d, J=7.6 Hz, 2H), 7.48-7.52 (m, 2H), 7.2-7.15 (m, 5H), 6.57 (dd, J=9.2, 18.0 Hz, 1H), 6.37 (d, J=18.0 Hz, 1H), 5.87 (d, J=9.2 Hz, 1H). MS (ESI, m/e) [M+1]$^+$ 466.1.

Compound 79: 8-Amino-5-oxo-2-(4-phenoxyphenyl)-4,5-dihydropyrazolo[1,5-a]quinazoline-3-carboxamide

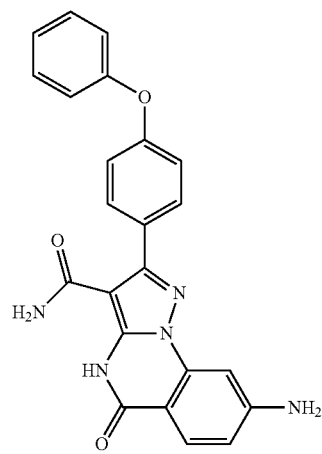 [SMILES: NC(=O)c1c(-c2ccc(Oc3ccccc3)cc2)nn2c1[nH]c(=O)c1ccc(N)cc12]

The desired product was prepared from methyl 2-chloro-4-nitrobenzoate and 5-amino-3-(4-phenoxyphenyl)-1H-pyrazole-4-carboxamide using the procedures similar to those for compound 76 and 77. $^1$H NMR (400 MHz, DMSO-d$_6$) δ 10.61 (s, 1H), 7.77 (d, J=8.4 Hz, 1H), 7.71 (d, J=8.0 Hz, 2H), 7.44-7.36 (m, 2H), 7.19-7.02 (m, 6H), 6.64 (d. J=8.4 Hz, 1H), 6.55 (br s, 2H). MS (ESI, m/e) [M+1]$^+$ 412.1.

Example 28: Synthesis of Compounds 80-81

Compound 80: 5-Oxo-2-(4-phenoxyphenyl)-7-(piperidin-4-yl)-4,5-dihydropyrazolo [1,5-a]pyrimidine-3-carboxamide

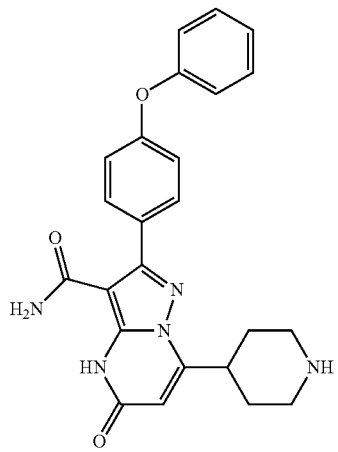 [SMILES: NC(=O)c1c(-c2ccc(Oc3ccccc3)cc2)nn2c(C3CCNCC3)cc(=O)[nH]c12]

Step 1: tert-Butyl 4-(2,2-dimethyl-4,6-dioxo-1,3-dioxane-5-carbonyl)piperidine-1-carboxylate

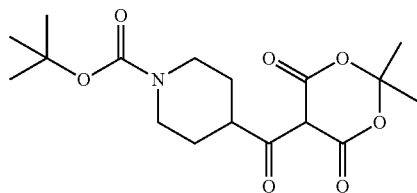 [SMILES: CC(C)(C)OC(=O)N1CCC(C(=O)C2C(=O)OC(C)(C)OC2=O)CC1]

To a stirred mixture of 1-(tert-butoxycarbonyl)piperidine-4-carboxylic acid (1.15 g, 5 mmol) and DMAP (61 mg, 0.5 mmol) in DCM (50 mL) was added DCC (1.14 g, 5.5 mmol) and 2,2-dimethyl-1,3-dioxane-4,6-dione (0.8 g, 5.5 mmol). The resulting mixture was stirred at rt for 16 hr and filtered. The filtrate was concentrated under vacuum to afford tert-butyl 4-(2,2-dimethyl-4,6-dioxo-1,3-dioxane-5-carbonyl)piperidine-1-carboxylate 2 g (crude) as a yellow oil, which was used in the next step without further purification. MS (ESI) m/e [M+23]$^+$ 378.1.

Step 2: tert-Butyl 4-(3-ethoxy-3-oxopropanoyl)piperidine-1-carboxylate

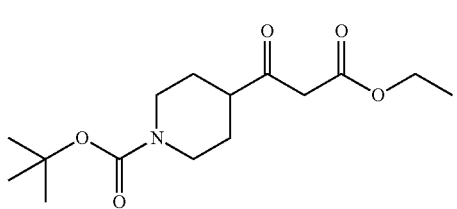 [SMILES: CCOC(=O)CC(=O)C1CCN(C(=O)OC(C)(C)C)CC1]

A solution of tert-butyl 4-(2,2-dimethyl-4,6-dioxo-1,3-dioxane-5-carbonyl) piperidine-1-carboxylate (2 g, 5.63 mmol) in ethanol (50 ml) was refluxed for 20 h, then the solvent was removed under vacuum, and the residue was purified by silica gel chromatography eluted with DCM to afford 0.5 g (30%) of tert-butyl 4-(3-ethoxy-3-oxopropanoyl)piperidine-1-carboxylate as a reddish oil. MS (ESI) m/e [M+23]$^+$ 322.2.

Step 3: 5-Oxo-2-(4-phenoxyphenyl)-7-(piperidin-4-yl)-4,5-dihydropyrazolo[1,5-a]pyrimidine-3-carboxamide

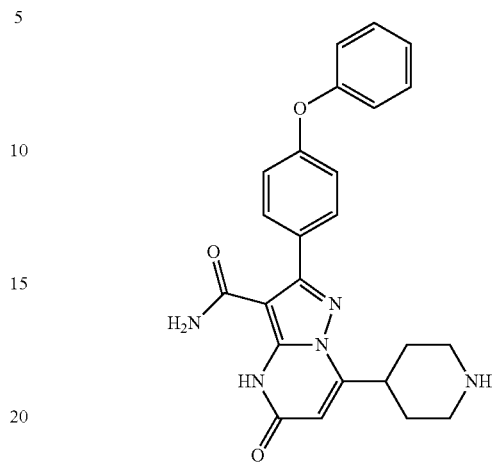

A mixture of 5-amino-3-(4-phenoxyphenyl)-1H-pyrazole-4-carboxamide (412 mg, 1.4 mmol) and tert-butyl 4-(3-ethoxy-3-oxopropanoyl)piperidine-1-carboxylate (420 mg, 1.4 mmol) in HOAc (20 mL) was stirred at 90° C. for 16 hr. The solvent was removed under vacuum, and the residue was partitioned between aq. NaHCO$_3$ and ethyl acetate. The organic layer was washed with brine, dried over Na$_2$SO$_4$ and concentrated under vacuum. The residue was purified by Pre-HPLC eluting from 25% to 90% CH$_3$CN in 0.1% TFA in H$_2$O. Fractions containing the desired product were combined and lyophilized overnight to afford 5-oxo-2-(4-phenoxyphenyl)-7-(piperidin-4-yl)-4,5-dihydropyrazolo[1,5-a]pyrimidine-3-carboxamide (0.3 g, 50%) as a white solid. $^1$H NMR (400 MHz. DMSO-d$_6$) δ 11.71 (br s, 1H), 8.68-8.65 (m, 1H), 8.42-8.39 (m, 1H), 7.74 (d, J=8.4 Hz, 2H), 7.47-7.41 (m, 2H), 7.22-7.18 (m, 1H), 7.14-7.09 (m, 4H), 5.72 (s, 1H), 3.50-3.35 (m, 2H), 3.17-3.06 (m, 1H), 3.01-2.87 (m, 2H), 2.15-2.05 (m, 2H), 1.83-1.72 (m, 2H). MS (ESI) m/e [M+1]$^+$ 430.1.

Compound 81: 5-Oxo-2-(4-phenoxyphenyl)-7-(1-propionylpiperidin-4-yl)-4,5-dihydropyrazolo[1,5-a]pyrimidine-3-carboxamide

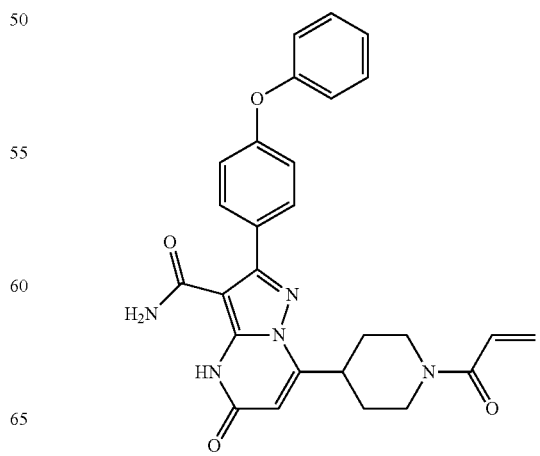

The desired product was prepared from compound 80 and acryloyl chloride using the procedure similar to that for compound 8. ¹H NMR (400 MHz, DMSO-d₆) δ 11.74 (s, 1H), 7.75 (d, J=8.4 Hz, 2H), 7.47-7.41 (m, 2H), 7.20 (t, J=7.2 Hz, 1H), 7.12-7.09 (m, 4H), 6.85 (dd, J=10.6, 16.6 Hz, 1H), 6.12 (dd, J=2.4, 16.6 Hz, 1H), 5.76 (s, 1H), 5.69 (dd, J=2.4, 10.6 Hz, 1H), 4.63-4.58 (m, 1H), 4.24-4.20 (m, 1H), 3.15-3.05 (m, 2H), 2.69-2.63 (m, 1H), 1.99-1.91 (m, 2H), 1.61-1.58 (m, 2H). MS (ESI) m/e [M+1]⁺ 483.9.

Example 29: Synthesis of Compounds 82-83

Compound 82: 2-Oxo-6-(4-phenoxyphenyl)-1,2-dihydrospiro[imidazo[1,2-b] pyrazole-3,4'-piperidine]-7-carboxamide

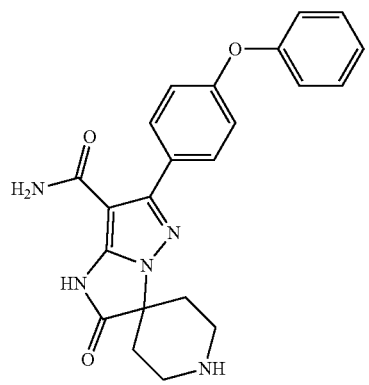 [SMILES: NC(=O)c1c(-c2ccc(Oc3ccccc3)cc2)nn2c1NC(=O)C21CCNCC1]

Step 1: 1'-Benzyl-2-oxo-6-(4-phenoxyphenyl)-1,2-dihydrospiro[imidazo[1,2-b] pyrazole-3,4'-piperidine]-7-carbonitrile

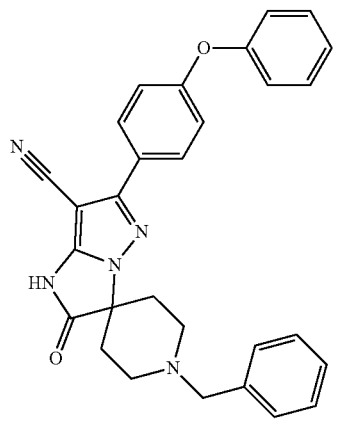 [SMILES: N#Cc1c(-c2ccc(Oc3ccccc3)cc2)nn2c1NC(=O)C21CCN(Cc2ccccc2)CC1]

A mixture of ethyl 1-benzyl-4-hydrazinylpiperidine-4-carboxylate hydrochloride (350 mg, 1.0 mmol), 2-(methoxy (4-phenoxyphenyl)methylene)malononitrile (276 mg, 1.0 mmol) and K₂CO₃ (414 mg, 3.0 mmol) in MeOH (20 mL) was heated to reflux for 16 hr. The mixture was filtered and the filtrate was concentrated to give the crude product (280 mg, 58.9%) as a yellow solid. MS (ESI, m/e) [M+1]⁺ 475.9.

Step 2: 1'-Benzyl-2-oxo-6-(4-phenoxyphenyl)-1,2-dihydrospiro[imidazo[1,2-b] pyrazole-3,4'-piperidine]-7-carboxamide

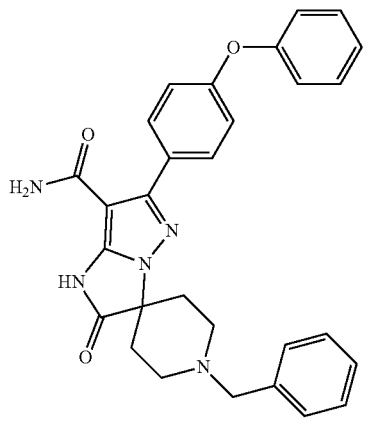 [SMILES: NC(=O)c1c(-c2ccc(Oc3ccccc3)cc2)nn2c1NC(=O)C21CCN(Cc2ccccc2)CC1]

A solution of 1'-benzyl-2-oxo-6-(4-phenoxyphenyl)-1,2-dihydrospiro[imidazo[1,2-b]pyrazole-3,4'-piperidine]-7-carbonitrile (200 mg, 0.42 mmol) in H₃PO₄ (15 mL) was heated to 120° C. for 2 hr. The solution was poured to water (10 mL) and extracted with EA (10 mL×3). The combined organic layers were dried over Na₂SO₄ and concentrated to give the crude product (120 mg, 58.0%) as an off-white solid. MS (ESI, m/e) [M+1]⁺ 493.9.

Step 3: 2-Oxo-6-(4-phenoxyphenyl)-1,2-dihydrospiro[imidazo[1,2-b]pyrazole-3,4'-piperidine]-7-carboxamide

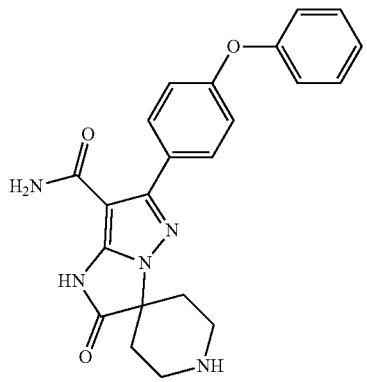 [SMILES: NC(=O)c1c(-c2ccc(Oc3ccccc3)cc2)nn2c1NC(=O)C21CCNCC1]

To a solution of 1'-benzyl-2-oxo-6-(4-phenoxyphenyl)-1, 2-dihydrospiro[imidazo [1,2-b]pyrazole-3,4'-piperidine]-7-carboxamide (120 mg, 0.24 mmol) in MeOH (10 mL) was added 10% w/w Pd(OH)₂/C (5 mg) and stirred for 16 hr under H₂. The mixture was filtered and the filtrate was concentrated to give the crude product (280 mg, 58.9%) as a yellow solid. MS (ESI, m/e) [M+1]⁺ 403.9.

Compound 83: 1'-Acryloyl-2-oxo-6-(4-phenoxyphenyl)-1,2-dihydrospiro[imidazo [1,2-b]pyrazole-3,4'-piperidine]-7-carboxamide

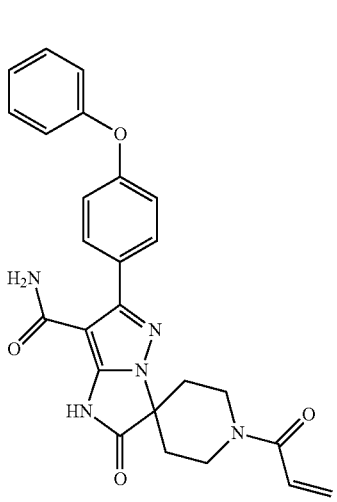 [SMILES: C=CC(=O)N1CCC2(CC1)C(=O)Nc1c(C(N)=O)c(-c3ccc(Oc4ccccc4)cc3)nn12]

The desired product was prepared from compound 82 and acryloyl chloride using the procedure similar to that for compound 8. ¹H NMR (400 MHz, DMSO-$d_6$) δ 11.91 (s, 1H), 7.71 (d, J=8.4 Hz, 2H), 7.47-7.37 (m, 2H), 7.25 (br s, 1H), 7.17 (t, J=7.6 Hz, 1H), 7.08-7.02 (m, 4H), 6.88 (dd, J=16.6, 10.4 Hz, 1H), 6.80 (br s, 1H), 6.16 (d, J=16.6 Hz, 1H), 5.72 (d, J=10.4 Hz, 1H), 4.32-4.14 (m, 1H), 4.12-3.99 (m, 1H), 3.97-3.81 (m, 1H), 3.76-3.60 (m, 1H), 1.86-1.91 (m, 4H). MS (ESI, m/e) [M+1]⁺ 457.9.

Example 30: Synthesis of Compounds 84-85

Compound 84: 6-Amino-2-(4-phenoxyphenyl)-4,5,6,7-tetrahydropyrazolo[1,5-a] pyrimidine-3-carboxamide

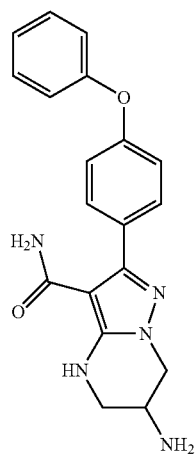 [SMILES: NC(=O)c1c(-c2ccc(Oc3ccccc3)cc2)nn2c1NCC(N)C2]

Step 1: 6-Nitro-2-(4-phenoxyphenyl)pyrazolo[1,5-a]pyrimidine-3-carbonitrile

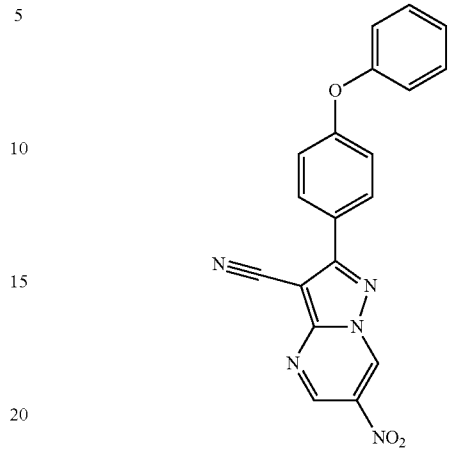

To a solution of 5-amino-3-(4-phenoxyphenyl)-1H-pyrazole-4-carbonitrile (83 mg, 0.3 mmol) in HOAc (2 mL) was added sodium 2-nitro-1,3-dioxopropan-2-ide (47 mg, 0.3 mmol). After stirring at RT for 1 hr, water (2 mL) was added. The mixture was partitioned between EA (25 mL) and brine (25 mL). The combined organic layers were washed with brine (25 mL×2), dried over $Na_2SO_4$ and concentrated to afford 90 mg of 6-nitro-2-(4-phenoxyphenyl)pyrazolo[1,5-a]pyrimidine-3-carbonitrile (84%) as a yellow solid. MS (ESI) m/e [M+1]⁺ 358.2.

Step 2: 6-Nitro-2-(4-phenoxyphenyl)-4,5,6,7-tetrahydropyrazolo[1,5-a]pyrimidine-3-carbonitrile

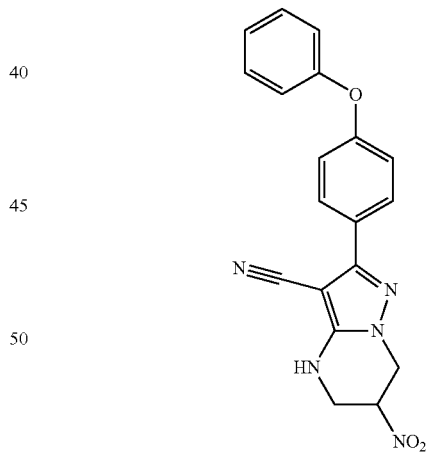

To a solution of 6-nitro-2-(4-phenoxyphenyl)pyrazolo[1,5-a]pyrimidine-3-carbonitrile (90 mg, 0.25 mmol) in 2 mL of ethanol and 2 mL of DCM was added $NaBH_4$ (19 mg, 0.5 mmol) at RT. After stirring at RT for 30 min, 5 mL of water was added. The mixture was concentrated. The residue was partitioned between 50 mL of DCM and 50 mL of brine. The combined organic layers were washed with brine (50 mL×2), dried over $Na_2SO_4$ and concentrated to afford 50 mg of 6-nitro-2-(4-phenoxyphenyl)-4,5,6,7-tetrahydropyrazolo[1,5-a]pyrimidine-3-carbonitrile (55%) as a yellow solid. MS (ESI) m/e [M+1]⁺ 362.1.

Step 3: 6-Amino-2-(4-phenoxyphenyl)-4,5,6,7-tetrahydro-pyrazolo[1,5-a]pyrimidine-3-carbonitrile

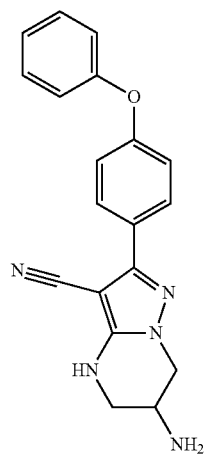 [SMILES: N#Cc1c(-c2ccc(Oc3ccccc3)cc2)nn2c1NCC(N)C2]

To a solution of 6-nitro-2-(4-phenoxyphenyl)-4,5,6,7-tetrahydropyrazolo[1,5-a]pyrimidine-3-carbonitrile (600 mg, 1.67 mmol) in 30 mL of methanol and 10 mL of DCM was added 10% w/w Pd/C (100 mg). The mixture was stirred at RT under $H_2$ for 2 hr and filtered. The filtrate was concentrated and purified by chromatography column on silica gel eluting with PE/EA to afford 200 mg (36%) of 6-amino-2-(4-phenoxyphenyl)-4,5,6,7-tetrahydropyrazolo[1,5-a]pyrimidine-3-carbonitrile as a white solid. MS (ESI) m/e $[M+1]^+$ 332.1.

Step 4: 6-Amino-2-(4-phenoxyphenyl)-4,5,6,7-tetrahydropyrazolo[1,5-a]pyrimidine-3-carboxamide

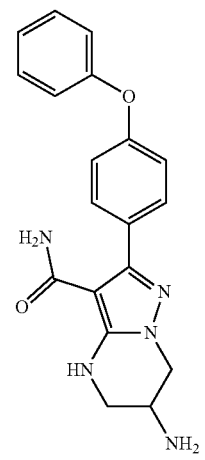 [SMILES: NC(=O)c1c(-c2ccc(Oc3ccccc3)cc2)nn2c1NCC(N)C2]

The desired product was prepared from 6-amino-2-(4-phenoxyphenyl)-4,5,6,7-tetrahydropyrazolo[1,5-a]pyrimidine-3-carbonitrile using the procedure similar to step 2 for compound 2. $^1$H NMR (400 MHz, DMSO-$d_6$) δ 7.53-7.48 (m, 2H), 7.46-7.40 (m, 2H), 7.22-7.16 (m, 1H), 7.11-7.03 (m, 4H), 6.58 (br s, 1H), 4.15-4.08 (m, 1H), 3.72-3.67 (m, 1H), 3.40-3.30 (m, 2H) and 3.06-2.98 (m, 1H). MS (ESI) m/e $[M+1]^+$ 350.2.

Compound 85: 6-Acrylamido-2-(4-phenoxyphenyl)-4,5,6,7-tetrahydropyrazolo[1,5-a]pyrimidine-3-carboxamide

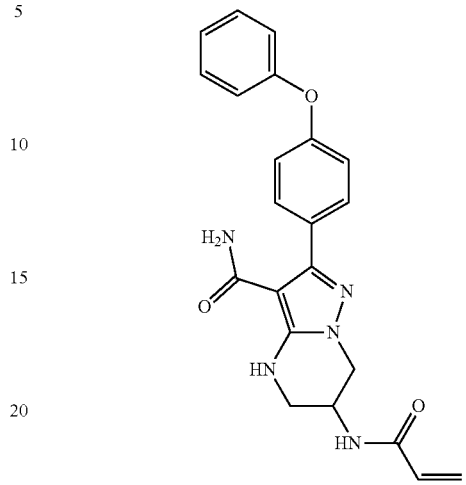

The desired product was prepared from compound 84 and acryloyl chloride using the procedure similar to that for compound 8. $^1$H NMR (400 MHz, DMSO-$d_6$) δ 8.47 (d, J=7.2 Hz, 1H), 7.52 (d. J=8.8 Hz, 2H), 7.46-7.38 (m, 2H), 7.18 (dd, J=7.2, 7.6 Hz, 1H), 7.09 (d. J=8.0 Hz, 2H), 7.05 (d, J=8.8 Hz, 2H), 6.67 (br s, 1H), 6.34 (dd, J=10.0, 17.2 Hz, 1H), 6.15 (dd, J=2.0, 17.2 Hz, 1H), 5.63 (dd, J=2.0, 10.0 Hz, 1H), 4.32-4.40 (m, 1H), 4.22 (dd, J=4.8, 12.4 Hz, 1H), 3.91 (dd, J=4.8, 12.4 Hz, 1H), 3.40 (m, 1H) and 3.26 (dd, J=5.2 Hz, J=12.0 Hz, 1H). MS (ESI) m/e $[M+1]^+$ 404.1.

Example 31: Synthesis of Compound 86

Compound 86: 6-(Acrylamidomethyl)-2-(4-phenoxyphenyl)-4,5,6,7-tetrahydro pyrazolo[1,5-a]pyrimidine-3-carboxamide

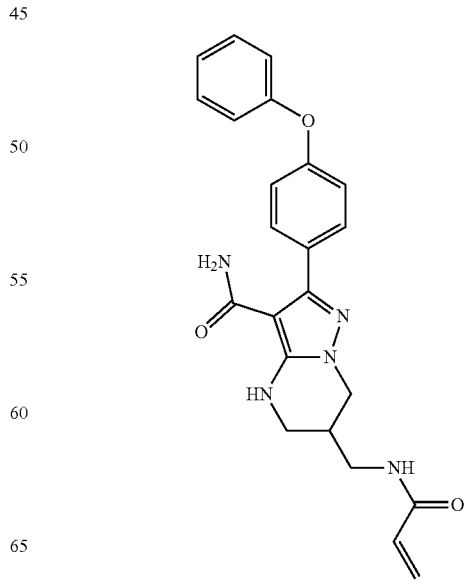

Step 1: Ethyl 3-cyano-2-(4-phenoxyphenyl)pyrazolo[1,5-a]pyrimidine-6-carboxylate

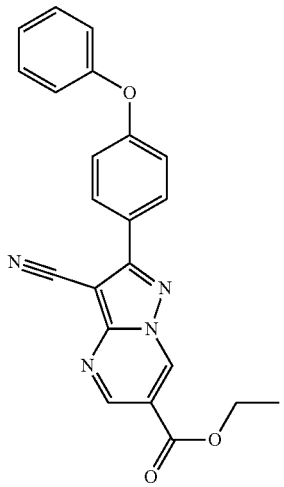 [SMILES: CCOC(=O)c1cnc2c(C#N)c(-c3ccc(Oc4ccccc4)cc3)nn2c1]

To a solution of 5-amino-3-(4-phenoxyphenyl)-1H-pyrazole-4-carbonitrile (276 mg, 1.0 mmol) in EtOH (10 mL) was added ethyl 2-formyl-3-oxopropanoate (144 mg, 1.0 mmol) and HOAc (5 drops). After stirring at RT for 16 hr, the mixture was filtered. The cake was washed with $H_2O$ (10 mL×2) and dried to afford 250 mg (65%) of ethyl 3-cyano-2-(4-phenoxyphenyl)pyrazolo[1,5-a]pyrimidine-6-carboxylate as a yellow solid. MS (ESI) m/e $[M+1]^+$ 384.9.

Step 2: 6-(Hydroxymethyl)-2-(4-phenoxyphenyl)-4,5,6,7-tetrahydropyrazolo[1,5-a]pyrimidine-3-carbonitrile

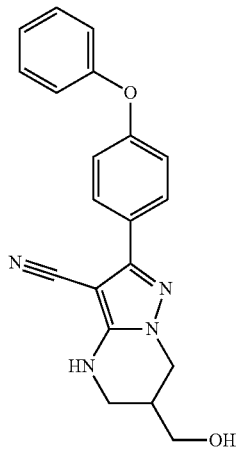 [SMILES: N#Cc1c(-c2ccc(Oc3ccccc3)cc2)nn2c1NCC(CO)C2]

To a solution of ethyl 3-cyano-2-(4-phenoxyphenyl)pyrazolo[1,5-a]pyrimidine-6-carboxylate (250 mg, 0.65 mmol) in DCM (5 mL) and $CH_3OH$ (5 mL) was added $NaBH_4$ (250 mg, 6.5 mmol). After stirring at RT for 16 hr, the mixture was partitioned between $DCM/CH_3OH$ (100 mL/5 mL) and brine (100 mL). The organic layer was separated from aqueous layers, dried over $Na_2SO_4$ and concentrated to afford 250 mg (100%) of 6-(hydroxymethyl)-2-(4-phenoxyphenyl)-4,5,6,7-tetrahydro pyrazolo[1,5-a]pyrimidine-3-carbonitrile. MS (ESI) m/e $[M+1]^+$ 346.9.

Step 3: 6-(Hydroxymethyl)-2-(4-phenoxyphenyl)-4,5,6,7-tetrahydropyrazolo[1,5-a] pyrimidine-3-carboxamide

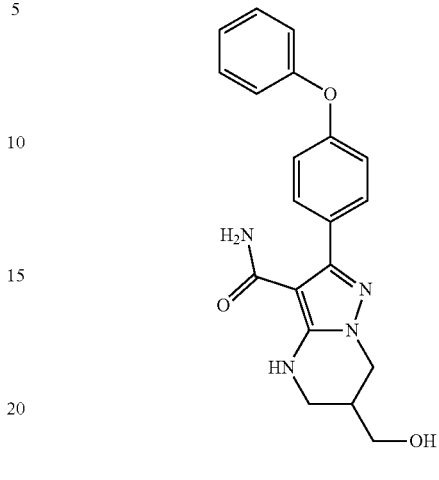

The desired product was prepared form 6-(hydroxymethyl)-2-(4-phenoxyphenyl)-4,5,6,7-tetrahydropyrazolo[1,5-a] pyrimidine-3-carbonitrile using the procedure similar to step 2 for compound 2. MS (ESI) m/e $[M+1]^+$ 364.9.

Step 4: 6-((1,3-Dioxoisoindolin-2-yl)methyl)-2-(4-phenoxyphenyl)-4,5,6,7-tetrahydro pyrazolo[1,5-a]pyrimidine-3-carboxamide

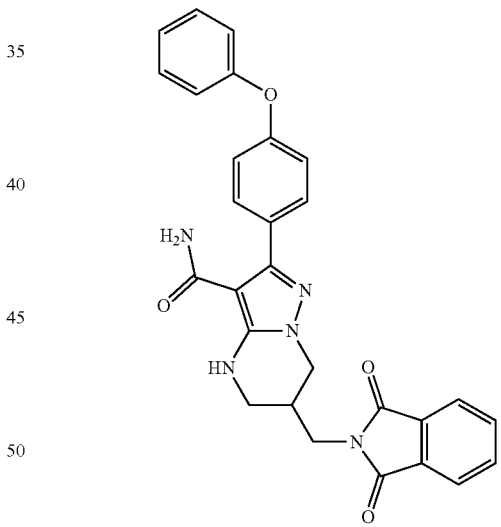

To a solution of isoindoline-1,3-dione (74 mg, 0.5 mmol) in THF (20 mL) was added $PPh_3$ (393 mg, 1.5 mmol) and 6-(hydroxymethyl)-2-(4-phenoxyphenyl)-4,5,6,7-tetrahydropyrazolo[1,5-a]pyrimidine-3-carboxamide (180 mg, 0.5 mmol). DIAD (253 mg, 1.25 mmol) was added dropwise at 0° C. and stirred for 10 min. The mixture was allowed to warm to it and stirred for 16 hr. Concentrated and purified by chromatography column on 5 g of silica gel eluting with $DCM/CH_3OH$ to afford 200 mg (62%) of 6-((1,3-dioxoisoindolin-2-yl)methyl)-2-(4-phenoxyphenyl)-4,5,6,7-tetrahydropyrazolo[1,5-a]pyrimidine-3-carboxamide as a yellow solid. MS (ESI) m/e $[M+1]^+$ 493.9.

Step 5: 6-(Aminomethyl)-2-(4-phenoxyphenyl)-4,5,6,7-tetrahydropyrazolo[1,5-a]pyrimidine-3-carboxamide

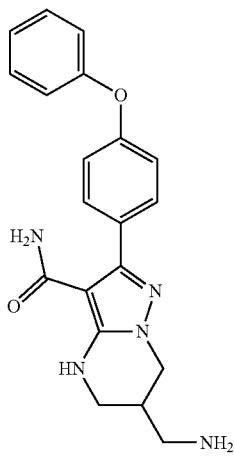 [SMILES: NCC1CNc2c(C(N)=O)c(-c3ccc(Oc4ccccc4)cc3)nn2C1]

To a solution of 6-((1,3-dioxoisoindolin-2-yl)methyl)-2-(4-phenoxyphenyl)-4,5,6,7-tetrahydropyrazolo[1,5-a]pyrimidine-3-carboxamide (200 mg, 0.40 mmol) in CH$_3$OH (5 mL) was added hydrazine hydrate (1 mL, 80% of aqueous solution). The mixture was stirred at 70° C. under N$_2$ for 4 hr, concentrated and purified by chromatography column on 5 g of silica gel eluting with DCM/CH$_3$OH to afford 63 mg (43%) of 6-(aminomethyl)-2-(4-phenoxyphenyl)-4,5,6,7-tetrahydropyrazolo[1,5-a]pyrimidine-3-carboxamide as colorless oil. MS (ESI) m/e [M+1]$^+$ 363.9.

Step 6: 6-(Acrylamidomethyl)-2-(4-phenoxyphenyl)-4,5,6,7-tetrahydropyrazolo [1,5-a]pyrimidine-3-carboxamide

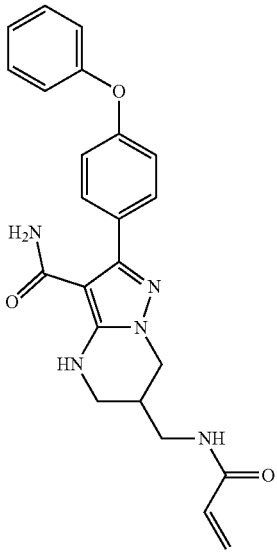 [SMILES: C=CC(=O)NCC1CNc2c(C(N)=O)c(-c3ccc(Oc4ccccc4)cc3)nn2C1]

The desired product was prepared form 6-(aminomethyl)-2-(4-phenoxyphenyl)-4,5,6,7-tetrahydropyrazolo[1,5-a]pyrimidine-3-carboxamide and acryloyl chloride using the procedure similar to that for compound 8. $^1$H NMR (400 MHz, DMSO-d$_6$) δ 8.31 (t, J=5.6 Hz, 1H), 7.51 (d, J=8.8 Hz, 2H), 7.46-7.38 (m, 2H), 7.17 (t, J=7.6 Hz, 1H), 7.08 (d, J=7.6 Hz, 2H), 7.04 (d, J=8.8 Hz, 2H), 6.61 (s, 1H), 6.25 (dd, J=17.1, 10.1 Hz, 1H), 6.11 (dd, J=17.1, 2.2 Hz, 1H), 5.62 (dd, J=10.1, 2.2 Hz, 1H), 4.07 (dd, J=12.4, 6.0 Hz, 1H), 3.73 (dd, J=12.4, 8.0 Hz, 1H), 3.41-3.34 (m, 1H), 3.27-3.21 (m, 2H), 3.09-2.96 (m, 1H), 2.37-2.24 (m, 1H). MS (ESI) m/e [M+1]+ 417.9.

Example 32: Synthesis of Compounds 87-88

Compound 87: 2'-(4-Phenoxyphenyl)-5',7'-dihydro-4'H-spiro[azetidine-3,6'-pyrazolo [1,5-a]pyrimidine]-3'-carboxamide

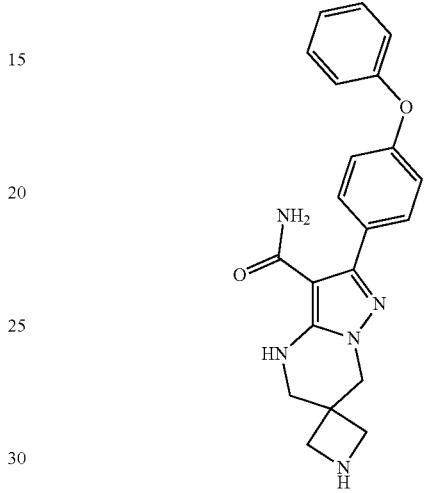

Step 1: Diethyl 1-benzylazetidine-3,3-dicarboxylate

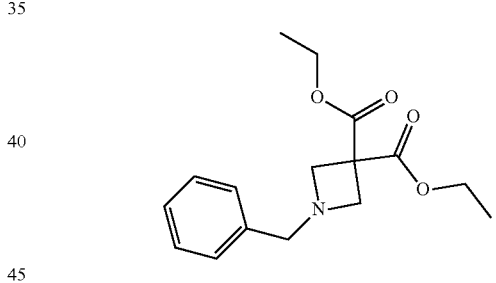

To a solution of diethyl 2,2-bis(hydroxymethyl)malonate (4.4 g, 20 mmol) in CH$_3$CN (50 mL) was added Tf$_2$O (7.1 mL, 11.85 g, 42 mmol) at −20° C., followed by two batches of DIEA (6.45 g, 50 mmol). After 0.5 hr, benzylamine (3.21 g, 35 mmol) was added at −20° C. The mixture was stirred at 70° C. for 2 hr. 100 mL of EA and 100 mL of brine were added. Organic layers were dried over Na$_2$SO$_4$. Purified by chromatography column on silica gel eluting with PE/EA to afford 4.8 g (82%) of diethyl 1-benzylazetidine-3,3-dicarboxylate as a yellow oil. $^1$H NMR (400 MHz, DMSO-d$_6$) δ 7.29-7.34 (m, 2H), 7.22-7.27 (m, 3H), 4.17 (q, J=7.2 Hz, 4H), 3.56 (s, 2H), 3.51 (s, 4H), 2.39 (s, 3H) and 1.17 (t, J=7.2 Hz, 6H).

Step 2: (1-Benzylazetidine-3,3-diyl)dimethanol

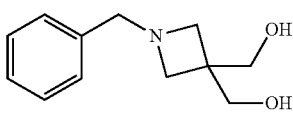 [SMILES: OCC1(CO)CN(Cc2ccccc2)C1]

To a solution of diethyl 1-benzylazetidine-3,3-dicarboxylate (4.8 g, 16.5 mmol) in CH$_3$OH (10 mL) was added NaBH$_4$ (1.25 g, 33 mmol). The mixture was stirred at RT for 1 hr. 100 mL of brine and 200 mL of DCM were added. Organic layers were separated from aqueous layers, dried over Na$_2$SO$_4$, concentrated to afford 2.328 g (68%) of (1-benzylazetidine-3,3-diyl)dimethanol as a yellow oil. $^1$H NMR (400 MHz. DMSO-d$_6$) δ 7.21-7.31 (m, 5H), 4.15-4.05 (m, 2H), 3.48 (d, J=4.8 Hz, 2H), 3.17 (d. J=4.8 Hz, 4H) and 2.89 (s, 2H).

Step 3: (1-Benzylazetidine-3,3-diyl)bis(methylene)dimethanesulfonate

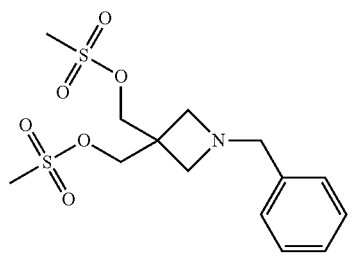 [SMILES: CS(=O)(=O)OCC1(COS(C)(=O)=O)CN(Cc2ccccc2)C1]

To a solution of (1-benzylazetidine-3,3-diyl)dimethanol (50 mg, 0.24 mmol) in DCM (10 mL) was added TEA (222 mg, 2.2 mmoL) and MsCl (249 mg, 2.2 mmol). After stirring for at RT for 4 hr, the mixture was concentrated. The residue was partitioned between brine (100 mL) and EA (100 mL). The organic layer was washed with brine (100 mL×2), dried over Na$_2$SO$_4$ and concentrated to afford 300 mg (83%) of crude (1-benzylazetidine-3,3-diyl)bis(methylene)dimethanesulfonate as a yellow oil. MS (ESI) m/e [M+1]$^+$ 363.9.

Step 4: 1-Benzyl-2'-(4-phenoxyphenyl)-5',7'-dihydro-4'H-spiro[azetidine-3,6'-pyrazolo[1,5-a]pyrimidine]-3'-carbonitrile

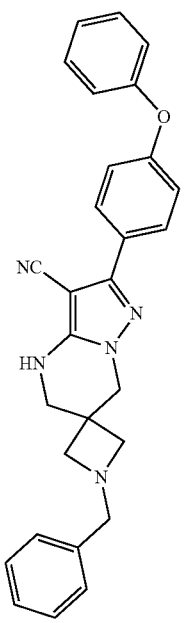 [SMILES: N#Cc1c(-c2ccc(Oc3ccccc3)cc2)nn2c1NCC1(CN(Cc3ccccc3)C1)C2]

To a solution of (1-benzylazetidine-3,3-diyl)bis(methylene)dimethanesulfonate (300 mg, 0.83 mmol) in DMF (10 mL) was added 5-amino-3-(4-phenoxyphenyl)-1H-pyrazole-4-carbonitrile (230 mg, 0.83 mmol) and K$_2$CO$_3$ (230 mg, 1.66 mmol). The mixture was stirred at 80° C. under N$_2$ for 16 hr. The mixture was concentrated. The residue was washed with H$_2$O (100 mL×2), dried and purified by pre-TLC (DCM/CH$_3$OH=10/1) to afford 30 mg (10%) of desired product as a yellow liquid. MS (ESI) m/e [M+1] 447.9.

Step 5: 1-Benzyl-2'-(4-phenoxyphenyl)-5',7'-dihydro-4'H-spiro[azetidine-3,6'-pyrazolo[1,5-a]pyrimidine]-3'-carboxamide

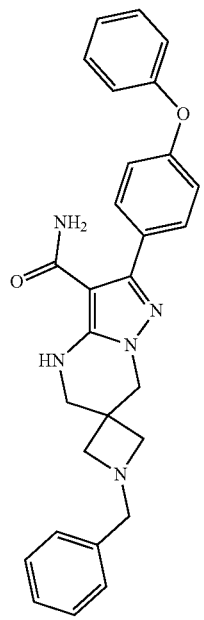 [SMILES: NC(=O)c1c(-c2ccc(Oc3ccccc3)cc2)nn2c1NCC1(CN(Cc3ccccc3)C1)C2]

The desired product was prepared from 1-benzyl-2'-(4-phenoxyphenyl)-5',7'-dihydro-4'H-spiro[azetidine-3,6'-pyrazolo[1,5-a]pyrimidine]-3'-carbonitrile using the procedure similar to step 2 for compound 2. MS (ESI) m/e [M+1]$^+$ 465.9.

Step 6: 2'-(4-Phenoxyphenyl)-5',7'-dihydro-4'H-spiro[azetidine-3,6'-pyrazolo[1,5-a]pyrimidine]-3'-carboxamide

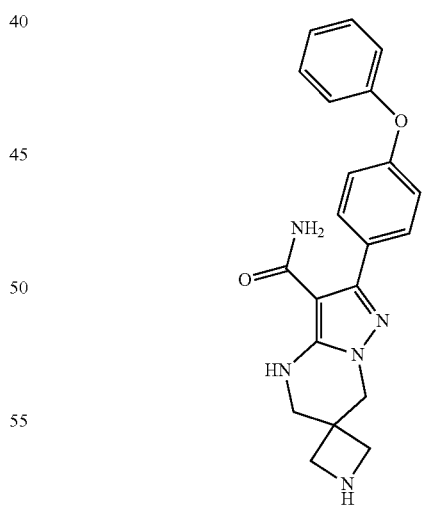

To a solution of 1-benzyl-2'-(4-phenoxyphenyl)-5',7'-dihydro-4'H-spiro[azetidine-3,6'-pyrazolo[1,5-a]pyrimidine]-3'-carboxamide (200 mg, 0.43 mmol) in 10 mL of DCM and 10 mL of CH$_3$OH was added 10% w/w Pd/C (100 mg). After stirring at RT under H$_2$ for 16 hr, the mixture was filtered and concentrated. The residue was purified by pre-HPLC eluting from 25% to 90% CH$_3$CN in 0.1% TFA in H$_2$O. Fractions containing the desired product were combined and lyophilized overnight to afford 30 mg (19%) of desired product as a white solid. ¹H NMR (400 MHz, DMSO-d₆) δ 8.94 (br s, 1H), 8.84 (br s, 1H), 7.50 (d, J=8.4 Hz, 2H), 7.46-7.38 (m, 2H), 7.18 (t, J=8.0 Hz, 1H), 7.08 (d, J=8.0 Hz, 2H), 7.05 (d, J=8.4 Hz, 2H), 6.81 (br s, 1H), 4.23 (s, 2H), 3.90-4.00 (m, 2H), 3.78-3.87 (m, 2H) and 3.47 (s, 2H). MS (ESI) m/e [M+1]⁺ 375.9.

Compound 88: 1-Acryloyl-2'-(4-phenoxyphenyl)-5',7'-dihydro-4'H-spiro[azetidine-3,6'-pyrazolo[1,5-a]pyrimidine]-3'-carboxamide

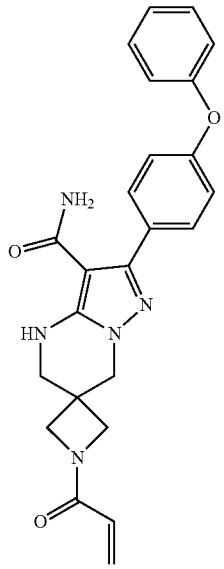 [SMILES: C=CC(=O)N1CC2(CNc3c(C(N)=O)c(-c4ccc(Oc5ccccc5)cc4)nn3C2)C1]

The desired product was prepared from compound 87 and acryloyl chloride using the procedure similar to that for compound 8. ¹H NMR (400 MHz, CD₃OD-d₄) δ 7.49 (d, J=7.6 Hz, 2H), 7.41-7.32 (m, 2H), 7.14 (t, J=8.0 Hz, 1H), 7.05 (d, J=8.0 Hz, 2H), 7.04 (d, J=7.6 Hz, 2H), 6.35 (dd, J=16.8, 10.1 Hz, 1H), 6.25 (dd, J=16.8, 1.6 Hz, 1H), 5.74 (dd, J=10.1, 1.6 Hz, 1H), 4.20-4.27 (m, 4H), 3.92-3.98 (m, 2H) and 3.54 (s, 2H). MS (ESI) m/e [M+1]⁺ 429.9.

Example 33: Synthesis of Compounds 89-90

Compound 89: 6-(2-Aminophenyl)-2-(4-phenoxyphenyl)-4,5,6,7-tetrahydropyrazolo[1,5-a]pyrimidine-3-carboxamide

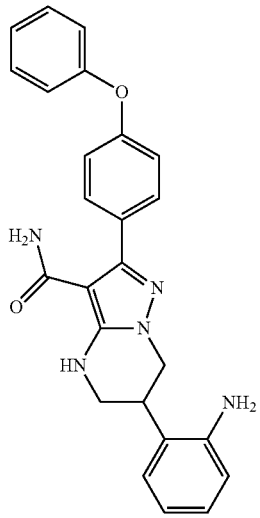 [SMILES: NC(=O)c1c(-c2ccc(Oc3ccccc3)cc2)nn2c1NCC(c1ccccc1N)C2]

Step 1: 6-Bromo-2-(4-phenoxyphenyl)pyrazolo[1,5-a]pyrimidine-3-carbonitrile

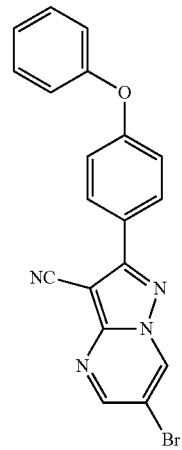 [SMILES: N#Cc1c(-c2ccc(Oc3ccccc3)cc2)nn2cc(Br)cnc12]

A mixture of 5-amino-3-(4-phenoxyphenyl)-1H-pyrazole-4-carbonitrile (28 mg, 0.1 mmol), 2-bromomalonaldehyde (15 mg, 0.1 mmol) in EtOH (5 mL) was stirred at RT for 2 hr. Then, the mixture was filtered to give the crude product (20 mg, 62.9%) as a yellow solid. ¹H NMR (400 MHz, DMSO-d₆) δ 9.89 (d, J=2.0 Hz, 1H), 8.95 (d, J=2.0 Hz, 1H), 8.08 (d, J=8.4 Hz, 2H), 7.52-7.43 (m, 2H), 7.27-7.19 (m, 3H), 7.15 (d, J=7.6 Hz, 2H). MS (ESI, m/e) [M+1]⁺ 391.9.

Step 2: 6-(2-Aminophenyl)-2-(4-phenoxyphenyl)pyrazolo[1,5-a]pyrimidine-3-carbonitrile

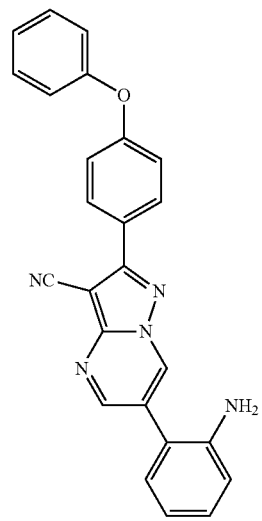 [SMILES: N#Cc1c(-c2ccc(Oc3ccccc3)cc2)nn2cc(-c3ccccc3N)cnc12]

A mixture of 6-bromo-2-(4-phenoxyphenyl)pyrazolo[1,5-a]pyrimidine-3-carbonitrile (500 mg, 1.28 mmol), 2-aminophenylboronic acid (175 mg, 1.28 mmol), Cs₂CO₃ (623 mg, 1.92 mmol) and Pd(PPh₃)₄ (74 mg, 0.06 mmol) in 1,4-dioxane (30 mL) and water (1.0 mL) was heated to 80° C. for 16 hr under N₂. The mixture was filtered and the filtrate was concentrated and purified by chromatography column on silica gel using 50% of EA in PE as eluant to give the crude product (320 mg, 59.1%) as a yellow solid. MS (ESI, m/e) [M+1]⁺ 403.9.

Step 3: 6-(2-Aminophenyl)-2-(4-phenoxyphenyl)-4,5-dihydropyrazolo[1,5-a]pyrimidine-3-carbonitrile

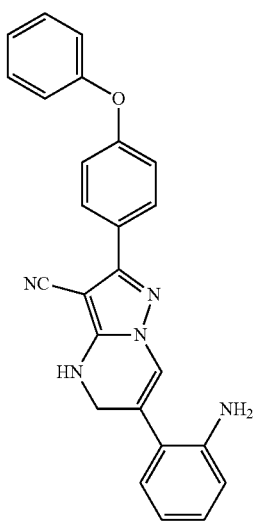

To a solution of 6-(2-aminophenyl)-2-(4-phenoxyphenyl) pyrazolo[1,5-a] pyrimidine-3-carbonitrile (320 mg, 0.79 mmol) in MeOH (20 mL) was added NaBH$_4$ (86 mg, 2.28 mmol). The solution was stirred at rt for 30 min then was poured into water (50 mL) and extracted with EA (50 mL×3). The organic combined layers were dried over Na$_2$SO$_4$ and concentrated to give the crude product (240 mg, 75%) as a yellow solid. MS (ESI, m/e) [M+1]$^+$ 406.0.

Step 4: 6-(2-Aminophenyl)-2-(4-phenoxyphenyl)-4,5,6,7-tetrahydropyrazolo[1,5-a]pyrimidine-3-carbonitrile

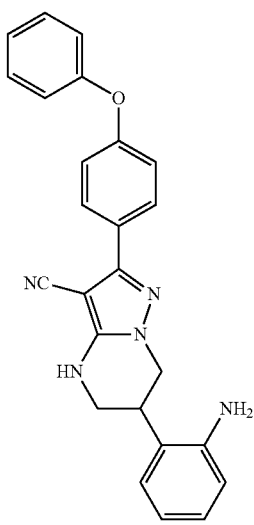 [SMILES: N#Cc1c(-c2ccc(Oc3ccccc3)cc2)nn2c1NCC(c1ccccc1N)C2]

The desired product was prepared from 6-(2-aminophenyl)-2-(4-phenoxyphenyl)-4,5-dihydropyrazolo[1,5-a] pyrimidine-3-carbonitrile using the procedure similar to step 8 for compound 68. MS (ESI, m/e) [M+1]$^+$ 407.9.

Step 5: 6-(2-Aminophenyl)-2-(4-phenoxyphenyl)-4,5,6,7-tetrahydropyrazolo[1,5-a]pyrimidine-3-carboxamide

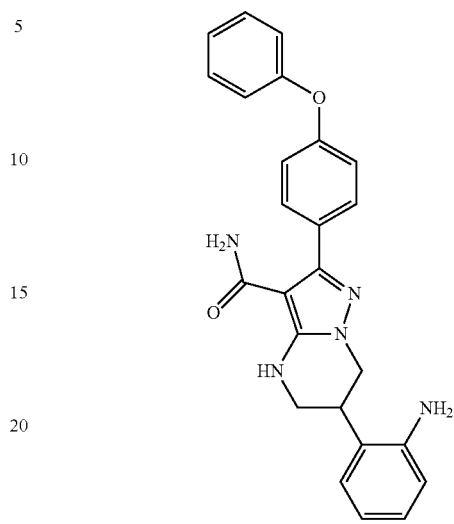

The desired product was prepared from 6-(2-aminophenyl)-2-(4-phenoxyphenyl)-4,5,6,7-tetrahydropyrazolo[1,5-a]pyrimidine-3-carbonitrile using the procedure similar to step 2 for compound 2. $^1$H NMR (400 MHz, DMSO-d$_6$) δ 7.58 (d, J=8.4 Hz, 2H), 7.53-7.44 (m, 2H), 7.24 (t. J=7.6 Hz, 1H), 7.19-7.09 (m, 4H), 7.06-7.99 (m, 2H), 6.84 (d, J=1.6 Hz, 1H), 6.74 (d, J=7.2 Hz, 1H), 6.61 (t, J=7.6 Hz, 1H), 5.20 (s, 2H), 4.24 (dd, J=4.0, 12.0, Hz, 1H), 4.07 (dd, J=12.0, 12.0 Hz, 1H), 3.56-3.41 (m, 3H). MS (ESI, m/e) [M+1]$^+$ 425.9.

Compound 90: 6-(3-Aminophenyl)-2-(4-phenoxyphenyl)-4,5,6,7-tetrahydropyrazolo [1,5-a]pyrimidine-3-carboxamide

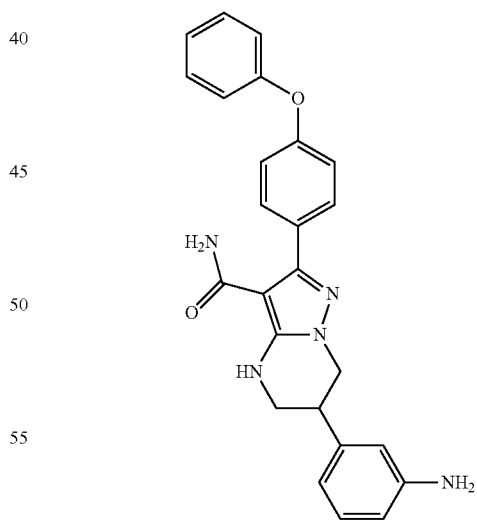

The desired product was prepared from 6-bromo-2-(4-phenoxyphenyl)pyrazolo[1,5-a]pyrimidine-3-carbonitrile and 3-aminophenylboronic acid according to the similar procedures (step 2 to 5) for compound 89 under appropriate conditions recognized by one of ordinary skill in the art. $^1$H NMR (400 MHz, DMSO-d$_6$) δ 7.59 (d, J=8.4 Hz, 2H), 7.52-7.45 (m, 2H), 7.24 (t, J=7.6 Hz, 1H), 7.15 (d, J=8.4 Hz, 2H), 7.12 (d, J=7.6 Hz, 2H), 7.07 (t, J=7.6 Hz, 1H), 6.85 (br s, 1H), 6.62-6.54 (m, 3H), 5.23 (br s, 2H), 4.24 (dd, J=12.0, 4.8 Hz, 1H), 4.09 (t, J=12.0 Hz, 1H), 3.56-3.50 (m, 1H), 3.40-3.35 (m, 1H), 3.28-3.19 (m, 1H). MS (ESI, m/e) [M+1]+ 425.9.

Example 34: Synthesis of Compound 91

Compound 91: 6-(3-(2-(Dimethylamino)ethoxy)phenyl)-2-(4-phenoxyphenyl)-4,5,6,7-tetrahydropyrazolo[1,5-a]pyrimidine-3-carboxamide

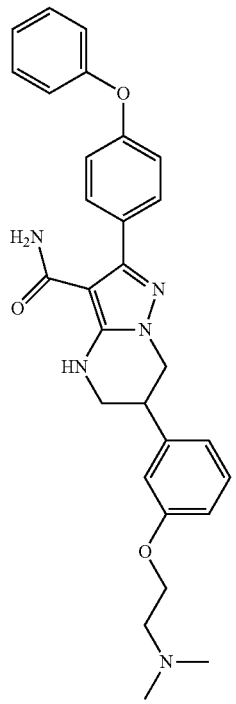 [SMILES: CN(C)CCOc1cccc(C2CNc3c(C(N)=O)c(-c4ccc(Oc5ccccc5)cc4)nn3C2)c1]

Step 1: 6-(3-Hydroxyphenyl)-2-(4-phenoxyphenyl)pyrazolo[1,5-a]pyrimidine-3-carbonitrile

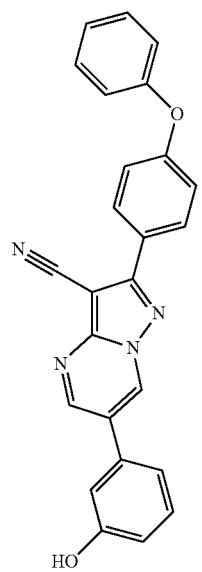 [SMILES: N#Cc1c(-c2ccc(Oc3ccccc3)cc2)nn2cc(-c3cccc(O)c3)cnc12]

To a solution of 6-bromo-2-(4-phenoxyphenyl)pyrazolo[1,5-a]pyrimidine-3-carbonitrile (782 mg, 2.0 mmol) in dioxane (10 mL) and H₂O (10 mL) was added 3-hydroxyphenylboronic acid (276 mg, 2.0 mmol), Pd(PPh₃)₄ (240 mg, 0.2 mmol) and Na₂CO₃ (424 mg, 4.0 mmol). After stirring at 65° C. under N₂ for 16 hr, the mixture was concentrated and 100 mL of DCM, 10 mL of CH₃OH, 100 mL of H₂O were added. Organic layers were separated from aqueous layers and dried over Na₂SO₄ and purified by chromatography column on silica gel eluting with DCM/CH₃OH to afford 500 mg (62%) of 6-(3-hydroxyphenyl)-2-(4-phenoxyphenyl) pyrazolo[1,5-a]pyrimidine-3-carbonitrile as a yellow solid. MS (ESI) m/e [M+1]+ 404.9.

Step 2: 6-(3-Hydroxyphenyl)-2-(4-phenoxyphenyl)-6,7-dihydropyrazolo[1,5-a]pyrimidine-3-carbonitrile and 6-(3-hydroxyphenyl)-2-(4-phenoxyphenyl)-4,5-dihydro pyrazolo[1,5-a] pyrimidine-3-carbonitrile

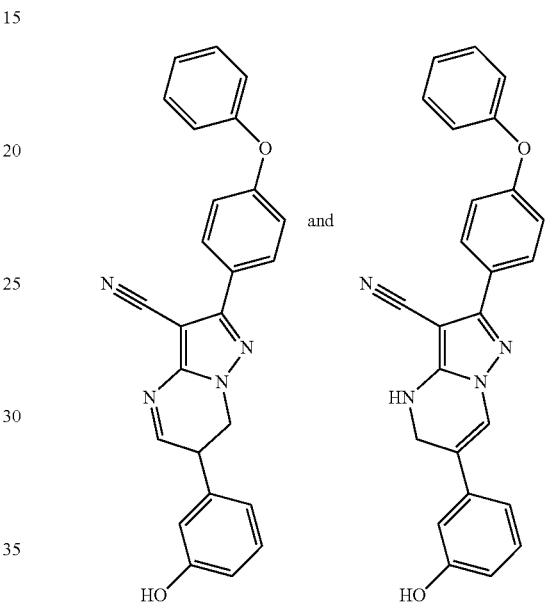

The desired product was prepared from 6-(3-hydroxyphenyl)-2-(4-phenoxyphenyl)pyrazolo[1,5-a]pyrimidine-3-carbonitrile using the procedure similar to step 3 for compound 89. MS (ESI) m/e [M+1]+ 406.9.

Step 3: 6-(3-Hydroxyphenyl)-2-(4-phenoxyphenyl)-4,5,67-tetrahydropyrazolo[1,5-a]pyrimidine-3-carbonitrile

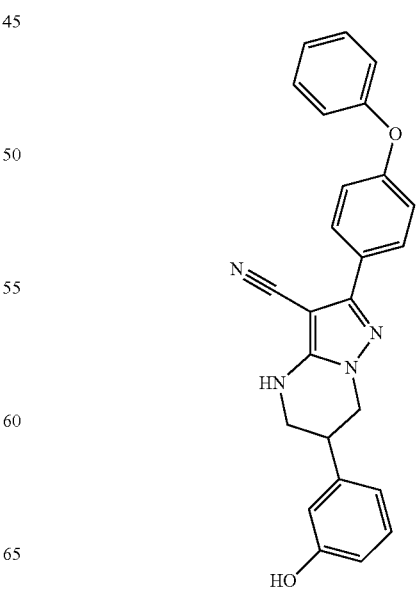

The desired product was prepared from intermediate in the last step using the procedure similar to step 4 for compound 89. MS (ESI) m/e [M+1]⁺ 408.9.

Step 4: 6-(3-Hydroxyphenyl)-2-(4-phenoxyphenyl)-4,5,6,7-tetrahydropyrazolo[1,5-a]pyrimidine-3-carboxamide

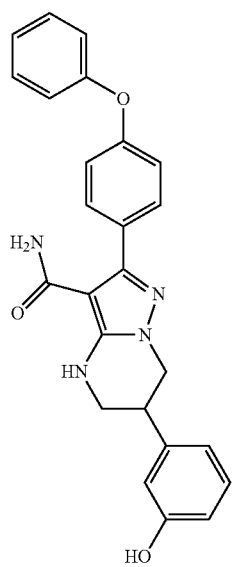 [SMILES: NC(=O)c1c(-c2ccc(Oc3ccccc3)cc2)nn2c1NCC(c1cccc(O)c1)C2]

The desired product was prepared from 6-(3-hydroxyphenyl)-2-(4-phenoxyphenyl)-4,5,6,7-tetrahydropyrazolo[1,5-a] pyrimidine-3-carbonitrile using the procedure similar to step 2 for compound 2. MS (ESI) m/e [M+1]⁺ 426.9.

Step 5: 6-(3-(2-(Dimethylamino)ethoxy)phenyl)-2-(4-phenoxyphenyl)-4,5,6,7-tetra hydropyrazolo[1,5-a]pyrimidine-3-carboxamide

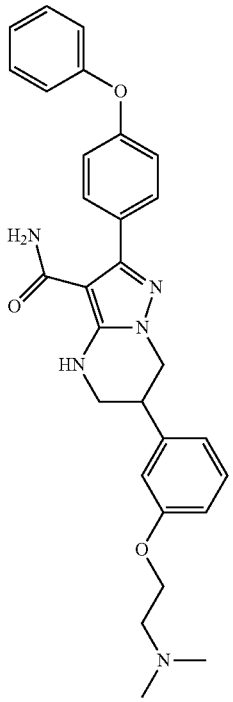

The desired product was prepared from 6-(3-hydroxyphenyl)-2-(4-phenoxyphenyl)-4,5,6,7-tetrahydropyrazolo[1,5-a] pyrimidine-3-carboxamide and 2-chloro-N,N-dimethylethanamine hydrochloride using the procedure similar to step 7 for compound 9. ¹H NMR (400 MHz, DMSO-d₆) δ 7.52 (d, J=8.4 Hz, 2H), 7.46-7.38 (m, 2H), 7.29 (t, J=7.6 Hz, 1H), 7.18 (t, J=7.6 Hz, 1H), 7.10-7.05 (m, 4H), 6.98-6.96 (m, 2H), 6.90-6.88 (m, 1H), 6.81 (d, J=2.4 Hz, 1H), 4.25-4.20 (m, 1H), 4.16-4.11 (m, 3H), 3.50-3.47 (m, 1H), 3.43-3.38 (m, 2H), 2.96-2.84 (m, 2H) and 2.43 (s, 6H). MS (ESI) m/e [M+1]⁺ 497.9.

Compound 178: N1-(2-(4-((E)-4-(4-((S)-3-carbamoyl-2-(4-phenoxyphenyl)-4,5,6,7-tetrahydropyrazolo[1,5-a]pyrimidin-7-yl)piperidin-1-yl)-4-oxobut-2-en-1-yl)piperazin-1-yl)ethyl)-N5-(15-oxo-19-((3aR,4R,6aS)-2-oxohexahydro-1H-thieno[3,4-d]imidazol-4-yl)-4,7,10-trioxa-14-azanonadecyl) glutaramide trifluoroacetate

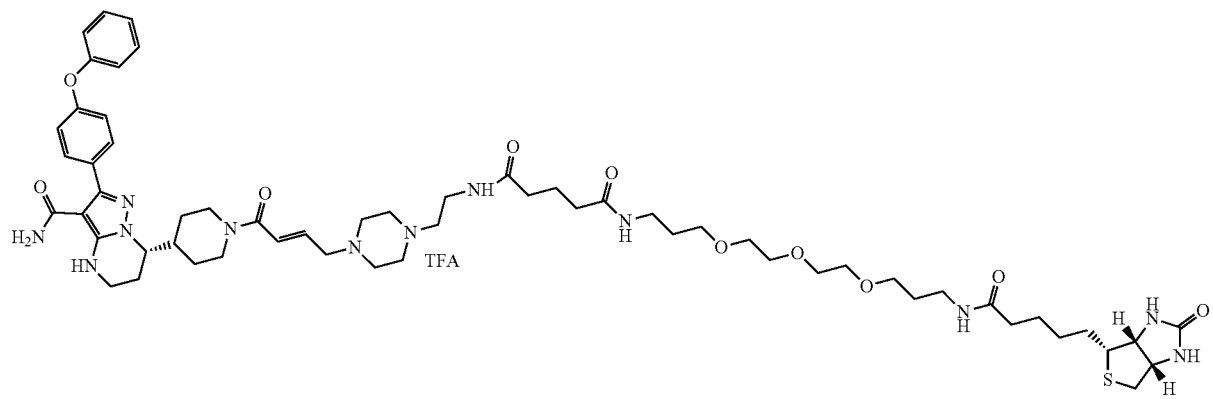 [SMILES: NC(=O)c1c(-c2ccc(Oc3ccccc3)cc2)nn2c1NCC[C@H]2C1CCN(C(=O)/C=C/CN2CCN(CCNC(=O)CCCC(=O)NCCCOCCOCCOCCCNC(=O)CCCC[C@H]3SC[C@H]4NC(=O)N[C@H]43)CC2)CC1]

The desired compound was prepared according to the scheme, step and intermediates described below.
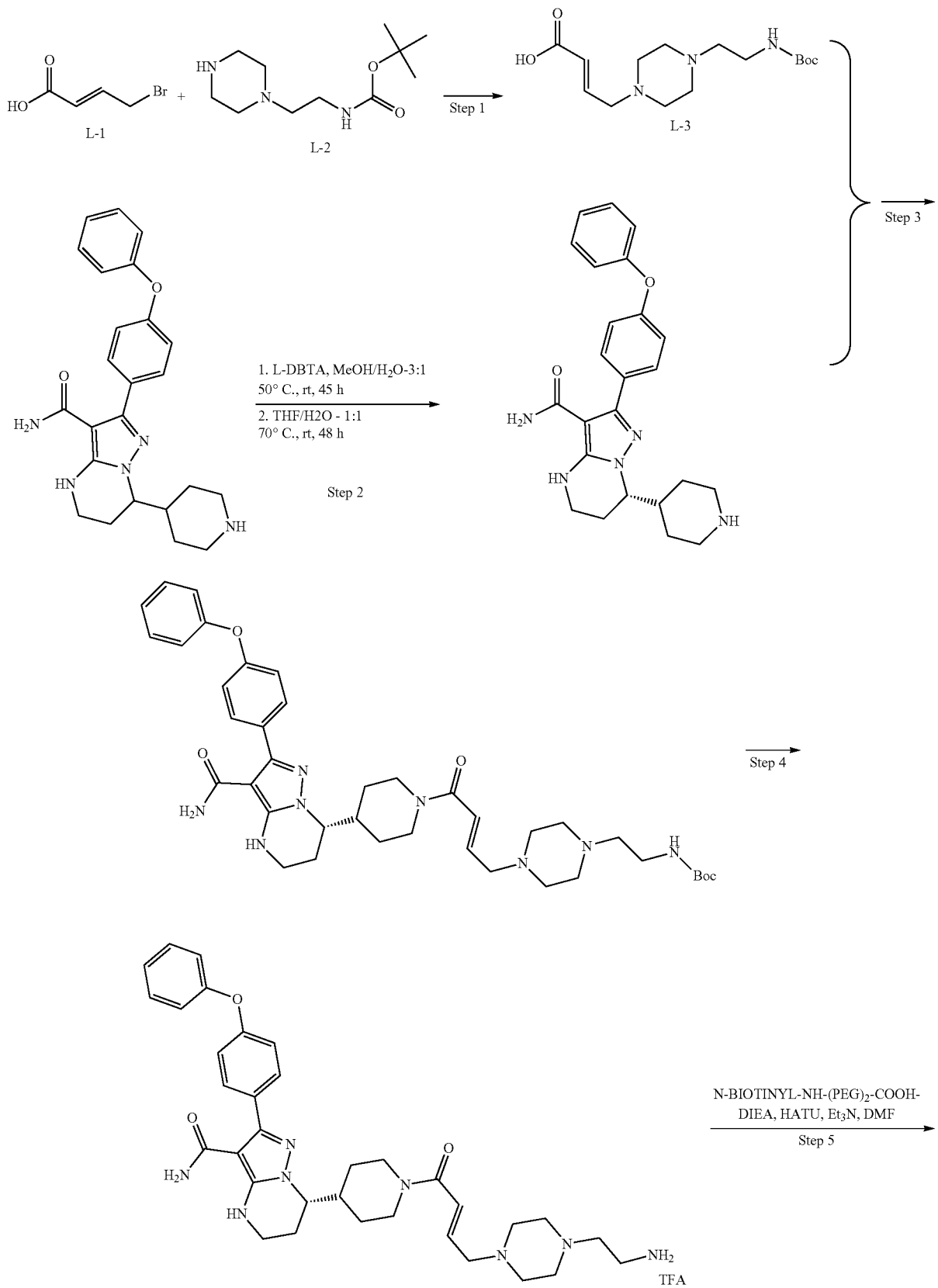

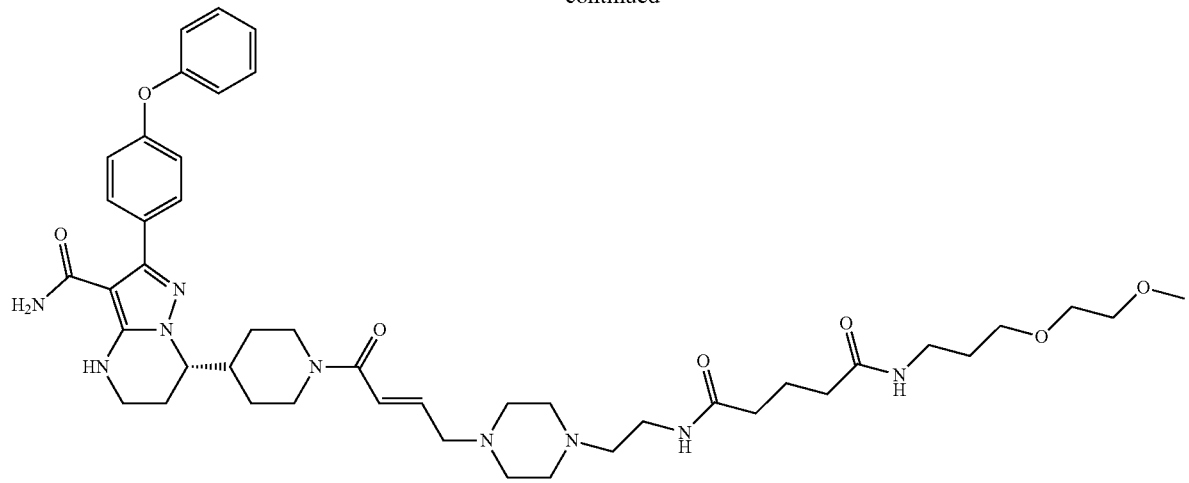

TFA

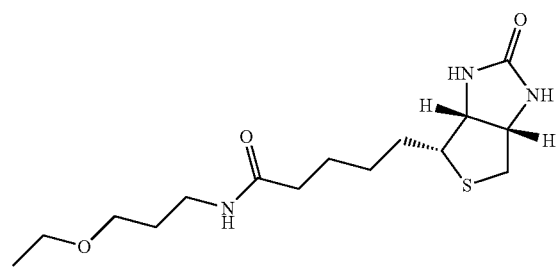

Step 1: (E)-4-(4-(2-((tert-butoxycarbonyl)amino)ethyl)piperazin-1-yl)but-2-enoic acid

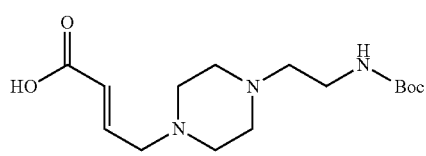 [SMILES: CC(C)(C)OC(=O)NCCN1CCN(C/C=C/C(=O)O)CC1]

A mixture of (E)-4-bromobut-2-enoic acid (500 mg, 3.03 mmol), tert-butyl (2-(piperazin-1-yl)ethyl)carbamate (694 mg, 3.03 mmol) and Et₃N (612 mg, 6.06 mmol) in 20 mL of THF was stirred at RT for 15 h. The mixture was concentrated and used in the next step without further purification. MS (ESI) m/e [M+1]⁺ 314.0.

Step 2: (S)-2-(4-phenoxyphenyl)-7-(piperidin-4-yl)-4,5,6,7-tetrahydropyrazolo[1,5-a]pyrimidine-3-carboxamide

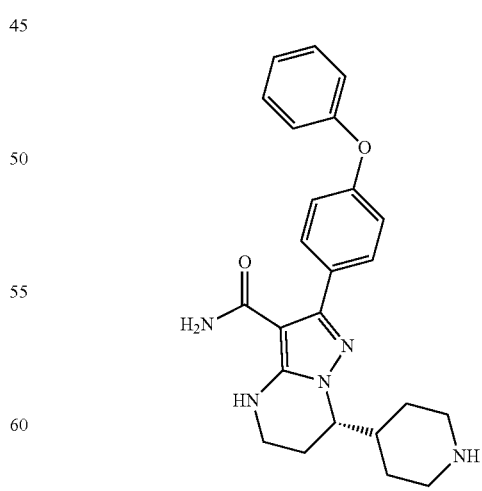

A solution of 2-(4-phenoxyphenyl)-7-(piperidin-4-yl)-4,5,6,7-tetrahydropyrazolo [1,5-a]pyrimidine-3-carboxamide (2.0 g, 4.8 mmol) in MeOH/H₂O=3/1 (110 mL) was warmed to 50° C. and stirred for about 20 min until all starting material dissolved, then to solution was added a solution of L-DBTA (600 mg, 1.6 mmol) in MeOH/H$_2$O=3/1 (10 mL), the solution was stirred at 50° C. for about 30 min. then slowly cooled to 40° C. (about 2 h). To the solution was added crystal seed (10 mg). The mixture was stirred at 40° C. for 2 h, then slowly cooled to ambient temperature and stirred for about 48 h. Filtered, the solid was washed with MeOH/H$_2$O=3/1 (5 mL), dried under reduced pressure to give the product as a white solid about 1.1 g (38% yield, 93% ee value). The solid (500 mg) was added to the solvent of THF/H$_2$O=1/1 (20 mL), the solution was warmed to 70° C. and stirred for about 1 h until all solid dissolved, then slowly cooled to 40° C. (3 h) and added crystal seed (10 mg), after stirring for about 2 h, the solution was slowly cooled to ambient temperature and stirred for about 48 h. Filtered, solid was washed with water (4 mL), dried under reduced pressure to give the product as a white solid about 330 mg (65% yield, >99.5% ee value) as its L-DBTA salt. Suitable single crystal of this L-DBTA salt was obtained by slow cooling in MeOH/H$_2$O (1:1, v/v). Configuration of chiral carbon in freebase was determined to be S. The DBTA salt was converted to the free base by using aqueous NaOH solution and extracting with DCM.

The chiral analysis conditions for the chiral resolution are shown below.

| Column | CHIRALPAK IC |
| --- | --- |
| Column size | 0.46 cm I.D. × 15 cm L, 5 um |
| Injection | 2 uL |
| Mobile phase | n-Hexane/EtOH(0.1% triethylamine) = 50/50 (v/v) |
| Flow rate | 1.0 mL/min |
| Wave length | UV 214, 254 nm |

Step 3: (S,E)-tert-butyl (2-(4-(4-(4-(3-carbamoyl-2-(4-phenoxyphenyl)-4,5,6,7-tetrahydropyrazolo[1,5-a]pyrimidin-7-yl)piperidin-1-yl)-4-oxobut-2-en-1-yl)piperazin-1-yl)ethyl)carbamate

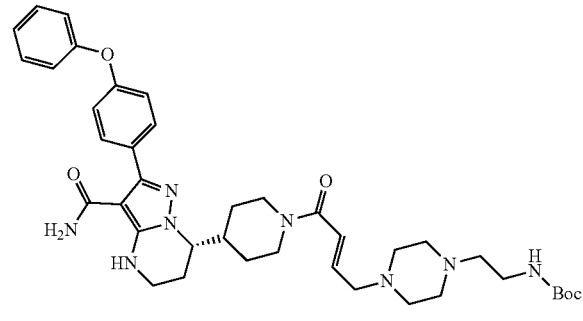 [SMILES: CC(C)(C)OC(=O)NCCN1CCN(C/C=C/C(=O)N2CCC([C@@H]3CCNc4c(C(N)=O)c(-c5ccc(Oc6ccccc6)cc5)nn43)CC2)CC1]

A mixture of (S)-2-(4-phenoxyphenyl)-7-(piperidin-4-yl)-4,5,6,7-tetrahydropyrazolo[1,5-a]pyrimidine-3-carboxamide (1.26 g, 3.03 mmol), (E)-4-(4-(2-((tert-butoxycarbonyl)amino)ethyl)piperazin-1-yl)but-2-enoic acid (948.4 mg, 3.03 mmol), HATU (1.21 g, 3.18 mmol), DIEA (782 mg, 6.06 mmol) in 30 mL of DMF was stirred at RT for 15 hr. The mixture was poured into 300 mL of water and extracted with EA (100 mL). The organic phase was washed with water (100 mL×3) and concentrated to give 1.25 g (58%) of product as a yellow solid. $^1$H NMR (400 MHz, DMSO-d$_6$) δ 7.50 (d, J=8.4 Hz, 2H), 7.42 (t, J=8.4 Hz, 2H), 7.17 (t, J=7.4 Hz, 1H), 7.12-7.02 (m, 4H), 6.67 (br s, 1H), 6.64-6.53 (m, 3H), 4.53-4.40 (m, 1H), 4.14-4.05 (m, 1H), 3.32-3.25 (m, 2H), 3.10-2.91 (m, 5H), 2.45-2.15 (m, 11H), 2.10-2.00 (m, 1H), 1.96-1.84 (m, 1H), 1.78-1.65 (m, 1H), 1.62-1.50 (m, 1H), 1.37 (s, 9H), 1.31-1.10 (m, 3H). MS (ESI) m/e [M+1]$^+$ 713.0.

Step 4: (S,E)-7-(1-(4-(4-(2-aminoethyl)piperazin-1-yl)but-2-enoyl)piperidin-4-yl)-2-(4-phenoxyphenyl)-4,5,6,7-tetrahydropyrazolo[1,5-a]pyrimidine-3-carboxamide trifluoroacetate

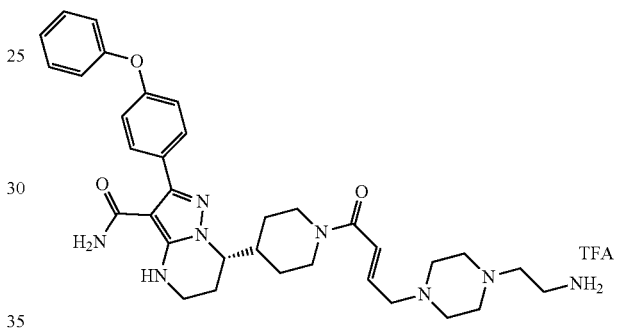

To a solution of (S,E)-tert-butyl (2-(4-(4-(4-(3-carbamoyl-2-(4-phenoxyphenyl)-4,5,6,7-tetrahydropyrazolo[1,5-a]pyrimidin-7-yl)piperidin-1-yl)-4-oxobut-2-en-1-yl)piperazin-1-yl)ethyl)carbamate (150 mg, 0.21 mmol) in 10 mL of DCM was added 2 mL of TFA. The reaction mixture was stirred at RT for 15 hr and concentrated to remove the solvent. The residue was used in the next step without further purification. MS (ESI) m/e [M+1]$^+$ 613.0.

Compound 178: N1-(2-(4-((E)-4-(4-((S)-3-carbamoyl-2-(4-phenoxyphenyl)-4,5,6,7-tetrahydropyrazolo[1,5-a]pyrimidin-7-yl)piperidin-1-yl)-4-oxobut-2-en-1-yl)piperazin-1-yl)ethyl)-N5-(15-oxo-19-((3aR,4R,6aS)-2-oxohexahydro-1H-thieno[3,4-d]imidazol-4-yl)-4,7,10-trioxa-14-azanonadecyl)glutaramide trifluoroacetate

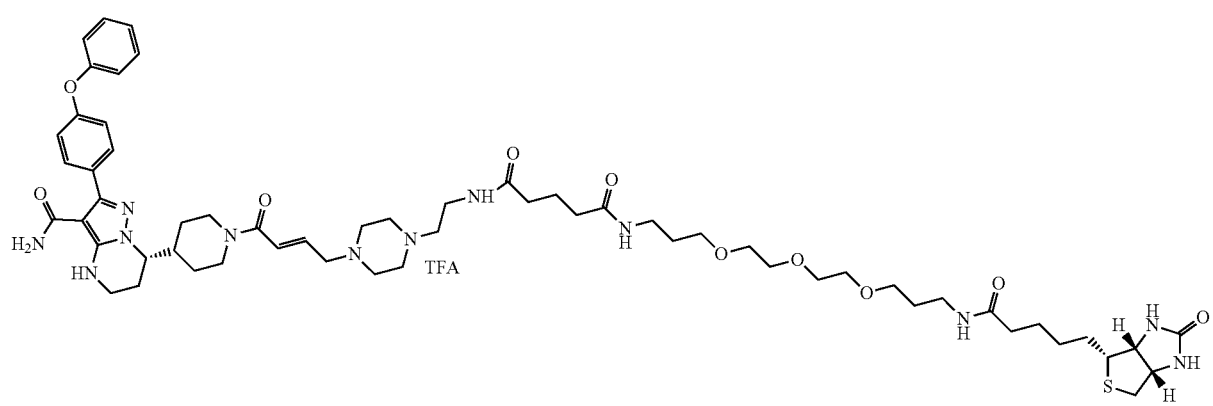 [SMILES: NC(=O)c1c(-c2ccc(Oc3ccccc3)cc2)nn2c1NCC[C@H]2C1CCN(C(=O)/C=C/CN2CCN(CCNC(=O)CCCC(=O)NCCCOCCOCCOCCCNC(=O)CCCC[C@H]3SC[C@H]4NC(=O)N[C@H]43)CC2)CC1]

A mixture of (S,E)-7-(1-(4-(4-(2-aminoethyl)piperazin-1-yl)but-2-enoyl)piperidin-4-yl)-2-(4-phenoxyphenyl)-4,5,6,7-tetrahydropyrazolo[1,5-a]pyrimidine-3-carboxamide trifluoroacetate (129 mg, 0.21 mmol, crude), N—BIOTINYL—NH—(PEG)2—COOH-DIEA (118 mg, 0.21 mmol), HATU (80 mg, 0.21 mmol), TEA (63.6 mg, 0.63 mmol) in 5 mL of DMF was stirred at 40° C. for 15 hr. The mixture was concentrated and purified by Pre-HPLC to afford 160 mg (60%) of product as a white solid. $^1$H NMR (400 MHz, DMSO-$d_6$) δ 8.04 (t. J=5.2 Hz, 1H), 7.80 (t, J=5.6 Hz, 1H), 7.76 (t, J=5.6 Hz, 1H), 7.50 (d, J=8.5 Hz, 2H), 7.42 (t, J=8.5 Hz, 2H), 7.18 (t, J=7.6 Hz, 1H), 7.12-7.03 (m, 4H), 6.89-6.77 (m, 1H), 6.62-6.51 (m, 1H), 6.44 (s, 1H), 4.55-4.40 (m, 1H), 4.35-4.27 (m, 1H), 4.17-3.95 (m, 3H), 3.74-3.60 (m, 2H), 3.55-3.44 (m, 9H), 3.41-3.27 (m, 10H), 3.14-3.02 (m, 9H), 2.82 (dd. J=12.4, 5.0 Hz, 1H), 2.65-2.53 (m, 3H), 2.36-2.18 (m, 1H), 2.13-2.00 (m, 7H), 1.96-1.85 (m, 1H), 1.80-1.67 (m, 3H), 1.66-1.55 (m, 6H), 1.55-1.40 (m, 3H), 1.38-1.21 (m, 4H). MS (ESI) m/e [M+1]$^+$ 1155.0, [M+23]$^+$ 1176.9.

Compound 181: (S)-7-(1-(2-cyano-3-cyclopropylacryloyl)piperidin-4-yl)-2-(4-phenoxyphenyl)-4,5,6,7-tetrahydropyrazolo[1,5-a]pyrimidine-3-carboxamide

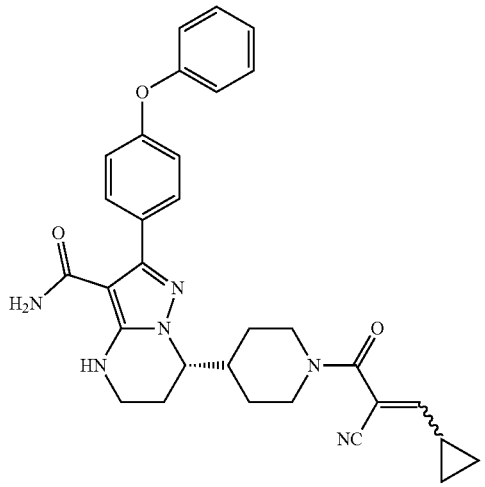 [SMILES: N#CC(=CC1CC1)C(=O)N1CCC([C@@H]2CCNc3c(C(N)=O)c(-c4ccc(Oc5ccccc5)cc4)nn32)CC1]

A mixture of compound 180 (60 mg, 0.124 mmol), cyclopropanecarbaldehyde (43.4 mg, 0.62 mmol) and piperdine (52.7 mg, 0.62 mmol) in MeOH (10 mL) was stirred at RT for 15 h. After concentration, to the residue was added EA (50 mL) and water (50 mL). The organic phase was concentrated and purified by chromatography column on silica gel eluting with DCM/MeOH (50/1) to afford 30 mg (45%) of desired compound as a white solid. MS (ESI) m/e [M+1]$^+$ 537.0.

Compound 182: (S)-7-(1-cyanopiperidin-4-yl)-2-(4-phenoxyphenyl)-4,5,6,7-tetra hydropyrazolo[1,5-a]pyrimidine-3-carboxamide

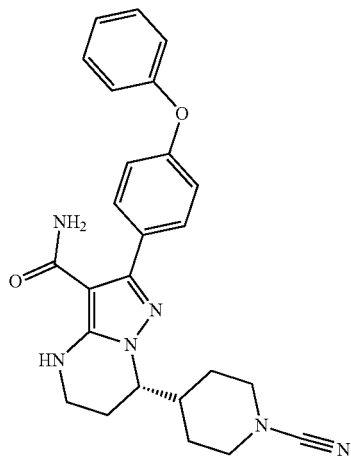 [SMILES: N#CN1CCC([C@@H]2CCNc3c(C(N)=O)c(-c4ccc(Oc5ccccc5)cc4)nn32)CC1]

To a solution of (S)-2-(4-phenoxyphenyl)-7-(piperidin-4-yl)-4,5,6,7-tetrahydropyrazolo[1,5-a]pyrimidine-3-carboxamide (417 mg, 1 mmol) in DCM (20 mL) was added NaHCO$_3$ (168 mg, 2 mmol) and water (5 mL), followed by BrCN (127 mg, 1.2 mmol). The mixture was stirred at RT for 16 h. To the mixture was added DCM (50 mL) and brine (20 mL). The organic phase was further washed with brine (100 mL), dried over Na$_2$SO$_4$. Concentrated and purified by Pre-TLC (DCM/MeOH, 50/1) to afford 330 mg (75%) of white solid. MS (ESI) m/e [M+1]$^+$ 443.0.

A variety of other compounds have been prepared by methods substantially similar to those of above described Examples. The characterization data for some of these compounds are summarized in Table 1 below and include LC/MS (observed), chiral HPLC and $^1$H NMR data.

TABLE 1

Characterization Data for Selected Compounds

| No. | Name | ¹H NMR data, Chiral HPLC and LC/MS m/z (M + 1) | Structure |
|-----|------|------------------------------------------------|-----------|
| 92 | (E)-7-(2-(4-(dimethylamino)but-2-enamido)phenyl)-2-(4-phenoxyphenyl)-4,5,6,7-tetrahydropyrazolo[1,5-a]pyrimidine-3-carboxamide | ¹H NMR (DMSO-$d_6$) δ 9.74 (s, 1H), 7.52-7.44 (m, 3H), 7.44-7.36 (m, 2H), 7.29 (t, J = 7.6 Hz, 1H), 7.21-7.04 (m, 2H), 7.11-6.97 (m, 4H), 6.88-6.67 (m, 2H), 6.64 (d, J = 7.6 Hz, 1H), 6.37 (d, J = 15.1 Hz, 1H), 5.81-5.74 (m, 1H), 3.32-3.22 (m, 1H), 3.07 (d, J = 5.6 Hz, 2H), 3.03-2.93 (m, 1H), 2.38-2.26 (m, 1H), 2.19 (s, 6H), 2.05-1.95 (m, 1H). MS (ESI) m/e [M + 1]⁺ 536.9. | 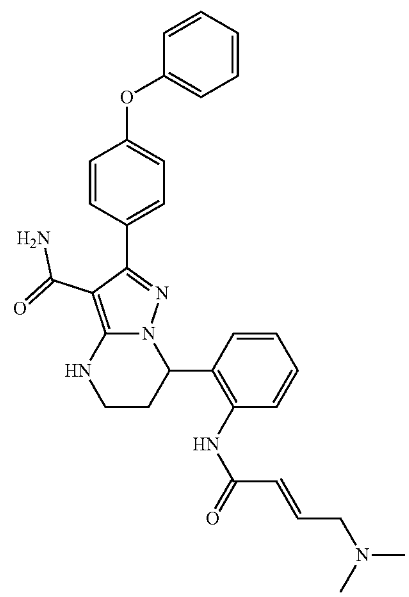 [SMILES: CN(C)C/C=C/C(=O)Nc1ccccc1C1CCNc2c(C(N)=O)c(-c3ccc(Oc4ccccc4)cc3)nn21] |
| 93 | 7-(2-Aminophenyl)-2-(4-methoxyphenyl)-4,5,6,7-tetrahydropyrazolo[1,5-a]pyrimidine-3-carboxamide | ¹H NMR (DMSO-$d_6$) δ 7.40 (d, J = 8.8 Hz, 2H), 6.98 (d, J = 8.8 Hz, 2H), 6.94 (d, J = 8.0 Hz, 1H), 6.75 (s, 1H), 6.67 (d, J = 8.0 Hz, 1H), 6.49 (t, J = 7.6 Hz, 1H), 6.27 (d, J = 7.6 Hz, 1H), 5.57 (s, 1H), 5.16 (s, 2H), 3.78 (s, 3H), 3.28-3.21 (m, 1H), 2.99-2.91 (m, 1H), 2.26-2.04 (m, 2H). MS (ESI) m/e [M + 1]⁺ 363.9. | 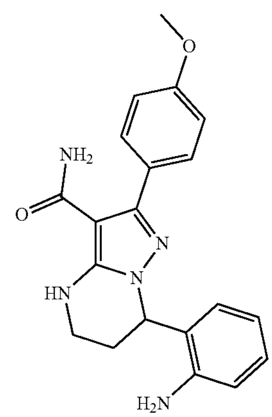 [SMILES: COc1ccc(-c2nn3c(c2C(N)=O)NCCC3c2ccccc2N)cc1] |
| 94 | 7-(2-acrylamidophenyl)-2-(4-methoxyphenyl)-4,5,6,7-tetrahydropyrazolo[1,5-a]pyrimidine-3-carboxamide | ¹H NMR (DMSO-$d_6$) δ 9.84 (s, 1H), 7.45 (d, J = 8.0 Hz, 1H), 7.40 (d, J = 8.8 Hz, 2H), 7.30 (t, J = 7.6 Hz, 1H), 7.21 (t, J = 7.6 Hz, 1H), 6.98 (d, J = 8.8 Hz, 2H), 6.82 (s, 1H), 6.64 (d, J = 8.0 Hz, 1H), 6.53 (dd, J = 17.0, 10.2 Hz, 1H), 6.27 (dd, J = 17.0, 1.8 Hz, 1H), 5.82-5.74 (m, 2H), 3.77 (s, 3H), 3.31-3.19 (m, 1H), 3.03-2.91 (m, 1H), 2.38-2.24 (m, 1H), 2.02-1.92 (m, 1H). MS (ESI) m/e [M + 1]⁺ 417.9. | 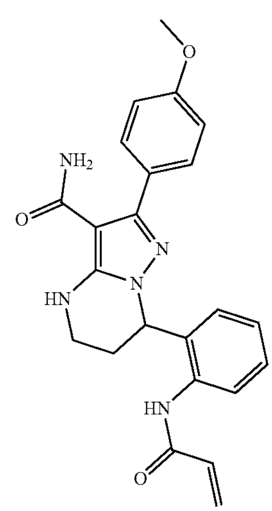 [SMILES: C=CC(=O)Nc1ccccc1C1CCNc2c(C(N)=O)c(-c3ccc(OC)cc3)nn21] |

TABLE 1-continued

Characterization Data for Selected Compounds

| No. | Name | ¹H NMR data, Chiral HPLC and LC/MS m/z (M + 1) | Structure |
|---|---|---|---|
| 95 | 7-(5-amino-2-chlorophenyl)-2-(4-phenoxyphenyl)-4,5,6,7-tetrahydropyrazolo[1,5-a]pyrimidine-3-carboxamide | ¹H NMR (CD$_3$OD-d$_4$) δ 7.52-7.44 (m, 2H), 7.40-7.31 (m, 2H), 7.19-7.06 (m, 2H), 7.06-6.98 (m, 4H), 6.58 (dd, J = 8.4, 2.6 Hz, 1H), 6.10 (d, J = 2.6 Hz, 1H), 5.71 (dd, J = 2.0, 5.2 Hz, 1H), 3.37 (dt, J = 12.4, 3.6 Hz, 1H), 3.21 (td, J = 12.4, 3.6 Hz, 1H), 2.50-2.40 (m, 1H), 2.30-2.23 (m, 1H). MS (ESI) m/e [M + 1]$^+$ 460.1. | 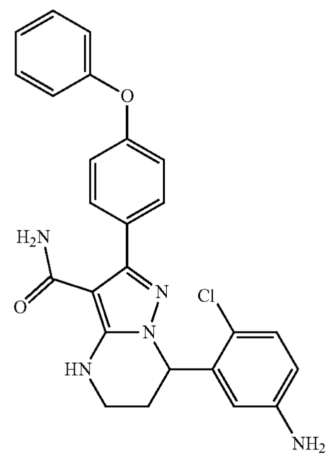 [SMILES: NC(=O)c1c(-c2ccc(Oc3ccccc3)cc2)nn2c1NCCC2c1cc(N)ccc1Cl] |
| 96 | 7-(5-acrylamido-2-chlorophenyl)-2-(4-phenoxyphenyl)-4,5,6,7-tetrahydropyrazolo[1,5-a]pyrimidine-3-carboxamide | ¹H NMR (DMSO-d$_6$) δ 10.32 (s, 1H), 8.14 (s, 1H), 7.88 (dd, J = 8.4, 2.0 Hz, 1H), 7.51-7.46 (m, 3H), 7.40 (t, 2H, J = 7.6, 7.6 Hz), 7.16 (t, J = 7.6 Hz, 1H), 7.07-7.01 (m, 5H), 6.95 (br s, 1H), 6.37 (dd, J = 17.0, 10.0 Hz, 1H), 6.23 (dd, J = 17.0, 1.4 Hz, 1H), 5.74 (dd, J = 10.0, 1.4 Hz, 1H), 5.68-5.64 (m, 1H), 3.12-3.02 (m, 1H), 2.46-2.39 (m, 2H), 2.10-2.05 (m, 1H). MS (ESI) m/e [M + 1]$^+$ 513.9. | 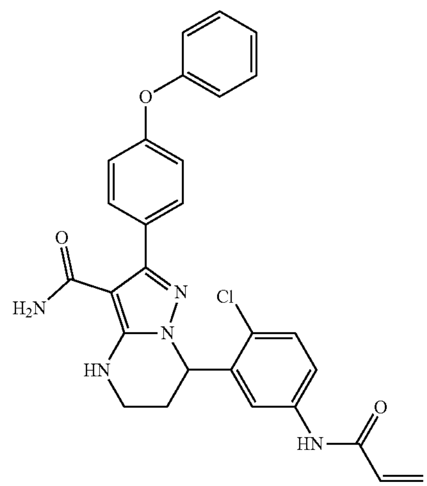 [SMILES: C=CC(=O)Nc1ccc(Cl)c(C2CCNc3c(C(N)=O)c(-c4ccc(Oc5ccccc5)cc4)nn32)c1] |
| 97 | 7-(3-acrylamido-4-chlorophenyl)-2-(4-phenoxyphenyl)-4,5,6,7-tetrahydropyrazolo[1,5-a]pyrimidine-3-carboxamide | ¹H NMR (DMSO-d$_6$) δ 9.77 (s, 1H), 7.57 (s, 1H), 7.53-7.46 (m, 3H), 7.44-7.35 (m, 2H), 7.16 (t, J = 7.6 Hz, 1H), 7.08-7.00 (m, 4H), 6.91 (d, J = 7.6 Hz, 1H), 6.83 (br s, 1H), 6.59 (dd, J = 17.1, 10.0 Hz, 1H), 6.27 (d, J = 17.1 Hz, 1H), 5.78 (d, J = 10.0 Hz, 1H), 5.50-5.45 (m, 1H), 3.33 (m, 1H), 3.13-3.03 (m, 1H), 2.42-2.31 (m, 1H), 2.14-2.04 (m, 1H). MS (ESI) m/e [M + 1]$^+$ 513.9. | 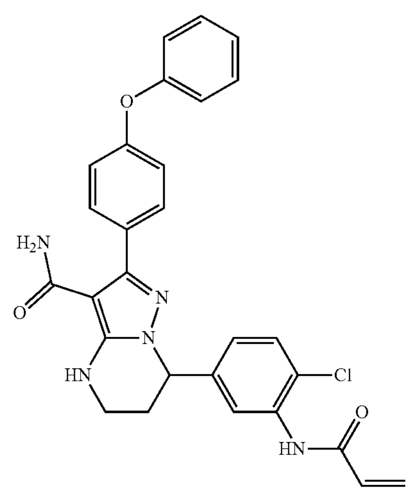 [SMILES: C=CC(=O)Nc1cc(C2CCNc3c(C(N)=O)c(-c4ccc(Oc5ccccc5)cc4)nn32)ccc1Cl] |

TABLE 1-continued

Characterization Data for Selected Compounds

| No. | Name | ¹H NMR data, Chiral HPLC and LC/MS m/z (M + 1) | Structure |
|---|---|---|---|
| 98 | 7-(4-aminophenyl)-2-(4-phenoxyphenyl)-4,5,6,7-tetrahydropyrazolo[1,5-a]pyrimidine-3-carboxamide | ¹H NMR (DMSO-d6) δ 7.50 (d, J = 8.4 Hz, 2H), 7.41-7.32 (m, 2H), 7.11 (t, J = 7.6 Hz, 1H), 7.03-6.98 (m, 4H), 6.69-6.67 (m, 3H), 6.48 (d, J = 8.4 Hz, 2H), 5.24-5.19 (m, 1H), 4.99 (s, 2H), 3.26-3.22 (m, 1H), 3.07-3.00 (m, 1H), 2.28-2.20 (m, 1H), 2.00-1.95 (m, 1H). MS (ESI) m/e [M + 1]⁺ 426.0. | 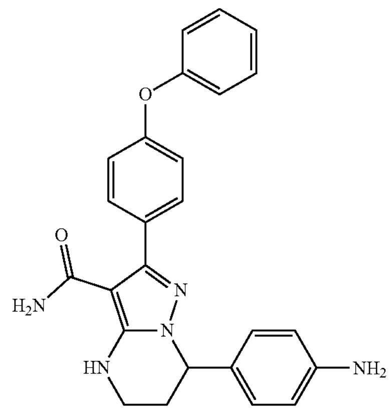 [SMILES: NC(=O)c1c(-c2ccc(Oc3ccccc3)cc2)nn2c1NCCC2c1ccc(N)cc1] |
| 99 | 7-(4-Acrylamidophenyl)-2-(4-phenoxyphenyl)-4,5,6,7-tetrahydropyrazolo[1,5-a]pyrimidine-3-carboxamide | ¹H NMR (DMSO-d₆) δ 10.14 (s, 1H), 7.60 (d, J = 8.4 Hz, 2H), 7.46 (d, J = 8.8 Hz, 2H), 7.40-7.32 (m, 2H), 7.12 (t, J = 7.6 Hz, 1H), 6.94-7.06 (m, 6H), 6.75 (s, 1H), 6.39 (dd, J = 10.1, 17.0 Hz, 1H), 6.21 (dd, J = 1.8, 17.0 Hz, 1H), 5.71 (dd, J = 1.8, 10.1 Hz, 1H), 5.41-5.36 (m, 1H), 3.27-3.22 (m, 1H), 3.07-2.97 (m, 1H), 2.37-2.24 (m, 1H), 2.08-1.95 (m, 1H). MS (ESI) m/e [M + 1]⁺ 480. | 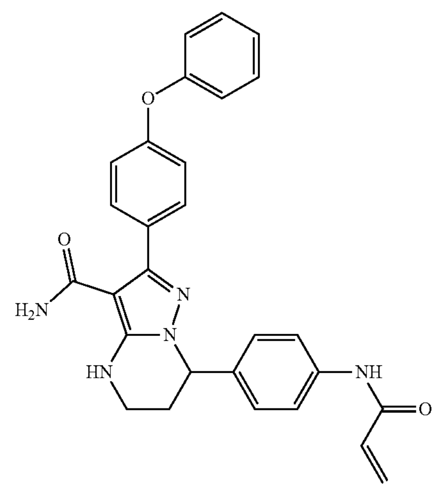 [SMILES: C=CC(=O)Nc1ccc(C2CCNc3c(C(N)=O)c(-c4ccc(Oc5ccccc5)cc4)nn32)cc1] |
| 100 | 2-(4-phenoxyphenyl)-7-(pyridin-4-yl)-4,5,6,7-tetrahydropyrazolo[1,5-a]pyrimidine-3-carboxamide | ¹H NMR (DMSO-d₆) δ 8.57 (d, J = 6.0 Hz, 2H), 7.50 (d, J = 8.8 Hz, 2H), 7.45-7.37 (m, 2H), 7.22-7.10 (m, 3H), 7.07-7.03 (m, 4H), 6.86-6.83 (m, 1H), 5.56-5.10 (m, 1H), 3.35-3.29 (m, 1H), 3.00-2.94 (m, 1H), 2.48-2.38 (m, 1H), 2.18-2.14 (m, 1H). MS (ESI) m/e [M + 1]⁺ 412.2. | 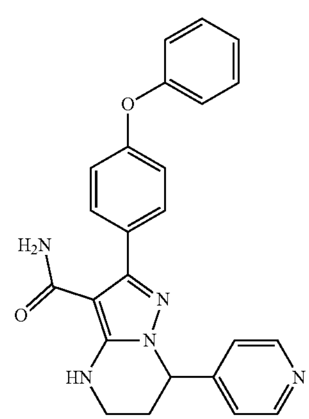 [SMILES: NC(=O)c1c(-c2ccc(Oc3ccccc3)cc2)nn2c1NCCC2c1ccncc1] |

TABLE 1-continued

Characterization Data for Selected Compounds

| No. | Name | $^1$H NMR data, Chiral HPLC and LC/MS m/z (M + 1) | Structure |
|---|---|---|---|
| 101 | 2-(4-phenoxyphenyl)-7-(pyridin-3-yl)-4,5,6,7-tetrahydropyrazolo[1,5-a]pyrimidine-3-carboxamide | $^1$H NMR (DMSO-d$_6$) δ 8.51 (dd, J = 1.6, 4.8 Hz, 1H), 8.37 (d, J = 1.6 Hz, 1H), 7.52-7.44 (m, 3H), 7.42-7.38 (m, 3H), 7.19-7.13 (m, 1H), 7.07-7.02 (m, 4H), 6.84 (br s, 1H), 5.56-5.51 (m, 1H), 3.34-3.30 (m, 1H), 3.13-3.03 (m, 1H), 2.46-2.40 (m, 1H), 2.21-2.14 (m, 1H). MS (ESI) m/e [M + 1]$^+$ 411.9. | 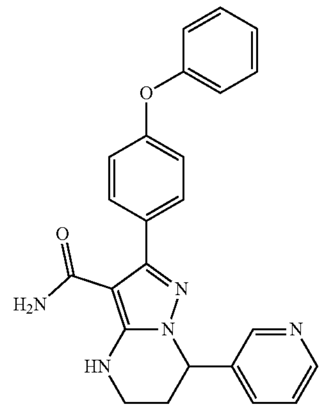 [SMILES: NC(=O)c1c(-c2ccc(Oc3ccccc3)cc2)nn2c1NCCC2c1cccnc1] |
| 102 | 2-(4-phenoxyphenyl)-7-(pyridin-2-yl)-4,5,6,7-tetrahydropyrazolo[1,5-a]pyrimidine-3-carboxamide | $^1$H NMR (DMSO-d$_6$) δ 8.57 (d, J = 4.4 Hz, 1H), 7.79 (td, J = 1.6, 7.6 Hz, 1H), 7.49 (d, J = 8.6 Hz, 2H), 7.40 (t, J = 8.0 Hz, 2H), 7.36-7.28 (m, 1H), 7.16 (t, J = 8.0 Hz, 1H), 7.09-7.00 (m, 5H), 6.81 (br s, 1H), 5.48-5.43 (m, 1H), 3.31-3.25 (m, 1H), 3.10-3.02 (m, 1H), 2.42-2.28 (m, 2H). MS (ESI) m/e [M + 1]$^+$ 411.9. | 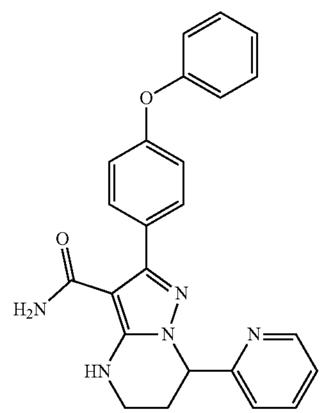 [SMILES: NC(=O)c1c(-c2ccc(Oc3ccccc3)cc2)nn2c1NCCC2c1ccccn1] |
| 103 | 7-(1-acryloylpyrrolidin-2-yl)-2-(4-phenoxyphenyl)-4,5,6,7-tetrahydropyrazolo[1,5-a]pyrimidine-3-carboxamide | $^1$H NMR (DMSO-d$_6$) δ 7.49 (d, J = 8.6 Hz, 2H), 7.46-7.38 (m, 2H), 7.20-7.15 (m, 1H), 7.09 (d, J = 8.0 Hz, 2H), 7.06 (d, J = 8.6 Hz, 2H), 6.76 (s, 1H), 6.62 (dd, J = 16.8, 10.3 Hz, 1H), 6.16 (dd, J = 16.8, 2.2 Hz, 1H), 5.70 (dd, J = 10.3, 2.2 Hz, 1H), 4.47-4.40 (m, 1H), 4.36-4.28 (m, 1H), 3.65-3.50 (m, 2H), 3.50-3.40 (m, 1H), 3.37-3.33 (m, 1H), 2.06-1.74 (m, 6H). MS (ESI) m/e [M + 1]$^+$ 457.9. | 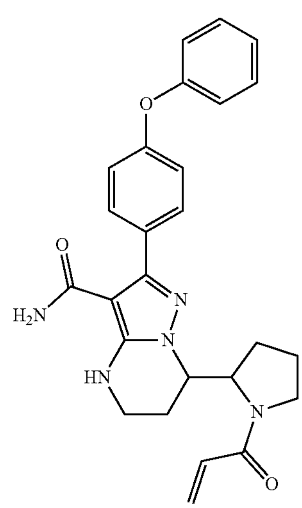 [SMILES: C=CC(=O)N1CCCC1C1CCNc2c(C(N)=O)c(-c3ccc(Oc4ccccc4)cc3)nn21] |

TABLE 1-continued

Characterization Data for Selected Compounds

| No. | Name | ¹H NMR data, Chiral HPLC and LC/MS m/z (M + 1) | Structure |
|---|---|---|---|
| 104 | 7-(1-acryloylazetidin-3-yl)-2-(4-(benzyloxy)phenyl)-4,5,6,7-tetrahydropyrazolo[1,5-a]pyrimidine-3-carboxamide | ¹H NMR (DMSO-d₆) δ 7.49-7.45 (m, 2H),, 7.44-7.37 (m, 4H), 7.37-7.31 (m, 1H), 7.10-7.07 (m, 2H), 6.68 (s, 1H), 6.38-6.25 (m, 1H), 6.12-6.04 (m, 1H), 5.69-5.57 (m, 1H), 5.17-5.12 (m, 2H), 4.42-3.78 (m, 5H), 3.31-3.25 (m, 2H), 3.04-2.88 (m, 1H), 2.15-2.04 (m, 1H), 1.79-1.68 (m, 1H). MS (ESI) m/e [M + 1]⁺ 457.9. | 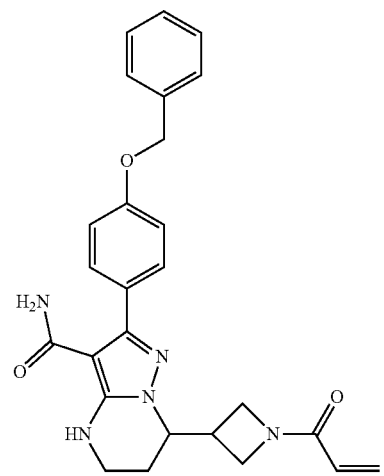 [SMILES: C=CC(=O)N1CC(C2CCNc3c(C(N)=O)c(-c4ccc(OCc5ccccc5)cc4)nn32)C1] |
| 105 | 7-(1-acryloylazetidin-3-yl)-2-(4-(pyridin-2-ylmethoxy)phenyl)-4,5,6,7-tetrahydropyrazolo[1,5-a]pyrimidine-3-carboxamide | ¹H NMR (400 MHz, dmso) δ 8.61-8.57 (m, 1H), 7.90-7.78 (m, 1H), 7.56-7.52 (m, 1H), 7.44-7.39 (m, 2H), 7.38-7.34 (m, 1H), 7.12-7.08 (m, 2H), 6.68 (s, 1H), 6.39-6.23 (m, 1H), 6.12-6.01 (m, 1H), 5.68-5.59 (m, 1H), 5.24-5.21 (m, 2H), 4.44-4.23 (m, 2.5H), 4.19-4.07 (m, 1.H), 4.04-3.94 (m, 1H), 3.88-3.78 (m, 0.5H), 3.31-3.24 (m, 2H), 3.02-2.88 (m, 1H), 2.15-2.03 (m, 1H), 1.80-1.68 (m, 1H). MS (ESI) m/e [M + 1]⁺ 458.9 | 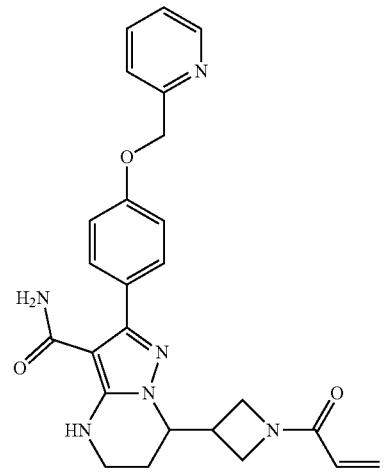 [SMILES: C=CC(=O)N1CC(C2CCNc3c(C(N)=O)c(-c4ccc(OCc5ccccn5)cc4)nn32)C1] |
| 106 | 7-(1-acryloylazetidin-3-yl)-2-(4-(4-chlorophenoxy)phenyl)-4,5,6,7-tetrahydropyrazolo[1,5-a]pyrimidine-3-carboxamide | ¹H NMR (DMSO-d₆) δ 7.52 (d, J = 8.8 Hz, 2H), 7.46 (d, J = 8.8 Hz, 2H), 7.11 (d, J = 8.8 Hz, 2H), 7.08 (d, J = 8.8 Hz, 2H), 6.69 (s, 1H), 6.38-6.22 (m, 1H), 6.13-6.03 (m, 1H), 5.70-5.60 (m, 1H), 4.43-4.26 (m, 2.5H), 4.19-4.08 (m, 1H), 4.05-3.95 (m, 1H), 3.87-3.79 (m, 0.5H), 3.31-3.25 (m, 2H), 3.04-2.90 (m, 1H), 2.15-2.05 (m, 1H), 1.80-1.66 (m, 1H). MS (ESI) m/e [M + 1]⁺ 477.9. | 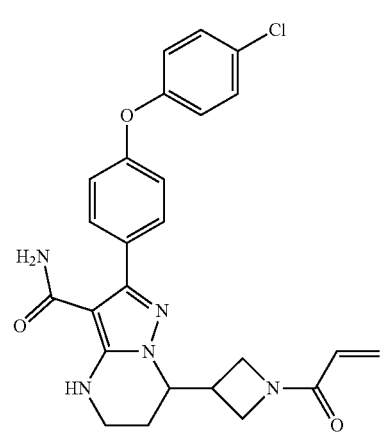 [SMILES: C=CC(=O)N1CC(C2CCNc3c(C(N)=O)c(-c4ccc(Oc5ccc(Cl)cc5)cc4)nn32)C1] |

TABLE 1-continued

Characterization Data for Selected Compounds

| No. | Name | ¹H NMR data, Chiral HPLC and LC/MS m/z (M + 1) | Structure |
|---|---|---|---|
| 107 | 7-(1-acryloylazetidin-3-yl)-2-(4-(3-chlorophenoxy)phenyl)-4,5,6,7-tetrahydropyrazolo[1,5-a]pyrimidine-3-carboxamide | ¹H NMR (DMSO-$d_6$) δ 7.54 (d, J = 8.4 Hz, 2H), 7.46-7.40 (m, 1H), 7.25-7.19 (m, 1H), 7.18-7.15 (m, 1H), 7.11 (d, J = 8.4 Hz, 2H), 7.07-7.02 (m, 1H), 6.69 (s, 1H), 6.39-6.26 (m, 1H), 6.13-6.01 (m, 1H), 5.69-5.60 (m, 1H), 4.45-4.24 (m, 2.5H), 4.19-4.09 (m, 1H), 4.06-3.94 (m, 1H), 3.88-3.80 (m, 0.5H), 3.32-3.24 (m, 2H), 3.05-2.90 (m, 1H), 2.15-2.04 (m, 1H), 1.80-1.68 (m, 1H). MS (ESI) m/e [M + 1]⁺ 477.9. | 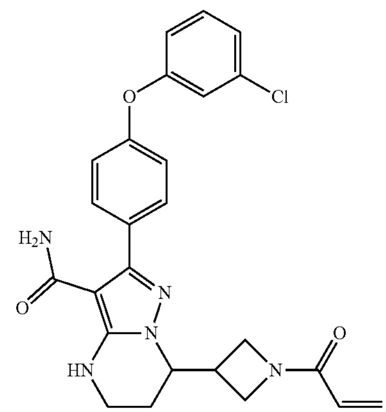 [SMILES: C=CC(=O)N1CC(C2CCNc3c(C(N)=O)c(-c4ccc(Oc5cccc(Cl)c5)cc4)nn32)C1] |
| 108 | 7-(1-acrylamidocyclopropyl])-2-(4-phenoxyphenyl)-4,5,6,7-tetrahydropyrazolo[1,5-a]pyrimidine-3-carboxamide | ¹H NMR (DMSO-$d_6$) δ 8.41 (s, 1H), 7.52 (d, J = 8.6 Hz, 2H), 7.46-7.38 (m, 2H), 7.21-7.15 (m, 1H), 7.11-7.04 (m, 4H), 6.75 (s, 1H), 6.21 (dd, J = 17.1, 9.9 Hz, 1H), 6.09 (dd, J = 17.1, 2.4 Hz, 1H), 5.58 (dd, J = 9.9, 2.4 Hz, 1H), 4.36-4.30 (m, 1H), 3.44-3.35 (m, 2H), 2.31-2.19 (m, 1H), 1.96-1.82 (m, 1H), 1.08-1.00 (m, 1H), 0.81-0.73 (m, 1H), 0.72-0.59 (m, 2H). MS (ESI) m/e [M + 1]⁺ 443.9. | 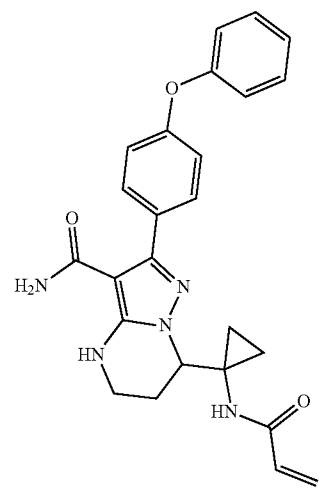 [SMILES: C=CC(=O)NC1(C2CCNc3c(C(N)=O)c(-c4ccc(Oc5ccccc5)cc4)nn32)CC1] |
| 109 | 7-(2-acrylamidopropan-2-yl)-2-(4-phenoxyphenyl)-4,5,6,7-tetrahydropyrazolo[1,5-a]pyrimidine-3-carboxamide | ¹H NMR (DMSO-$d_6$) δ 8.06 (s, 1H), 7.53 (d, J = 8.6 Hz, 2H), 7.46-7.37 (m, 2H), 7.17 (t, J = 8.0 Hz, 1H), 7.08 (d, J = 8.0 Hz, 2H), 7.06 (d, J = 8.6 Hz, 2H), 6.77 (s, 1H), 6.28 (dd, J = 17.1, 10.1 Hz, 1H), 6.06 (dd, J = 17.1, 1.6 Hz, 1H), 5.56 (dd, J = 10.1, 1.6 Hz, 1H), 4.80 (t, J = 5.4 Hz, 1H), 3.32-3.26 (m, 2H), 2.11-1.82 (m, 2H). MS (ESI) m/e [M + 1]⁺ 445.9. | 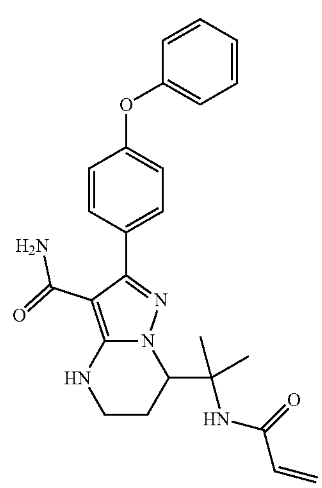 [SMILES: C=CC(=O)NC(C)(C)C1CCNc2c(C(N)=O)c(-c3ccc(Oc4ccccc4)cc3)nn21] |

TABLE 1-continued

Characterization Data for Selected Compounds

| No. | Name | $^1$H NMR data, Chiral HPLC and LC/MS m/z (M + 1) | Structure |
|---|---|---|---|
| 110 | 7-(aminomethyl)-2-(4-(benzyloxy)phenyl)-4,5,6,7-tetrahydropyrazolo[1,5-a]pyrimidine-3-carboxamide trifluoroacetate | $^1$H NMR (DMSO-d$_6$) δ 7.97 (s. 3H), 7.50-7.44 (m, 4H), 7.43-7.38 (m, 2H), 7.37-7.31 (m, 1H), 7.11 (d, J = 8.8 Hz, 2H), 6.80 (s, 1H), 5.15 (s, 2H), 4.43-4.29 (m, 1H), 3.35-3.21 (m, 4H), 2.20-2.09 (m, 1H), 2.04-1.91 (m, 1H). MS (ESI) m/e [M + 1]$^+$ 337.9. | 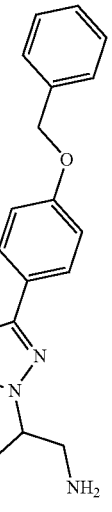 CF3COOH |
| 111 | 7-(acrylamidomethyl)-2-(4-(benzyloxy)phenyl)-4,5,6,7-tetrahydropyrazolo[1,5-a]pyrimidine-3-carboxamide | $^1$H NMR (DMSO-d$_6$) δ 8.29 (t, J = 6.1 Hz, 1H), 7.51-7.31 (m, 6H), 7.10 (d, J = 8.8 Hz, 1H), 6.68 (s, 1H), 6.26 (dd, J = 17.1, 10.1 Hz, 1H), 6.11 (dd, J = 17.1, 2.1 Hz, 1H), 5.62 (dd, J = 10.1, 2.1 Hz, 1H), 5.15 (s, 2H), 4.21-4.12 (m, 1H), 3.84-3.68 (m, 1H), 3.45-3.36 (m, 1H), 3.32-3.23 (m, 2H), 2.10-1.85 (m, 2H). MS (ESI) m/e [M + 1]$^+$ 431.9. | 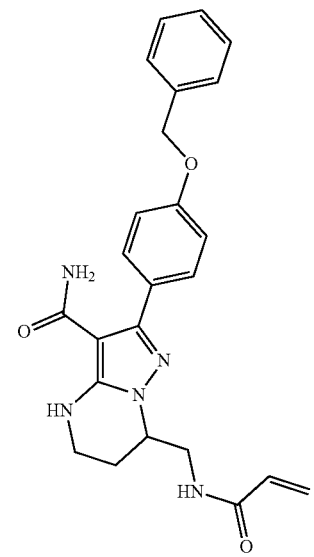 [SMILES: C=CC(=O)NCC1CCNc2c(C(N)=O)c(-c3ccc(OCc4ccccc4)cc3)nn21] |
| 112 | 7-(aminomethyl)-2-(4-(cyclopropylmethoxy)phenyl)-4,5,6,7-tetrahydropyrazolo[1,5-a]pyrimidine-3-carboxamide | $^1$H NMR (DMSO-d$_6$) δ 7.39 (d, J = 8.6 Hz, 2H), 6.99 (d, J = 8.6 Hz, 2H), 6.63 (s, 1H), 4.06-3.94 (m, 1H), 3.85 (d, J = 7.0 Hz, 2H), 3.04 (dd, J = 12.8, 6.8 Hz, 1H), 2.87 (dd, J = 12.8, 6.8 Hz, 1H), 2.12-1.91 (m, 2H), 1.30-1.18 (m, 2H), 0.62-0.50 (m, 2H), 0.36-0.28 (m, 2H). MS (ESI) m/e [M + 1]$^+$ 342.0. | 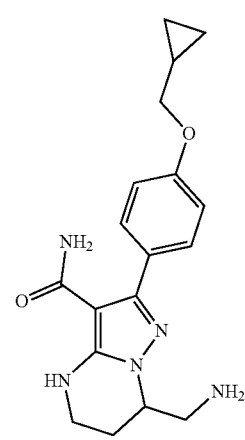 [SMILES: NCC1CCNc2c(C(N)=O)c(-c3ccc(OCC4CC4)cc3)nn21] |

TABLE 1-continued

Characterization Data for Selected Compounds

| No. | Name | ¹H NMR data, Chiral HPLC and LC/MS m/z (M + 1) | Structure |
|---|---|---|---|
| 113 | 7-(acrylamidomethyl)-2-(4-(cyclopropylmethoxy)phenyl)-4,5,6,7-tetrahydropyrazolo[1,5-a]pyrimidine-3-carboxamide | ¹H NMR (CD$_3$OD-d$_4$) δ 7.43 (d, J = 8.4 Hz, 2H), 7.01 (d, J = 8.4 Hz, 2H), 6.32-6.18 (m, 2H), 5.70-5.65 (m, 1H), 4.32-4.22 (m, 1H), 3.87 (d, J = 6.9 Hz, 2H), 3.80-3.66 (m, 2H), 3.52-3.36 (m, 2H), 2.22-1.96 (m, 2H), 1.34-1.20 (m, 1H), 0.66-0.57 (m, 2H), 0.39-0.30 (m, 2H). MS (ESI) m/e [M + 1]⁺ 395.9. | 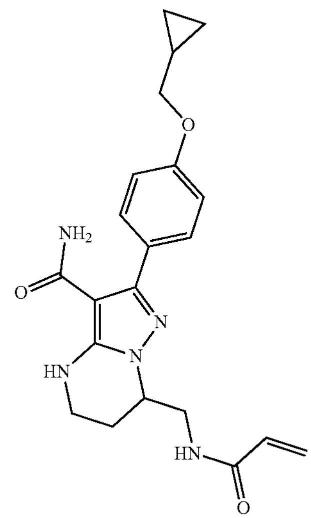 [SMILES: C=CC(=O)NCC1CCNc2c(C(N)=O)c(-c3ccc(OCC4CC4)cc3)nn21] |
| 114 | Cis-7-(1-tert-Butoxycarbonyl)-2-(4-phenoxyphenyl)-5,5a,6,7,8,8a-hexahydro-4H-pyrazolo[1,5-a]pyrrolo[3,4-e]pyrimidine-3-carboxamide | ¹H NMR (DMSO-d$_6$) δ 7.52 (d, J = 7.6 Hz, 2H), 7.46-7.38 (m, 2H), 7.18 (t, J = 7.6 Hz, 1H), 7.11-7.03 (m, 4H), 6.71 (br s, 1H), 4.61-4.54 (m, 1H), 3.87 (t, J = 11.6 Hz, 1H), 3.67-3.48 (m, 2H), 3.30-3.12 (m, 3H), 3.06-2.85 (m, 1H), 1.36 (d, 9H). MS (ESI) m/e [M + 1]⁺ 476.0. | 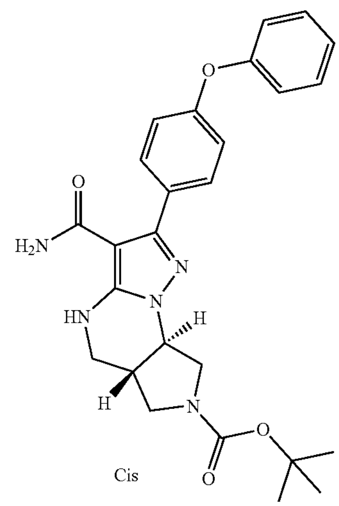 [SMILES: CC(C)(C)OC(=O)N1C[C@@H]2CNc3c(C(N)=O)c(-c4ccc(Oc5ccccc5)cc4)nn3[C@H]2C1] |
| 115 | Cis-2-(4-phenoxyphenyl)-5,5a,6,7,8,8a-hexahydro-4H-pyrazolo[1,5-a]pyrrolo[3,4-e]pyrimidine-3-carboxamide | ¹H NMR (DMSO-d$_6$ and D$_2$O) δ 7.53 (d, J = 8.8 Hz, 2H), 7.44-7.40 (m, 2H), 7.23-7.16 (m, 1H), 7.13-7.04 (m, 4H), 4.79-4.73 (m, 1H), 3.78 (d, J = 12.8 Hz, 1H), 3.57-3.27 (m, 4H), 3.14-3.03 (m, 2H). MS (ESI) m/e [M + 1]⁺ 376.0. | 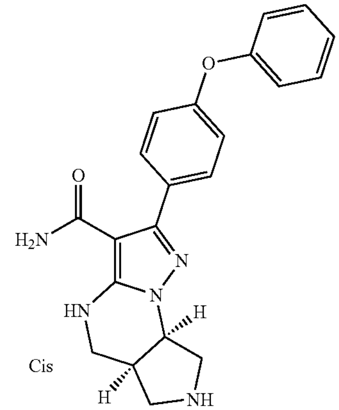 [SMILES: NC(=O)c1c(-c2ccc(Oc3ccccc3)cc2)nn2c1NC[C@@H]1CNC[C@@H]12] |

TABLE 1-continued

Characterization Data for Selected Compounds

| No. | Name | ¹H NMR data, Chiral HPLC and LC/MS m/z (M + 1) | Structure |
|---|---|---|---|
| 116 | Cis-7-acryloyl-2-(4-phenoxyphenyl)-5,5a,6,7,8,8a-hexahydro-4H-pyrazolo[1,5-a]pyrrolo[3,4-e]pyrimidine-3-carboxamide | ¹H NMR (DMSO-$d_6$) δ 7.51 (dd, J = 2.0, 8.4 Hz, 2H), 7.45-7.38 (m, 2H), 7.18 (t, J = 7.6 Hz, 1H), 7.08 (d, J = 8.0 Hz, 2H), 7.04 (d, J = 8.4 Hz, 2H), 6.75 (s, 1H), 6.62-6.48 (m, 1H), 6.14-6.04 (m, 1H), 5.69-5.61 (m, 1H), 4.70-4.61 (m, 1H), 4.20-4.10 (m, 1H), 3.98-3.86 (m, 1H), 3.72-3.67 (m, 1H), 3.50-3.40 (m, 1H), 3.42-3.38 (m, 1H), 3.33-3.28 (m, 1H), 3.13-2.94 (m, 1H). MS (ESI) m/e [M + 1]⁺ 430.0. | 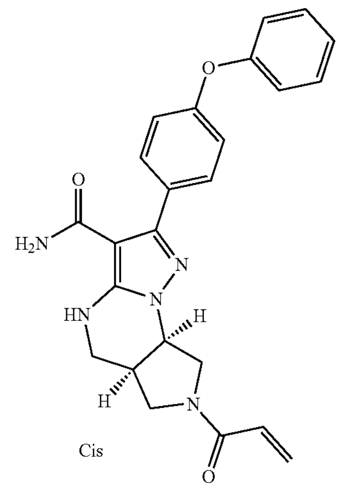 [SMILES: C=CC(=O)N1C[C@H]2CNc3c(C(N)=O)c(-c4ccc(Oc5ccccc5)cc4)nn3[C@H]2C1] |
| 117 | 2(1-acryloylpyrrolidin-3-yl)-6-(4-phenoxyphenyl)-1H-imidazo[1,2-b]pyrazole-7-carboxamide | ¹H NMR (DMSO-$d_6$) δ 11.76 (s, 1H), 7.67 (d, J = 8.0 Hz, 2H), 7.56 (s, 1H), 7.47-7.38 (m, 2H), 7.17 (t, J = 7.6 Hz, 1H), 7.109 (d, J = 7.6 Hz, 2H), 7.04 (d, J = 8.0 Hz, 2H), 6.60 (ddd, J = 2.2, 10.3, 16.6 Hz, 1H), 6.16 (dd, J = 2.2, 16.6 Hz, 1H), 5.69 (dd, J = 2.2, 10.3 Hz, 1H), 4.09-3.95 (m, 1H), 3.94-3.73 (m, 1H), 3.70-3.37 (m, 3H), 2.42-2.24 (m, 1H), 2.21-2.01 (m, 1H). MS (ESI) m/e [M + 1]⁺ 441.9. | 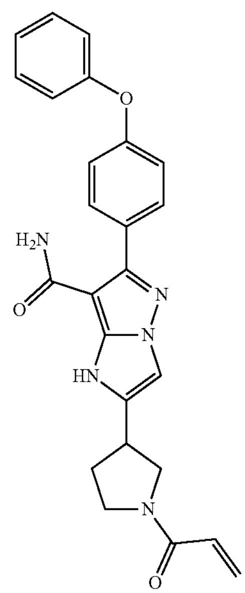 [SMILES: C=CC(=O)N1CCC(c2cn3nc(-c4ccc(Oc5ccccc5)cc4)c(C(N)=O)c3[nH]2)C1] |
| 118 | 2'-(4-phenoxyphenyl)-5',6'-dihydro-4'H-spiro[azetidine-3,7'-pyrazolo[1,5-a]pyrimidine]-3'-carboxamide | ¹H NMR (DMSO-$d_6$) δ 7.63 (d, J = 8.4 Hz, 2H), 7.55-7.47 (m, 2H), 7.21-7.14 (m, 4H), 6.88 (s, 1H), 4.47 (d, J = 9.8 Hz, 2H), 3.81 (d, J = 9.8 Hz, 2H), 3.35-3.33 (m, 2H), 2.51-2.44 (m, 2H). MS (ESI) m/e [M + 1]⁺ 375.9. | 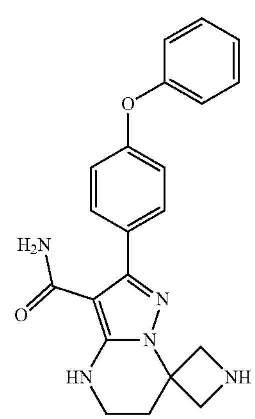 [SMILES: NC(=O)c1c(-c2ccc(Oc3ccccc3)cc2)nn2c1NCCC21CNC1] |

TABLE 1-continued

Characterization Data for Selected Compounds

| No. | Name | $^1$H NMR data, Chiral HPLC and LC/MS m/z (M + 1) | Structure |
|---|---|---|---|
| 119 | 1-acryloyl-2'-(4-phenoxyphenyl)-5',6'-dihydro-4'H-spiro[azetidine-3,7'-pyrazolo[1,5-a]pyrimidine]-3'-carboxamide | $^1$H NMR (DMSO-d$_6$) δ 7.54 (d, J = 8.6 Hz, 2H), 7.46-7.38 (m, 2H), 7.17 (t, J = 7.6 Hz, 1H), 7.11-7.05 (m, 4H), 6.79 (s, 1H), 6.35 (dd, J = 17.0, 10.3 Hz, 1H), 6.14 (dd, J = 17.0, 2.1 Hz, 1H), 5.70 (dd, J = 10.3, 2.1 Hz, 1H), 4.66 (d, J = 8.8 Hz, 1H), 4.38 (d, J = 10.0 Hz, 1H), 4.32 (d, J = 8.8 Hz, 1H), 4.03 (d, J = 10.0 Hz, 1H), 3.31-3.26 (m, 2H), 2.38-2.31 (m, 2H). MS (ESI) m/e [M + 1]$^+$ 429.9. | 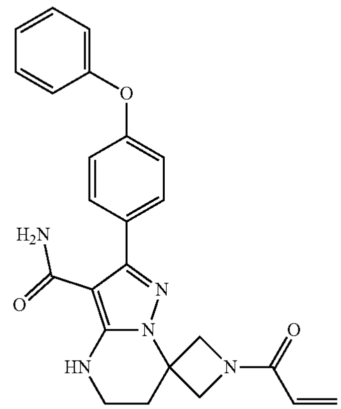 [SMILES: C=CC(=O)N1CC2(CCNc3c(C(N)=O)c(-c4ccc(Oc5ccccc5)cc4)nn32)C1] |
| 120 | 2-(4-phenoxyphenyl)-4,5,6,7,8,9-hexahydropyrazolo[1',5':1,2]imidazo[4,5-d]azepine-3-carboxamide | $^1$H NMR (DMSO-d$_6$) δ 11.74 (br s, 1H), 9.06 (br s, 2H), 7.65 (d, J = 8.4 Hz, 2H), 7.47-7.39 (m, 2H), 7.18 (t, J = 7.6 Hz, 1H), 7.09 (d, J = 7.6 Hz, 2H), 7.07 (d, J = 8.4 Hz, 2H), 3.19-3.14 (m, 2H), 3.10-3.05 (m, 2H). MS (ESI) m/e [M + 1]$^+$ 387.9. | 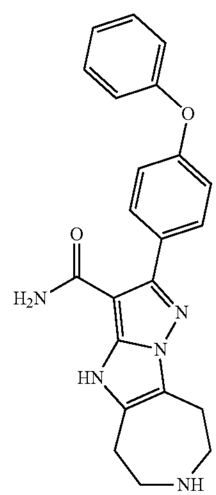 [SMILES: NC(=O)c1c(-c2ccc(Oc3ccccc3)cc2)nn2c3c([nH]c12)CCNCC3] |
| 121 | 7-acryloyl-2-(4-phenoxyphenyl)-4,5,6,7,8,9-hexahydropyrazolo[1',5':1,2]imidazo[4,5-d]azepine-3-carboxamide | $^1$H NMR (CD$_3$OD-d$_4$) δ 7.64-7.60 (m, 2H), 7.43-7.37 (m, 2H), 7.19-7.14 (m, 1H), 7.12-7.05 (m, 4H), 6.97-6.85 (m, 1H), 6.32 (dd, J = 2.0, 16.8 Hz, 1H), 5.81 (dd, J = 2.0, 8.4 Hz, 1H), 4.04-3.91 (m, 4H), 3.17-3.09 (m, 2H), 3.07-3.01 (m, 2H). MS (ESI) m/e [M + 1]$^+$ 441.9. | 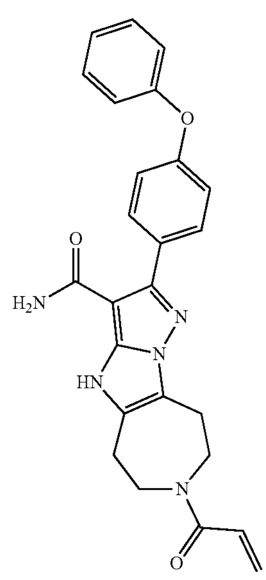 [SMILES: C=CC(=O)N1CCc2[nH]c3c(C(N)=O)c(-c4ccc(Oc5ccccc5)cc4)nn3c2CC1] |

TABLE 1-continued

Characterization Data for Selected Compounds

| No. | Name | $^1$H NMR data, Chiral HPLC and LC/MS m/z (M + 1) | Structure |
|---|---|---|---|
| 122 | (E)-7-(4-(dimethylamino)but-2-enoyl)-2-(4-phenoxyphenyl)-4,5,6,7,8,9-hexahydropyrazolo[1',5':1,2]imidazo[4,5-d]azepine-3-carboxamide | $^1$H NMR (CD$_3$OD-d$_4$) δ 7.59 (d, J = 8.4 Hz, 2H), 7.41-7.32 (m, 2H), 7.15 (t, J = 7.6 Hz, 1H), 7.10-6.99 (m, 5H), 6.80-6.70 (m, 1H), 4.08-3.84 (m, 6H), 3.15-3.08 (m, 2H), 3.06-3.01 (m, 2H), 2.90 (s, 3H), 2.89 (s, 3H). MS (ESI) m/e [M + 1]$^+$ 498.9. | 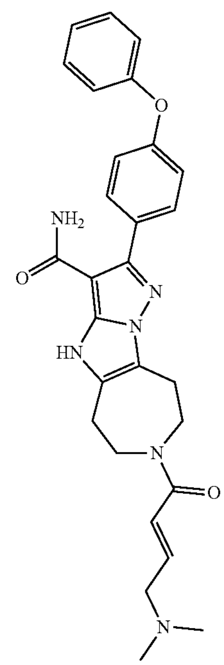 [SMILES: CN(C)C/C=C/C(=O)N1CCc2[nH]c3c(C(N)=O)c(-c4ccc(Oc5ccccc5)cc4)nn3c2CC1] |
| 123 | 8-acryloyl-2-(4-phenoxyphenyl)-4,5,6,7,8,9-hexahydropyrazolo[5',1':2,3]imidazo[4,5-c]azepine-3-carboxamide As a byproduct in the preparation of compound 121 | $^1$H NMR (CD$_3$OD-d$_4$) δ 7.61 (dd, J = 2.4, 8.8 Hz, 2H), 7.41-7.33 (m, 2H), 7.14 (t, J = 8.0 Hz, 1H), 7.11-7.02 (m, 4H), 6.82 (dd, J = 10.6, 16.8 Hz, 1H), 6.19 (dd, J = 1.8, 16.8 Hz, 1H), 5.74 (dd, J = 1.8, 10.6 Hz, 1H), 4.98 (d, J = 12.4 Hz, 2H), 4.06-3.80 (m, 2H), 2.96-2.89 (m, 2H), 2.12-1.93 (m, 2H). MS (ESI) m/e [M + 1]$^+$ 441.9. | 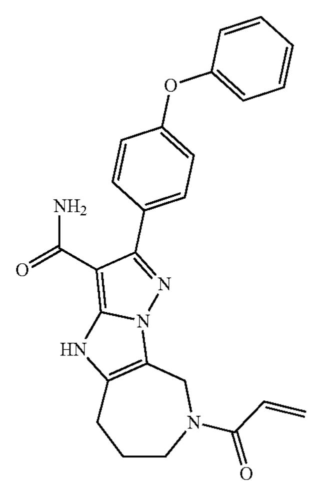 [SMILES: C=CC(=O)N1CCCc2[nH]c3c(C(N)=O)c(-c4ccc(Oc5ccccc5)cc4)nn3c2C1] |

TABLE 1-continued

Characterization Data for Selected Compounds

| No. | Name | $^1$H NMR data, Chiral HPLC and LC/MS m/z (M + 1) | Structure |
|---|---|---|---|
| 124 | (E)-8-(4-(dimethylamino)but-2-enoyl)-2-(4-phenoxyphenyl)-4,5,6,7,8,9-hexahydropyrazolo[5',1':2,3]imidazo[4,5-c]azepine-3-carboxamide As a byproduct in the preparation of compound 122 | $^1$H NMR (CD$_3$OD-d$_4$) δ 7.54 (dd, J = 2.4, 8.8 Hz, 2H), 7.34-7.26 (m, 2H), 7.10-7.04 (m, 1H), 7.03-6.95 (m, 4H), 6.75-6.50 (m, 2H), 4.90 (d, J = 11.6 Hz, 2H), 3.89-3.77 (m, 2H), 3.17-3.12 (m, 2H), 2.88-2.82 (m, 2H), 2.28 (s, 3H), 2.19 (s, 3H), 2.02-1.90 (m, 2H). MS (ESI) m/e [M + 1]$^+$ 498.9. | 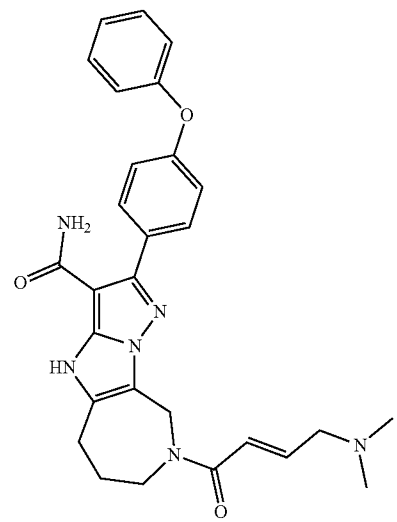 [SMILES: CN(C)C/C=C/C(=O)N1CCCc2[nH]c3c(C(N)=O)c(-c4ccc(Oc5ccccc5)cc4)nn3c2C1] |
| 125 | 2-(4-(benzyloxy)phenyl)-5,6,7,8-tetrahydro-4H-pyrazolo[5',1':2,3]imidazo[4,5-c]pyridine-3-carboxamide formate | $^1$H NMR (DMSO-d$_6$) δ 11.94 (s, 1H), 9.78 (s, 1H), 9.33 (s, 2H), 7.30-7.22 (m, 5H), 7.18-7.13 (m, 1H), 6.95-6.85 (m, 1H), 4.41 (s, 2H), 3.91 (s, 2H), 2.94-2.87 (m, 2H). MS (ESI) m/e [M + 1]$^+$ 387.9. | 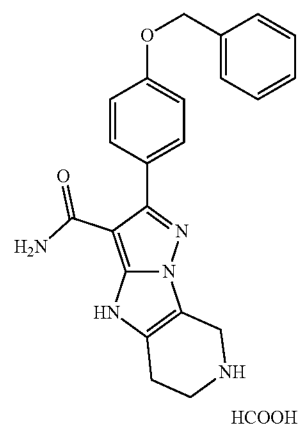 [SMILES: NC(=O)c1c(-c2ccc(OCc3ccccc3)cc2)nn2c3c([nH]c12)CCNC3 ; "HCOOH"] |
| 126 | 7-Acryloyl-2-(4-(benzyloxy)phenyl)-5,6,7,8-tetrahydro-4H-pyrazolo[5',1':2,3]imidazo[4,5-c]pyridine-3-carboxamide | $^1$H NMR (DMSO-d$_6$) δ 9.70 (s, 1H), 7.40 (d, J = 8.2 Hz, 2H), 7.35-7.29 (m, 2H), 7.28-7.23 (m, 1H), 7.19 (d, J = 8.2 Hz, 2H), 6.95-6.87 (m, 1H), 6.86-6.83 (m, 2H), 6.20-6.07 (m, 1H), 5.74-5.73 (m, 3H), 4.80-4.72 (m, 2H), 3.89-3.87 (m, 2H), 2.69-2.67 (m, 2H). MS (ESI) m/e [M + 1]$^+$ 441.9. | 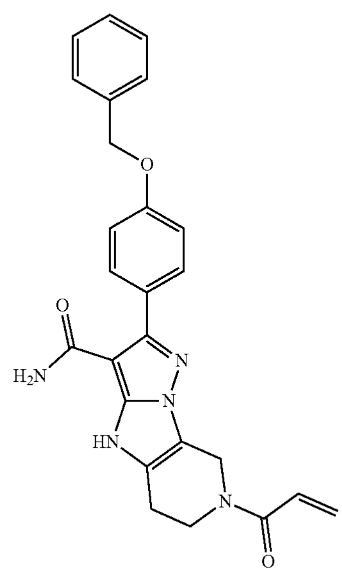 [SMILES: C=CC(=O)N1CCc2[nH]c3c(C(N)=O)c(-c4ccc(OCc5ccccc5)cc4)nn3c2C1] |

TABLE 1-continued

Characterization Data for Selected Compounds

| No. | Name | $^1$H NMR data, Chiral HPLC and LC/MS m/z (M + 1) | Structure |
|---|---|---|---|
| 127 | 7-acryloyl-2-(4-(cyclopropylmethoxy)phenyl)-5,6,7,8-tetrahydro-4H-pyrazolo[5',1':2,3]imidazo[4,5-c]pyridine-3-carboxamide | $^1$H NMR (DMSO-d$_6$) δ 9.67 (s, 1H), 7.39 (d, J = 8.4 Hz, 2H), 7.01-6.89 (m, 1H), 6.84 (d, J = 8.4 Hz, 2H), 6.22-6.11 (m, 1H), 5.80-5.70 (m, 1H), 4.85-4.70 (m, 2H), 4.30-4.26 (m, 2H), 3.99-3.90 (m, 2H), 2.90-2.80 (m, 2H), 1.18-1.06 (m, 1H), 0.44-0.30 (m, 4H). MS (ESI) m/e [M + 1]$^+$ 405.9. | 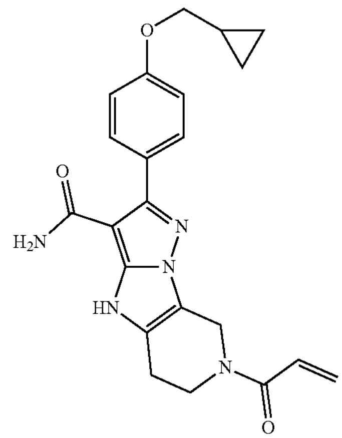 [SMILES: C=CC(=O)N1CCc2[nH]c3c(C(N)=O)c(-c4ccc(OCC5CC5)cc4)nn3c2C1] |
| 128 | 6-nitro-2-(4-phenoxyphenyl)-4H-benzo[4,5]imidazo[1,2-b]pyrazole-3-carboxamide | $^1$H NMR (DMSO-d$_6$) δ 12.78 (s, 1H), 8.29 (s, 1H), 8.14-8.08 (m, 1H), 8.04-7.96 (m, 1H), 7.91-7.81 (m, 2H), 7.49-7.39 (m, 2H), 7.19 (t, J = 7.6 Hz, 1H), 7.15-7.05 (m, 4H). MS (ESI) m/e [M + 1]$^+$ 413.9. | 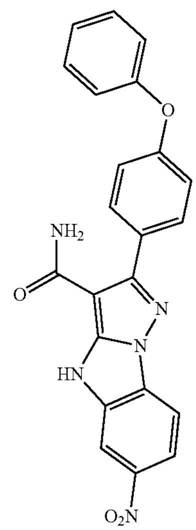 |
| 129 | 6-amino-2-(4-phenoxyphenyl)-4H-benzo[4,5]imidazo[1,2-b]pyrazole-3-carboxamide | $^1$H NMR (DMSO-d$_6$) δ 11.64 (s, 1H), 8.24 (s, 1H), 7.73 (d, J = 8.8 Hz, 2H), 7.47-7.39 (m, 3H), 7.18 (t, J = 7.6 Hz, 1H), 7.12-7.05 (m, 4H), 6.69 (d, J = 1.8 Hz, 1H), 6.50 (dd, J = 1.8, 8.8 Hz, 1H), 5.21 (br s, 2H). MS (ESI) m/e [M + 1]$^+$ 383.9. | 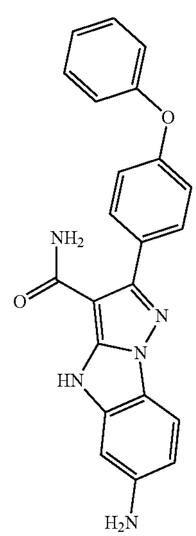 [SMILES: NC(=O)c1c(-c2ccc(Oc3ccccc3)cc2)nn2c1[nH]c1cc([N+](=O)[O-])ccc12] |

TABLE 1-continued

Characterization Data for Selected Compounds

| No. | Name | $^1$H NMR data, Chiral HPLC and LC/MS m/z (M + 1) | Structure |
|---|---|---|---|
| 130 | 6-acrylamido-2-(4-phenoxyphenyl)-4H-benzo[4,5]imidazo[1,2-b]pyrazole-3-carboxamide | $^1$H NMR (CD$_3$OD-d$_4$) δ 8.14 (s, 1H), 7.68 (d, J = 8.8 Hz, 1H), 7.62 (d, J = 8.8 Hz, 2H), 7.38-7.24 (m, 3H), 7.12-6.94 (m, 5H), 6.46-6.25 (m, 2H), 5.71 (dd, J = 2.0, 9.6 Hz, 1H). MS (ESI) m/e [M + 1]$^+$ 437.9. | 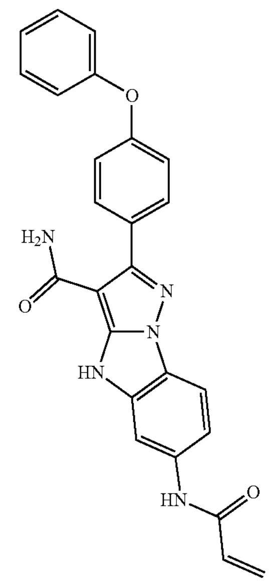 [SMILES: C=CC(=O)Nc1ccc2c(c1)[nH]c1c(C(N)=O)c(-c3ccc(Oc4ccccc4)cc3)nn12] |
| 131 | 8-amino-2-(4-phenoxyphenyl)-4H-benzo[4,5]imidazo[1,2-b]pyrazole-3-carboxamide | $^1$H NMR (DMSO-d$_6$) δ 11.87 (s, 1H), 7.78 (d, J = 8.4 Hz, 2H), 7.48-7.39 (m, 2H), 7.18 (t, J = 7.6 Hz, 1H), 7.13-7.07 (m, 4H), 7.02 (t, J = 8.0 Hz, 1H), 6.70 (d, J = 8.0 Hz, 1H), 6.50 (d, J = 8.0 Hz, 1H), 5.56 (s, 2H). MS (ESI) m/e [M + 1]$^+$ 383.9. | 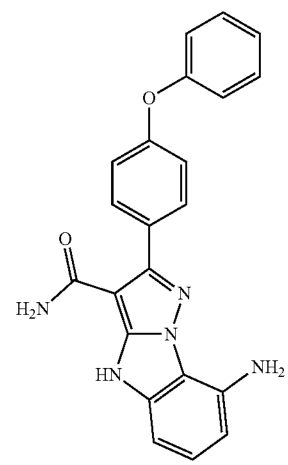 [SMILES: NC(=O)c1c(-c2ccc(Oc3ccccc3)cc2)nn2c1[nH]c1cccc(N)c12] |
| 132 | 7-(1-acryloylazetidin-3-yl)-2-(4-(3,4-dichlorophenoxy)phenyl)-4,5,6,7-tetrahydropyrazolo[1,5-a]pyrimidine-3-carboxamide | $^1$H NMR (DMSO-d$_6$) δ 7.61 (dd, J = 8.9, 2.8 Hz, 1H), 7.51 (d, J = 8.4 Hz, 2H), 7.36 (d, J = 2.8 Hz, 1H), 7.10 (d, J = 8.4 Hz, 2H), 7.08-7.03 (m, 1H), 6.66 (s, 1H), 6.35-6.22 (m, 1H), 6.09-6.01 (m, 1H), 5.65-5.55 (m, 1H), 4.40-4.30 (m, 2H), 4.29-4.21 (m, 0.5H), 4.15-4.06 (m, 1H), 4.02-3.92 (m, 1H), 3.84-3.76 (m, 0.5H), 3.28-3.21 (m, 1H), 3.03-2.87 (m, 1H), 2.21-2.00 (m, 1H), 1.77-1.66 (m, 1H). MS (ESI) m/e [M + 1]$^+$ 511.8, 513.8. | 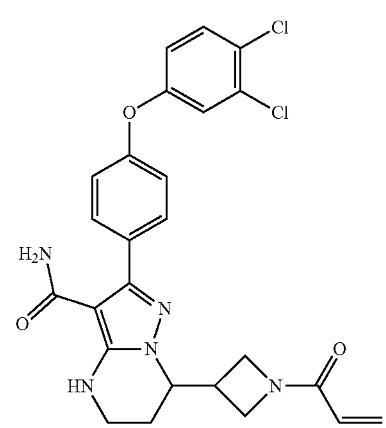 [SMILES: C=CC(=O)N1CC(C2CCNc3c(C(N)=O)c(-c4ccc(Oc5ccc(Cl)c(Cl)c5)cc4)nn32)C1] |

TABLE 1-continued

Characterization Data for Selected Compounds

| No. | Name | $^1$H NMR data, Chiral HPLC and LC/MS m/z (M + 1) | Structure |
| --- | --- | --- | --- |
| 133 | 7-(2-acrylamidophenyl)-2-(3-methoxy-4-methylphenyl)-4,5,6,7-tetrahydropyrazolo[1,5-a]pyrimidine-3-carboxamide | $^1$H NMR (DMSO-d$_6$) δ 9.82 (s, 1H), 7.42 (d, J = 7.4 Hz, 1H), 7.27 (t, J = 7.4 Hz, 1H), 7.19 (d, J = 7.4 Hz, 1H), 7.15 (d, J = 7.4 Hz, 1H), 6.96 (s, 1H), 6.93 (d, J = 7.4 Hz, 1H), 6.83 (s, 1H), 6.61 (d, J = 7.4 Hz, 1H), 6.50 (dd, J = 17.1, 10.0 Hz, 1H), 6.24 (d, J = 17.1 Hz, 1H), 5.80-5.70 (m, 2H), 3.74 (s, 3H), 3.28-3.19 (m, 1H), 2.99-2.87 (m, 1H), 2.33-2.19 (m, 1H), 2.13 (s, 3H), 1.99-1.89 (m, 1H). MS (ESI) m/e [M + 1]$^+$ 431.9. | 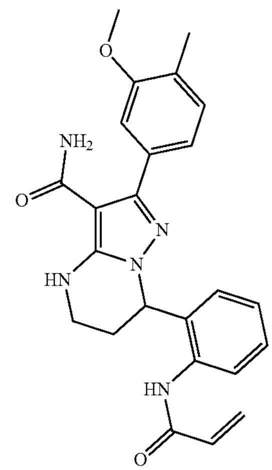 [SMILES: C=CC(=O)Nc1ccccc1C1CCNc2c(C(N)=O)c(-c3ccc(C)c(OC)c3)nn21] |
| 133a (peak 1) | (R or S) 7-(2-acrylamidophenyl)-2-(3-methoxy-4-methylphenyl)-4,5,6,7-tetrahydropyrazolo[1,5-a]pyrimidine-3-carboxamide | Chiral HPLC analysis condition: Instrument: Agilent 1260 HPLC Column: CHIRALCEL OJ-H Column size: 0.46 cm I.D. × 15 cm L, 5 um Mobile phase: n-Hexane/EtOH(0.1% triethyl amine) = 85/15(v/v) Column temperature: 35° C. Flow rate: 1.0 ml/min retention time: 5.86 min | 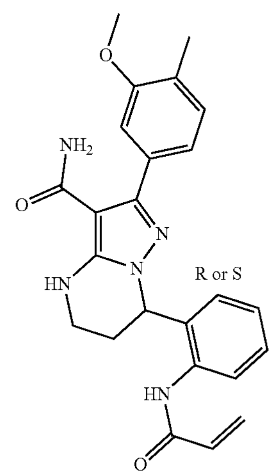 [SMILES: C=CC(=O)Nc1ccccc1C1CCNc2c(C(N)=O)c(-c3ccc(C)c(OC)c3)nn21] |
| 133b (peak 2) | (S or R) 7-(2-acrylamidophenyl)-2-(3-methoxy-4-methylphenyl)-4,5,6,7-tetrahydropyrazolo[1,5-a]pyrimidine-3-carboxamide | retention time: 6.64 min | 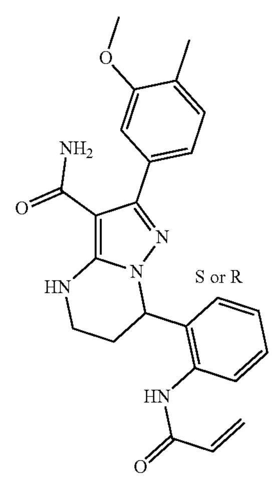 [SMILES: C=CC(=O)Nc1ccccc1C1CCNc2c(C(N)=O)c(-c3ccc(C)c(OC)c3)nn21] |

TABLE 1-continued

Characterization Data for Selected Compounds

| No. | Name | $^1$H NMR data, Chiral HPLC and LC/MS m/z (M + 1) | Structure |
|---|---|---|---|
| 134 | 7-(2-acrylamidophenyl)-2-(4-chlorophenyl)-4,5,6,7-tetrahydropyrazolo[1,5-a]pyrimidine-3-carboxamide | $^1$H NMR (DMSO-d$_6$) δ 9.81 (s, 1H), 7.48 (d, J = 8.6 Hz, 2H), 7.45-7.38 (m, 3H), 7.27 (t, J = 7.2 Hz, 1H), 7.17 (t, J = 7.2 Hz, 1H), 6.76 (s, 1H), 6.59 (d, J = 7.2 Hz, 1H), 6.50 (dd, J = 17.0, 10.2 Hz, 1H), 6.24 (dd, J = 17.0, 1.8 Hz, 1H), 5.79-5.67 (m, 2H), 3.26-3.18 (m, 1H), 2.99-2.89 (m, 1H), 2.35-2.20 (m, 1H), 1.99-1.88 (m, 1H). MS (ESI) m/e [M + 1]$^+$ 421.8, 423.8. | 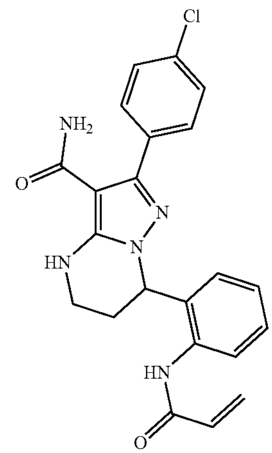 [SMILES: C=CC(=O)Nc1ccccc1C1CCNc2c(C(N)=O)c(-c3ccc(Cl)cc3)nn21] |
| 134a (peak 1) | (R or S) 7-(2-acrylamidophenyl)-2-(4-chlorophenyl)-4,5,6,7-tetrahydropyrazolo[1,5-a]pyrimidine-3-carboxamide | Chiral HPLC analysis condition: Instrument: Agilent 1260 HPLC Column: CHIRALPAK AD-H Column size: 0.46 cm I.D. × 15 cm L, 5 um Mobile phase: n-Hexane/EtOH (0.1% triethyl amine) = 70/30 (v/v) Column temperature: 35° C. Flow rate: 1.0 ml/min retention time: 4.15 min | 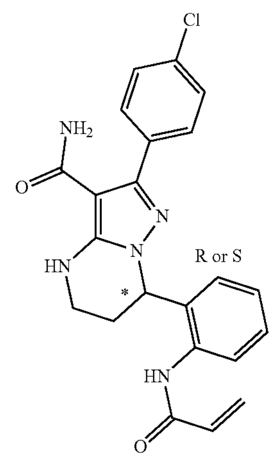 [SMILES: C=CC(=O)Nc1ccccc1C1CCNc2c(C(N)=O)c(-c3ccc(Cl)cc3)nn21] |
| 134b (peak 2) | (S or R) 7-(2-acrylamidophenyl)-2-(4-chlorophenyl)-4,5,6,7-tetrahydropyrazolo[1,5-a]pyrimidine-3-carboxamide | retention time: 10.52 min | 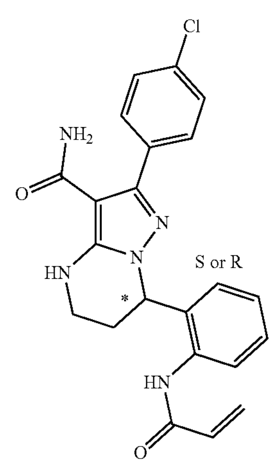 [SMILES: C=CC(=O)Nc1ccccc1C1CCNc2c(C(N)=O)c(-c3ccc(Cl)cc3)nn21] |

TABLE 1-continued

Characterization Data for Selected Compounds

| No. | Name | ¹H NMR data, Chiral HPLC and LC/MS m/z (M + 1) | Structure |
|---|---|---|---|
| 135 | 7-(1-acryloylazetidin-3-yl)-2-(4-(2-cyanophenoxy)phenyl)-4,5,6,7-tetrahydropyrazolo[1,5-a]pyrimidine-3-carboxamide | ¹H NMR (DMSO-d$_6$) δ 7.91-7.85 (m, 1H), 7.71-7.61 (m, 1H), 7.58-7.52 (m, 2H), 7.33-7.24 (m, 1H), 7.20-7.14 (m, 2H), 7.11-7.05 (m, 1H), 6.61 (br s, 1H), 6.36-6.22 (m, 1H), 6.10-6.00 (m, 1H), 5.67-5.54 (m, 1H), 4.42-4.30 (m, 2H), 4.30-4.22 (m, 0.5H), 4.16-4.07 (m, 1H), 4.03-3.92 (m, 1H), 3.87-3.73 (m, 0.5H), 3.30-3.20 (m, 2H), 3.05-2.85 (m, 1H), 2.15-1.97 (m, 1H), 1.78-1.64 (m, 1H). MS (ESI) m/e [M + 1]⁺ 468.9. | 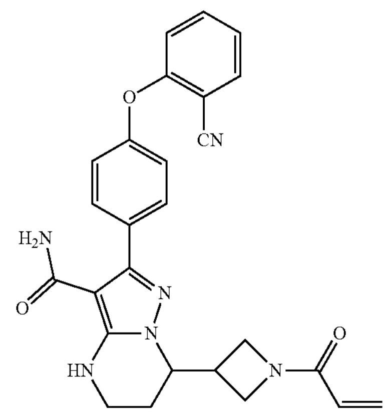 [SMILES: C=CC(=O)N1CC(C2CCNc3c(C(N)=O)c(-c4ccc(Oc5ccccc5C#N)cc4)nn32)C1] |
| 136 | 3-(1-acryloylpiperidin-4-yl)-6-(4-phenoxyphenyl)-1H-imidazo[1,2-b]pyrazole-7-carboxamide | ¹H NMR (DMSO-d$_6$) δ 11.53 (s, 1H), 7.64 (d, J = 8.4 Hz, 2H), 7.40 (d, J = 7.6 Hz, 1H), 7.38 (d, J = 7.6 Hz, 1H), 7.14 (t, J = 7.6 Hz, 1H), 7.05 (d, J = 8.0 Hz, 2H), 7.02 (d, J = 8.0 Hz, 2H), 6.96 (s, 1H), 6.80 (dd, J = 16.8, 10.1 Hz, 1H), 6.40 (brs, 2H), 6.07 (dd, J = 16.8, 2.0 Hz, 1H), 5.64 (dd, J = 10.1, 2.0 Hz, 1H), 4.46 (d, J = 12.8 Hz, 1H), 4.10 (d, J = 12.8 Hz, 1H), 3.24-3.04 (m, 2H), 2.80 (t, J = 12.8 Hz, 1H), 2.20-2.05 (m, 2H), 1.64-1.46 (m, 2H). MS (ESI) m/e [M + 1]⁺ 455.9. | 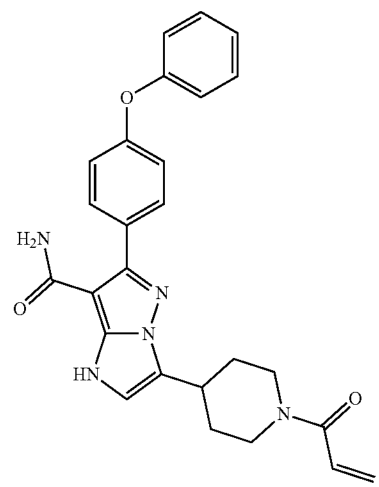 [SMILES: C=CC(=O)N1CCC(c2c[nH]c3c(C(N)=O)c(-c4ccc(Oc5ccccc5)cc4)nn23)CC1] |
| 137 | 7-(2-acrylamidophenyl)-2-(3,4-difluorophenyl)-4,5,6,7-tetrahydropyrazolo[1,5-a]pyrimidine-3-carboxamide | ¹H NMR (DMSO-d$_6$) δ 9.81 (s, 1H), 7.52-7.36 (m, 3H), 7.34-7.24 (m, 2H), 7.17 (t, J = 7.6 Hz, 1H), 6.74 (br s, 2H), 6.59 (d, J = 7.6 Hz, 1H), 6.50 (dd, J = 17.0, 10.2 Hz, 1H), 6.24 (dd, J = 17.0, 1.6 Hz, 1H), 5.80-5.70 (m, 2H), 3.28-3.18 (m, 1H), 3.01-2.87 (m, 1H), 2.34-2.20 (m, 1H), 2.01-1.89 (m, 1H). MS (ESI) m/e [M + 1]⁺ 423.9. | 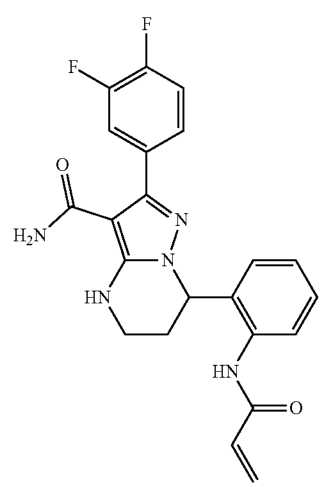 [SMILES: C=CC(=O)Nc1ccccc1C1CCNc2c(C(N)=O)c(-c3ccc(F)c(F)c3)nn21] |

TABLE 1-continued

Characterization Data for Selected Compounds

| No. | Name | ¹H NMR data, Chiral HPLC and LC/MS m/z (M + 1) | Structure |
|-----|------|------------------------------------------------|-----------|
| 138 | 7-(1-acryloylpiperidin-4-yl)-7-methyl-2-(4-phenoxyphenyl)-4,5,6,7-tetrahydropyrazolo[1,5-a]pyrimidine-3-carboxamide | ¹H NMR (DMSO-$d_6$) δ 7.50 (d, J = 8.6 Hz, 2H), 7.45-7.37 (m, 2H), 7.17 (t, J = 7.4 Hz, 1H), 7.11-7.03 (m, 4H), 6.85-6.72 (m, 1H), 6.68 (s, 1H), 6.07 (dd, J = 16.7, 2.4 Hz, 1H), 5.64 (d, J = 10.6 Hz, 1H), 4.58-4.41 (m, 1H), 4.19-4.00 (m, 1H), 3.33-3.24 (m, 2H), 3.05-2.85 (m, 1H), 2.60-2.50 (m, 1H), 2.31-2.16 (m, 1H), 2.15-2.00 (m, 1H), 1.80-1.65 (m, 2H), 1.44 (s, 3H), 1.35-1.05 (m, 3H). MS (ESI) m/e [M + 1]⁺ 486.0. | 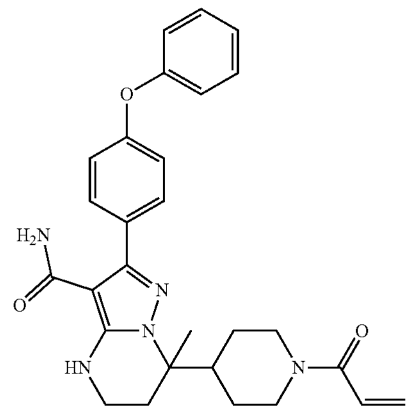 [SMILES: C=CC(=O)N1CCC(C2(C)CCNc3c(C(N)=O)c(-c4ccc(Oc5ccccc5)cc4)nn32)CC1] |
| 139 | 7-(1-acryloylazetidin-3-yl)-2-(3-chloro-4-phenoxyphenyl)-4,5,6,7-tetrahydropyrazolo[1,5-a]pyrimidine-3-carboxamide | ¹H NMR (DMSO-$d_6$) δ 7.70-7.66 (m, 1H), 7.52-7.46 (m, 1H), 7.44-7.36 (m, 2H), 7.19-7.07 (m, 2H), 7.04 (d, J = 8.6 Hz, 2H), 6.66 (s, 1H), 6.40-6.25 (m, 1H), 6.13-6.05 (m, 1H), 5.70-5.60 (m, 1H), 4.45-4.36 (m, 2H), 4.33-4.26 (m, 0.5H), 4.21-4.08 (m, 1H), 4.07-3.95 (m, 1H), 3.88-3.80 (m, 0.5H), 3.31-3.24 (m, 2H), 3.04-2.90 (m, 1H), 2.15-2.04 (m, 1H), 1.81-1.67 (m, 1H). MS (ESI) m/e [M + 1]⁺ 477.9. | 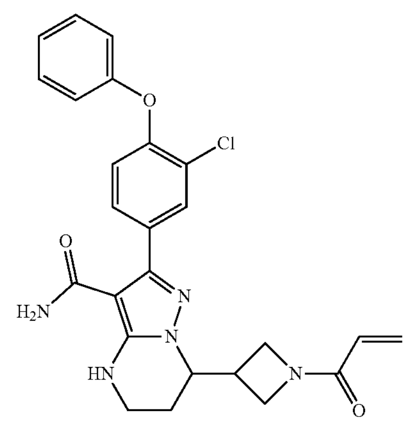 [SMILES: C=CC(=O)N1CC(C2CCNc3c(C(N)=O)c(-c4ccc(Oc5ccccc5)c(Cl)c4)nn32)C1] |
| 140 | 7-(1-acryloylazetidin-3-yl)-2-(3-methoxy-4-phenoxyphenyl)-4,5,6,7-tetrahydropyrazolo[1,5-a]pyrimidine-3-carboxamide formate | ¹H NMR (CD₃OD-$d_4$) δ 8.38 (br s, 1H), 7.31-7.19 (m, 3H), 7.15-7.10 (m, 1H), 7.06-6.96 (m, 2H), 6.88 (d, J = 8.1 Hz, 2H), 6.17-6.11 (m, 2H), 5.64-5.54 (m, 1H), 4.24-4.08 (m, 2H), 4.06-3.95 (m, 1H), 3.85-3.70 (m, 4H), 3.55-3.45 (m, 2H), 3.30-3.20 (m, 1H), 3.05-2.90 (m, 1H), 2.48-2.36 (m, 1H), 1.40-1.25 (m, 1H). MS (ESI) m/e [M + 1]⁺ 473.9. | 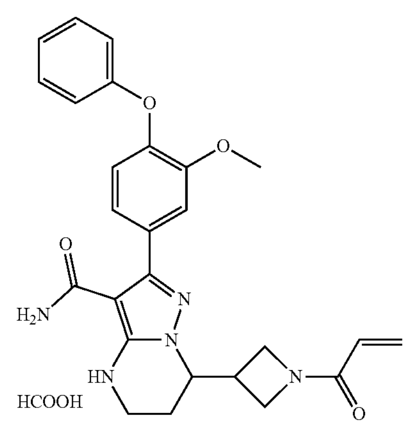 [SMILES: "HCOOH" ; C=CC(=O)N1CC(C2CCNc3c(C(N)=O)c(-c4ccc(Oc5ccccc5)c(OC)c4)nn32)C1] |

TABLE 1-continued

Characterization Data for Selected Compounds

| No. | Name | ¹H NMR data, Chiral HPLC and LC/MS m/z (M + 1) | Structure |
|---|---|---|---|
| 141 | 7-(1-acryloylazetidin-3-yl)-2-(4-phenethoxyphenyl)-4,5,6,7-tetrahydropyrazolo[1,5-a]pyrimidine-3-carboxamide | ¹H NMR (CD$_3$OD-d$_4$) δ 7.41-7.35 (m, 2H), 7.32-7.24 (m, 4H), 7.22-7.15 (m, 1H), 7.03-7.96 (m, 2H), 6.31 (dd, J = 17.0, 10.2 Hz, 1H), 6.19 (dd, J = 17.0, 2.0 Hz, 1H), 5.74-5.66 (m, 1H), 4.55-4.26 (m, 3H), 4.25-3.94 (m, 4H), 3.48-3.34 (m, 2H), 3.13-3.03 (m, 3H), 2.26-2.14 (m, 1H), 2.04-1.88 (m, 1H). MS (ESI) m/e [M + 1]⁺ 471.9. | 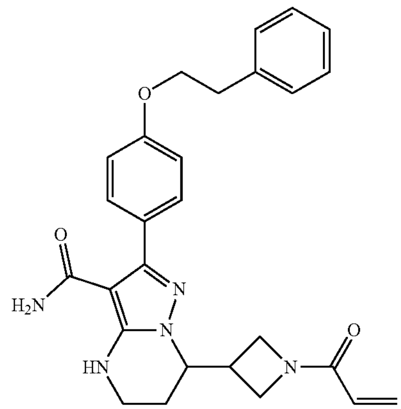 [SMILES: C=CC(=O)N1CC(C2CCNc3c(C(N)=O)c(-c4ccc(OCCc5ccccc5)cc4)nn32)C1] |
| 142 | 7-(acrylamidomethyl)-2-(4-(benzyloxy)-3-methoxyphenyl)-4,5,6,7-tetrahydropyrazolo[1,5-a]pyrimidine-3-carboxamide | ¹H NMR (DMSO-d$_6$) δ 8.31 (t, J = 6.0 Hz, 1H), 7.50-7.44 (m, 2H), 7.44-7.31 (m, 3H), 7.17-7.05 (m, 2H), 7.04-6.99 (m, 1H), 6.72 (s, 1H), 6.26 (dd, J = 17.1, 10.1 Hz, 1H), 6.11 (dd, J = 17.1, 1.8 Hz, 1H), 5.62 (dd, J = 10.1, 1.8 Hz, 1H), 5.12 (s, 2H), 4.22-4.12 (m, 1H), 3.85-3.72 (m, 4H), 3.48-3.33 (m, 3H), 2.07-1.87 (m, 2H). MS (ESI) m/e [M + 1]⁺ 461.9. | 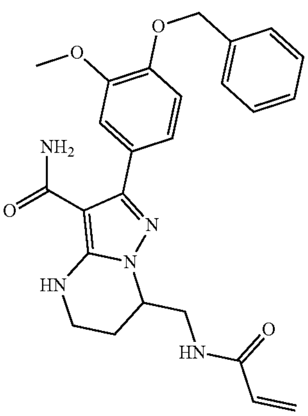 [SMILES: C=CC(=O)NCC1CCNc2c(C(N)=O)c(-c3ccc(OCc4ccccc4)c(OC)c3)nn21] |
| 143 | 7-(acrylamidomethyl)-7-methyl-2-(4-phenoxyphenyl)-4,5,6,7-tetrahydropyrazolo[1,5-a]pyrimidine-3-carboxamide | ¹H NMR (DMSO-d$_6$) δ 8.08 (t, J = 6.4 Hz, 1H), 7.53-7.45 (m, 2H), 7.42-7.34 (m, 2H), 7.14 (t, J = 7.4 Hz, 1H), 7.08-7.00 (m, 4H), 6.66 (s, 1H), 6.29 (dd, J = 17.1, 10.2 Hz, 1H), 6.08 (dd, J = 17.1, 2.2 Hz, 1H), 5.58 (dd, J = 10.2, 2.2 Hz, 1H), 3.66 (dd, J = 13.5, 6.8 Hz, 1H), 3.47 (dd, J = 13.5, 6.8 Hz, 1H), 2.05-1.94 (m, 1H), 1.79-1.69 (m, 1H), 1.38 (s, 3H). MS (ESI) m/e [M + 1]⁺ 431.9. | 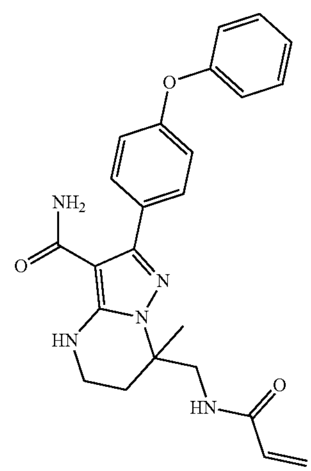 [SMILES: C=CC(=O)NCC1(C)CCNc2c(C(N)=O)c(-c3ccc(Oc4ccccc4)cc3)nn21] |

TABLE 1-continued

Characterization Data for Selected Compounds

| No. | Name | ¹H NMR data, Chiral HPLC and LC/MS m/z (M + 1) | Structure |
|---|---|---|---|
| 144 | 7-(1-acryloylpiperidin-4-yl)-2-phenyl-4,5,6,7-tetrahydropyrazolo[1,5-a]pyrimidine-3-carboxamide trifluoroacetate | ¹H NMR (CD$_3$OD-d$_4$) δ 7.54-7.42 (m, 5H), 6.75 (dd, J = 16.8, 10.7 Hz, 1H), 6.15 (dd, J = 16.8, 1.6 Hz, 1H), 5.70 (dd, J = 10.7, 1.6 Hz, 1H), 4.70-4.55 (m, 1H), 4.25-4.00 (m, 2H), 3.50-3.40 (m, 2H), 3.14-3.03 (m, 1H), 2.73-2.61 (m, 1H), 2.39-2.14 (m, 2H), 2.10-1.94 (m, 1H), 1.84-1.66 (m, 2H), 1.51-1.30 (m, 2H). MS (ESI) m/e [M + 1]⁺ 380.0. | 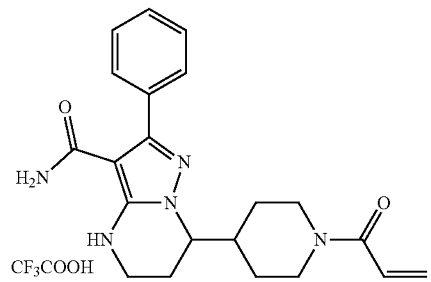 [SMILES: "CF3COOH" ; C=CC(=O)N1CCC(C2CCNc3c(C(N)=O)c(-c4ccccc4)nn32)CC1] |
| 145 | 7-(1-acryloylazetidin-3-yl)-2-(4-chlorophenyl)-4,5,6,7-tetrahydropyrazolo[1,5-a]pyrimidine-3-carboxamide | ¹H NMR (DMSO-d$_6$) δ 7.50 (d, J = 8.6 Hz, 2H), 7.45 (d, J = 8.6 Hz, 2H), 6.62 (s, 1H), 6.35-6.22 (m, 1H), 6.10-6.01 (m, 1H), 5.65-5.55 (m, 1H), 4.40-4.21 (m, 2.5H), 4.14-4.06 (m, 1H), 4.04-3.90 (m, 1H), 3.85-3.75 (m, 0.5H), 3.27-3.21 (m, 2H), 3.00-2.86 (m, 1H), 2.12-1.98 (m, 1H), 1.77-1.63 (m, 1H). | 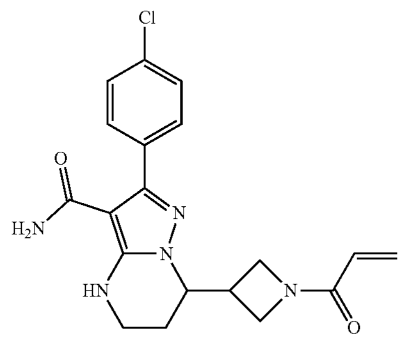 [SMILES: C=CC(=O)N1CC(C2CCNc3c(C(N)=O)c(-c4ccc(Cl)cc4)nn32)C1] |
| 146 | 7-(2-Acrylamidophenyl)-2-(3-chloro-4-(pyridin-2-ylmethoxy)phenyl)-4,5,6,7-tetrahydropyrazolo[1,5-a]pyrimidine-3-carboxamide | ¹H NMR (400 MHz, DMSO-d$_6$) δ 9.83 (s, 1H), 8.59 (d, J = 4.2 Hz, 1H), 7.86 (dt, J = 7.6, 2.0 Hz, 1H), 7.56 (d, J = 7.6 Hz, 1H), 7.54 (d, J = 2.0 Hz, 2H), 7.48-7.40 (m, 2H), 7.39-7.33 (m, 1H), 7.33-7.24 (m, 2H), 7.21 (t, J = 7.6 Hz, 1H), 6.77 (s, 1H), 6.63 (d, J = 8.0 Hz, 1H), 6.53 (dd, J = 16.8, 10.2 Hz, 1H), 6.27 (dd, J = 16.8, 1.8 Hz, 1H), 5.82-5.74 (m, 2H), 5.30 (s, 2H), 3.30-3.20 (m, 1H), 3.02-2.92 (m, 1H), 2.37-2.23 (m, 1H), 2.02-1.93 (m, 1H). MS (ESI) m/e [M + 1]⁺ 528.9. | 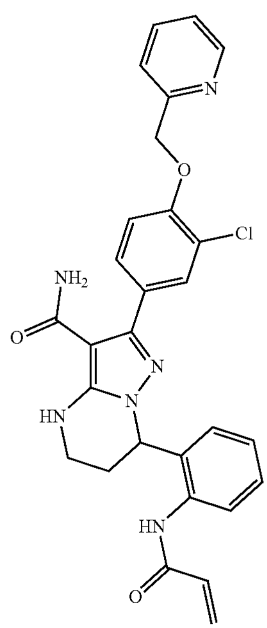 [SMILES: C=CC(=O)Nc1ccccc1C1CCNc2c(C(N)=O)c(-c3ccc(OCc4ccccn4)c(Cl)c3)nn21] |

TABLE 1-continued

Characterization Data for Selected Compounds

| No. | Name | $^1$H NMR data, Chiral HPLC and LC/MS m/z (M + 1) | Structure |
|---|---|---|---|
| 147 | 7-(2-Acrylamido-4-chlorophenyl)-2-(4-(cyclopropylmethoxy)phenyl)-4,5,6,7-tetrahydropyrazolo[1,5-a]pyrimidine-3-carboxamide | MS (ESI) m/e [M + 1]$^+$ 491.9. | 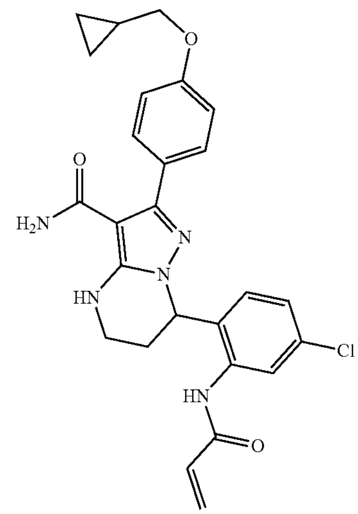 [SMILES: C=CC(=O)Nc1cc(Cl)ccc1C1CCNc2c(C(N)=O)c(-c3ccc(OCC4CC4)cc3)nn21] |
| 148 | 7-(2-Acrylamido-4-methylphenyl)-2-(4-(cyclopropylmethoxy)phenyl)-4,5,6,7-tetrahydropyrazolo[1,5-a]pyrimidine-3-carboxamide | MS (ESI) m/e [M + 1]$^+$ 471.9. | 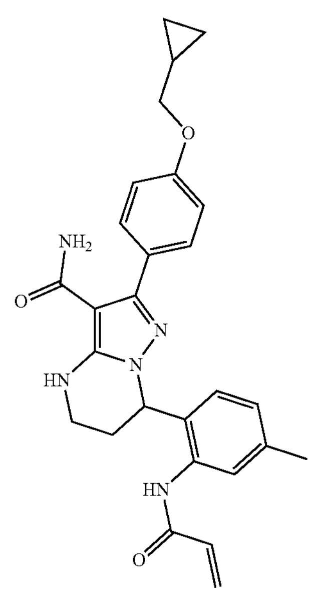 [SMILES: C=CC(=O)Nc1cc(C)ccc1C1CCNc2c(C(N)=O)c(-c3ccc(OCC4CC4)cc3)nn21] |

TABLE 1-continued

Characterization Data for Selected Compounds

| No. | Name | ¹H NMR data, Chiral HPLC and LC/MS<br>m/z (M + 1) | Structure |
|---|---|---|---|
| 149 | 7-(2-Acrylamidophenyl)-2-(4-(trifluoromethoxy)phenyl)-4,5,6,7-tetrahydropyrazolo[1,5-a]pyrimidine-3-carboxamide | MS (ESI) m/e [M + 1]⁺ 471.9. | 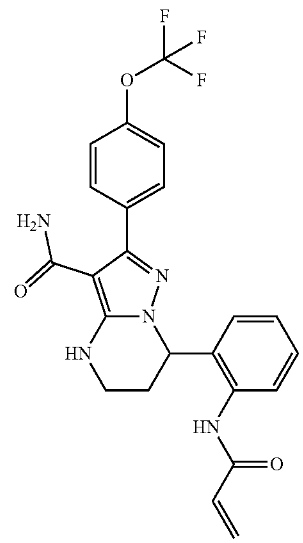 [SMILES: C=CC(=O)Nc1ccccc1C1CCNc2c(C(N)=O)c(-c3ccc(OC(F)(F)F)cc3)nn21] |
| 150 | 7-(2-Acrylamidophenyl)-2-phenyl-4,5,6,7-tetrahydropyrazolo[1,5-a]pyrimidine-3-carboxamide | MS (ESI) m/e [M + 1]⁺ 387.9. | 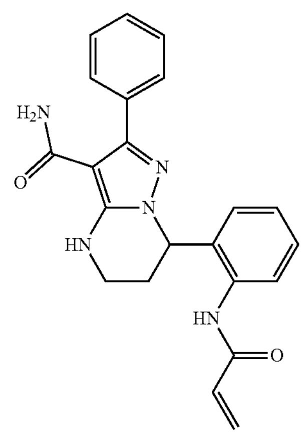 [SMILES: C=CC(=O)Nc1ccccc1C1CCNc2c(C(N)=O)c(-c3ccccc3)nn21] |
| 151 | 7-(2-Acrylamidophenyl)-2-(4-fluorophenyl)-4,5,6,7-tetrahydropyrazolo[1,5-a]pyrimidine-3-carboxamide | MS (ESI) m/e [M + 1]⁺ 405.9. | 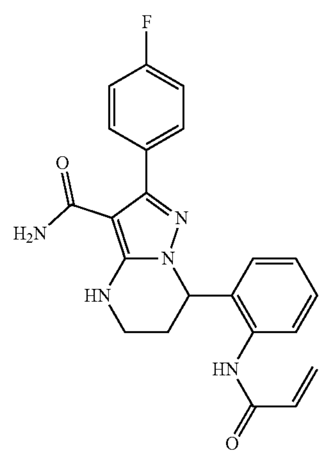 [SMILES: C=CC(=O)Nc1ccccc1C1CCNc2c(C(N)=O)c(-c3ccc(F)cc3)nn21] |

TABLE 1-continued

Characterization Data for Selected Compounds

| No. | Name | ¹H NMR data, Chiral HPLC and LC/MS m/z (M + 1) | Structure |
|---|---|---|---|
| 152 | 7-(2-Acrylamidophenyl)-2-(3-bromo-4-fluorophenyl)-4,5,6,7-tetrahydropyrazolo[1,5-a]pyrimidine-3-carboxamide | ¹H NMR (400 MHz, DMSO-d$_6$) δ 9.83 (s, 1H), 7.77 (dd, J = 6.8, 2.0 Hz, 1H), 7.58-7.51 (m, 1H), 7.45 (d, J = 7.6 Hz, 1H), 7.39 (t, J = 8.6 Hz, 1H), 7.31 (t, J = 7.6 Hz, 1H), 7.21 (t, J = 7.6 Hz, 1H), 6.77 (s, 1H), 6.63 (d, J = 7.6 Hz, 1H), 6.53 (dd, J = 17.0, 10.2 Hz, 1H), 6.28 (dd, J = 17.0, 1.8 Hz, 1H), 5.82-5.75 (m, 2H), 3.31-3.21 (m, 1H), 3.03-2.91 (m, 1H), 2.37-2.22 (m, 1H), 2.03-1.91 (m, 1H). MS (ESI) m/e [M + 1]⁺ 483.8, 485.8. | 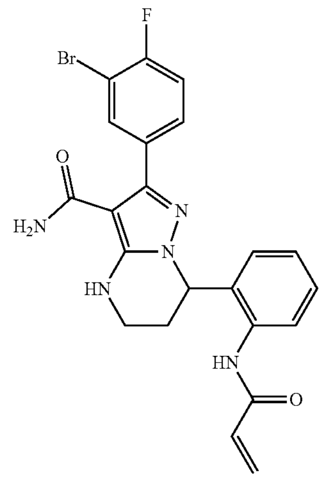 [SMILES: C=CC(=O)Nc1ccccc1C1CCNc2c(C(N)=O)c(-c3ccc(F)c(Br)c3)nn21] |
| 153 | (E)-2-(3-Chloro-4-fluorophenyl)-7-(2-(4-(piperidin-1-yl)but-2-enamido)phenyl)-4,5,6,7-tetrahydropyrazolo[1,5-a]pyrimidine-3-carboxamide | MS (ESI) m/e [M + 1]⁺ 536.9. | 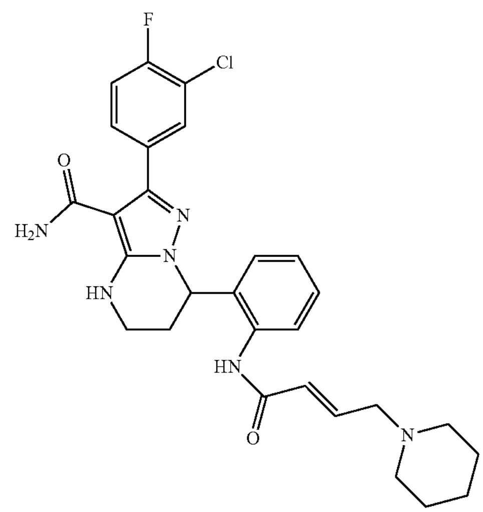 [SMILES: NC(=O)c1c(-c2ccc(F)c(Cl)c2)nn2c1NCCC2c1ccccc1NC(=O)/C=C/CN1CCCCC1] |
| 154 | 7-(2-Acrylamidophenyl)-2-(4-chloro-3-fluorophenyl)-4,5,6,7-tetrahydropyrazolo[1,5-a]pyrimidine-3-carboxamide | ¹H NMR (400 MHz, DMSO-d$_6$) δ 9.83 (s, 1H), 7.65 (dd, J = 7.3, 2.0 Hz, 1H), 7.54-7.48 (m, 1H), 7.47-7.39 (m, 2H), 7.31 (t, J = 7.6 Hz, 1H), 7.21 (t, J = 7.6 Hz, 1H), 6.77 (s, 1H), 6.63 (d, J = 7.8 Hz, 1H), 6.53 (dd, J = 17.0, 10.3 Hz, 1H), 6.27 (dd, J = 17.0, 1.8 Hz, 1H), 5.83-5.75 (m, 2H), 3.30-3.21 (m, 1H), 3.03-2.97 (m, 1H), 2.36-2.24 (m, 1H), 2.04-1.93 (m, 1H). MS (ESI) m/e [M + 1]⁺ 439.9. | 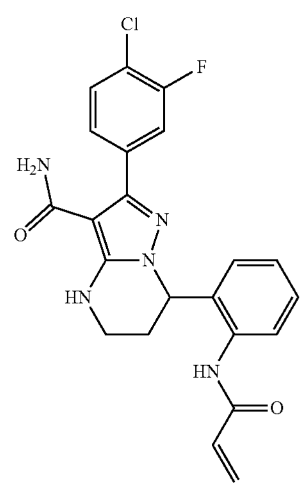 [SMILES: C=CC(=O)Nc1ccccc1C1CCNc2c(C(N)=O)c(-c3ccc(Cl)c(F)c3)nn21] |

TABLE 1-continued

Characterization Data for Selected Compounds

| No. | Name | $^1$H NMR data, Chiral HPLC and LC/MS m/z (M + 1) | Structure |
|---|---|---|---|
| 155 | 7-(2-Acrylamidophenyl)-2-(3-chlorophenyl)-4,5,6,7-tetrahydropyrazolo[1,5-a]pyrimidine-3-carboxamide | MS (ESI) m/e [M + 1]$^+$ 421.9. | 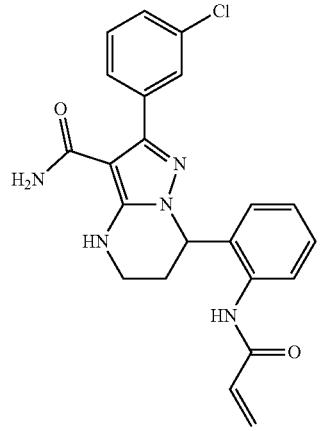 [SMILES: C=CC(=O)Nc1ccccc1C1CCNc2c(C(N)=O)c(-c3cccc(Cl)c3)nn21] |
| 156 | 7-(2-Acrylamidophenyl)-2-(3,4-dichlorophenyl)-4,5,6,7-tetrahydropyrazolo[1,5-a]pyrimidine-3-carboxamide | $^1$H NMR (400 MHz, DMSO-d$_6$) δ 9.83 (s, 1H), 7.71 (d, J = 1.6 Hz, 1H), 7.63 (d, J = 8.4 Hz, 1H), 7.50 (dd, J = 8.4, 1.6 Hz, 1H), 7.45 (d, J = 7.6 Hz, 1H), 7.31 (t, J = 7.6 Hz, 1H), 7.21 (t, J = 7.6 Hz, 1H), 6.77 (s, 1H), 6.63 (d, J = 7.6 Hz, 1H), 6.53 (dd, J = 16.8, 10.2 Hz, 1H), 6.28 (d, J = 16.8 Hz, 1H), 5.84-5.75 (m, 2H), 3.31-3.21 (m, 1H), 3.05-2.92 (m, 1H), 2.38-2.23 (m, 1H), 2.03-1.94 (m, 1H). MS (ESI) m/e [M + 1]$^+$ 455.8. | 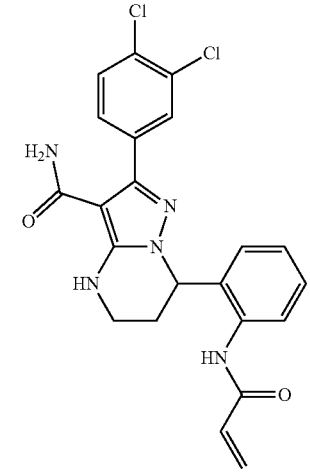 [SMILES: C=CC(=O)Nc1ccccc1C1CCNc2c(C(N)=O)c(-c3ccc(Cl)c(Cl)c3)nn21] |
| 157 | 7-(2-Acrylamidophenyl)-2-(4-fluoro-3-methylphenyl)-4,5,6,7-tetrahydropyrazolo[1,5-a]pyrimidine-3-carboxamide | MS (ESI) m/e [M + 1]$^+$ 419.9. | 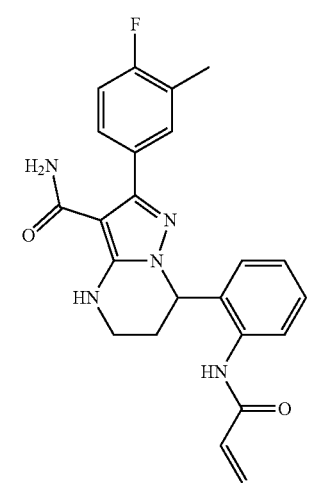 [SMILES: C=CC(=O)Nc1ccccc1C1CCNc2c(C(N)=O)c(-c3ccc(F)c(C)c3)nn21] |

TABLE 1-continued

Characterization Data for Selected Compounds

| No. | Name | $^1$H NMR data, Chiral HPLC and LC/MS m/z (M + 1) | Structure |
|---|---|---|---|
| 158 | 7-(2-Acrylamidophenyl)-2-(3-chloro-4,5-difluorophenyl)-4,5,6,7-tetrahydropyrazolo[1,5-a]pyrimidine-3-carboxamide | MS (ESI) m/e [M + 1]$^+$ 457.9. | 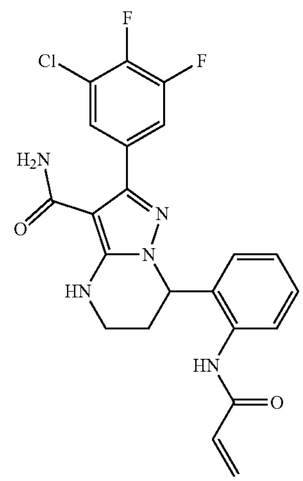 [SMILES: C=CC(=O)Nc1ccccc1C1CCNc2c(C(N)=O)c(-c3cc(F)c(F)c(Cl)c3)nn21] |
| 159 | 7-(2-Acrylamidophenyl)-2-(4-fluoro-3-methoxyphenyl)-4,5,6,7-tetrahydropyrazolo[1,5-a]pyrimidine-3-carboxamide | MS (ESI) m/e [M + 1]$^+$ 435.9. | 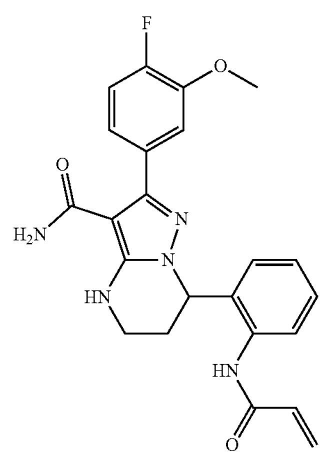 [SMILES: C=CC(=O)Nc1ccccc1C1CCNc2c(C(N)=O)c(-c3ccc(F)c(OC)c3)nn21] |
| 160 | 7-(2-Acrylamidophenyl)-2-(4-chloro-3-methoxyphenyl)-4,5,6,7-tetrahydropyrazolo[1,5-a]pyrimidine-3-carboxamide | MS (ESI) m/e [M + 1]$^+$ 451.8. | 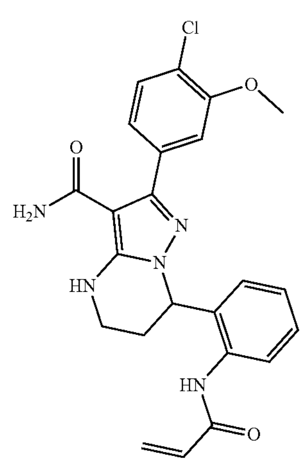 [SMILES: C=CC(=O)Nc1ccccc1C1CCNc2c(C(N)=O)c(-c3ccc(Cl)c(OC)c3)nn21] |

TABLE 1-continued

Characterization Data for Selected Compounds

| No. | Name | ¹H NMR data, Chiral HPLC and LC/MS m/z (M + 1) | Structure |
|---|---|---|---|
| 161 | 7-(2-Acrylamidophenyl)-2-(4-(trifluoromethyl)phenyl)-4,5,6,7-tetrahydropyrazolo[1,5-a]pyrimidine-3-carboxamide | MS (ESI) m/e [M + 1]⁺ 455.9. | 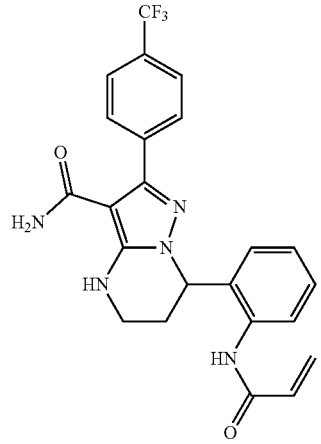 [SMILES: C=CC(=O)Nc1ccccc1C1CCNc2c(C(N)=O)c(-c3ccc(C(F)(F)F)cc3)nn21] |
| 162 | 7-(2-Acrylamidophenyl)-2-(3-chloro-4-(trifluoromethyl)phenyl)-4,5,6,7-tetrahydropyrazolo[1,5-a]pyrimidine-3-carboxamide | MS (ESI) m/e [M + 1]⁺ 489.8. | 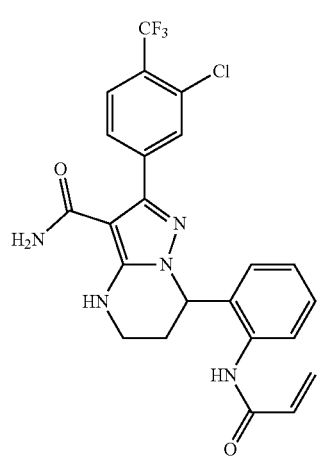 [SMILES: C=CC(=O)Nc1ccccc1C1CCNc2c(C(N)=O)c(-c3ccc(C(F)(F)F)c(Cl)c3)nn21] |
| 163 | 7-(2-Acrylamidophenyl)-2-(4-chloro-3-(trifluoromethyl)phenyl)-4,5,6,7-tetrahydropyrazolo[1,5-a]pyrimidine-3-carboxamide | MS (ESI) m/e [M + 1]⁺ 489.8. | 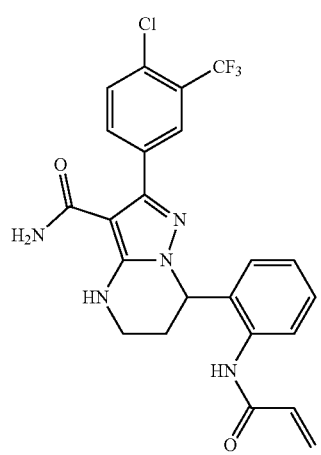 [SMILES: C=CC(=O)Nc1ccccc1C1CCNc2c(C(N)=O)c(-c3ccc(Cl)c(C(F)(F)F)c3)nn21] |

TABLE 1-continued

Characterization Data for Selected Compounds

| No. | Name | $^1$H NMR data, Chiral HPLC and LC/MS m/z (M + 1) | Structure |
|-----|------|---------------------------------------------------|-----------|
| 164 | 7-(2-Acrylamidophenyl)-2-(p-tolyl)-4,5,6,7-tetrahydropyrazolo[1,5-a]pyrimidine-3-carboxamide | MS (ESI) m/e [M + 1]$^+$ 401.9. | 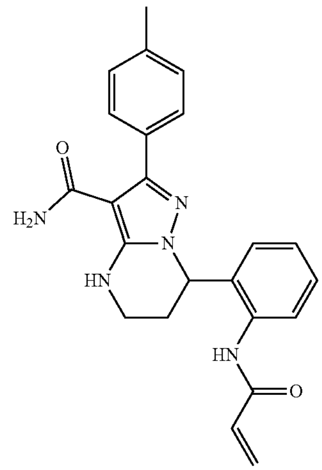 [SMILES: C=CC(=O)Nc1ccccc1C1CCNc2c(C(N)=O)c(-c3ccc(C)cc3)nn21] |
| 165 | (E)-7-(2-(4-(Dimethylamino)but-2-enamido)phenyl)-2-(3-methoxy-4-methylphenyl)-4,5,6,7-tetrahydropyrazolo[1,5-a]pyrimidine-3-carboxamide | MS (ESI) m/e [M + 1]$^+$ 489.0. | 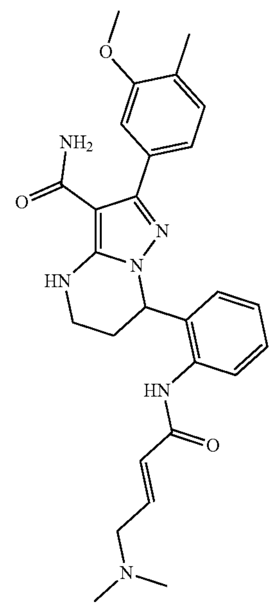 [SMILES: COc1cc(-c2nn3c(c2C(N)=O)NCCC3c2ccccc2NC(=O)/C=C/CN(C)C)ccc1C] |
| 166 | 7-(2-Acrylamidophenyl)-2-(3-methoxyphenyl)-4,5,6,7-tetrahydropyrazolo[1,5-a]pyrimidine-3-carboxamide | MS (ESI) m/e [M + 1]$^+$ 417.9. | 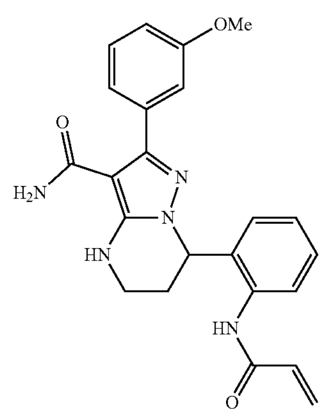 [SMILES: C=CC(=O)Nc1ccccc1C1CCNc2c(C(N)=O)c(-c3cccc(OC)c3)nn21] |

TABLE 1-continued

Characterization Data for Selected Compounds

| No. | Name | ¹H NMR data, Chiral HPLC and LC/MS m/z (M + 1) | Structure |
|---|---|---|---|
| 167 | 7-(2-Acrylamidophenyl)-2-(3,4,5-trimethoxyphenyl)-4,5,6,7-tetrahydropyrazolo[1,5-a]pyrimidine-3-carboxamide | MS (ESI) m/e [M + 1]⁺ 477.9. | 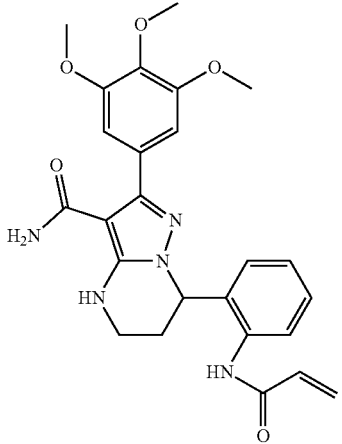 [SMILES: C=CC(=O)Nc1ccccc1C1CCNc2c(C(N)=O)c(-c3cc(OC)c(OC)c(OC)c3)nn21] |
| 168 | 7-(2-Acrylamidophenyl)-2-(3,4-dimethoxyphenyl)-4,5,6,7-tetrahydropyrazolo[1,5-a]pyrimidine-3-carboxamide | MS (ESI) m/e [M + 1]⁺ 447.9. | 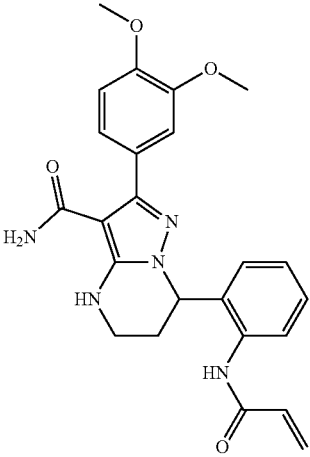 [SMILES: C=CC(=O)Nc1ccccc1C1CCNc2c(C(N)=O)c(-c3ccc(OC)c(OC)c3)nn21] |
| 169 | 7-(2-Acrylamidophenyl)-2-(3,5-dichloro-4-methoxyphenyl)-4,5,6,7-tetrahydropyrazolo[1,5-a]pyrimidine-3-carboxamide | MS (ESI) m/e [M + 1]⁺ 485.8. | 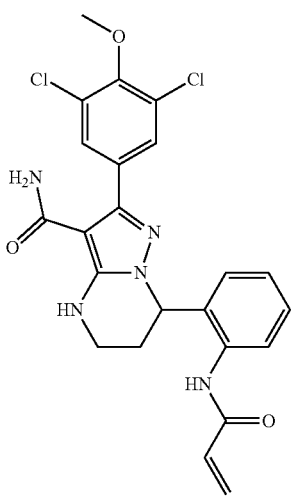 [SMILES: C=CC(=O)Nc1ccccc1C1CCNc2c(C(N)=O)c(-c3cc(Cl)c(OC)c(Cl)c3)nn21] |

TABLE 1-continued

Characterization Data for Selected Compounds

| No. | Name | ¹H NMR data, Chiral HPLC and LC/MS m/z (M + 1) | Structure |
|---|---|---|---|
| 170 | (E)-2-(4-Phenoxyphenyl)-7-(1-(4-(piperidin-1-yl)but-2-enoyl)piperidin-4-yl)-4,5,6,7-tetrahydropyrazolo[1,5-a]pyrimidine-3-carboxamide | MS (ESI) m/e [M + 1]⁺ 569.0. | 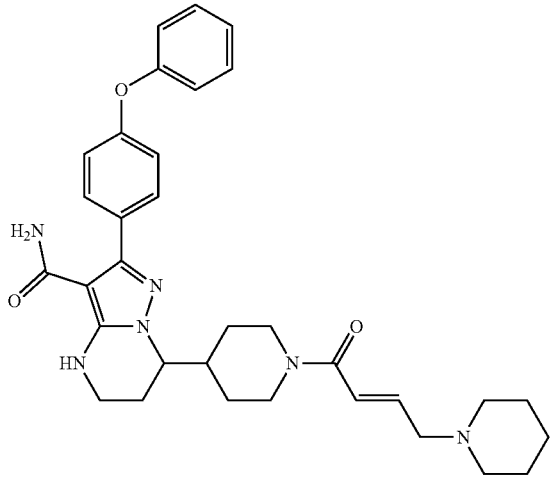 [SMILES: NC(=O)c1c(-c2ccc(Oc3ccccc3)cc2)nn2c1NCCC2C1CCN(C(=O)/C=C/CN2CCCCC2)CC1] |
| 171 | (R or S) (E)-7-(1-(4-(Dimethylamino)but-2-enoyl)piperidin-4-yl)-2-(4-phenoxyphenyl)-4,5,6,7-tetrahydropyrazolo[1,5-a]pyrimidine-3-carboxamide | MS (ESI) m/e [M + 1]⁺ 529.0. | 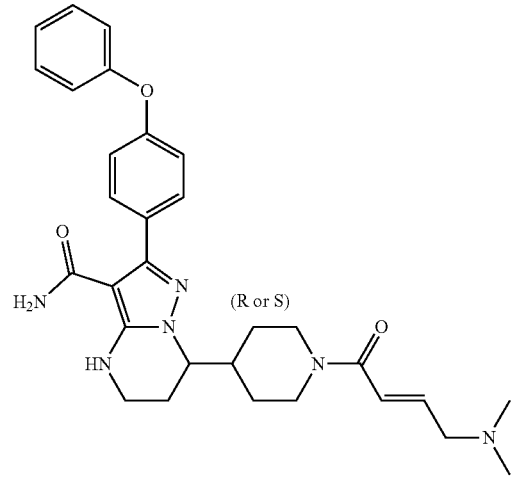 [SMILES: CN(C)C/C=C/C(=O)N1CCC(C2CCNc3c(C(N)=O)c(-c4ccc(Oc5ccccc5)cc4)nn32)CC1] |
| 172 | 7-(1-Acryloylpiperidin-4-yl)-2-(3-methoxy-4-phenoxyphenyl)-4,5,6,7-tetrahydropyrazolo[1,5-a]pyrimidine-3-carboxamide | MS (ESI) m/e [M + 1]⁺ 501.9. | 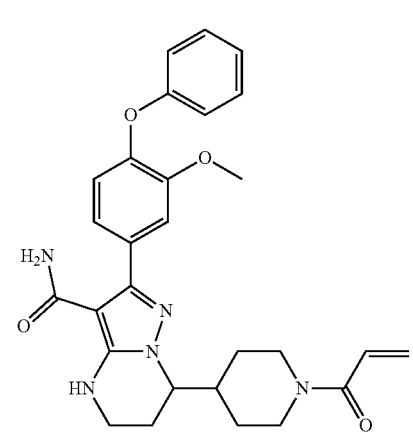 [SMILES: C=CC(=O)N1CCC(C2CCNc3c(C(N)=O)c(-c4ccc(Oc5ccccc5)c(OC)c4)nn32)CC1] |

TABLE 1-continued

Characterization Data for Selected Compounds

| No. | Name | ¹H NMR data, Chiral HPLC and LC/MS<br>m/z (M + 1) | Structure |
| --- | --- | --- | --- |
| 173 | 7-(1-Acryloylpiperidin-4-yl)-2-(3-chloro-4-phenoxyphenyl)-4,5,6,7-tetrahydropyrazolo[1,5-a]pyrimidine-3-carboxamide | MS (ESI) m/e [M + 1]⁺ 505.9. | 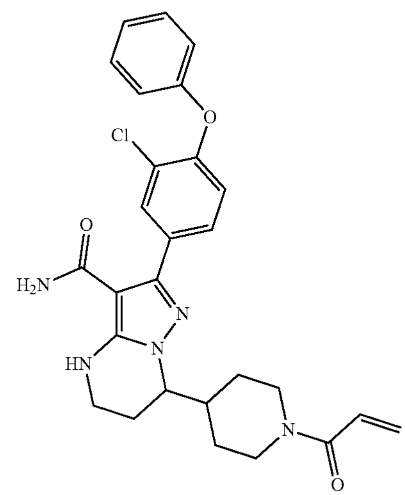 [SMILES: C=CC(=O)N1CCC(C2CCNc3c(C(N)=O)c(-c4ccc(Oc5ccccc5)c(Cl)c4)nn32)CC1] |
| 174 | 7-(1-Acryloylpiperidin-4-yl)-2-(3-methoxy-4-methylphenyl)-4,5,6,7-tetrahydropyrazolo[1,5-a]pyrimidine-3-carboxamide | MS (ESI) m/e [M + 1]⁺ 424.0. | 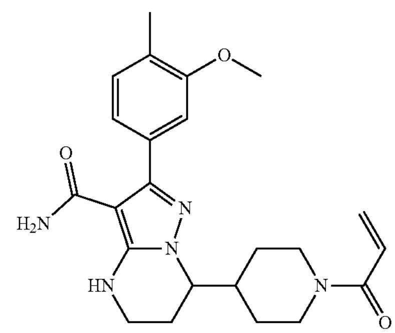 [SMILES: C=CC(=O)N1CCC(C2CCNc3c(C(N)=O)c(-c4ccc(C)c(OC)c4)nn32)CC1] |
| 175 | 7-(1-Acryloylazetidin-3-yl)-7-methyl-2-(4-phenoxyphenyl)-4,5,6,7-tetrahydropyrazolo[1,5-a]pyrimidine-3-carboxamide | MS (ESI) m/e [M + 1]⁺ 457.9. | 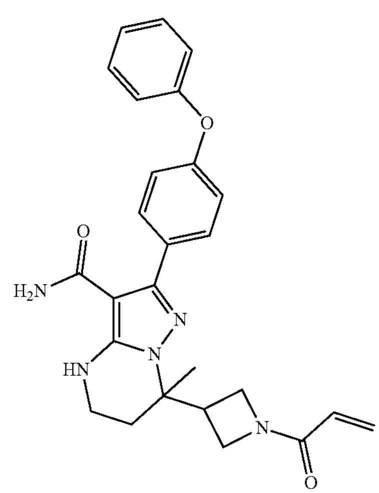 [SMILES: C=CC(=O)N1CC(C2(C)CCNc3c(C(N)=O)c(-c4ccc(Oc5ccccc5)cc4)nn32)C1] |

TABLE 1-continued

Characterization Data for Selected Compounds

| No. | Name | $^1$H NMR data, Chiral HPLC and LC/MS m/z (M + 1) | Structure |
|---|---|---|---|
| 176 | (S)-7-(1-(But-2-ynoyl)piperidin-4-yl)-2-(4-phenoxyphenyl)-4,5,6,7-tetrahydropyrazolo[1,5-a]pyrimidine-3-carboxamide | $^1$H NMR (400 MHz, DMSO-d$_6$) δ 7.50 (d, J = 7.2 Hz, 2 H), 7.42 (dd, J = 8.4, 8.4 Hz, 2H), 7.17 (t, J = 7.2 Hz, 1H), 7.11-7.03 (m, 4H), 6.68 (s, 1 H), 4.40-4.24 (m, 2 H), 4.06-3.97 (m, 1 H), 3.33-3.27 (m, 1 H), 3.12-3.00 (m, 1 H), 2.66-2.54 (m, 1H), 2.32-2.20 (m, 1H), 2.07-2.00 (m, 1H), 2.00 (s, 3 H), 1.96-1.86 (m, 1 H), 1.81-1.67 (m, 1 H), 1.63-1.52 (m, 1 H), 1.36-1.08 (m, 2 H). MS (ESI) m/e [M + 1]$^+$ 483.9. | 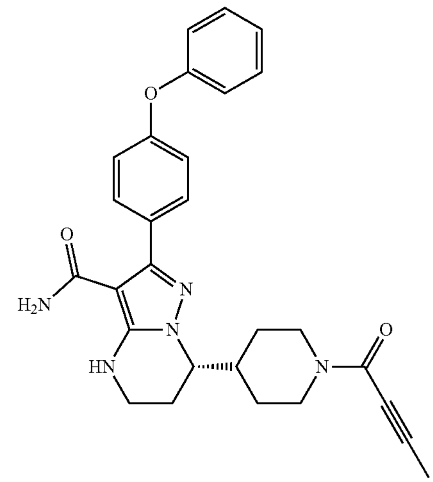 [SMILES: CC#CC(=O)N1CCC([C@@H]2CCNc3c(C(N)=O)c(-c4ccc(Oc5ccccc5)cc4)nn32)CC1] |
| 177 | (S)-7-(1-(3-chloropropanoyl)piperidin-4-yl)-2-(4-phenoxyphenyl)-4,5,6,7-tetrahydropyrazolo[1,5-a]pyrimidine-3-carboxamide | $^1$H NMR (400 MHz, DMSO-d$_6$) δ 7.54-7.47 (m, 2H), 7.45-7.38 (m, 2H), 7.21-7.14 (m, 1H), 7.12-7.02 (m, 4H), 6.69 (s, 1H), 4.45 (d, J = 12.1 Hz, 1H), 4.06-3.97 (m, 1H), 3.90 (t, J = 10.3 Hz, 1H), 3.82-3.72 (m, 2H), 3.33-3.25 (m, 2H), 3.02-2.72 (m, 3H), 2.58-2.43 (m, 1H), 2.35-2.15 (m, 1H), 2.10-1.84 (m, 2H), 1.70 (t, J = 12.1 Hz, 1H), 1.54 (t, J = 12.1 Hz, 1H), 1.41-1.08 (m, 2H). MS (ESI) m/e [M + 1]$^+$ 507.9, 509.9. | 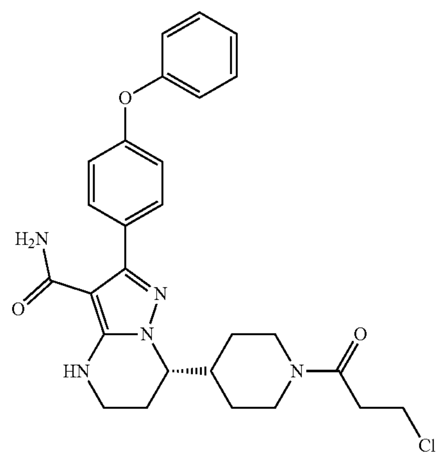 [SMILES: NC(=O)c1c(-c2ccc(Oc3ccccc3)cc2)nn2c1NCC[C@H]2C1CCN(C(=O)CCCl)CC1] |
| 179 | 7-(1-(But-2-ynoyl)piperidin-4-yl)-2-(4-(2,4-difluorophenoxy)phenyl)-4,5,6,7-tetrahydropyrazolo[1,5-a]pyrimidine-3-carboxamide | $^1$H NMR (400 MHz, DMSO-d$_6$) δ 7.55-7.45 (m, 3H), 7.41-7.32 (m, 1H), 7.21-7.12 (m, 1H), 7.05-6.99 (m, 2H), 6.67 (s, 1H), 4.39-4.22 (m, 2H), 4.06-3.97 (m, 1H), 3.33-3.25 (m, 2H), 3.12-2.97 (m, 1H), 2.69-2.52 (m, 1H), 2.35-2.17 (m, 1H), 2.08-2.00 (m, 1H), 2.00 (s, 3H), 1.96-1.84 (m, 1H), 1.81-1.65 (m, 1H), 1.63-1.51 (m, 1H), 1.36-1.09 (m, 2H). MS (ESI) m/e [M + 1]$^+$ 519.9. | 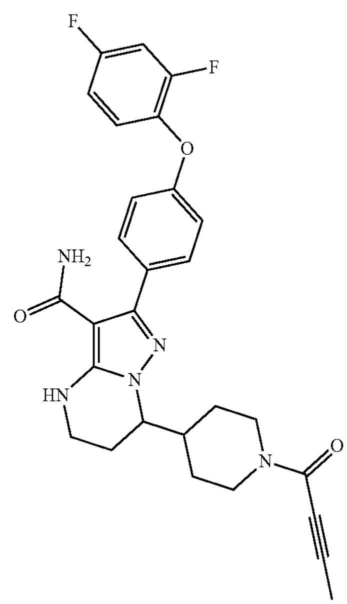 [SMILES: CC#CC(=O)N1CCC(C2CCNc3c(C(N)=O)c(-c4ccc(Oc5ccc(F)cc5F)cc4)nn32)CC1] |

TABLE 1-continued

Characterization Data for Selected Compounds

| No. | Name | $^1$H NMR data, Chiral HPLC and LC/MS m/z (M + 1) | Structure |
|---|---|---|---|
| 180 | (S)-7-(1-(2-Cyanoacetyl)piperidin-4-yl)-2-(4-phenoxyphenyl)-4,5,6,7-tetrahydropyrazolo[1,5-a]pyrimidine-3-carboxamide | MS (ESI) m/e [M + 1]$^+$ 484.9. | 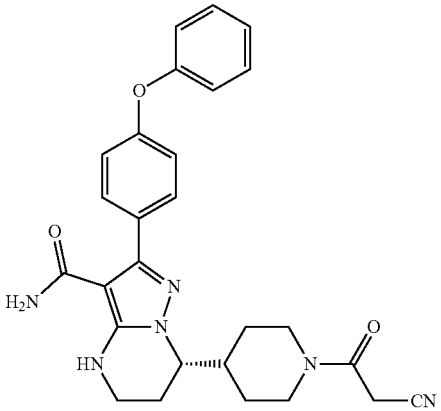 [SMILES: N#CCC(=O)N1CCC([C@@H]2CCNc3c(C(N)=O)c(-c4ccc(Oc5ccccc5)cc4)nn32)CC1] |
| 183 | 7-(1-Acryloylpiperidin-4-yl)-2-(4-(2,4-difluorophenoxy)phenyl)-4,5,6,7-tetrahydropyrazolo[1,5-a]pyrimidine-3-carboxamide | $^1$H NMR (400 MHz, DMSO-d$_6$) δ 7.58-7.44 (m, 3H), 7.41-7.30 (m, 1H), 7.20-7.10 (m, 1H), 7.02 (d, J = 8.5 Hz, 2H), 6.85-6.73 (m, 1H), 6.67 (br s, 1H), 6.07 (d, J = 16.4 Hz, 1H), 5.64 (d, J = 10.5 Hz, 1H), 4.55-4.39 (m, 1H), 4.17-3.95 (m, 2H), 3.74-3.38 (m, 3H), 3.06-2.89 (m, 1H), 2.35-2.15 (m, 1H), 2.09-1.83 (m, 2H), 1.78-1.65 (m, 1H), 1.62-1.49 (m, 1H), 1.34-1.07 (m, 2H). MS (ESI) m/e [M + 1]$^+$ 507.9. | 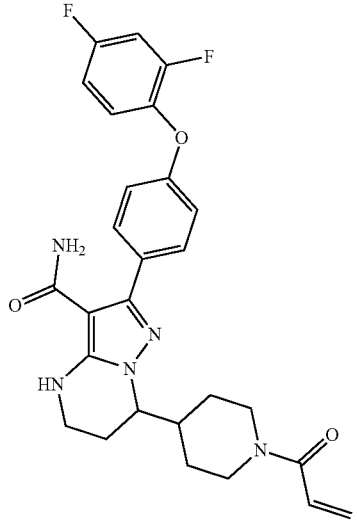 [SMILES: C=CC(=O)N1CCC(C2CCNc3c(C(N)=O)c(-c4ccc(Oc5ccc(F)cc5F)cc4)nn32)CC1] |
| 184 | 7-(1-(But-2-ynoyl)azetidin-3-yl)-2-(4-phenoxyphenyl)-4,5,6,7-tetrahydropyrazolo[1,5-a]pyrimidine-3-carboxamide | $^1$H NMR (400 MHz, DMSO-d$_6$) δ 7.53-7.46 (m, 2H), 7.45-7.38 (m, 2H), 7.21-7.13 (m, 1H), 7.12-7.01 (m, 4H), 6.72-6.66 (m, 1H), 4.43-4.34 (m, 1H), 4.33-4.27 (m, 0.5H), 4.26-4.15 (m, 1H), 4.11-4.04 (m, 1H), 4.02-3.92 (m, 1H), 3.85-3.77 (m, 0.5H), 3.30-3.23 (m, 2H), 3.03-2.90 (m, 1H), 2.15-2.04 (m, 1H), 2.00-1.90 (m, 3H), 1.82-1.67 (m, 1H). MS (ESI) m/e [M + 1]$^+$ 455.9. | 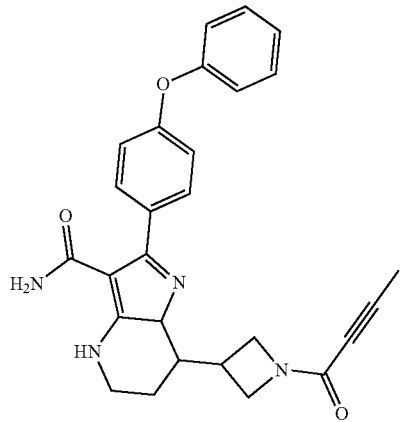 [SMILES: CC#CC(=O)N1CC(C2CCNC3=C(C(N)=O)C(c4ccc(Oc5ccccc5)cc4)=NC32)C1] |

TABLE 1-continued

Characterization Data for Selected Compounds

| No. | Name | $^1$H NMR data, Chiral HPLC and LC/MS m/z (M + 1) | Structure |
|---|---|---|---|
| 185 | 7-(But-2-ynamidomethyl)-2-(4-phenoxyphenyl)-4,5,6,7-tetrahydropyrazolo[1,5-a]pyrimidine-3-carboxamide | $^1$H NMR (400 MHz, DMSO-d$_6$) δ 8.67 (t, J = 6.0 Hz, 1H), 7.56-7.49 (m, 2H), 7.46-7.37 (m, 2H), 7.21-7.13 (m, 1H), 7.12-7.01 (m, 4H), 6.68 (s, 1H), 4.20-4.09 (m, 1H), 3.76-3.65 (m, 1H), 3.36-3.24 (m, 3H), 2.09-1.83 (m, 5H). MS (ESI) m/e [M + 1]$^+$ 429.9. | 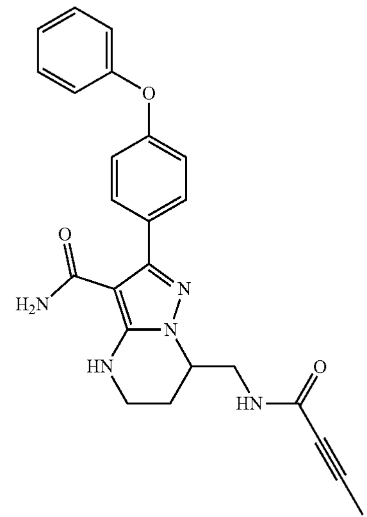 [SMILES: CC#CC(=O)NCC1CCNc2c(C(N)=O)c(-c3ccc(Oc4ccccc4)cc3)nn21] |
| 186 | (S)-7-(1-(Pent-2-ynoyl)piperidin-4-yl)-2-(4-phenoxyphenyl)-4,5,6,7-tetrahydropyrazolo[1,5-a]pyrimidine-3-carboxamide | $^1$H NMR (400 MHz, DMSO-d$_6$) δ 7.50 (d, J = 8.1 Hz, 2H), 7.45-7.38 (m, 2H), 7.17 (t, J = 7.4 Hz, 1H), 7.12-7.02 (m, 4H), 6.68 (s, 1H), 4.41-4.24 (m, 2H), 4.09-3.97 (m, 1H), 3.33-3.26 (m, 2H), 3.14-2.99 (m, 1H), 2.68-2.53 (m, 1H), 2.43-2.33 (m, 2H), 2.31-2.19 (m, 1H), 2.07-1.83 (m, 2H), 1.82-1.66 (m, 1H), 1.63-1.50 (m, 1H), 1.40-1.13 (m, 2H), 1.11 (t, J = 7.5 Hz, 3H). MS (ESI) m/e [M + 1]$^+$ 498.0. | 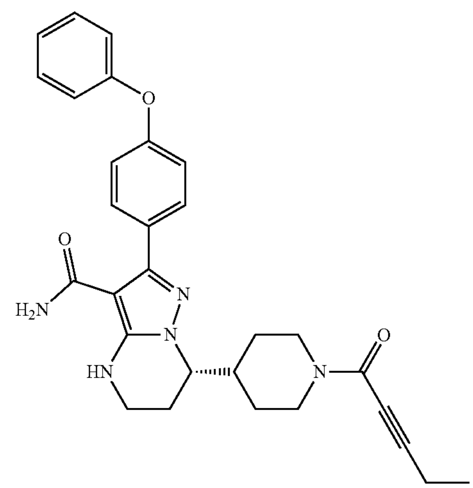 [SMILES: CCC#CC(=O)N1CCC([C@@H]2CCNc3c(C(N)=O)c(-c4ccc(Oc5ccccc5)cc4)nn32)CC1] |
| 187 | (S)-2-(4-Phenoxyphenyl)-7-(1-(4-(pyrrolidin-1-yl)but-2-ynoyl)piperidin-4-yl)-4,5,6,7-tetrahydropyrazolo[1,5-a]pyrimidine-3-carboxamide | $^1$H NMR (400 MHz, DMSO-d$_6$) δ 7.50 (d, J = 8.2 Hz, 2H), 7.45-7.37 (m, 2H), 7.17 (t, J = 7.4 Hz, 1H), 7.11-7.02 (m, 4H), 6.67 (s, 1H), 4.41-4.22 (m, 2H), 4.08-3.99 (m, 1H), 3.69 (s, 2H), 3.18-3.04 (m, 1H), 2.75-2.55 (m, 5H), 2.35-2.20 (m, 1H), 2.09-1.85 (m, 2H), 1.83-1.66 (m, 5H), 1.66-1.53 (m, 1H), 1.40-1.11 (m, 4H). MS (ESI) m/e [M + 1]$^+$ 553.0. | 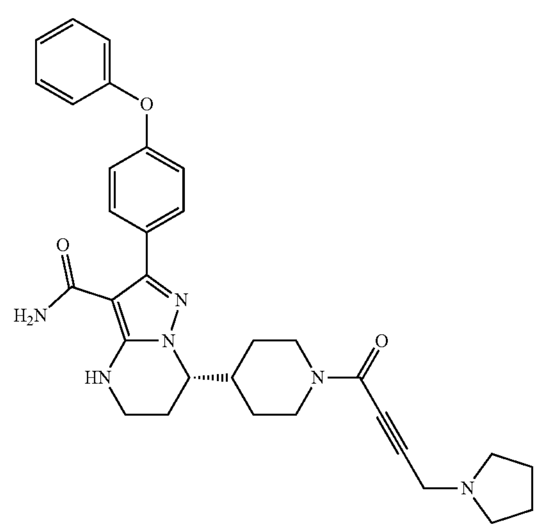 [SMILES: NC(=O)c1c(-c2ccc(Oc3ccccc3)cc2)nn2c1NCC[C@H]2C1CCN(C(=O)C#CCN2CCCC2)CC1] |

TABLE 1-continued

Characterization Data for Selected Compounds

| No. | Name | $^1$H NMR data, Chiral HPLC and LC/MS m/z (M + 1) | Structure |
|---|---|---|---|
| 188 | (S)-7-(1-(4-(Dimethylamino)but-2-ynoyl)piperidin-4-yl)-2-(4-phenoxyphenyl)-4,5,6,7-tetrahydropyrazolo[1,5-a]pyrimidine-3-carboxamide | $^1$H NMR (400 MHz, DMSO-d$_6$) δ 7.53-7.47 (m, 2H), 7.46-7.38 (m, 2H), 7.20-7.14 (m, 1H), 7.12-7.02 (m, 4H), 6.69-6.64 (m, 1H), 4.45-4.23 (m, 2H), 4.08-3.99 (m, 1H), 3.52 (s, 2H), 3.19-3.05 (m, 1H), 2.72-2.57 (m, 1H), 2.54-2.49 (m, 1H), 2.36-2.18 (m, 7H), 2.10-1.86 (m, 2H), 1.83-1.68 (m, 1H), 1.67-1.53 (m, 1H), 1.41-1.11 (m, 3H). MS (ESI) m/e [M + 1]$^+$ 527.0. | 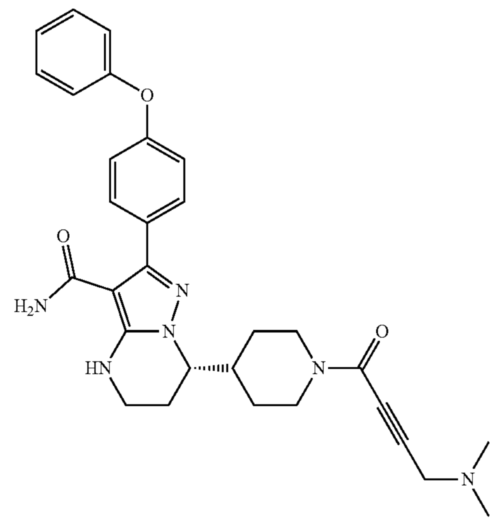 [SMILES: CN(C)CC#CC(=O)N1CCC([C@@H]2CCNc3c(C(N)=O)c(-c4ccc(Oc5ccccc5)cc4)nn32)CC1] |
| 189 | 7-(1-(But-2-ynoyl)azetidin-3-yl)-2-(4-(2,4-difluorophenoxy)phenyl)-4,5,6,7-tetrahydropyrazolo[1,5-a]pyrimidine-3-carboxamide | MS (ESI) m/e [M + 1]$^+$ 491.9. | 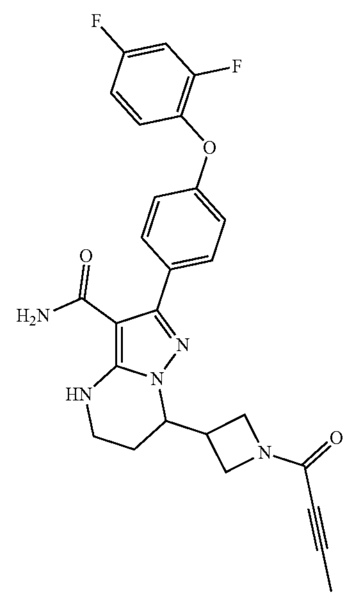 [SMILES: CC#CC(=O)N1CC(C2CCNc3c(C(N)=O)c(-c4ccc(Oc5ccc(F)cc5F)cc4)nn32)C1] |
| 190 | 7-(But-2-ynamidomethyl)-2-(4-(2,4-difluorophenoxy)phenyl)-4,5,6,7-tetrahydropyrazolo[1,5-a]pyrimidine-3-carboxamide | MS (ESI) m/e [M + 1]$^+$ 465.9. | 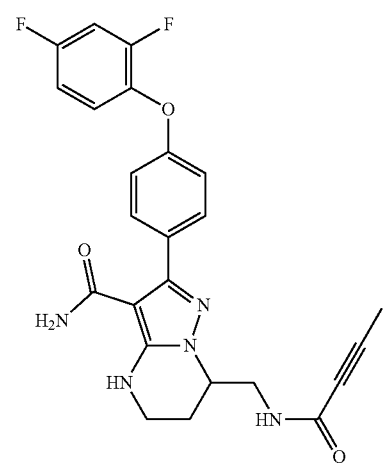 [SMILES: CC#CC(=O)NCC1CCNc2c(C(N)=O)c(-c3ccc(Oc4ccc(F)cc4F)cc3)nn21] |

| No. | Name | $^1$H NMR data, Chiral HPLC and LC/MS m/z (M + 1) | Structure |
| --- | --- | --- | --- |
| 191 | (S)-7-(1-(4-Hydroxybut-2-ynoyl)piperidin-4-yl)-2-(4-phenoxyphenyl)-4,5,6,7-tetrahydropyrazolo[1,5-a]pyrimidine-3-carboxamide | MS (ESI) m/e [M + 1]$^+$ 499.9. | 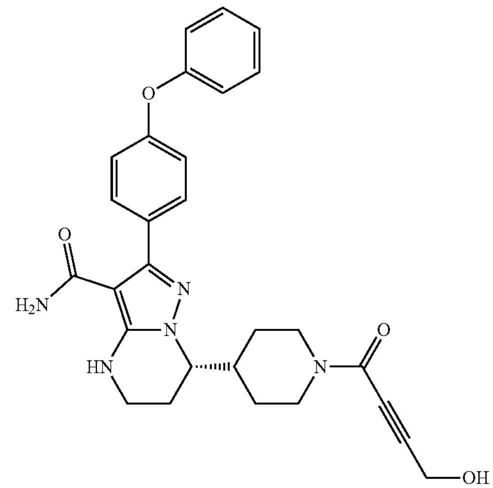 [SMILES: NC(=O)c1c(-c2ccc(Oc3ccccc3)cc2)nn2c1NCC[C@H]2C1CCN(C(=O)C#CCO)CC1] |
| 192 | (S)-7-(1-(4-Methoxybut-2-ynoyl)piperidin-4-yl)-2-(4-phenoxyphenyl)-4,5,6,7-tetrahydropyrazolo[1,5-a]pyrimidine-3-carboxamide | $^1$H NMR (400 MHz, DMSO-d$_6$) δ 7.54-7.47 (m, 2H), 7.45-7.38 (m, 2H), 7.21-7.14 (m, 1H), 7.12-7.03 (m, 4H), 6.69 (s, 1H), 4.41-4.32 (m, 1H), 4.30 (s, 2H), 4.29-4.20 (m, 1H), 4.09-3.98 (m, 1H), 3.33-3.26 (m, 2H), 3.29 (s, 3H), 3.19-3.05 (m, 1H), 2.72-2.57 (m, 1H), 2.36-2.21 (m, 1H), 2.09-1.98 (m, 1H), 2.09-1.97 (m, 1H), 1.84-1.68 (m, 1H), 1.66-1.50 (m, 1H), 1.41-1.10 (m, 2H). MS (ESI) m/e [M + 1]$^+$ 514.0. | 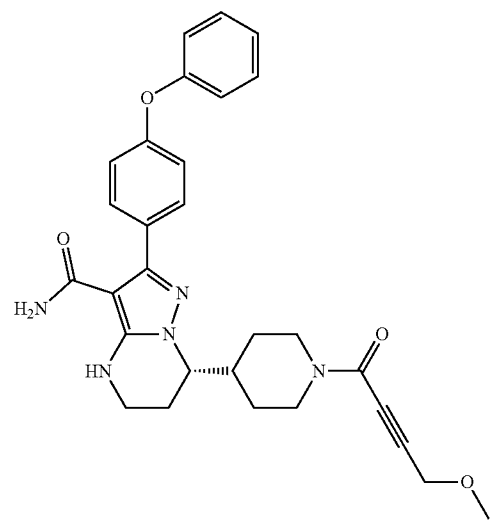 [SMILES: COCC#CC(=O)N1CCC([C@@H]2CCNc3c(C(N)=O)c(-c4ccc(Oc5ccccc5)cc4)nn32)CC1] |
| 193 | (S)-7-(1-(Hex-2-ynoyl)piperidin-4-yl)-2-(4-phenoxyphenyl)-4,5,6,7-tetrahydropyrazolo[1,5-a]pyrimidine-3-carboxamide | $^1$H NMR (400 MHz, DMSO-d$_6$) δ 7.54-7.48 (m, 2H), 7.45-7.38 (m, 2H), 7.21-7.14 (m, 1H), 7.12-7.02 (m, 4H), 6.68 (s, 1H), 4.42-4.22 (m, 2H), 4.06-3.98 (m, 1H), 3.33-3.25 (m, 2H), 3.15-3.01 (m, 1H), 2.69-2.53 (m, 1H), 2.36 (t, J = 6.9 Hz, 2H), 2.32-2.20 (m, 1H), 2.08-1.97 (m, 1H), 1.97-1.84 (m, 1H), 1.83-1.67 (m, 1H), 1.65-1.46 (m, 3H), 1.38-1.09 (m, 3H), 0.94 (t, J = 7.4 Hz, 3H). MS (ESI) m/e [M + 1]$^+$ 512.0. | 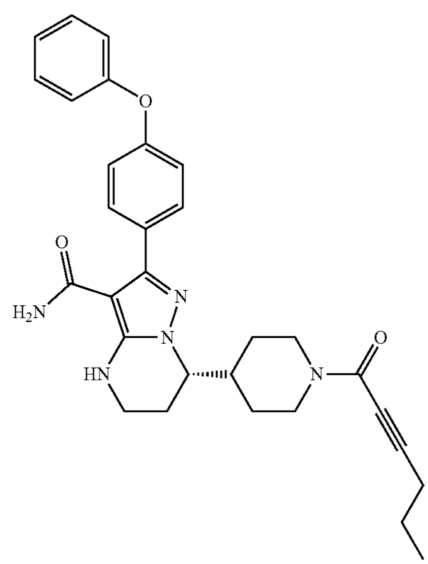 [SMILES: CCCC#CC(=O)N1CCC([C@@H]2CCNc3c(C(N)=O)c(-c4ccc(Oc5ccccc5)cc4)nn32)CC1] |

TABLE 1-continued

Characterization Data for Selected Compounds

| No. | Name | $^1$H NMR data, Chiral HPLC and LC/MS m/z (M + 1) | Structure |
|---|---|---|---|
| 194 | 7-(1-(But-2-ynoyl)piperidin-4-yl)-2-(4-(4-fluorophenoxy)phenyl)-4,5,6,7-tetrahydropyrazolo[1,5-a]pyrimidine-3-carboxamide | $^1$H NMR (400 MHz, DMSO-d$_6$) δ 7.53-7.46 (m, 2H), 7.30-7.21 (m, 2H), 7.18-7.11 (m, 2H), 7.07-7.00 (m, 2H), 6.64 (br s, 1H), 4.39-4.23 (m, 2H), 4.06-3.98 (m, 1H), 3.34-3.26 (m, 2H), 3.12-2.99 (m, 1H), 2.69-2.53 (m, 1H), 2.31-2.18 (m, 1H), 2.08-2.01 (m, 1H), 2.00 (s, 3H), 1.97-1.86 (m, 1H), 1.81-1.66 (m, 1H), 1.64-1.51 (m, 1H), 1.36-1.08 (m, 2H). MS (ESI) m/e [M + 1]$^+$ 501.9. | 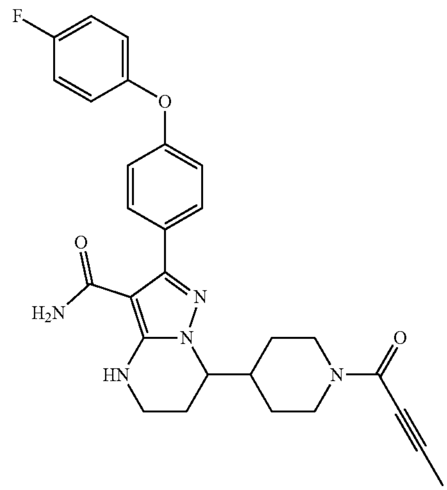 [SMILES: CC#CC(=O)N1CCC(C2CCNc3c(C(N)=O)c(-c4ccc(Oc5ccc(F)cc5)cc4)nn32)CC1] |
| 195 | 7-(1-(But-2-ynoyl)piperidin-4-yl)-2-(4-(3-chlorophenoxy)phenyl)-4,5,6,7-tetrahydropyrazolo[1,5-a]pyrimidine-3-carboxamide | $^1$H NMR (400 MHz, DMSO-d$_6$) δ 7.57-7.50 (m, 2H), 7.46-7.39 (m, 1H), 7.25-7.20 (m, 1H), 7.17-7.10 (m, 3H), 7.08-7.02 (m, 1H), 6.63 (br s, 1H), 4.40-4.22 (m, 2H), 4.06-3.98 (m, 1H), 3.34-3.26 (m, 2H), 3.13-3.00 (m, 1H), 2.69-2.54 (m, 1H), 2.31-2.19 (m, 1H), 2.08-2.00 (m, 1H), 2.00 (s, 3H), 1.96-1.87 (m, 1H), 1.82-1.66 (m, 1H), 1.64-1.52 (m, 1H), 1.35-1.09 (m, 2H). MS (ESI) m/e [M + 1]$^+$ 517.9, 519.9. | 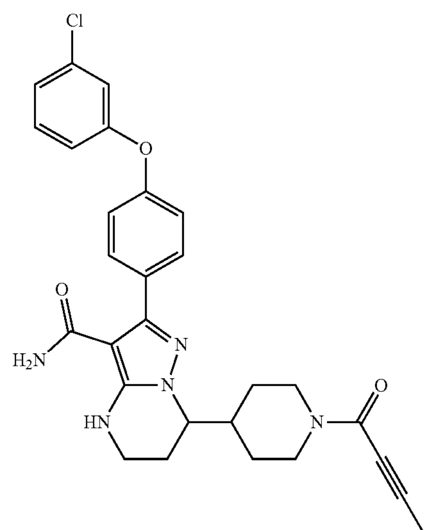 [SMILES: CC#CC(=O)N1CCC(C2CCNc3c(C(N)=O)c(-c4ccc(Oc5cccc(Cl)c5)cc4)nn32)CC1] |
| 196 | 7-(2-Acrylamidophenyl)-2-(3-chloro-4-fluorophenyl)-4,5,6,7-tetrahydropyrazolo[1,5-a]pyrimidine-3-carboxamide | $^1$H NMR (400 MHz, DMSO-d$_6$) δ 9.82 (s, 1H), 7.65 (dd, J = 7.4, 2.1 Hz, 1H), 7.55-7.47 (m, 1H), 7.47-7.38 (m, 2H), 7.31 (t, J = 7.1 Hz, 1H), 7.34-7.28 (m, 1H), 6.76 (br s, 1H), 6.63 (d, J = 7.4 Hz, 1H), 6.53 (dd, J = 17.2, 10.3 Hz, 1H), 6.27 (dd, J = 17.2, 1.9 Hz, 1H), 5.83-5.73 (m, 2H), 3.30-3.22 (m, 1H), 3.03-2.93 (m, 1H), 2.37-2.24 (m, 1H), 2.03-1.93 (m, 1H). MS (ESI) m/e [M + 1]$^+$ 439.8, 441.8. | 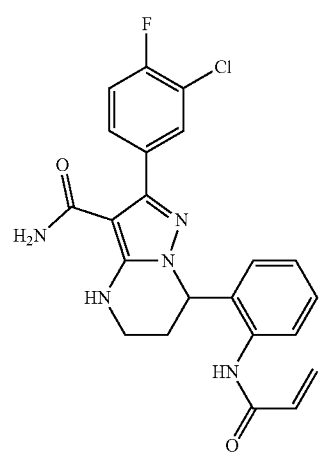 [SMILES: C=CC(=O)Nc1ccccc1C1CCNc2c(C(N)=O)c(-c3ccc(F)c(Cl)c3)nn21] |

Btk Kinase Assay

Compounds disclosed herein were tested for inhibition of Btk kinase activity in an assay based on time-resolved fluorescence resonance energy transfer methodology. Recombinant Btk was pre-incubated with the compounds disclosed herein at room temperature for 1 hour in an assay buffer containing 50 mM Tris pH7.4, 10 mM $MgCl_2$, 2 mM $MnCl_2$, 0.1 mM EDTA, 1 mM DTT, 20 nM SEB, 0.1% BSA, 0.005% tween-20. The reactions were initiated by the addition of ATP (at the concentration of ATP Km) and peptide substrate (Biotin-AVLESEEELYSSARQ-NH2). After incubating at room temperature for 1 h. an equal volume of stop solution containing 50 mM HEPES pH7.0, 800 mM KF, 20 mM EDTA, 0.1% BSA, Eu cryptate-conjugated p-Tyr66 antibody and streptavidin-labeled XL665 was added to stop the reaction. Plates were further incubated at room temperature for 1 hour, and then the TR-FRET signals (ex337 nm, em 620 nm/665 nm) were read on BMG PHERAstar FS instrument. The residual enzyme activity in presence of increasing concentrations of compounds was calculated based on the ratio of fluorescence at 615 nm to that at 665 nm. The $IC_{50}$ for each compound was derived from fitting the data to the four-parameter logistic equation by Graphpad Prism software.

BtkpY223 Cellular Assay

Btk pY223 cellular assay is a HTRF based assay intended to determine the endogenous levels of phosphorylated Btk at Tyr223. Phosphorylated Tyr223 is necessary for full activation of Btk. The assay was performed in Ramos cells (CRL-1596, ATCC) with a Btk pY223 assay kit (63IDC000, Cisbio).

Briefly, Ramos cells were serum starved in 0.5% FBS-containing RPM11640 for 2 hours. Following starvation, the cells were incubated with compounds to be detected at various concentrations in a $CO_2$ incubator for 1 hour. After incubation, cells were stimulated with 1 mM pervanadate (PV) or $Na_3VO_4$ (OV) for 20 min. Then, the cells were spinned down and lysed with 1× lysis buffer at RT for 10 min (4× lysis buffer supplied in the kit). During the incubation, 1× antibody mix was prepared by diluting anti-Btk-d2 and anti-pBtk-K in detection buffer (supplied in the kit). 2 ul/well of 1× antibody mixture was dispensed into the OptiPlate-384 assay plate (6005620, Perkin Elmer). After that, 18 ul of cell lysate was transferred to the assay plate pre-loaded with antibody solution. After mixing gently and spinning briefly, the plate was sealed up and kept in dark at RT for 18 hours. The fluorescence emission was measured at two different wavelengths (665 nm and 620 nm) on a compatible HTRF reader (PHERAstar FS, BMG). The potency of compounds was calculated basing on the inhibition of ratio between signal intensities at 665 nm and 620 nm. IC50 values were calculated with GraphPad Prism software using the sigmoidal dose-response function.

Representative compounds as disclosed herein were tested and found to inhibit Btk and autophosphorylation of Btk at Tyr-223 with IC50 values ranging from subnanomolar to 10 micromolar.

TABLE II

Assay data for representative compounds

| Compound No. | IC50 (nM) Btk | Btk pY223 |
|---|---|---|
| 1 | >10,000 | n.d. |
| 2 | 360 | n.d. |
| 2a (peak 1) | 270 | n.d. |
| 2b (peak 2) | 210 | n.d. |
| 3 | 3.6 | 12.7 |
| 3a (peak 1) | 2.5 | 8.7 |
| 3b (peak 2) | 1.7 | 2.0 |
| 4 | 26 | n.d. |
| 5 | 200 | n.d. |
| 6 | 0.71 | 3.1 |
| 6a (peak 1) | 0.4 | 3.0 |
| 6b (peak 2) | 120 | n.d. |
| 7 | >10,000 | n.d. |
| 8 | 860 | n.d. |
| 9 | 3,700 | n.d. |
| 10 | 1.5 | 8.0 |
| 10a (peak 1) | 0.51 | 2.2 |
| 10b (peak 2) | 42 | n.d. |
| 11 | 4,500 | n.d. |
| 12 | 1.7 | 23.6 |
| 13 | 1000 | n.d. |
| 14 | 4.7 | 232.6 |
| 15 | 2,700 | n.d. |
| 16 | 19 | n.d. |
| 17 | >10,000 | n.d. |
| 18 | 1.3 | 26.3 |
| 19 | 5,300 | n.d. |
| 20 | 1.6 | 12.6 |
| 20a (peak 1) | 1.2 | 2.5 |
| 20b (peak 2) | 110 | n.d. |
| 21 | >10,000 | n.d. |
| 22 | 2.7 | 16.7 |
| 23 | 3,200 | n.d. |
| 24 | 39 | n.d. |
| 25 | 3,100 | n.d. |
| 26 | 1700 | n.d. |
| 27 | 1 | 4.6 |
| 27a (peak 1) | 0.33 | 5.7 |
| 27b (peak 2) | 2 | 20.0 |
| 28 | 3,400 | n.d. |
| 29 | 0.48 | 18 |
| 29a (peak 1) | 0.43 | 1.6 |
| 29b (peak 2) | 1.3 | 4.1 |
| 30 | 1 | 4.0 |
| 30a (peak 1) | 0.66 | 5.6 |
| 30b (peak 2) | 16 | n.d. |
| 31 | 15 | n.d. |
| 32 | 1,700 | n.d. |
| 33 | 0.9 | 2.9 |
| 33a (peak 1) | 0.6 | 5.9 |
| 33b (peak 2) | 11 | 63.3 |
| 34 | 1,900 | n.d. |
| 35 | 1.1 | 7.9 |
| 36 | >10,000 | n.d. |
| 37 | 640 | n.d. |
| 38 | 490 | n.d. |
| 39 | 1,400 | n.d. |
| 40 | 13 | n.d. |
| 41 | 180 | n.d. |
| 42 | 330 | n.d. |
| 43 | 3.0 | 75.8 |
| 44 | 220 | n.d. |
| 45 | 510 | n.d. |
| 46 | 5 | 22.6 |
| 47 | 110 | n.d. |
| 48 | 150 | n.d. |
| 49 | 29 | n.d. |
| 50 | 2.7 | 8.0 |
| 51 | 310 | n.d. |
| 52 | 0.14 | <0.5 |
| 53 | 7.7 | n.d. |
| 54 | 0.19 | 6.4 |
| 55 | 82 | n.d. |

TABLE II-continued

Assay data for representative compounds

| Compound No. | IC50 (nM) Btk | IC50 (nM) Btk pY223 |
|---|---|---|
| 56 | 110 | n.d. |
| 57 | 37 | 232.9 |
| 58 | 0.43 | 4.6 |
| 59 | 43 | n.d. |
| 60 | 40 | n.d. |
| 61 | 140 | n.d. |
| 62 | 240 | n.d. |
| 63 | 0.18 | 1.5 |
| 64 | 0.17 | 4.8 |
| 65 | 320 | n.d. |
| 66 | 14 | 322.2 |
| 67 | 0.32 | 2.8 |
| 68 | 190 | n.d. |
| 69 | 7.8 | 34.4 |
| 70 | 19 | n.d. |
| 71 | 55 | n.d. |
| 72 | 4.1 | 10.5 |
| 73 | >10,000 | n.d. |
| 74 | 240 | n.d. |
| 75 | 41 | 222.9 |
| 76 | 5,500 | n.d. |
| 77 | 480 | n.d. |
| 78 | 21 | 139.6 |
| 79 | 50 | n.d. |
| 80 | >10,000 | n.d. |
| 81 | 5,900 | n.d. |
| 82 | 3,100 | n.d. |
| 83 | 130 | n.d. |
| 84 | 2,900 | n.d. |
| 85 | 32 | 73.2 |
| 86 | 2.2 | 4.4 |
| 87 | 2,000 | n.d. |
| 88 | 16.0 | n.d. |
| 89 | >10,000 | n.d. |
| 90 | 1,900 | n.d. |
| 91 | 1,900 | n.d. |
| 92 | 1.1 | 7.0 |
| 93 | 1,500 | n.d. |
| 94 | 1.9 | 6.7 |
| 95 | 470 | n.d. |
| 96 | 30 | n.d. |
| 97 | 1.1 | n.d. |
| 98 | 77 | n.d. |
| 99 | 9.5 | 43.4 |
| 100 | 260 | n.d. |
| 101 | 550 | n.d. |
| 102 | 830 | n.d. |
| 103 | 1.1 | 14 |
| 104 | 2.6 | 20.6 |
| 105 | 18 | n.d. |
| 106 | 1.4 | 30.3 |
| 107 | 0.48 | 11.2 |
| 108 | 3.5 | 18.9 |
| 109 | 41 | n.d. |
| 110 | 3,000 | n.d. |
| 111 | 24 | n.d. |
| 112 | >10,000 | n.d. |
| 113 | 94 | n.d. |
| 114 | 6,000 | n.d. |
| 115 | 8,200 | n.d. |
| 116 | 1 | 3.2 |
| 117 | 34 | n.d. |
| 118 | 410 | n.d. |
| 119 | 40 | n.d. |
| 120 | 180 | n.d. |
| 121 | 0.36 | 8.2 |
| 122 | 0.78 | 12.6 |
| 123 | 0.15 | 1.5 |
| 124 | 0.62 | 4.6 |
| 125 | 5,000 | n.d. |
| 126 | 20 | n.d. |
| 127 | 300 | n.d. |
| 128 | 930 | n.d. |
| 129 | 23 | n.d. |
| 130 | 14 | n.d. |
| 131 | 170 | n.d. |
| 132 | 1.7 | 6.2 |
| 133 | 0.53 | 1.8 |
| 133a (peak 1) | 0.23 | 2.9 |
| 133b (peak 2) | 16 | n.d. |
| 134 | 0.78 | 4.7 |
| 134a (peak 1) | 0.64 | 4.2 |
| 134b (peak 2) | 1500 | n.d. |
| 135 | 0.38 | 2.4 |
| 136 | 0.13 | 0.8 |
| 137 | 3.2 | 22.7 |
| 138 | 1.0 | 7.6 |
| 139 | 0.44 | 3.1 |
| 140 | 3000 | n.d. |
| 141 | 7.0 | n.d. |
| 142 | 54 | n.d. |
| 143 | 0.89 | 4.1 |
| 144 | 140 | n.d. |
| 145 | 72 | n.d. |
| 146 | 1.3 | 4.0 |
| 147 | 2.7 | n.d. |
| 148 | 5.6 | n.d. |
| 149 | 4.2 | n.d. |
| 150 | 4.7 | n.d. |
| 151 | 1.9 | 2.5 |
| 152 | 1.2 | 1.8 |
| 153 | 6.1 | 165.2 |
| 154 | 1.2 | 1.5 |
| 155 | 0.96 | n.d. |
| 156 | 0.55 | 6.8 |
| 157 | 0.38 | 20 |
| 158 | 2.9 | n.d. |
| 159 | 1 | 4.5 |
| 160 | 0.49 | 1.3 |
| 161 | 4.2 | n.d. |
| 162 | 2.1 | 3.2 |
| 163 | 7.3 | n.d. |
| 164 | 1.6 | 3.9 |
| 165 | 1.6 | 19.1 |
| 166 | 2.7 | n.d. |
| 167 | 2.4 | n.d. |
| 168 | 3.2 | n.d. |
| 169 | 0.15 | 7 |
| 170 | 3.8 | 33.7 |
| 171 | 1.4 | 10.9 |
| 172 | 1.1 | 0.8 |
| 173 | 0.81 | 2.1 |
| 174 | 4.8 | n.d. |
| 175 | 1.2 | 17.6 |
| 176 | 3 | 15.1 |
| 177 | 5.7 | 3.9 |
| 178 | 46 | >1000 |
| 179 | 48 | n.d. |
| 180 | 87 | n.d. |
| 181 | 25 | n.d. |
| 182 | 124 | n.d. |
| 183 | 1.2 | 2.9 |
| 184 | 4.7 | 6.7 |
| 185 | 4.3 | 4.4 |
| 186 | 1.1 | 10.3 |
| 187 | 2.1 | 7.3 |
| 188 | 1.1 | 8.5 |
| 189 | 42 | n.d. |
| 190 | 38 | n.d. |
| 191 | 0.67 | n.d. |
| 192 | 0.91 | n.d. |
| 193 | 3.9 | n.d. |
| 194 | 45 | n.d. |
| 195 | 8.0 | n.d. |
| 196 | 1.1 | 2.0 | n.d.: No data.

TABLE III
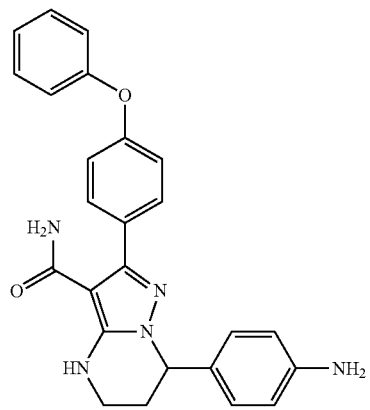 [SMILES: NC(=O)c1c(-c2ccc(Oc3ccccc3)cc2)nn2c1NCCC2c1ccc(N)cc1]
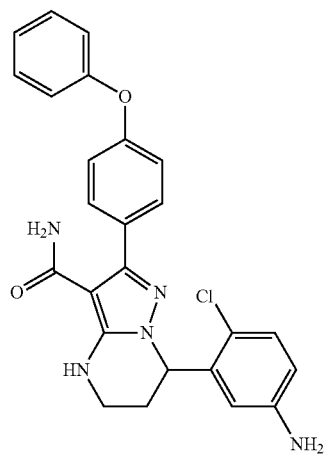 [SMILES: NC(=O)c1c(-c2ccc(Oc3ccccc3)cc2)nn2c1NCCC2c1cc(N)ccc1Cl]
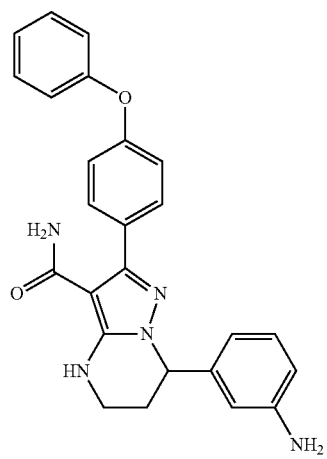 [SMILES: NC(=O)c1c(-c2ccc(Oc3ccccc3)cc2)nn2c1NCCC2c1cccc(N)c1]

TABLE III-continued
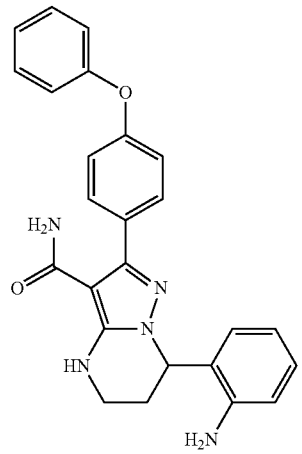 [SMILES: NC(=O)c1c(-c2ccc(Oc3ccccc3)cc2)nn2c1NCCC2c1ccccc1N]
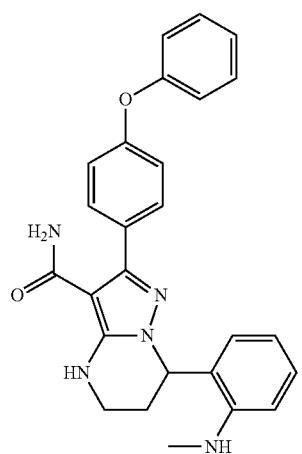 [SMILES: CNc1ccccc1C1CCNc2c(C(N)=O)c(-c3ccc(Oc4ccccc4)cc3)nn21]
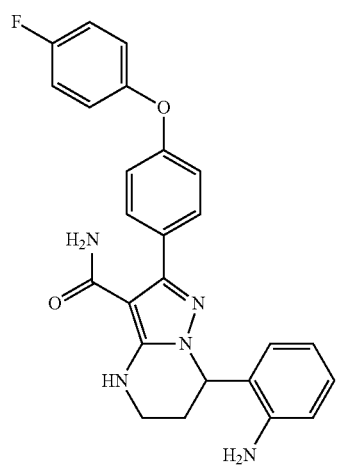 [SMILES: NC(=O)c1c(-c2ccc(Oc3ccc(F)cc3)cc2)nn2c1NCCC2c1ccccc1N]

TABLE III-continued
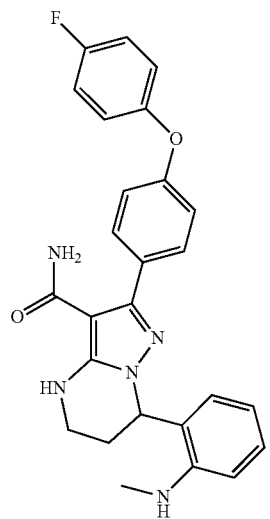 [SMILES: CNc1ccccc1C1CCNc2c(C(N)=O)c(-c3ccc(Oc4ccc(F)cc4)cc3)nn21]
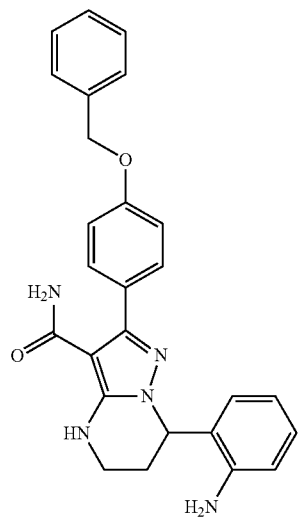 [SMILES: NC(=O)c1c(-c2ccc(OCc3ccccc3)cc2)nn2c1NCCC2c1ccccc1N]
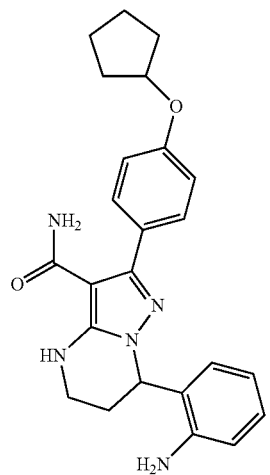 [SMILES: NC(=O)c1c(-c2ccc(OC3CCCC3)cc2)nn2c1NCCC2c1ccccc1N]

TABLE III-continued
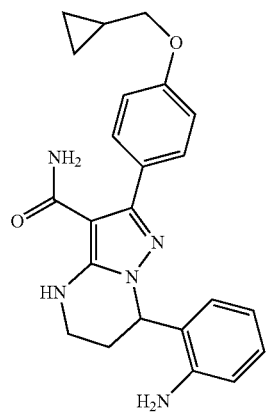 [SMILES: NC(=O)c1c(-c2ccc(OCC3CC3)cc2)nn2c1NCCC2c1ccccc1N]
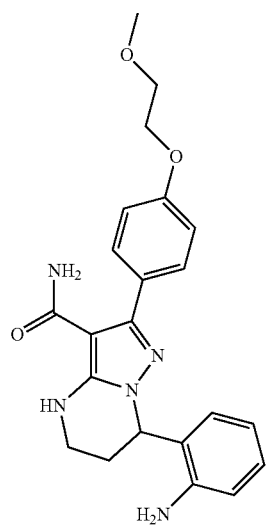 [SMILES: COCCOc1ccc(-c2nn3c(c2C(N)=O)NCCC3c2ccccc2N)cc1]
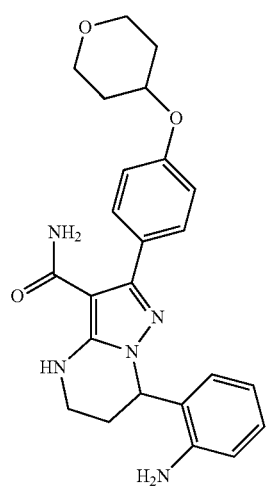 [SMILES: NC(=O)c1c(-c2ccc(OC3CCOCC3)cc2)nn2c1NCCC2c1ccccc1N]

TABLE III-continued
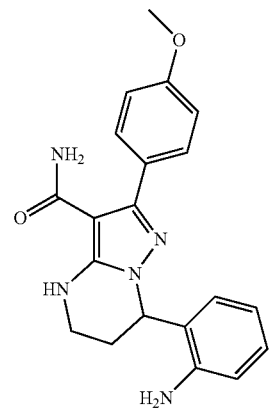 [SMILES: COc1ccc(-c2nn3c(c2C(N)=O)NCCC3c2ccccc2N)cc1]
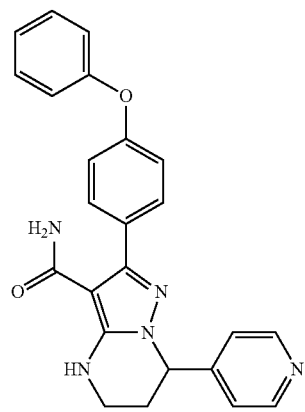 [SMILES: NC(=O)c1c(-c2ccc(Oc3ccccc3)cc2)nn2c1NCCC2c1ccncc1]
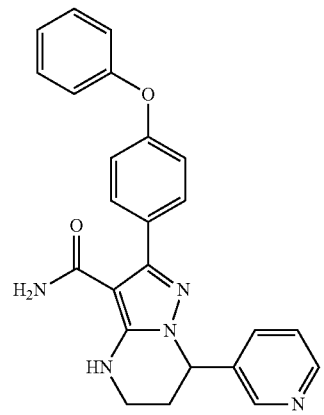 [SMILES: NC(=O)c1c(-c2ccc(Oc3ccccc3)cc2)nn2c1NCCC2c1cccnc1]
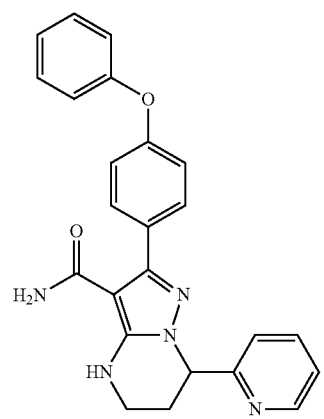 [SMILES: NC(=O)c1c(-c2ccc(Oc3ccccc3)cc2)nn2c1NCCC2c1ccccn1]

TABLE III-continued
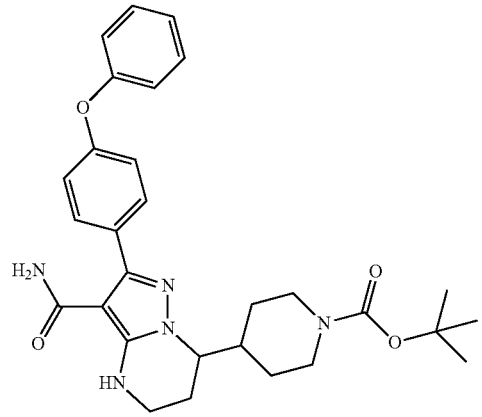 [SMILES: CC(C)(C)OC(=O)N1CCC(C2CCNc3c(C(N)=O)c(-c4ccc(Oc5ccccc5)cc4)nn32)CC1]
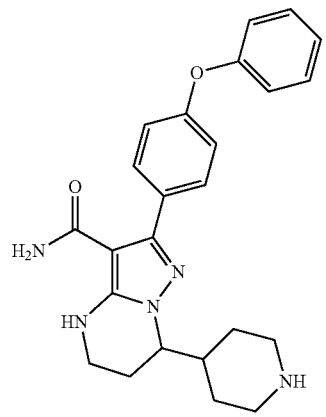 [SMILES: NC(=O)c1c(-c2ccc(Oc3ccccc3)cc2)nn2c1NCCC2C1CCNCC1]
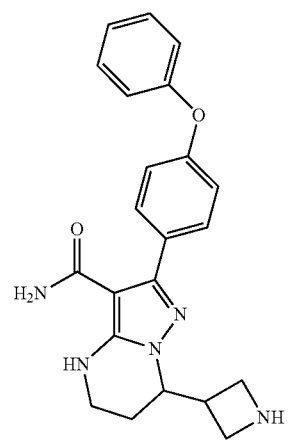 [SMILES: NC(=O)c1c(-c2ccc(Oc3ccccc3)cc2)nn2c1NCCC2C1CNC1]

TABLE III-continued
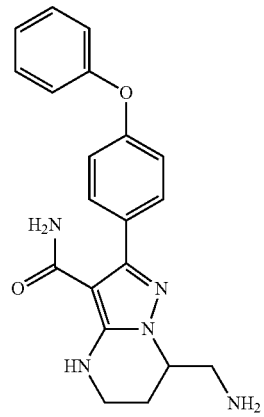 [SMILES: NCC1CCNc2c(C(N)=O)c(-c3ccc(Oc4ccccc4)cc3)nn21]
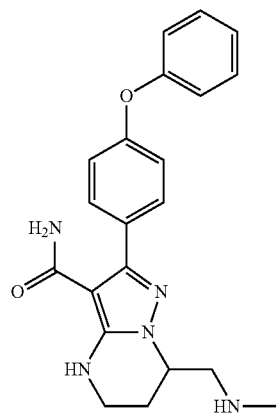 [SMILES: CNCC1CCNc2c(C(N)=O)c(-c3ccc(Oc4ccccc4)cc3)nn21]
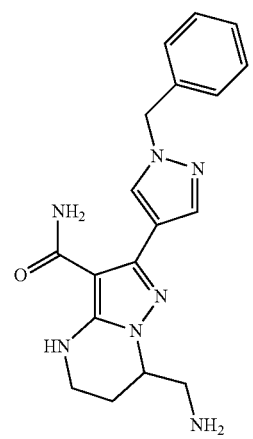 [SMILES: NCC1CCNc2c(C(N)=O)c(-c3cnn(Cc4ccccc4)c3)nn21]

TABLE III-continued
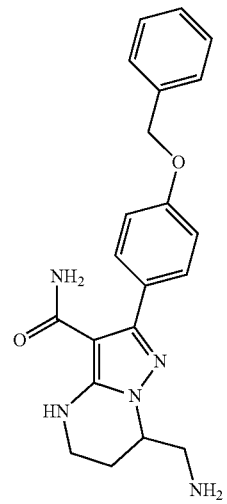 [SMILES: NCC1CCNc2c(C(N)=O)c(-c3ccc(OCc4ccccc4)cc3)nn21]
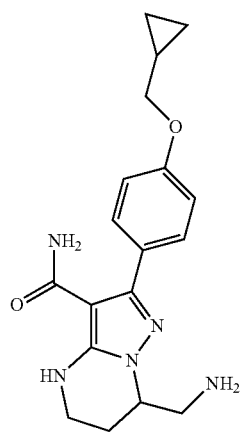 [SMILES: NCC1CCNc2c(C(N)=O)c(-c3ccc(OCC4CC4)cc3)nn21]
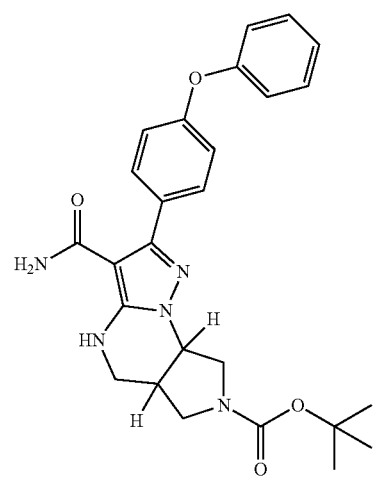 [SMILES: CC(C)(C)OC(=O)N1CC2CNc3c(C(N)=O)c(-c4ccc(Oc5ccccc5)cc4)nn3C2C1]

TABLE III-continued
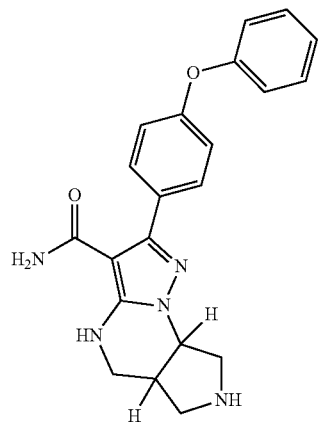 [SMILES: NC(=O)c1c(-c2ccc(Oc3ccccc3)cc2)nn2c1NCC1CNCC12]
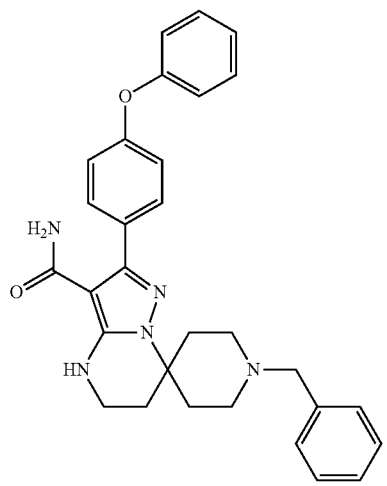 [SMILES: NC(=O)c1c(-c2ccc(Oc3ccccc3)cc2)nn2c1NCCC21CCN(Cc2ccccc2)CC1]
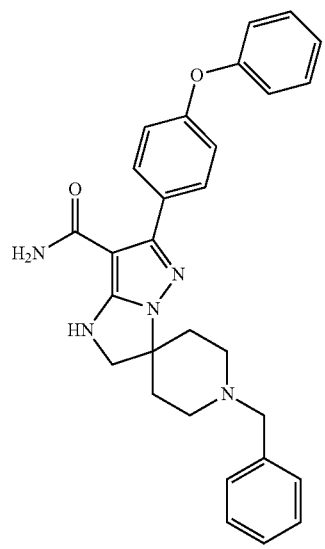 [SMILES: NC(=O)c1c(-c2ccc(Oc3ccccc3)cc2)nn2c1NCC21CCN(Cc2ccccc2)CC1]

TABLE III-continued
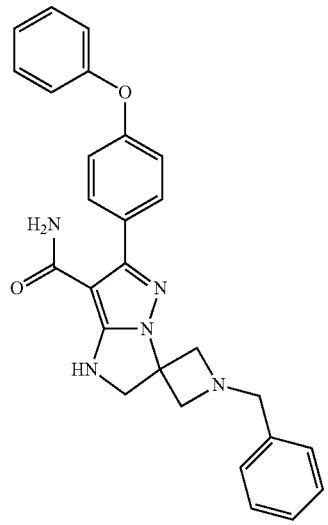 [SMILES: NC(=O)c1c(-c2ccc(Oc3ccccc3)cc2)nn2c1NCC21CN(Cc2ccccc2)C1]
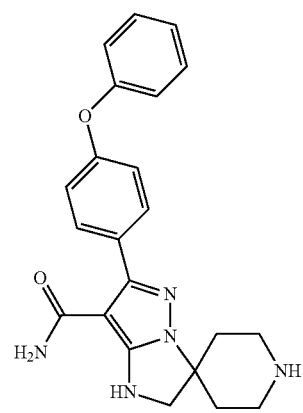 [SMILES: NC(=O)c1c(-c2ccc(Oc3ccccc3)cc2)nn2c1NCC21CCNCC1]
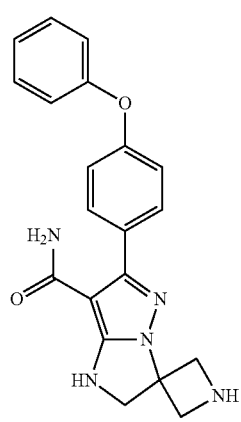 [SMILES: NC(=O)c1c(-c2ccc(Oc3ccccc3)cc2)nn2c1NCC21CNC1]

TABLE III-continued
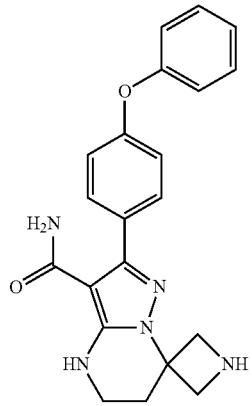 [SMILES: NC(=O)c1c(-c2ccc(Oc3ccccc3)cc2)nn2c1NCCC21CNC1]
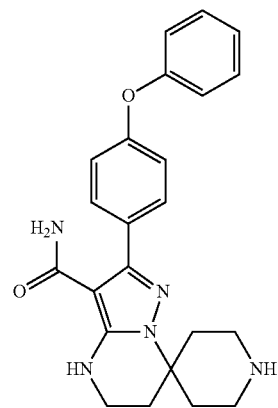 [SMILES: NC(=O)c1c(-c2ccc(Oc3ccccc3)cc2)nn2c1NCCC21CCNCC1]
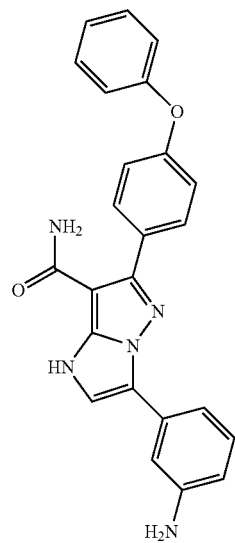 [SMILES: NC(=O)c1c(-c2ccc(Oc3ccccc3)cc2)nn2c(-c3cccc(N)c3)c[nH]c12]

TABLE III-continued
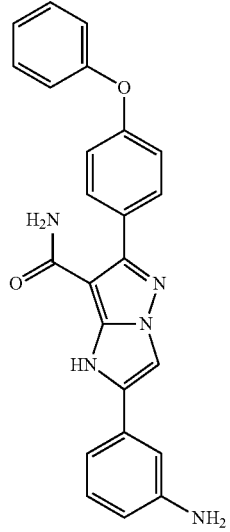 [SMILES: NC(=O)c1c(-c2ccc(Oc3ccccc3)cc2)nn2cc(-c3cccc(N)c3)[nH]c12]
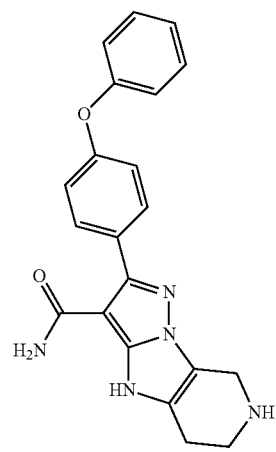 [SMILES: NC(=O)c1c(-c2ccc(Oc3ccccc3)cc2)nn2c3c([nH]c12)CCNC3]
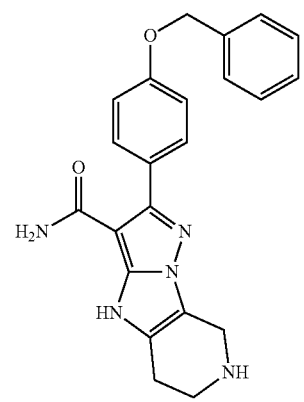 [SMILES: NC(=O)c1c(-c2ccc(OCc3ccccc3)cc2)nn2c3c([nH]c12)CCNC3]

TABLE III-continued
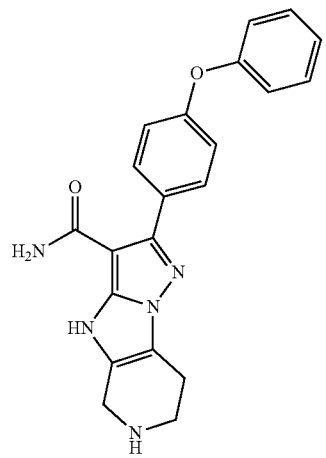 [SMILES: NC(=O)c1c(-c2ccc(Oc3ccccc3)cc2)nn2c3c([nH]c12)CNCC3]
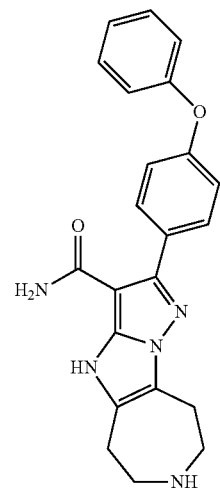 [SMILES: NC(=O)c1c(-c2ccc(Oc3ccccc3)cc2)nn2c3c([nH]c12)CCNCC3]
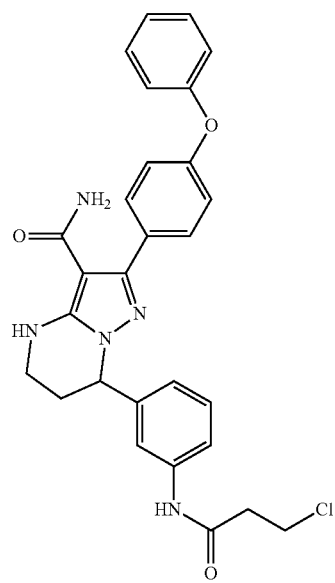 [SMILES: NC(=O)c1c(-c2ccc(Oc3ccccc3)cc2)nn2c1NCCC2c1cccc(NC(=O)CCCl)c1]

TABLE III-continued
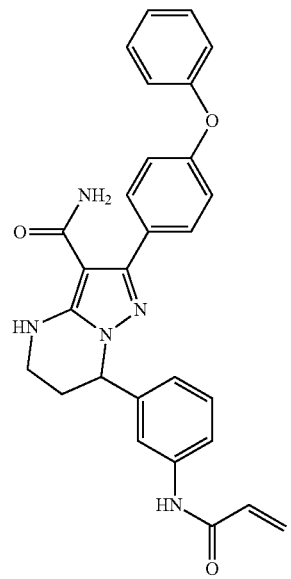 [SMILES: C=CC(=O)Nc1cccc(C2CCNc3c(C(N)=O)c(-c4ccc(Oc5ccccc5)cc4)nn32)c1]
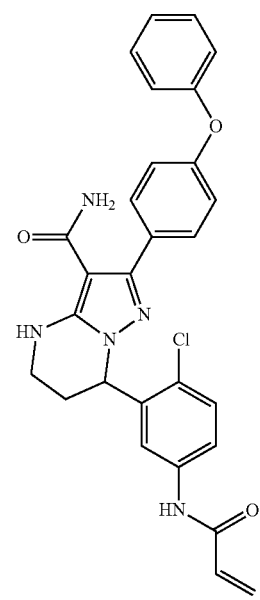 [SMILES: C=CC(=O)Nc1ccc(Cl)c(C2CCNc3c(C(N)=O)c(-c4ccc(Oc5ccccc5)cc4)nn32)c1]
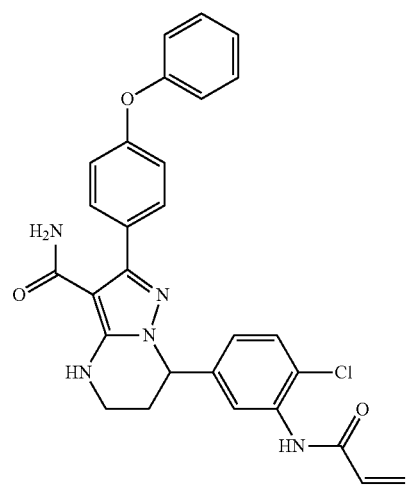 [SMILES: C=CC(=O)Nc1cc(C2CCNc3c(C(N)=O)c(-c4ccc(Oc5ccccc5)cc4)nn32)ccc1Cl]

TABLE III-continued
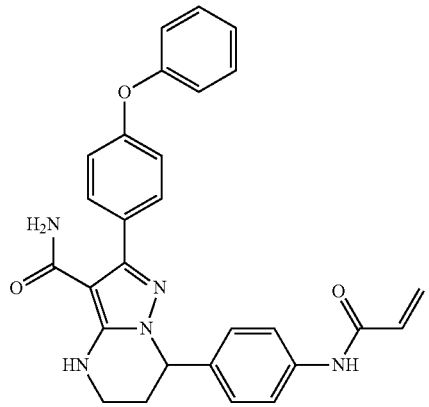 [SMILES: C=CC(=O)Nc1ccc(C2CCNc3c(C(N)=O)c(-c4ccc(Oc5ccccc5)cc4)nn32)cc1]
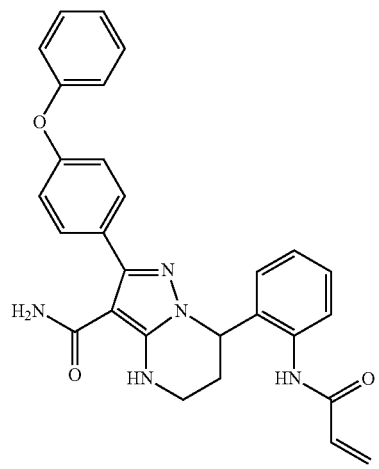 [SMILES: C=CC(=O)Nc1ccccc1C1CCNc2c(C(N)=O)c(-c3ccc(Oc4ccccc4)cc3)nn21]
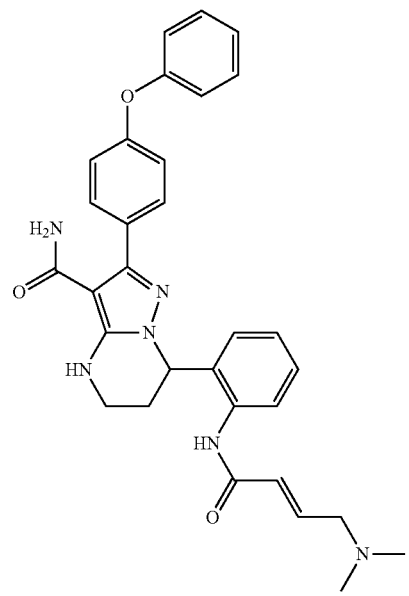 [SMILES: CN(C)C/C=C/C(=O)Nc1ccccc1C1CCNc2c(C(N)=O)c(-c3ccc(Oc4ccccc4)cc3)nn21]

TABLE III-continued
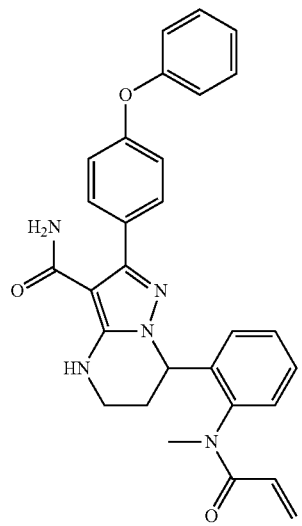 [SMILES: C=CC(=O)N(C)c1ccccc1C1CCNc2c(C(N)=O)c(-c3ccc(Oc4ccccc4)cc3)nn21]
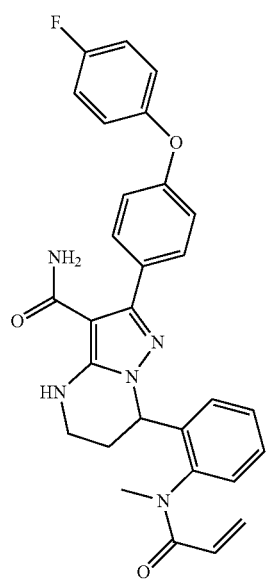 [SMILES: C=CC(=O)N(C)c1ccccc1C1CCNc2c(C(N)=O)c(-c3ccc(Oc4ccc(F)cc4)cc3)nn21]

TABLE III-continued
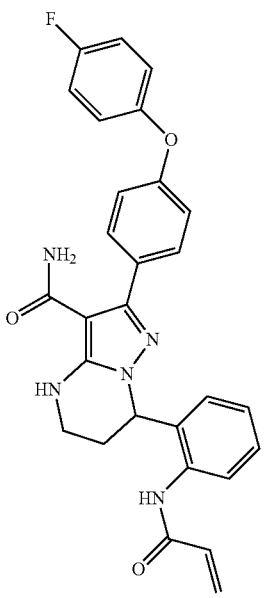 [SMILES: C=CC(=O)Nc1ccccc1C1CCNc2c(C(N)=O)c(-c3ccc(Oc4ccc(F)cc4)cc3)nn21]
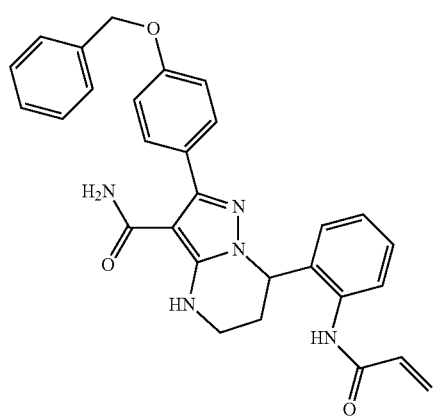 [SMILES: C=CC(=O)Nc1ccccc1C1CCNc2c(C(N)=O)c(-c3ccc(OCc4ccccc4)cc3)nn21]
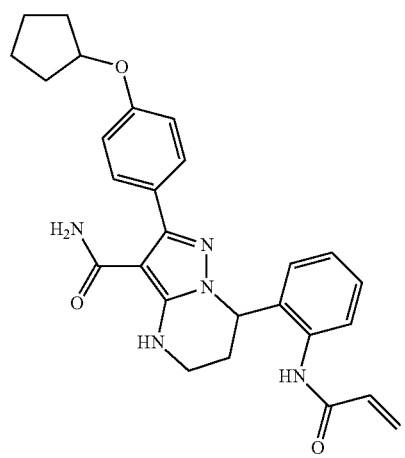 [SMILES: C=CC(=O)Nc1ccccc1C1CCNc2c(C(N)=O)c(-c3ccc(OC4CCCC4)cc3)nn21]

TABLE III-continued
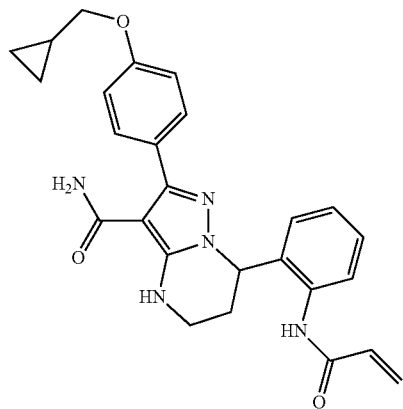 [SMILES: C=CC(=O)Nc1ccccc1C1CCNc2c(C(N)=O)c(-c3ccc(OCC4CC4)cc3)nn21]
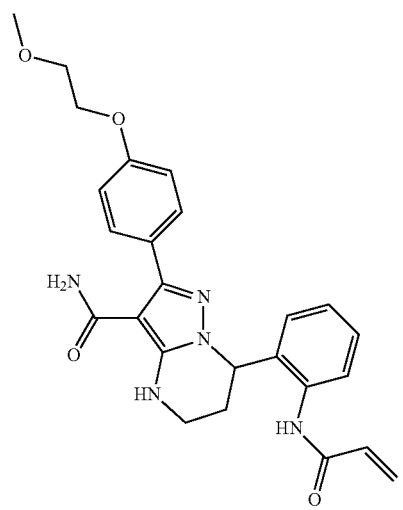 [SMILES: C=CC(=O)Nc1ccccc1C1CCNc2c(C(N)=O)c(-c3ccc(OCCOC)cc3)nn21]
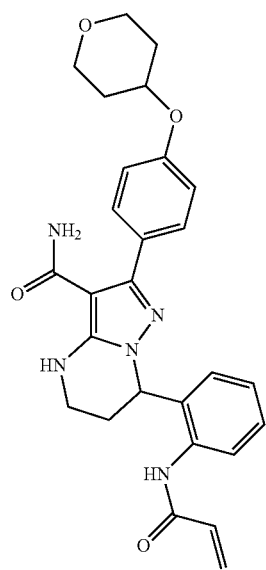 [SMILES: C=CC(=O)Nc1ccccc1C1CCNc2c(C(N)=O)c(-c3ccc(OC4CCOCC4)cc3)nn21]

TABLE III-continued
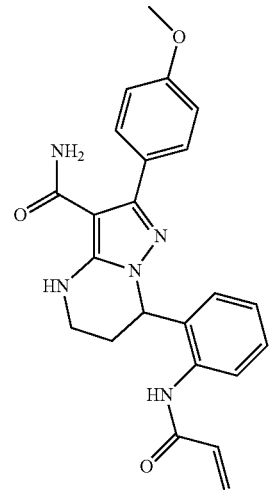 [SMILES: C=CC(=O)Nc1ccccc1C1CCNc2c(C(N)=O)c(-c3ccc(OC)cc3)nn21]
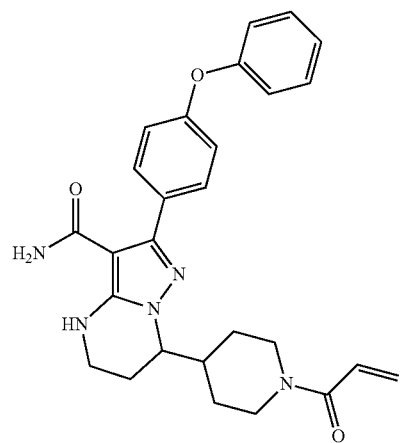 [SMILES: C=CC(=O)N1CCC(C2CCNc3c(C(N)=O)c(-c4ccc(Oc5ccccc5)cc4)nn32)CC1]
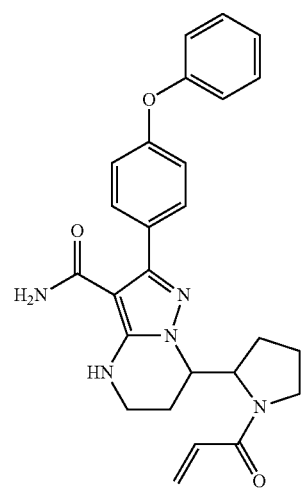 [SMILES: C=CC(=O)N1CCCC1C1CCNc2c(C(N)=O)c(-c3ccc(Oc4ccccc4)cc3)nn21]

TABLE III-continued
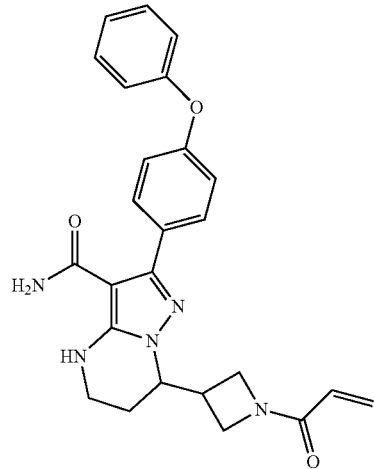 [SMILES: C=CC(=O)N1CC(C2CCNc3c(C(N)=O)c(-c4ccc(Oc5ccccc5)cc4)nn32)C1]
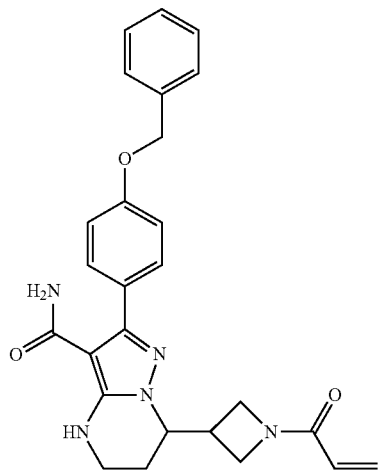 [SMILES: C=CC(=O)N1CC(C2CCNc3c(C(N)=O)c(-c4ccc(OCc5ccccc5)cc4)nn32)C1]
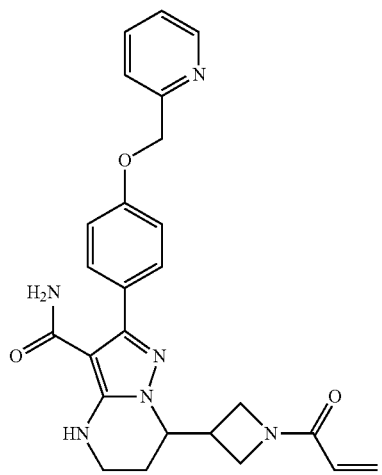 [SMILES: C=CC(=O)N1CC(C2CCNc3c(C(N)=O)c(-c4ccc(OCc5ccccn5)cc4)nn32)C1]

TABLE III-continued
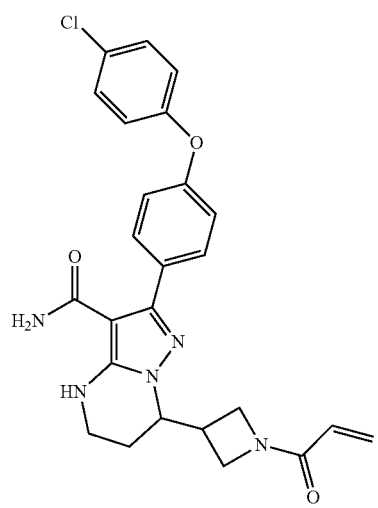 [SMILES: C=CC(=O)N1CC(C2CCNc3c(C(N)=O)c(-c4ccc(Oc5ccc(Cl)cc5)cc4)nn32)C1]
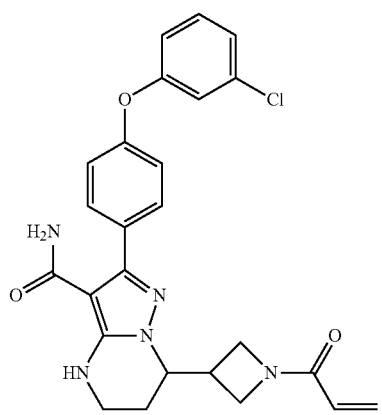 [SMILES: C=CC(=O)N1CC(C2CCNc3c(C(N)=O)c(-c4ccc(Oc5cccc(Cl)c5)cc4)nn32)C1]
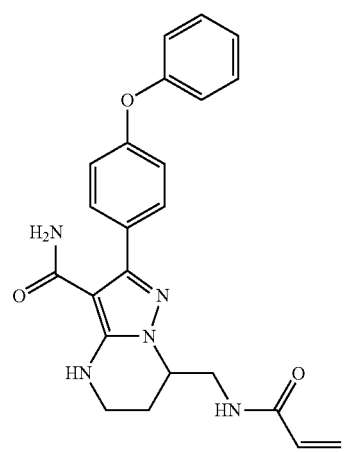 [SMILES: C=CC(=O)NCC1CCNc2c(C(N)=O)c(-c3ccc(Oc4ccccc4)cc3)nn21]

TABLE III-continued
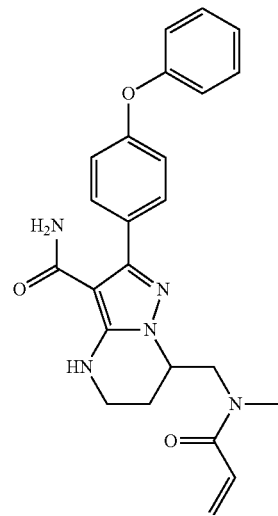 [SMILES: C=CC(=O)N(C)CC1CCNc2c(C(N)=O)c(-c3ccc(Oc4ccccc4)cc3)nn21]
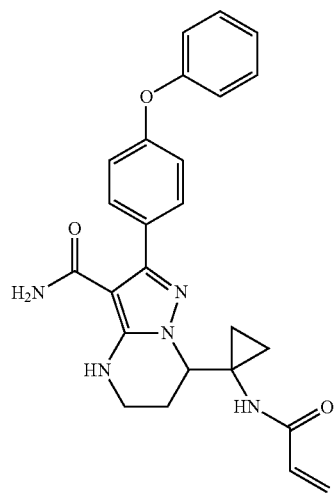 [SMILES: C=CC(=O)NC1(C2CCNc3c(C(N)=O)c(-c4ccc(Oc5ccccc5)cc4)nn32)CC1]
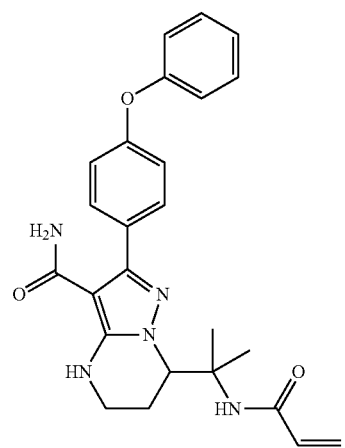 [SMILES: C=CC(=O)NC(C)(C)C1CCNc2c(C(N)=O)c(-c3ccc(Oc4ccccc4)cc3)nn21]

TABLE III-continued
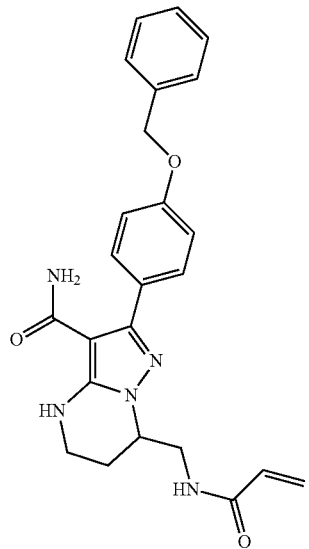 [SMILES: C=CC(=O)NCC1CCNc2c(C(N)=O)c(-c3ccc(OCc4ccccc4)cc3)nn21]
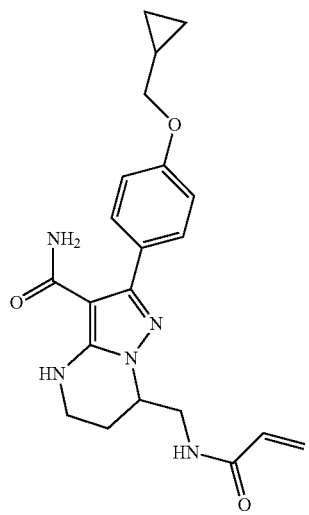 [SMILES: C=CC(=O)NCC1CCNc2c(C(N)=O)c(-c3ccc(OCC4CC4)cc3)nn21]
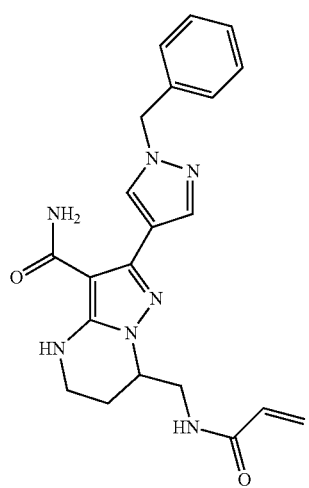 [SMILES: C=CC(=O)NCC1CCNc2c(C(N)=O)c(-c3cnn(Cc4ccccc4)c3)nn21]

TABLE III-continued
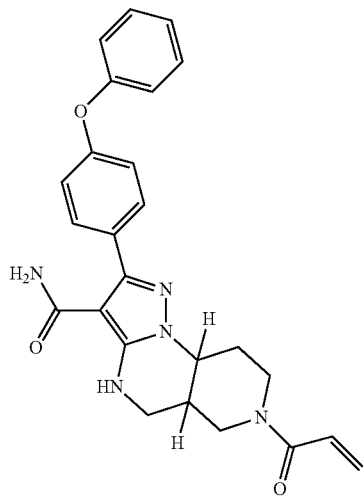 [SMILES: C=CC(=O)N1CCC2C(CNc3c(C(N)=O)c(-c4ccc(Oc5ccccc5)cc4)nn32)C1]
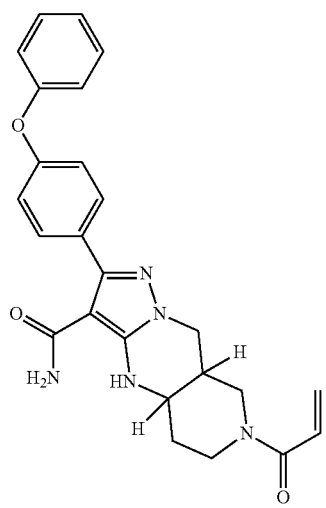 [SMILES: C=CC(=O)N1CCC2Nc3c(C(N)=O)c(-c4ccc(Oc5ccccc5)cc4)nn3CC2C1]
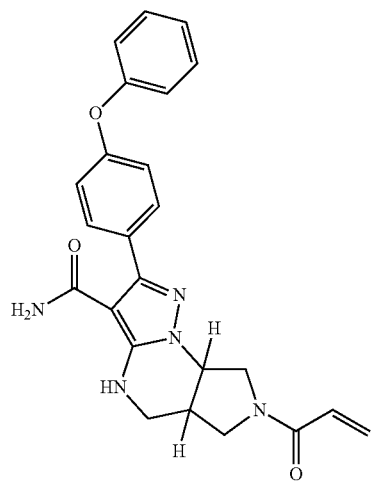 [SMILES: C=CC(=O)N1CC2CNc3c(C(N)=O)c(-c4ccc(Oc5ccccc5)cc4)nn3C2C1]

TABLE III-continued
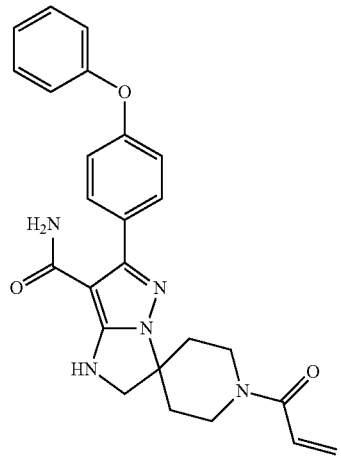 [SMILES: C=CC(=O)N1CCC2(CC1)CNc1c(C(N)=O)c(-c3ccc(Oc4ccccc4)cc3)nn12]
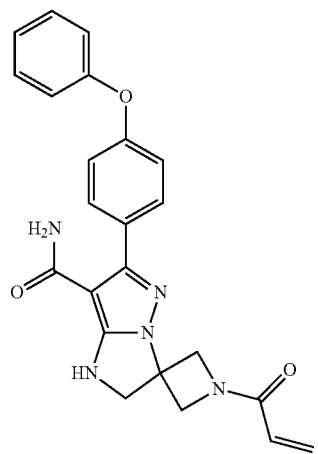 [SMILES: C=CC(=O)N1CC2(CNc3c(C(N)=O)c(-c4ccc(Oc5ccccc5)cc4)nn32)C1]
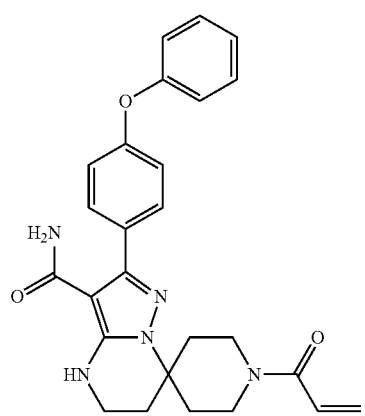 [SMILES: C=CC(=O)N1CCC2(CCNc3c(C(N)=O)c(-c4ccc(Oc5ccccc5)cc4)nn32)CC1]

TABLE III-continued
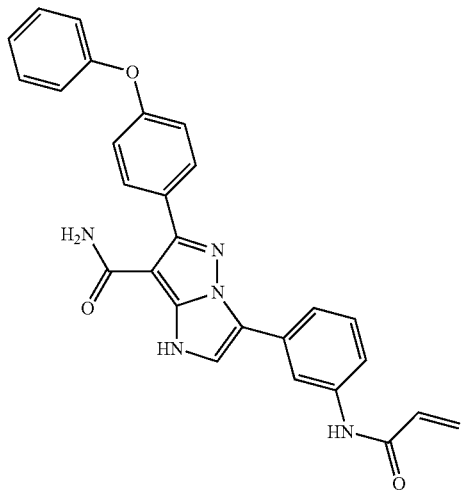 [SMILES: C=CC(=O)Nc1cccc(-c2c[nH]c3c(C(N)=O)c(-c4ccc(Oc5ccccc5)cc4)nn23)c1]
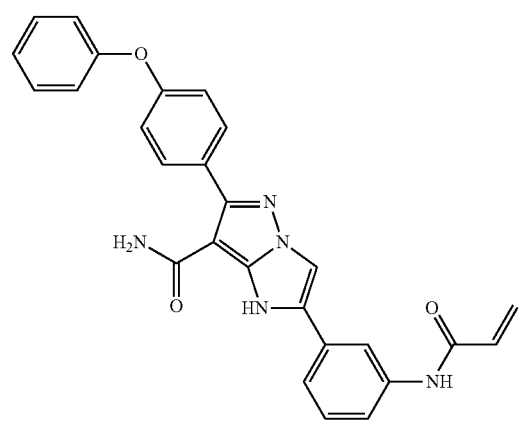 [SMILES: C=CC(=O)Nc1cccc(-c2cn3nc(-c4ccc(Oc5ccccc5)cc4)c(C(N)=O)c3[nH]2)c1]
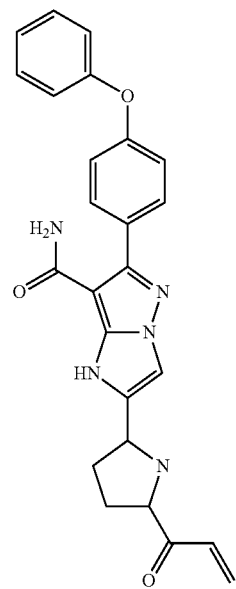 [SMILES: C=CC(=O)C1CCC(c2cn3nc(-c4ccc(Oc5ccccc5)cc4)c(C(N)=O)c3[nH]2)N1]

TABLE III-continued
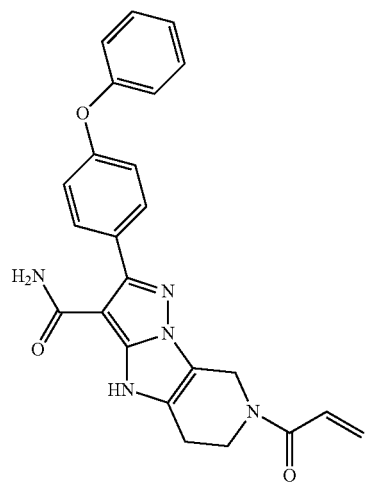 [SMILES: C=CC(=O)N1CCc2[nH]c3c(C(N)=O)c(-c4ccc(Oc5ccccc5)cc4)nn3c2C1]
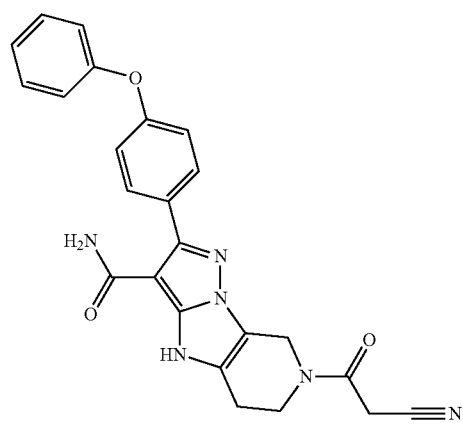 [SMILES: N#CCC(=O)N1CCc2[nH]c3c(C(N)=O)c(-c4ccc(Oc5ccccc5)cc4)nn3c2C1]
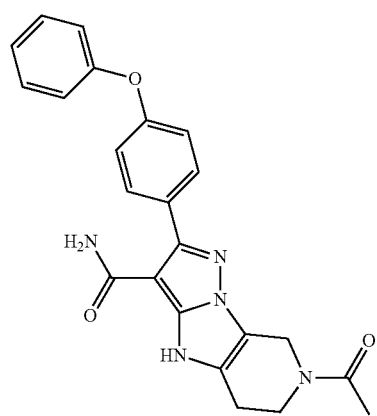 [SMILES: CC(=O)N1CCc2[nH]c3c(C(N)=O)c(-c4ccc(Oc5ccccc5)cc4)nn3c2C1]

TABLE III-continued
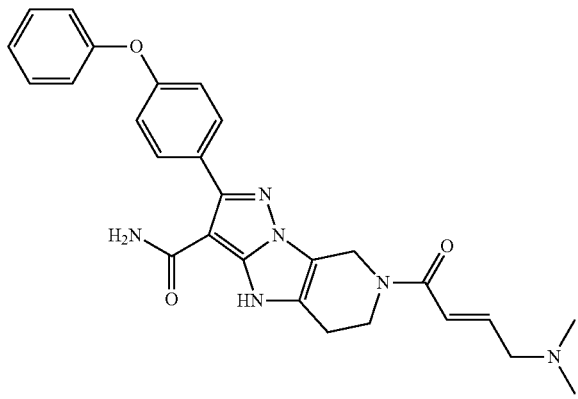 [SMILES: CN(C)C/C=C/C(=O)N1CCc2[nH]c3c(C(N)=O)c(-c4ccc(Oc5ccccc5)cc4)nn3c2C1]
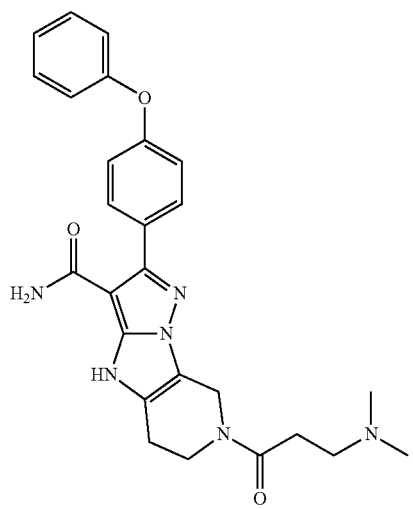 [SMILES: CN(C)CCC(=O)N1CCc2[nH]c3c(C(N)=O)c(-c4ccc(Oc5ccccc5)cc4)nn3c2C1]
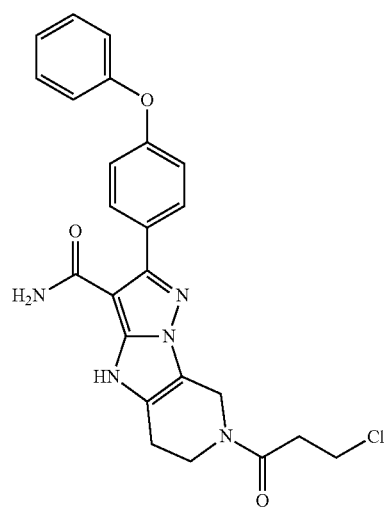 [SMILES: NC(=O)c1c(-c2ccc(Oc3ccccc3)cc2)nn2c3c([nH]c12)CCN(C(=O)CCCl)C3]

TABLE III-continued
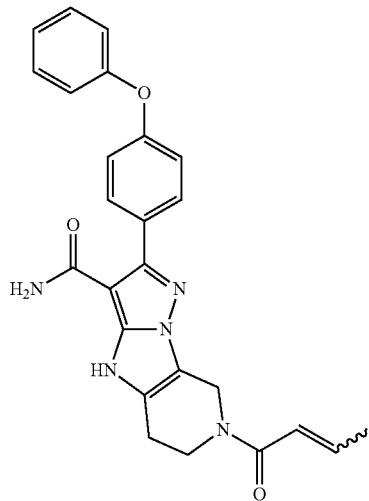
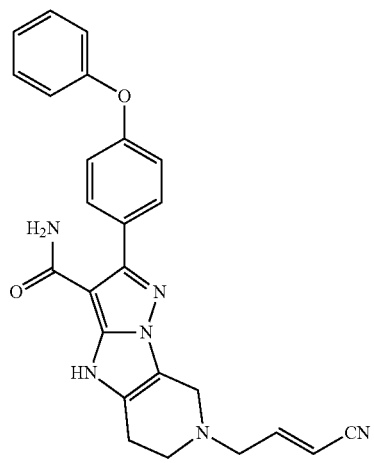 [SMILES: N#C/C=C/CN1CCc2[nH]c3c(C(N)=O)c(-c4ccc(Oc5ccccc5)cc4)nn3c2C1]
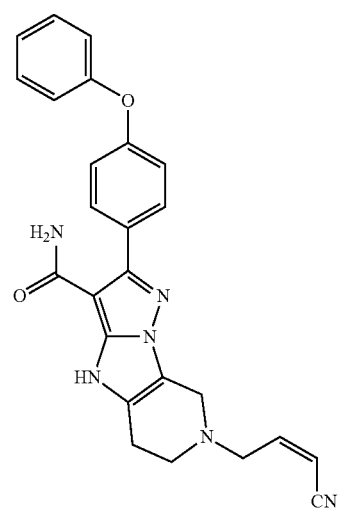 [SMILES: N#C/C=C\CN1CCc2[nH]c3c(C(N)=O)c(-c4ccc(Oc5ccccc5)cc4)nn3c2C1]

TABLE III-continued
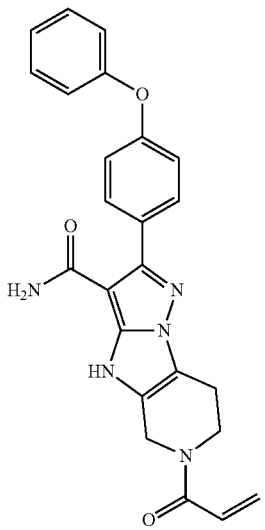 [SMILES: C=CC(=O)N1CCc2c([nH]c3c(C(N)=O)c(-c4ccc(Oc5ccccc5)cc4)nn23)C1]
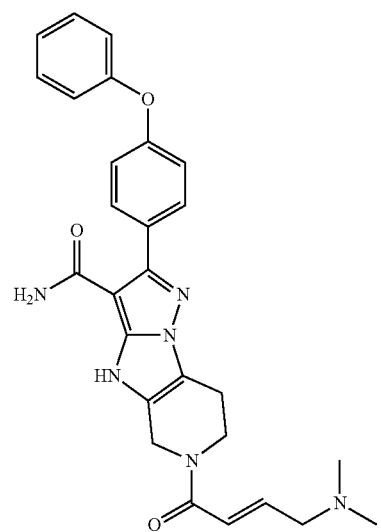 [SMILES: CN(C)C/C=C/C(=O)N1CCc2c([nH]c3c(C(N)=O)c(-c4ccc(Oc5ccccc5)cc4)nn23)C1]
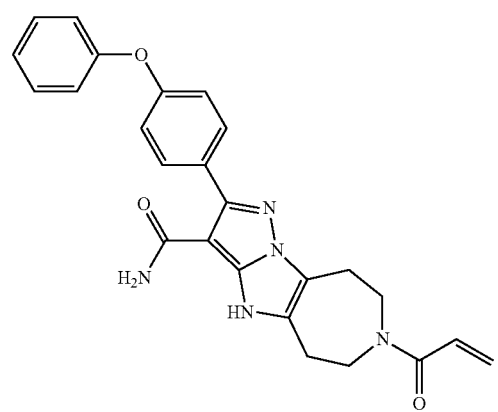 [SMILES: C=CC(=O)N1CCc2[nH]c3c(C(N)=O)c(-c4ccc(Oc5ccccc5)cc4)nn3c2CC1]

TABLE III-continued
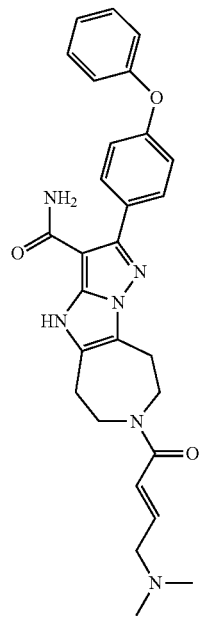 [SMILES: CN(C)C/C=C/C(=O)N1CCc2[nH]c3c(C(N)=O)c(-c4ccc(Oc5ccccc5)cc4)nn3c2CC1]
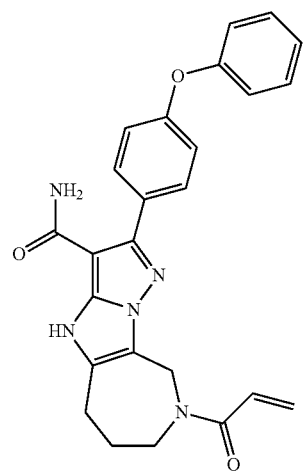 [SMILES: C=CC(=O)N1CCCc2[nH]c3c(C(N)=O)c(-c4ccc(Oc5ccccc5)cc4)nn3c2C1]
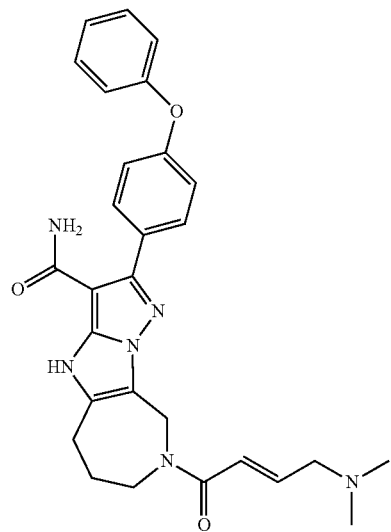 [SMILES: CN(C)C/C=C/C(=O)N1CCCc2[nH]c3c(C(N)=O)c(-c4ccc(Oc5ccccc5)cc4)nn3c2C1]

TABLE III-continued
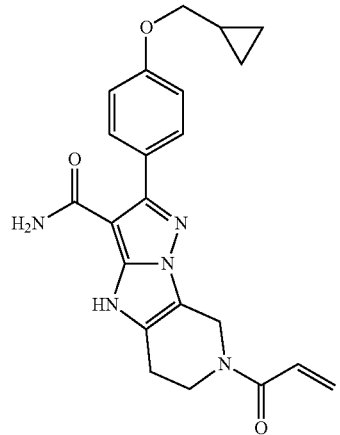 [SMILES: C=CC(=O)N1CCc2[nH]c3c(C(N)=O)c(-c4ccc(OCC5CC5)cc4)nn3c2C1]
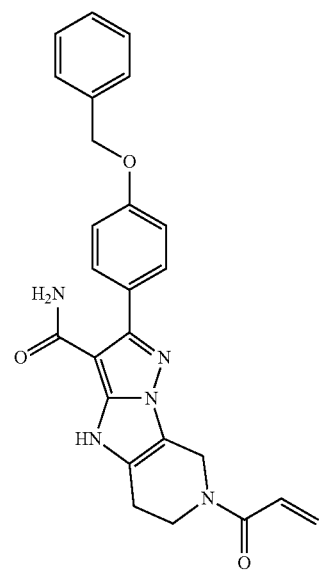 [SMILES: C=CC(=O)N1CCc2[nH]c3c(C(N)=O)c(-c4ccc(OCc5ccccc5)cc4)nn3c2C1]
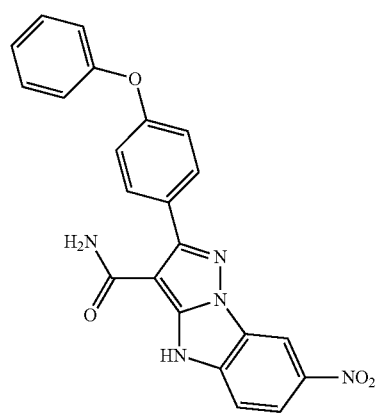 [SMILES: NC(=O)c1c(-c2ccc(Oc3ccccc3)cc2)nn2c1[nH]c1ccc([N+](=O)[O-])cc12]

TABLE III-continued
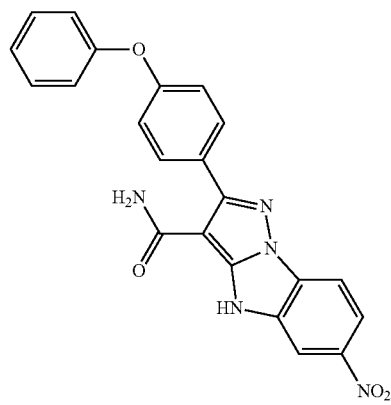
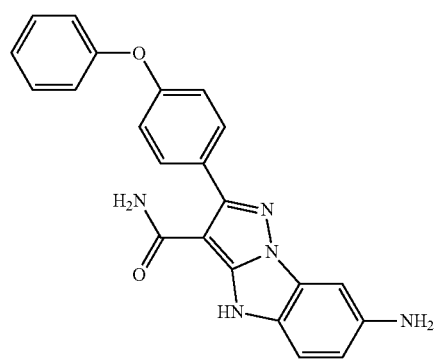 [SMILES: NC(=O)c1c(-c2ccc(Oc3ccccc3)cc2)nn2c1[nH]c1ccc(N)cc12]
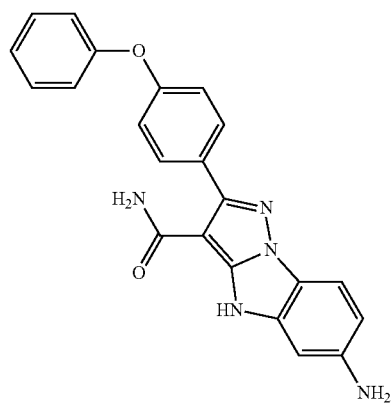 [SMILES: NC(=O)c1c(-c2ccc(Oc3ccccc3)cc2)nn2c1[nH]c1cc(N)ccc12]
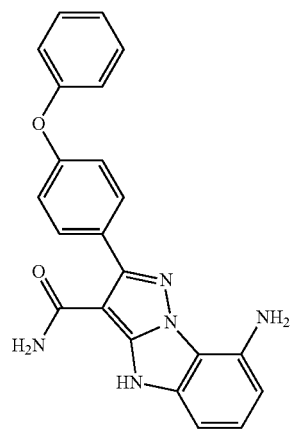 [SMILES: NC(=O)c1c(-c2ccc(Oc3ccccc3)cc2)nn2c1[nH]c1cccc(N)c12]

TABLE III-continued
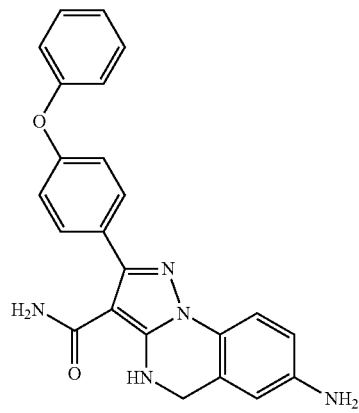 [SMILES: NC(=O)c1c(-c2ccc(Oc3ccccc3)cc2)nn2c1NCc1cc(N)ccc1-2]
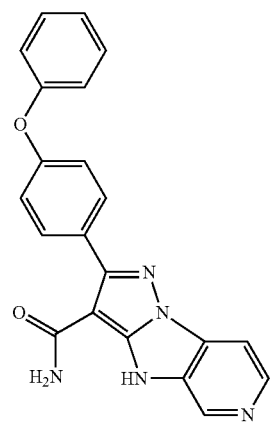 [SMILES: NC(=O)c1c(-c2ccc(Oc3ccccc3)cc2)nn2c1[nH]c1cnccc12]
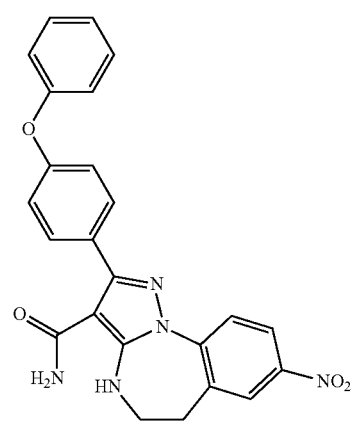

TABLE III-continued
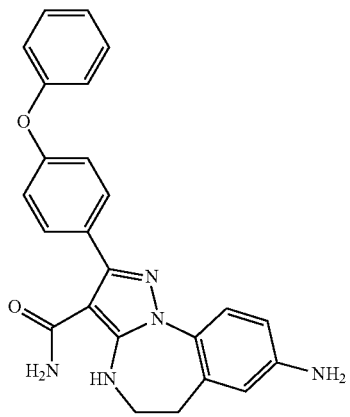 [SMILES: NC(=O)c1c(-c2ccc(Oc3ccccc3)cc2)nn2c1NCCc1cc([N+](=O)[O-])ccc1-2]
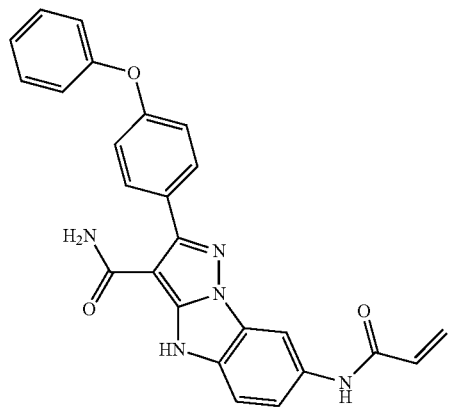 [SMILES: C=CC(=O)Nc1ccc2[nH]c3c(C(N)=O)c(-c4ccc(Oc5ccccc5)cc4)nn3c2c1]
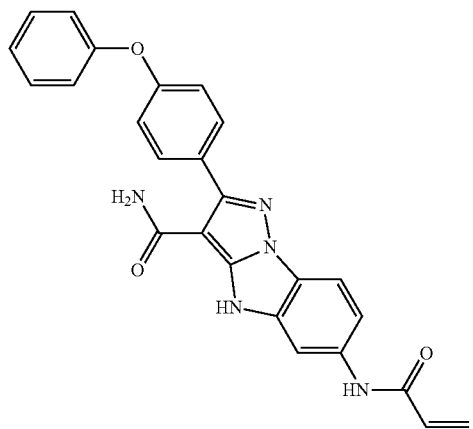 [SMILES: C=CC(=O)Nc1ccc2c(c1)[nH]c1c(C(N)=O)c(-c3ccc(Oc4ccccc4)cc3)nn12]
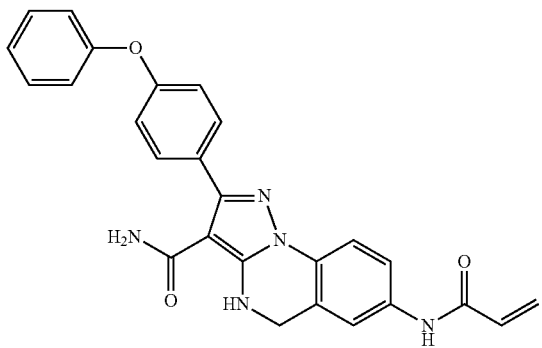 [SMILES: C=CC(=O)Nc1ccc2c(c1)CNc1c(C(N)=O)c(-c3ccc(Oc4ccccc4)cc3)nn1-2]

TABLE III-continued
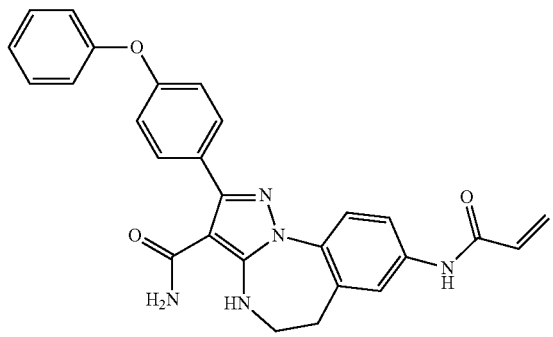 [SMILES: C=CC(=O)Nc1ccc2c(c1)CCNc1c(C(N)=O)c(-c3ccc(Oc4ccccc4)cc3)nn1-2]
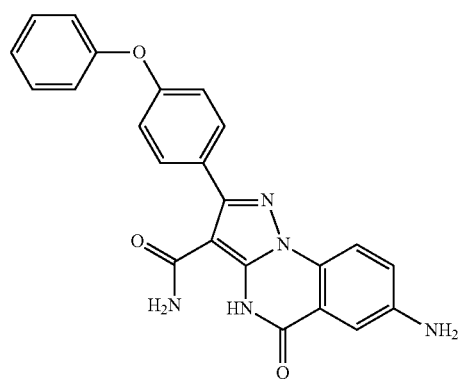 [SMILES: NC(=O)c1c(-c2ccc(Oc3ccccc3)cc2)nn2c1[nH]c(=O)c1cc(N)ccc12]
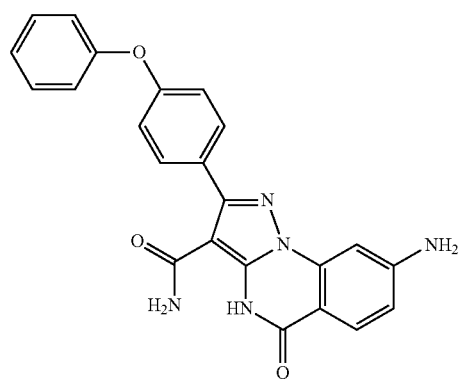 [SMILES: NC(=O)c1c(-c2ccc(Oc3ccccc3)cc2)nn2c1[nH]c(=O)c1ccc(N)cc12]
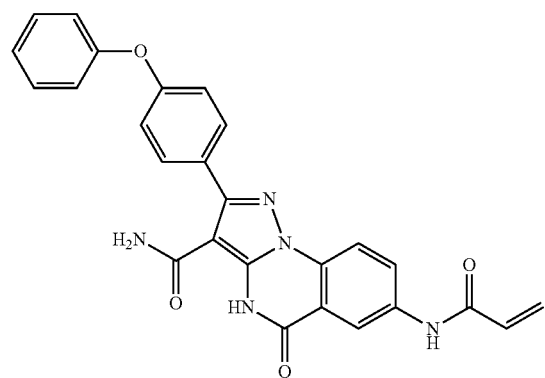 [SMILES: C=CC(=O)Nc1ccc2c(c1)c(=O)[nH]c1c(C(N)=O)c(-c3ccc(Oc4ccccc4)cc3)nn12]

TABLE III-continued
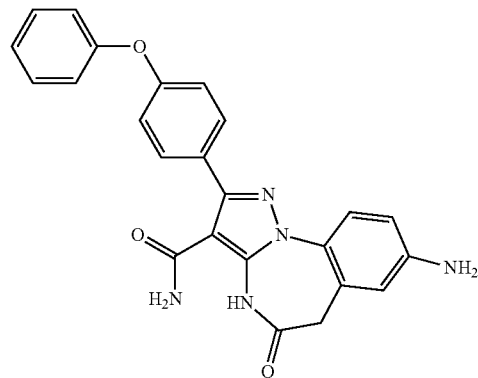 [SMILES: NC(=O)c1c(-c2ccc(Oc3ccccc3)cc2)nn2c1NC(=O)Cc1cc(N)ccc1-2]
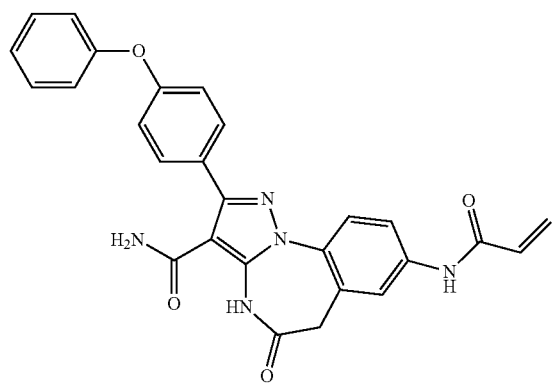 [SMILES: C=CC(=O)Nc1ccc2c(c1)CC(=O)Nc1c(C(N)=O)c(-c3ccc(Oc4ccccc4)cc3)nn1-2]
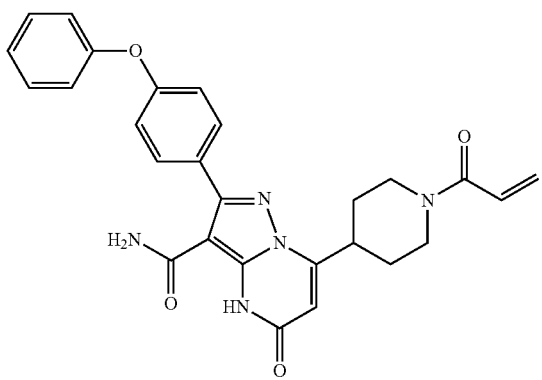 [SMILES: C=CC(=O)N1CCC(c2cc(=O)[nH]c3c(C(N)=O)c(-c4ccc(Oc5ccccc5)cc4)nn23)CC1]
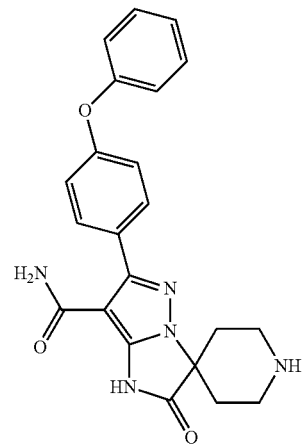 [SMILES: NC(=O)c1c(-c2ccc(Oc3ccccc3)cc2)nn2c1NC(=O)C21CCNCC1]

TABLE III-continued
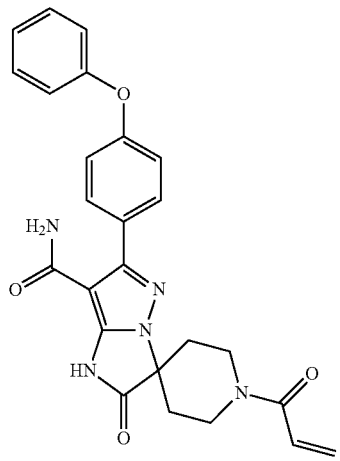 [SMILES: C=CC(=O)N1CCC2(CC1)C(=O)Nc1c(C(N)=O)c(-c3ccc(Oc4ccccc4)cc3)nn12]
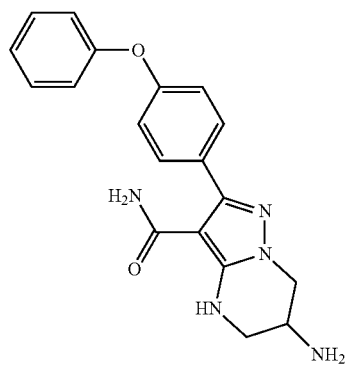 [SMILES: NC(=O)c1c(-c2ccc(Oc3ccccc3)cc2)nn2c1NCC(N)C2]
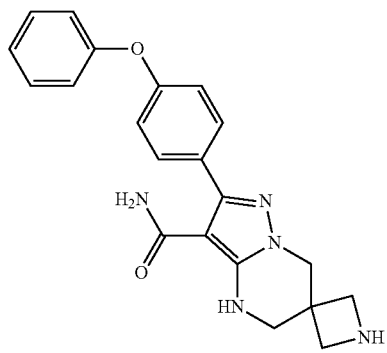 [SMILES: NC(=O)c1c(-c2ccc(Oc3ccccc3)cc2)nn2c1NCC1(CNC1)C2]

TABLE III-continued
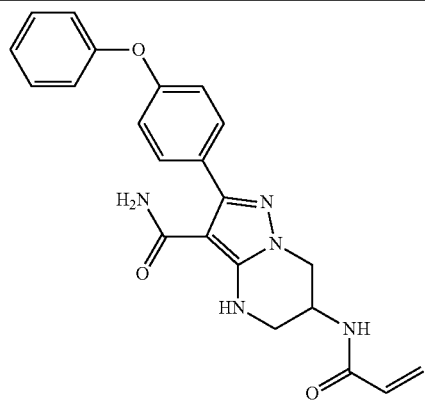
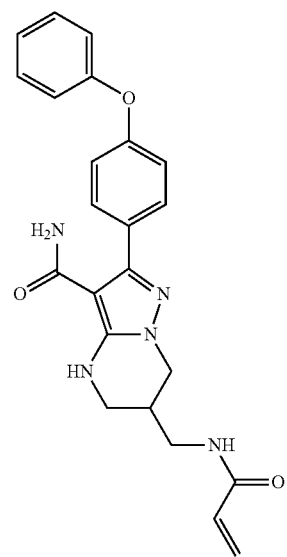 [SMILES: C=CC(=O)NCC1CNc2c(C(N)=O)c(-c3ccc(Oc4ccccc4)cc3)nn2C1]
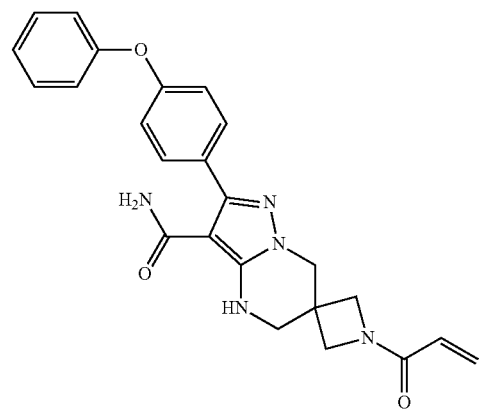 [SMILES: C=CC(=O)N1CC2(CNc3c(C(N)=O)c(-c4ccc(Oc5ccccc5)cc4)nn3C2)C1]

TABLE III-continued
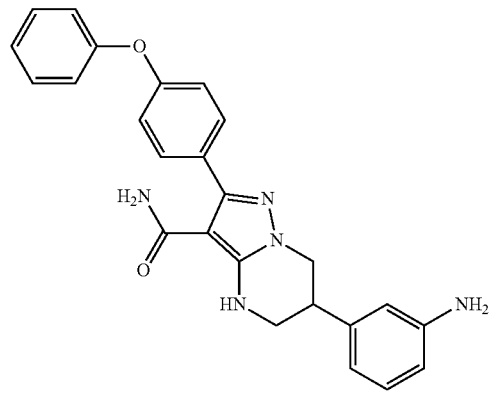 [SMILES: NC(=O)c1c(-c2ccc(Oc3ccccc3)cc2)nn2c1NCC(c1cccc(N)c1)C2]
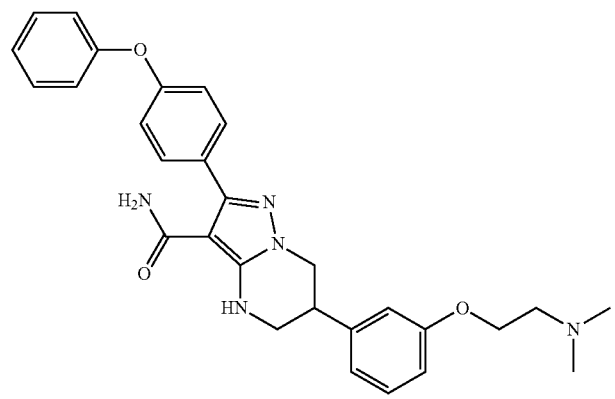 [SMILES: CN(C)CCOc1cccc(C2CNc3c(C(N)=O)c(-c4ccc(Oc5ccccc5)cc4)nn3C2)c1]
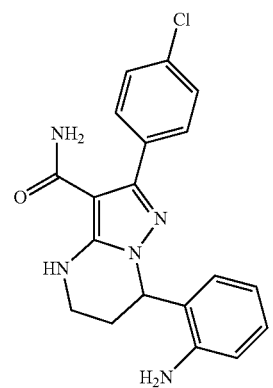 [SMILES: NC(=O)c1c(-c2ccc(Cl)cc2)nn2c1NCCC2c1ccccc1N]
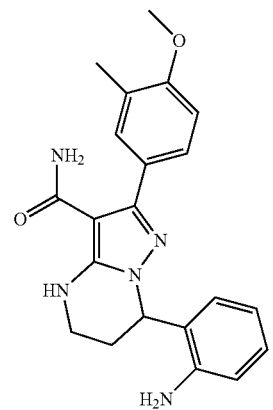 [SMILES: COc1ccc(-c2nn3c(c2C(N)=O)NCCC3c2ccccc2N)cc1C]

TABLE III-continued
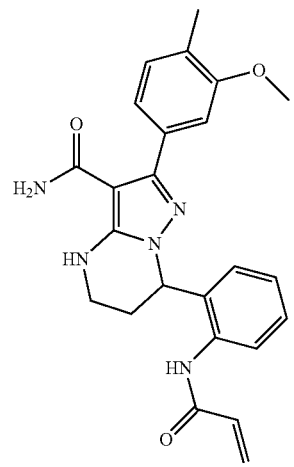 [SMILES: C=CC(=O)Nc1ccccc1C1CCNc2c(C(N)=O)c(-c3ccc(C)c(OC)c3)nn21]
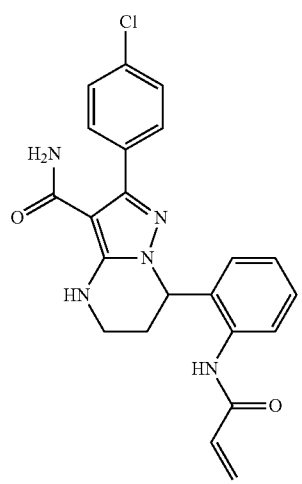 [SMILES: C=CC(=O)Nc1ccccc1C1CCNc2c(C(N)=O)c(-c3ccc(Cl)cc3)nn21]
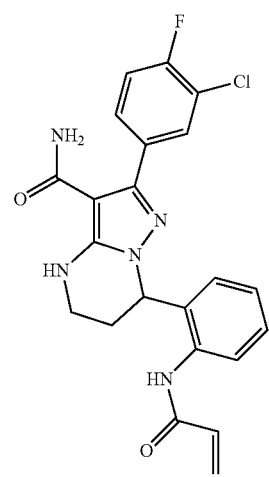 [SMILES: C=CC(=O)Nc1ccccc1C1CCNc2c(C(N)=O)c(-c3ccc(F)c(Cl)c3)nn21]

TABLE III-continued
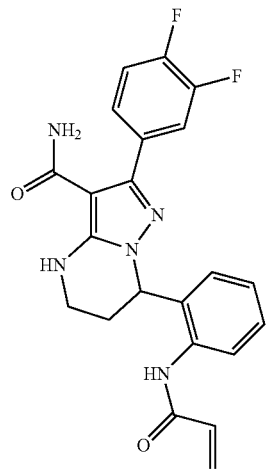 [SMILES: C=CC(=O)Nc1ccccc1C1CCNc2c(C(N)=O)c(-c3ccc(F)c(F)c3)nn21]
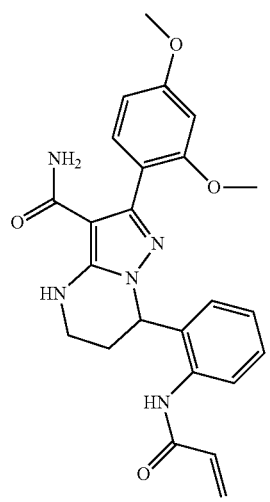 [SMILES: C=CC(=O)Nc1ccccc1C1CCNc2c(C(N)=O)c(-c3ccc(OC)cc3OC)nn21]
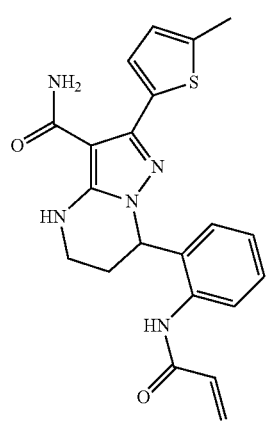 [SMILES: C=CC(=O)Nc1ccccc1C1CCNc2c(C(N)=O)c(-c3ccc(C)s3)nn21]

TABLE III-continued
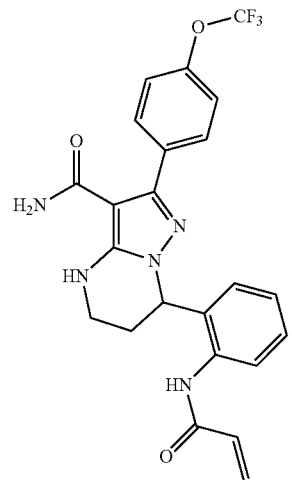 [SMILES: C=CC(=O)Nc1ccccc1C1CCNc2c(C(N)=O)c(-c3ccc(OC(F)(F)F)cc3)nn21]
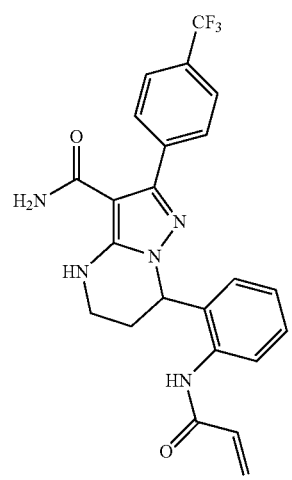 [SMILES: C=CC(=O)Nc1ccccc1C1CCNc2c(C(N)=O)c(-c3ccc(C(F)(F)F)cc3)nn21]
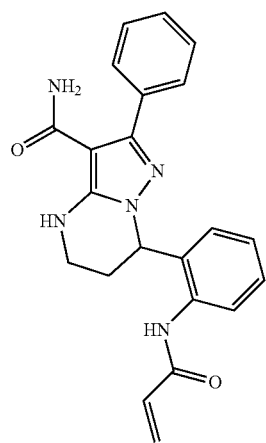 [SMILES: C=CC(=O)Nc1ccccc1C1CCNc2c(C(N)=O)c(-c3ccccc3)nn21]

TABLE III-continued
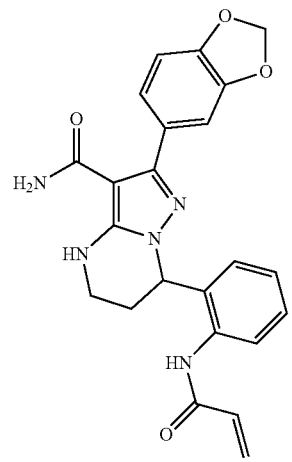 [SMILES: C=CC(=O)Nc1ccccc1C1CCNc2c(C(N)=O)c(-c3ccc4c(c3)OCO4)nn21]
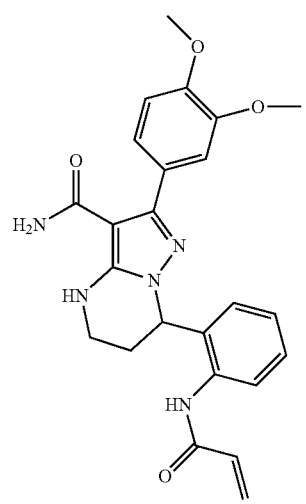 [SMILES: C=CC(=O)Nc1ccccc1C1CCNc2c(C(N)=O)c(-c3ccc(OC)c(OC)c3)nn21]
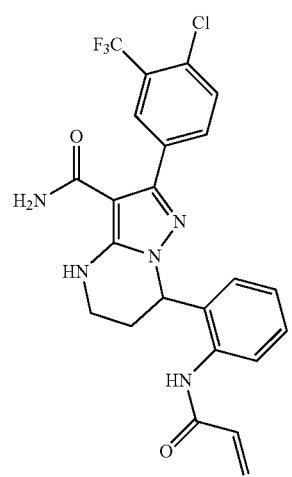 [SMILES: C=CC(=O)Nc1ccccc1C1CCNc2c(C(N)=O)c(-c3ccc(Cl)c(C(F)(F)F)c3)nn21]

TABLE III-continued
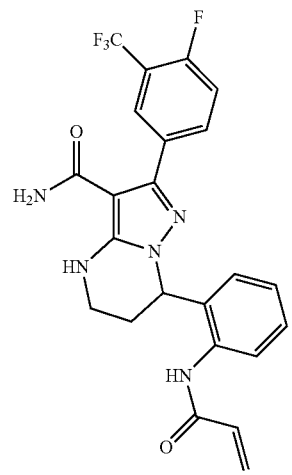 [SMILES: C=CC(=O)Nc1ccccc1C1CCNc2c(C(N)=O)c(-c3ccc(F)c(C(F)(F)F)c3)nn21]
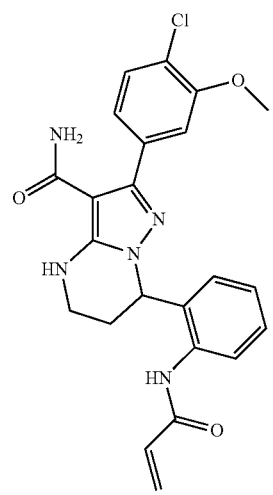
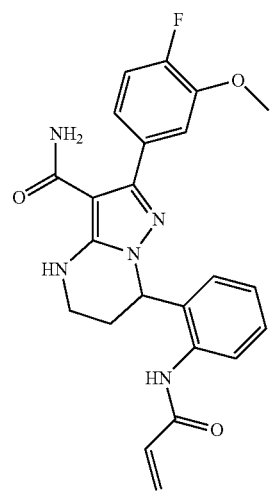 [SMILES: C=CC(=O)Nc1ccccc1C1CCNc2c(C(N)=O)c(-c3ccc(F)c(OC)c3)nn21]

TABLE III-continued
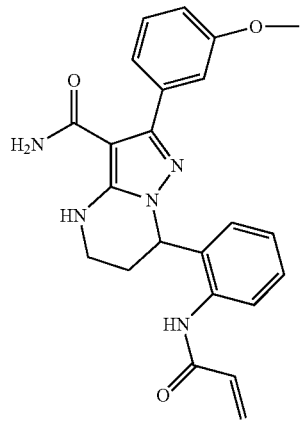 [SMILES: C=CC(=O)Nc1ccccc1C1CCNc2c(C(N)=O)c(-c3cccc(OC)c3)nn21]
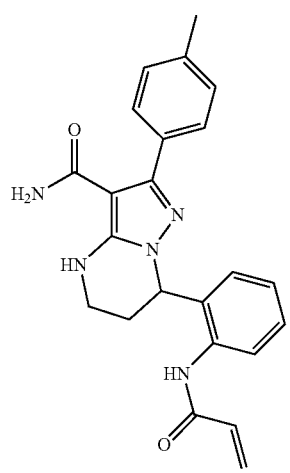
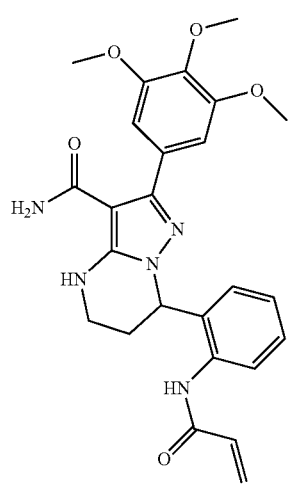 [SMILES: C=CC(=O)Nc1ccccc1C1CCNc2c(C(N)=O)c(-c3cc(OC)c(OC)c(OC)c3)nn21]

TABLE III-continued
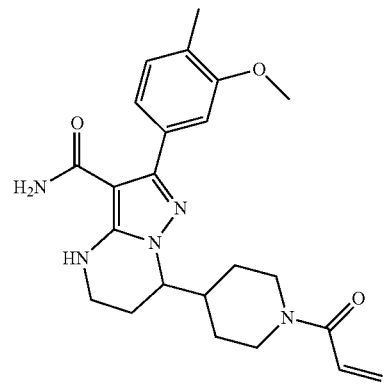 [SMILES: C=CC(=O)N1CCC(C2CCNc3c(C(N)=O)c(-c4ccc(C)c(OC)c4)nn32)CC1]
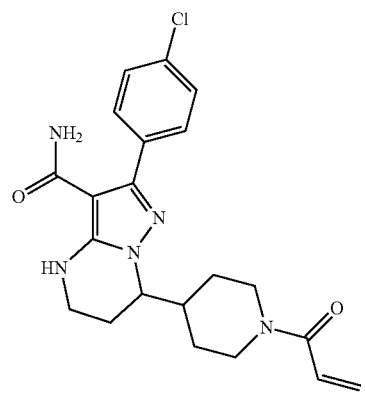 [SMILES: C=CC(=O)N1CCC(C2CCNc3c(C(N)=O)c(-c4ccc(Cl)cc4)nn32)CC1]
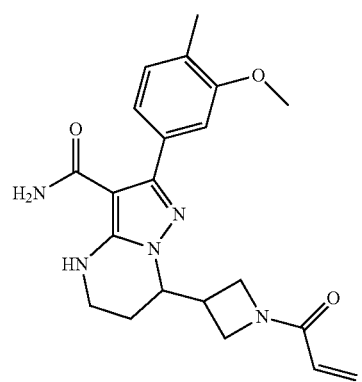 [SMILES: C=CC(=O)N1CC(C2CCNc3c(C(N)=O)c(-c4ccc(C)c(OC)c4)nn32)C1]
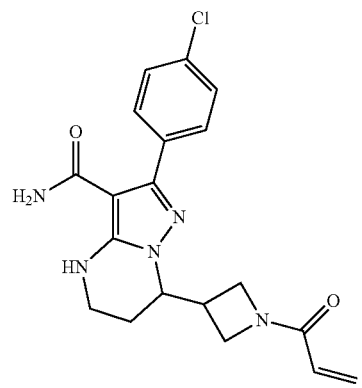 [SMILES: C=CC(=O)N1CC(C2CCNc3c(C(N)=O)c(-c4ccc(Cl)cc4)nn32)C1]

TABLE III-continued
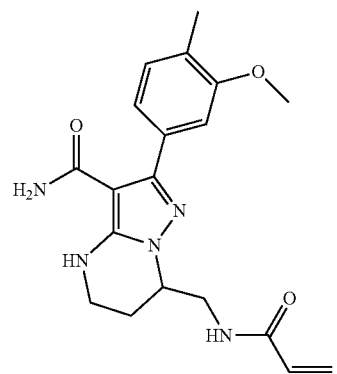 [SMILES: C=CC(=O)NCC1CCNc2c(C(N)=O)c(-c3ccc(C)c(OC)c3)nn21]
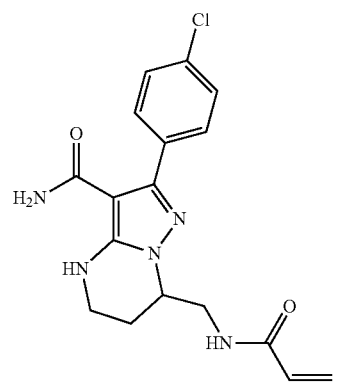 [SMILES: C=CC(=O)NCC1CCNc2c(C(N)=O)c(-c3ccc(Cl)cc3)nn21]
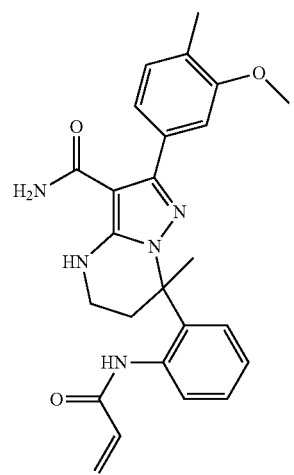 [SMILES: C=CC(=O)Nc1ccccc1C1(C)CCNc2c(C(N)=O)c(-c3ccc(C)c(OC)c3)nn21]

TABLE III-continued
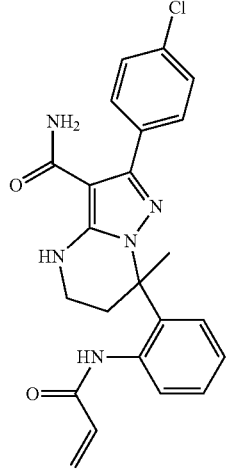 [SMILES: C=CC(=O)Nc1ccccc1C1(C)CCNc2c(C(N)=O)c(-c3ccc(Cl)cc3)nn21]
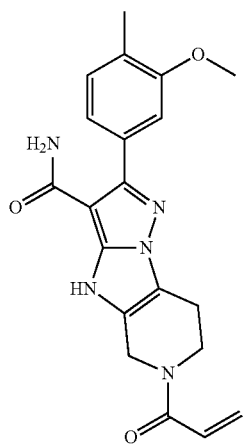 [SMILES: C=CC(=O)N1CCc2c([nH]c3c(C(N)=O)c(-c4ccc(C)c(OC)c4)nn23)C1]
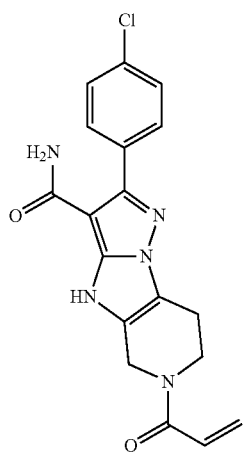 [SMILES: C=CC(=O)N1CCc2c([nH]c3c(C(N)=O)c(-c4ccc(Cl)cc4)nn23)C1]

TABLE III-continued
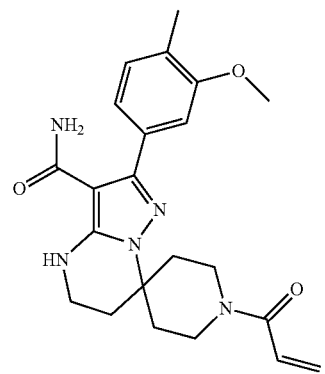 [SMILES: C=CC(=O)N1CCC2(CCNc3c(C(N)=O)c(-c4ccc(C)c(OC)c4)nn32)CC1]
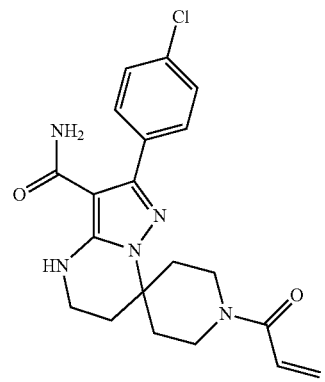 [SMILES: C=CC(=O)N1CCC2(CCNc3c(C(N)=O)c(-c4ccc(Cl)cc4)nn32)CC1]
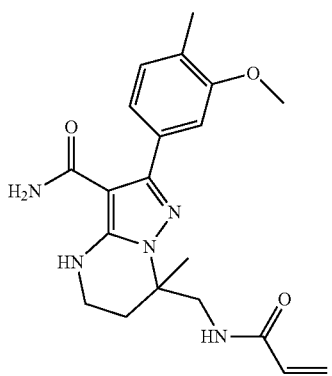 [SMILES: C=CC(=O)NCC1(C)CCNc2c(C(N)=O)c(-c3ccc(C)c(OC)c3)nn21]
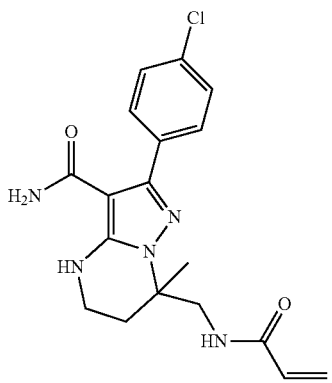 [SMILES: C=CC(=O)NCC1(C)CCNc2c(C(N)=O)c(-c3ccc(Cl)cc3)nn21]

TABLE III-continued
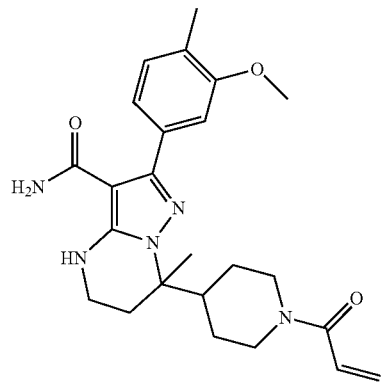 [SMILES: C=CC(=O)N1CCC(C2(C)CCNc3c(C(N)=O)c(-c4ccc(C)c(OC)c4)nn32)CC1]
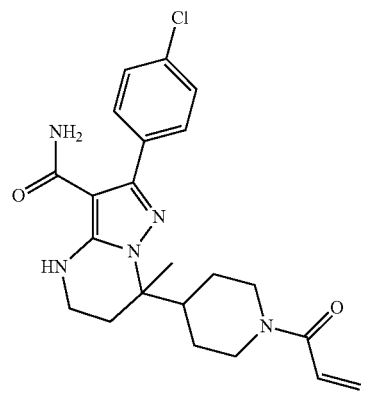 [SMILES: C=CC(=O)N1CCC(C2(C)CCNc3c(C(N)=O)c(-c4ccc(Cl)cc4)nn32)CC1]
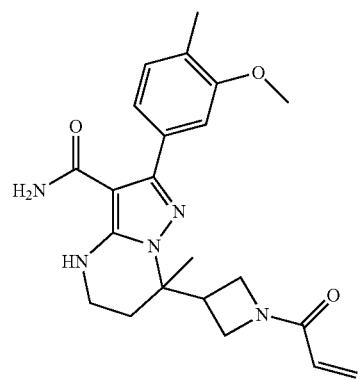 [SMILES: C=CC(=O)N1CC(C2(C)CCNc3c(C(N)=O)c(-c4ccc(C)c(OC)c4)nn32)C1]
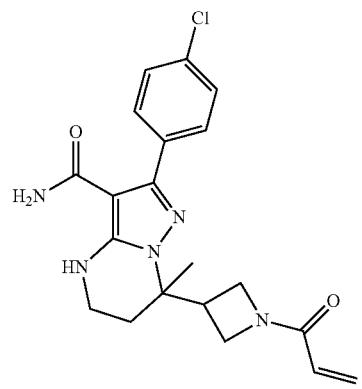 [SMILES: C=CC(=O)N1CC(C2(C)CCNc3c(C(N)=O)c(-c4ccc(Cl)cc4)nn32)C1]

TABLE III-continued
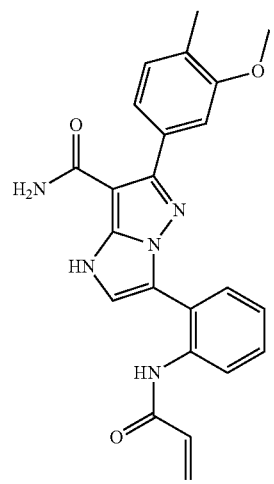 [SMILES: C=CC(=O)Nc1ccccc1-c1c[nH]c2c(C(N)=O)c(-c3ccc(C)c(OC)c3)nn12]
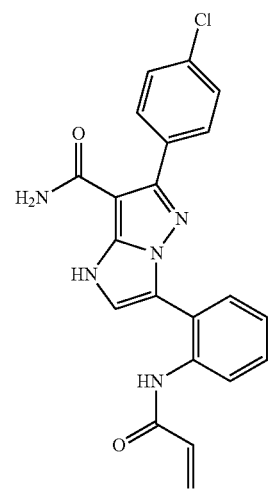 [SMILES: C=CC(=O)Nc1ccccc1-c1c[nH]c2c(C(N)=O)c(-c3ccc(Cl)cc3)nn12]
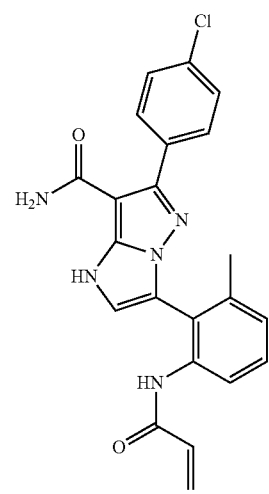 [SMILES: C=CC(=O)Nc1cccc(C)c1-c1c[nH]c2c(C(N)=O)c(-c3ccc(Cl)cc3)nn12]

TABLE III-continued
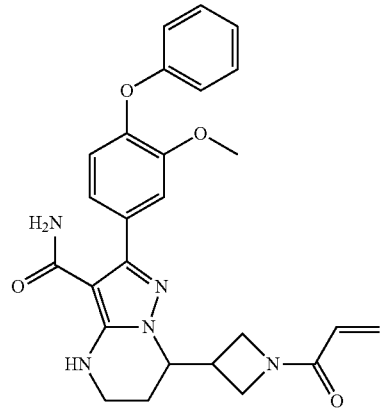 [SMILES: C=CC(=O)N1CC(C2CCNc3c(C(N)=O)c(-c4ccc(Oc5ccccc5)c(OC)c4)nn32)C1]
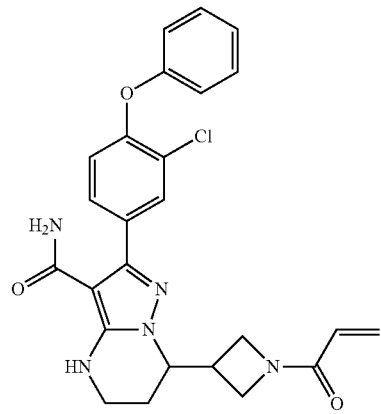 [SMILES: C=CC(=O)N1CC(C2CCNc3c(C(N)=O)c(-c4ccc(Oc5ccccc5)c(Cl)c4)nn32)C1]
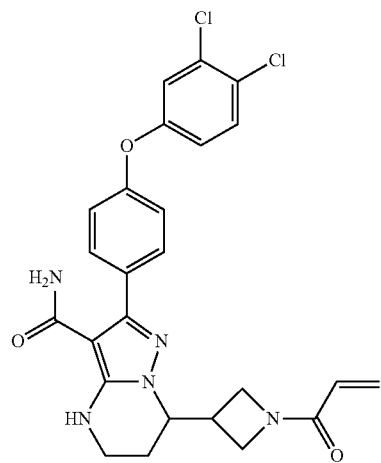 [SMILES: C=CC(=O)N1CC(C2CCNc3c(C(N)=O)c(-c4ccc(Oc5ccc(Cl)c(Cl)c5)cc4)nn32)C1]

TABLE III-continued
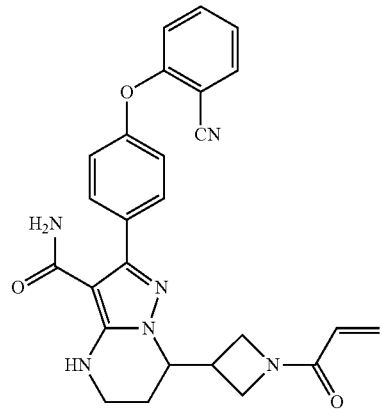 [SMILES: C=CC(=O)N1CC(C2CCNc3c(C(N)=O)c(-c4ccc(Oc5ccccc5C#N)cc4)nn32)C1]
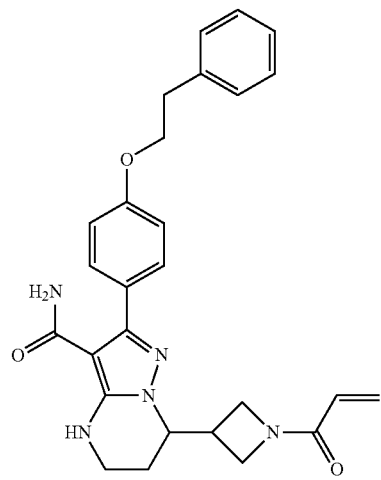 [SMILES: C=CC(=O)N1CC(C2CCNc3c(C(N)=O)c(-c4ccc(OCCc5ccccc5)cc4)nn32)C1]
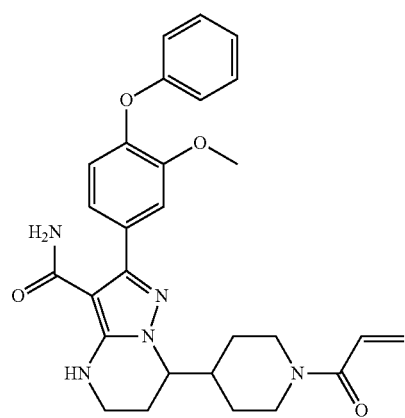 [SMILES: C=CC(=O)N1CCC(C2CCNc3c(C(N)=O)c(-c4ccc(Oc5ccccc5)c(OC)c4)nn32)CC1]

TABLE III-continued
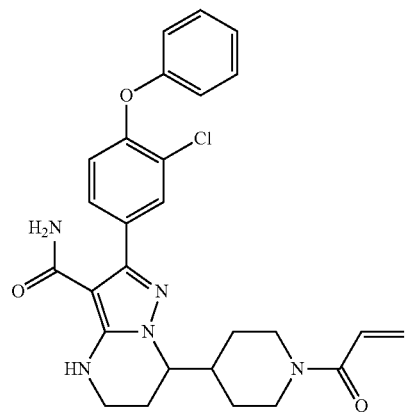 [SMILES: C=CC(=O)N1CCC(C2CCNc3c(C(N)=O)c(-c4ccc(Oc5ccccc5)c(Cl)c4)nn32)CC1]
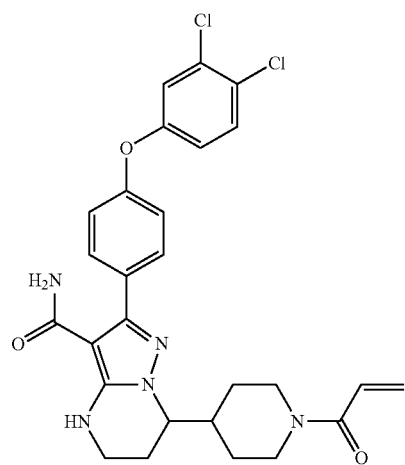 [SMILES: C=CC(=O)N1CCC(C2CCNc3c(C(N)=O)c(-c4ccc(Oc5ccc(Cl)c(Cl)c5)cc4)nn32)CC1]
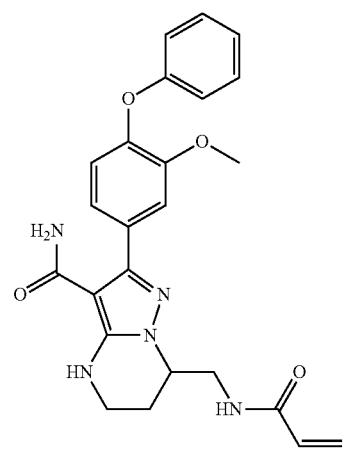 [SMILES: C=CC(=O)NCC1CCNc2c(C(N)=O)c(-c3ccc(Oc4ccccc4)c(OC)c3)nn21]

TABLE III-continued
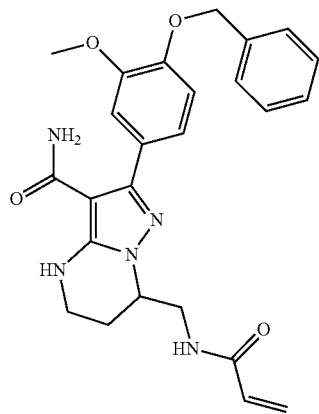 [SMILES: C=CC(=O)NCC1CCNc2c(C(N)=O)c(-c3ccc(OCc4ccccc4)c(OC)c3)nn21]
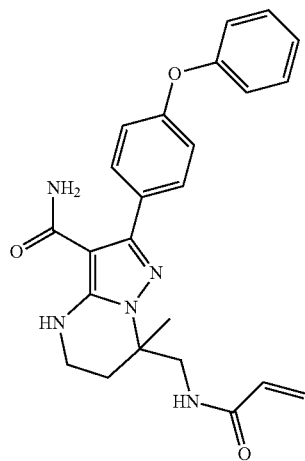 [SMILES: C=CC(=O)NCC1(C)CCNc2c(C(N)=O)c(-c3ccc(Oc4ccccc4)cc3)nn21]
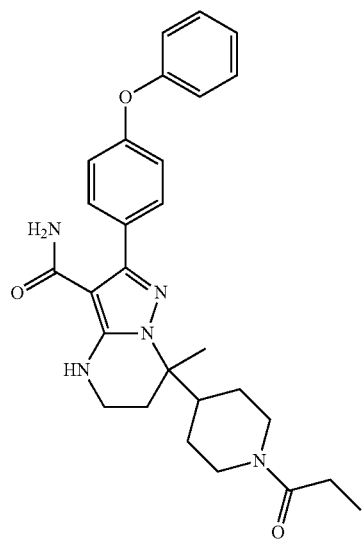 [SMILES: CCC(=O)N1CCC(C2(C)CCNc3c(C(N)=O)c(-c4ccc(Oc5ccccc5)cc4)nn32)CC1]

TABLE III-continued
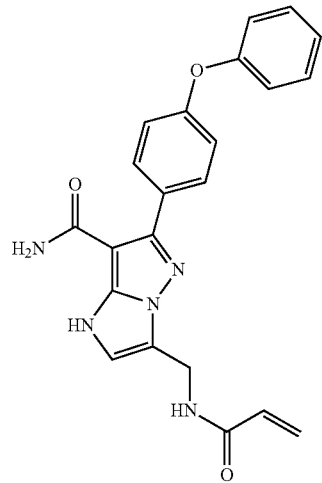 [SMILES: C=CC(=O)NCc1c[nH]c2c(C(N)=O)c(-c3ccc(Oc4ccccc4)cc3)nn12]
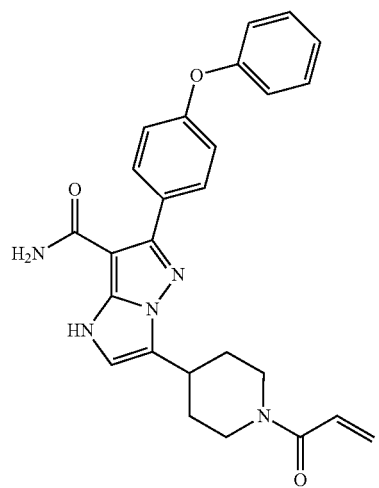 [SMILES: C=CC(=O)N1CCC(c2c[nH]c3c(C(N)=O)c(-c4ccc(Oc5ccccc5)cc4)nn23)CC1]
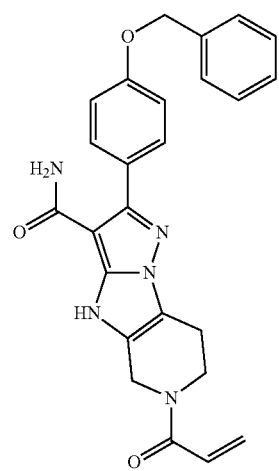 [SMILES: C=CC(=O)N1CCc2c([nH]c3c(C(N)=O)c(-c4ccc(OCc5ccccc5)cc4)nn23)C1]

TABLE III-continued
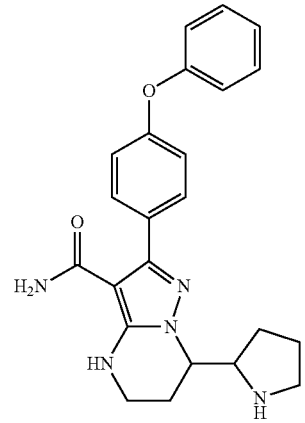 [SMILES: NC(=O)c1c(-c2ccc(Oc3ccccc3)cc2)nn2c1NCCC2C1CCCN1]
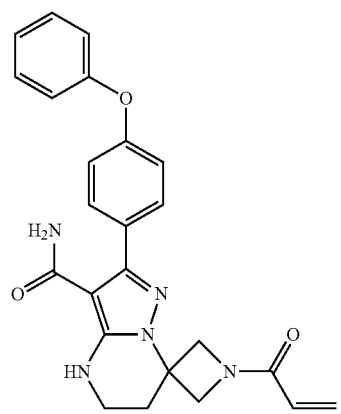 [SMILES: C=CC(=O)N1CC2(CCNc3c(C(N)=O)c(-c4ccc(Oc5ccccc5)cc4)nn32)C1]
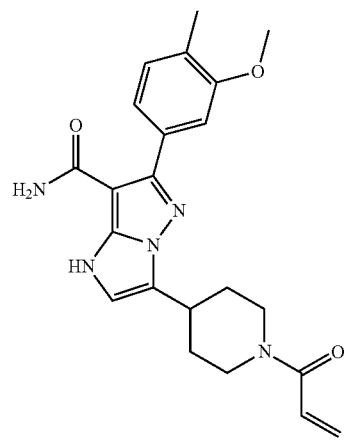 [SMILES: C=CC(=O)N1CCC(c2c[nH]c3c(C(N)=O)c(-c4ccc(C)c(OC)c4)nn23)CC1]

TABLE III-continued
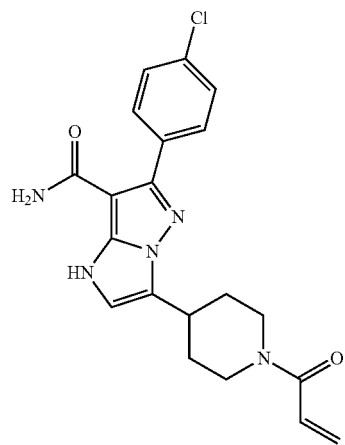 [SMILES: C=CC(=O)N1CCC(c2c[nH]c3c(C(N)=O)c(-c4ccc(Cl)cc4)nn23)CC1]
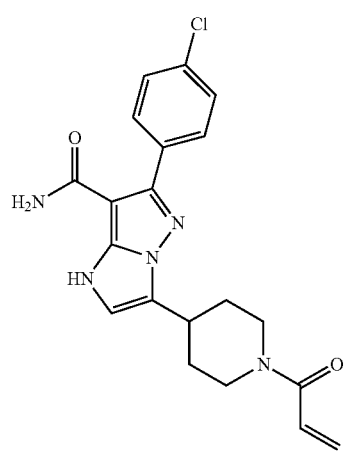 [SMILES: C=CC(=O)N1CCC(c2c[nH]c3c(C(N)=O)c(-c4ccc(Cl)cc4)nn23)CC1]
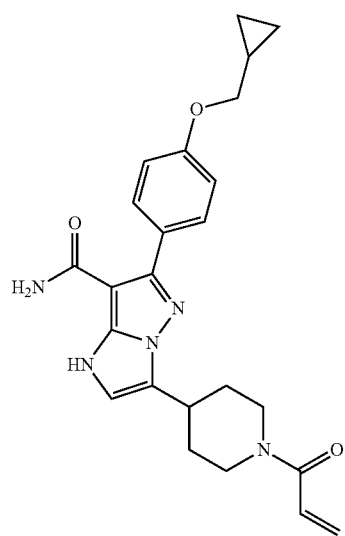 [SMILES: C=CC(=O)N1CCC(c2c[nH]c3c(C(N)=O)c(-c4ccc(OCC5CC5)cc4)nn23)CC1]

TABLE III-continued
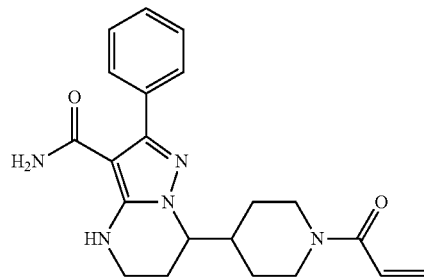 [SMILES: C=CC(=O)N1CCC(C2CCNc3c(C(N)=O)c(-c4ccccc4)nn32)CC1]
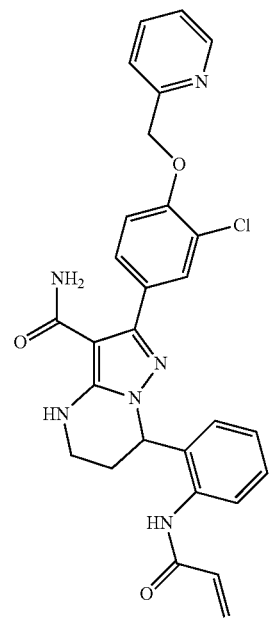 [SMILES: C=CC(=O)Nc1ccccc1C1CCNc2c(C(N)=O)c(-c3ccc(OCc4ccccn4)c(Cl)c3)nn21]
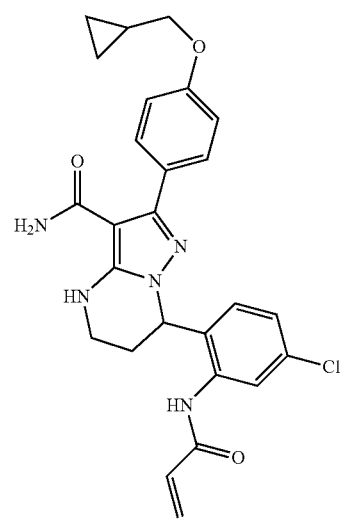 [SMILES: C=CC(=O)Nc1cc(Cl)ccc1C1CCNc2c(C(N)=O)c(-c3ccc(OCC4CC4)cc3)nn21]

TABLE III-continued
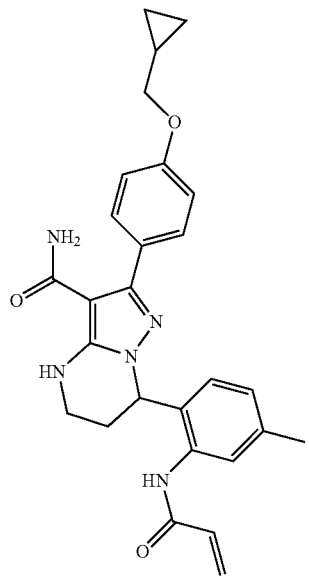 [SMILES: C=CC(=O)Nc1cc(C)ccc1C1CCNc2c(C(N)=O)c(-c3ccc(OCC4CC4)cc3)nn21]
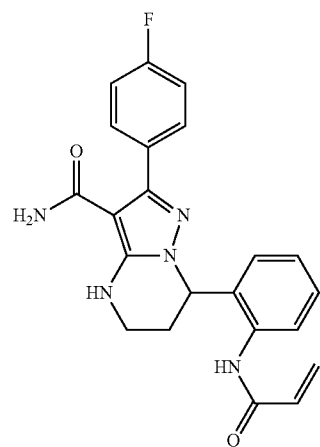 [SMILES: C=CC(=O)Nc1ccccc1C1CCNc2c(C(N)=O)c(-c3ccc(F)cc3)nn21]
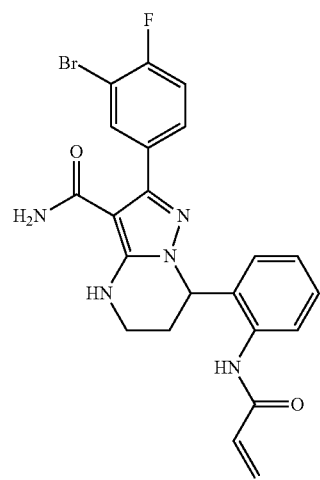 [SMILES: C=CC(=O)Nc1ccccc1C1CCNc2c(C(N)=O)c(-c3ccc(F)c(Br)c3)nn21]

TABLE III-continued
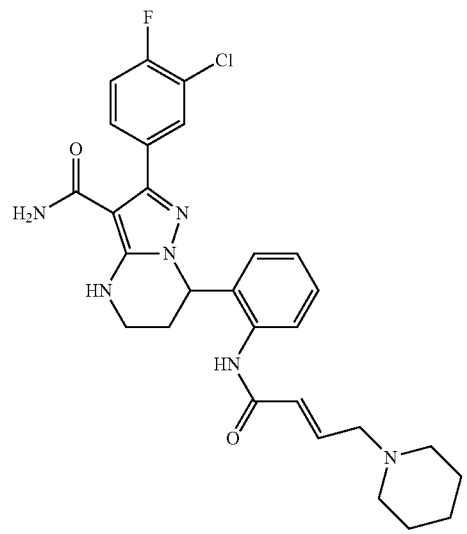 [SMILES: NC(=O)c1c(-c2ccc(F)c(Cl)c2)nn2c1NCCC2c1ccccc1NC(=O)/C=C/CN1CCCCC1]
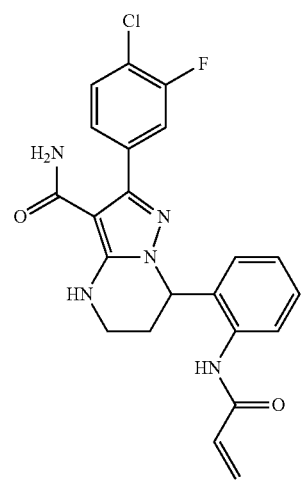 [SMILES: C=CC(=O)Nc1ccccc1C1CCNc2c(C(N)=O)c(-c3ccc(Cl)c(F)c3)nn21]
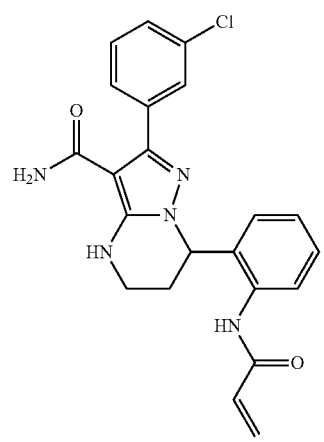 [SMILES: C=CC(=O)Nc1ccccc1C1CCNc2c(C(N)=O)c(-c3cccc(Cl)c3)nn21]

TABLE III-continued
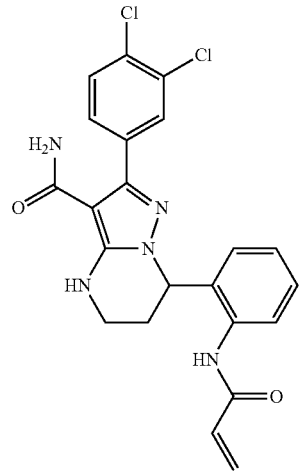
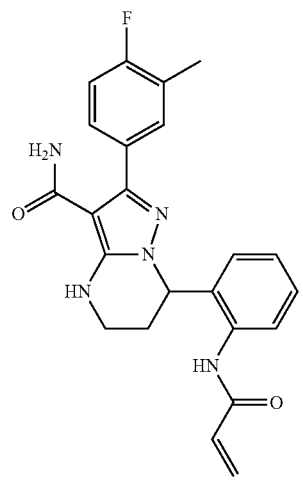 [SMILES: C=CC(=O)Nc1ccccc1C1CCNc2c(C(N)=O)c(-c3ccc(F)c(C)c3)nn21]
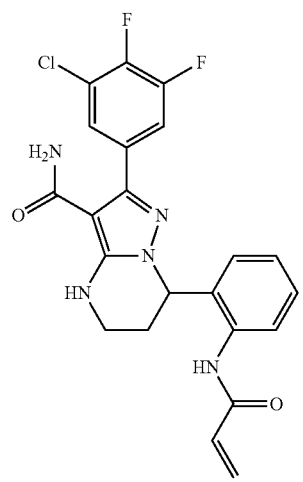 [SMILES: C=CC(=O)Nc1ccccc1C1CCNc2c(C(N)=O)c(-c3cc(F)c(F)c(Cl)c3)nn21]

TABLE III-continued
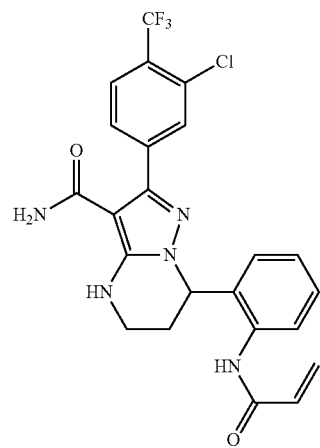 [SMILES: C=CC(=O)Nc1ccccc1C1CCNc2c(C(N)=O)c(-c3ccc(C(F)(F)F)c(Cl)c3)nn21]
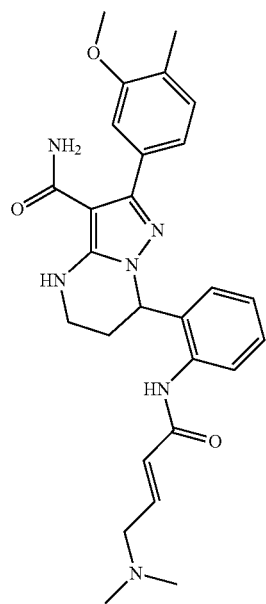 [SMILES: COc1cc(-c2nn3c(c2C(N)=O)NCCC3c2ccccc2NC(=O)/C=C/CN(C)C)ccc1C]
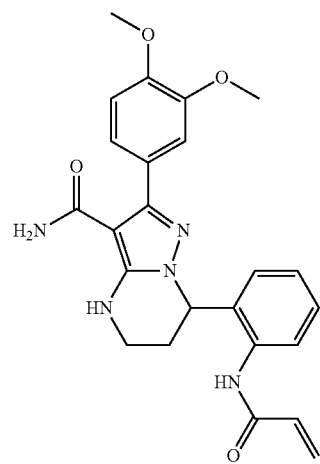 [SMILES: C=CC(=O)Nc1ccccc1C1CCNc2c(C(N)=O)c(-c3ccc(OC)c(OC)c3)nn21]

TABLE III-continued
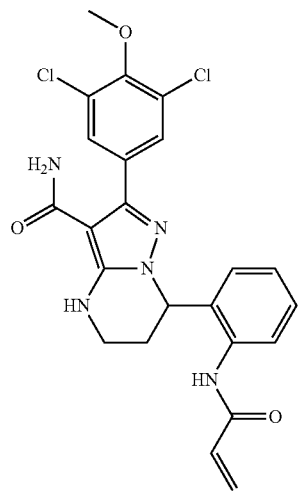 [SMILES: C=CC(=O)Nc1ccccc1C1CCNc2c(C(N)=O)c(-c3cc(Cl)c(OC)c(Cl)c3)nn21]
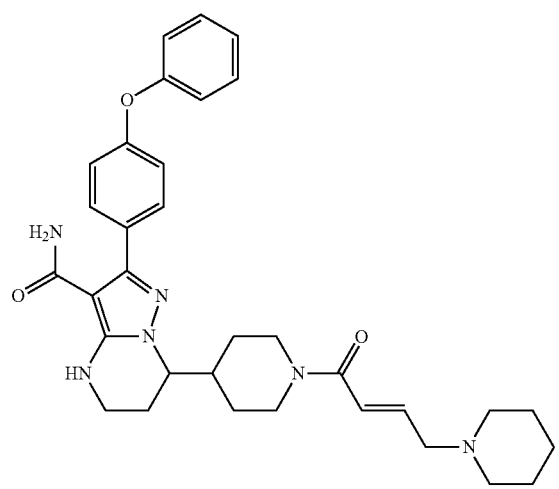 [SMILES: NC(=O)c1c(-c2ccc(Oc3ccccc3)cc2)nn2c1NCCC2C1CCN(C(=O)/C=C/CN2CCCCC2)CC1]
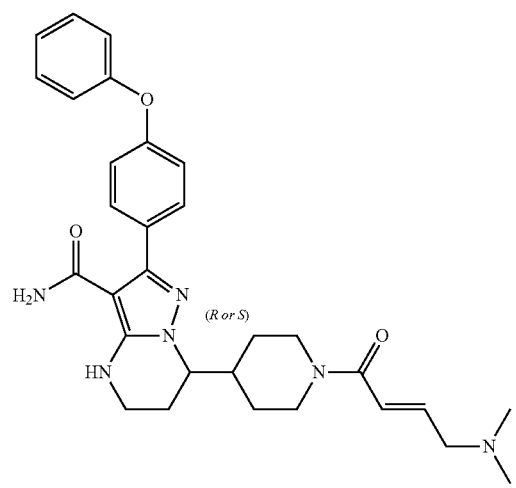 [SMILES: CN(C)C/C=C/C(=O)N1CCC(C2CCNc3c(C(N)=O)c(-c4ccc(Oc5ccccc5)cc4)nn32)CC1]

TABLE III-continued
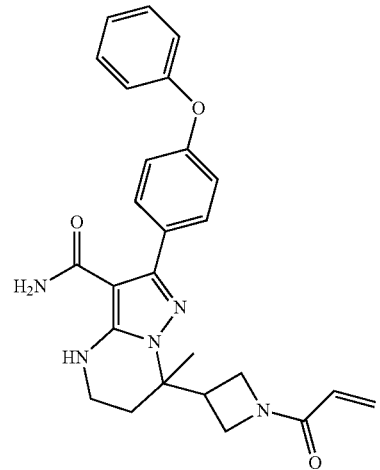 [SMILES: C=CC(=O)N1CC(C2(C)CCNc3c(C(N)=O)c(-c4ccc(Oc5ccccc5)cc4)nn32)C1]
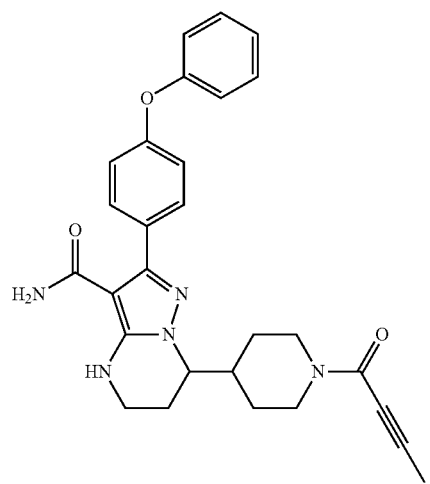 [SMILES: CC#CC(=O)N1CCC(C2CCNc3c(C(N)=O)c(-c4ccc(Oc5ccccc5)cc4)nn32)CC1]
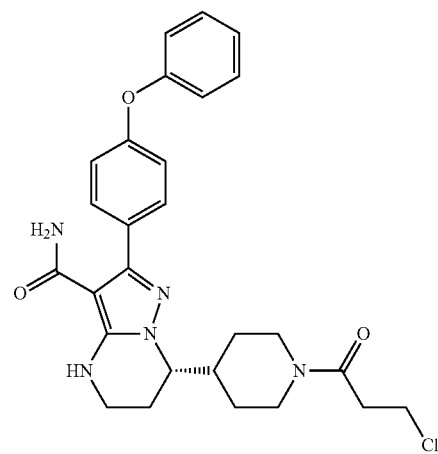 [SMILES: NC(=O)c1c(-c2ccc(Oc3ccccc3)cc2)nn2c1NCC[C@H]2C1CCN(C(=O)CCCl)CC1]

TABLE III-continued
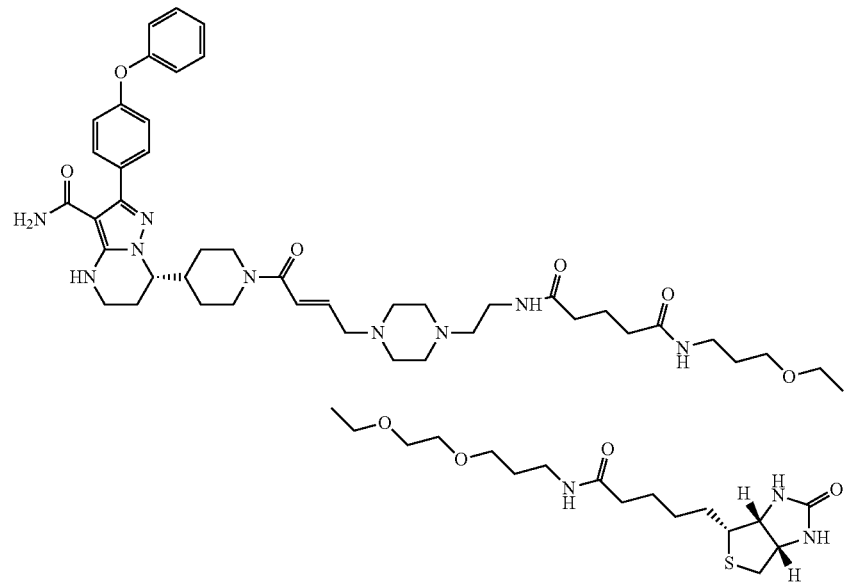
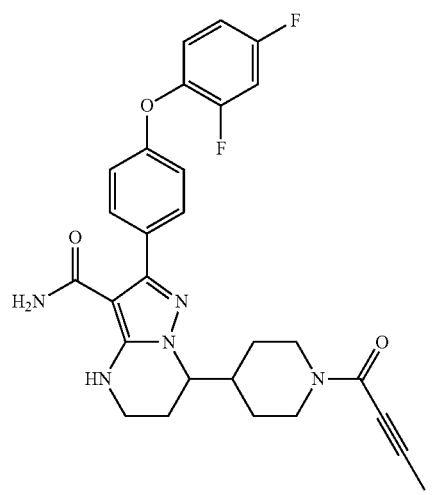 [SMILES: CC#CC(=O)N1CCC(C2CCNc3c(C(N)=O)c(-c4ccc(Oc5ccc(F)cc5F)cc4)nn32)CC1]
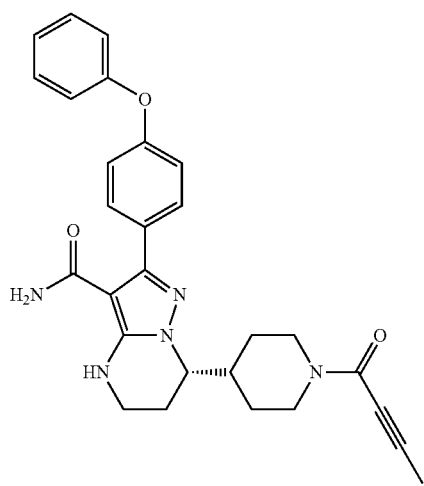 [SMILES: CC#CC(=O)N1CCC([C@@H]2CCNc3c(C(N)=O)c(-c4ccc(Oc5ccccc5)cc4)nn32)CC1]

TABLE III-continued
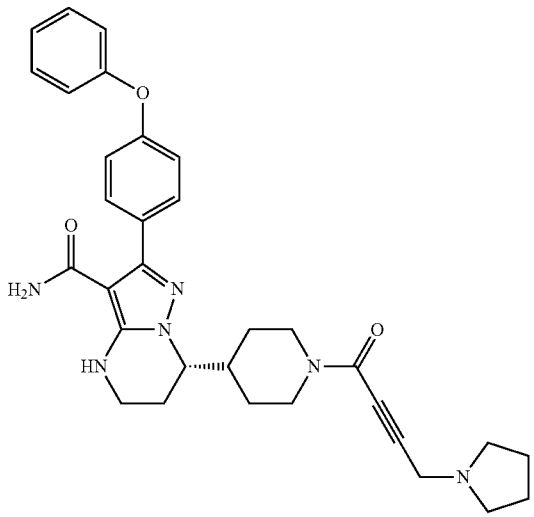 [SMILES: NC(=O)c1c(-c2ccc(Oc3ccccc3)cc2)nn2c1NCC[C@H]2C1CCN(C(=O)C#CCN2CCCC2)CC1]
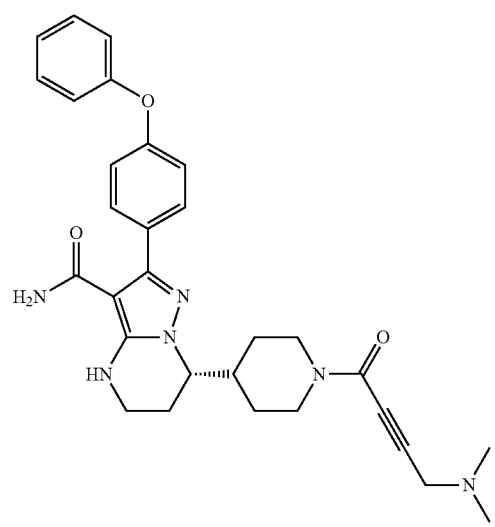 [SMILES: CN(C)CC#CC(=O)N1CCC([C@@H]2CCNc3c(C(N)=O)c(-c4ccc(Oc5ccccc5)cc4)nn32)CC1]
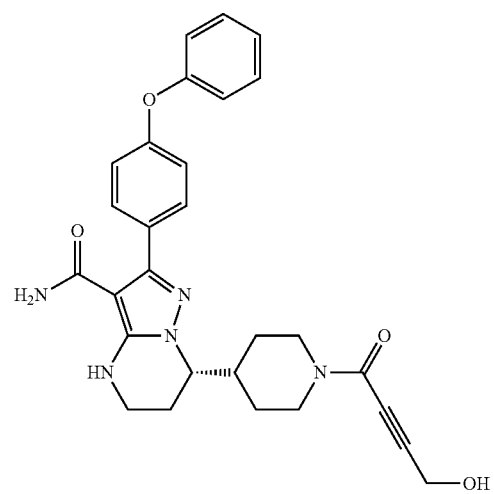 [SMILES: NC(=O)c1c(-c2ccc(Oc3ccccc3)cc2)nn2c1NCC[C@H]2C1CCN(C(=O)C#CCO)CC1]

TABLE III-continued
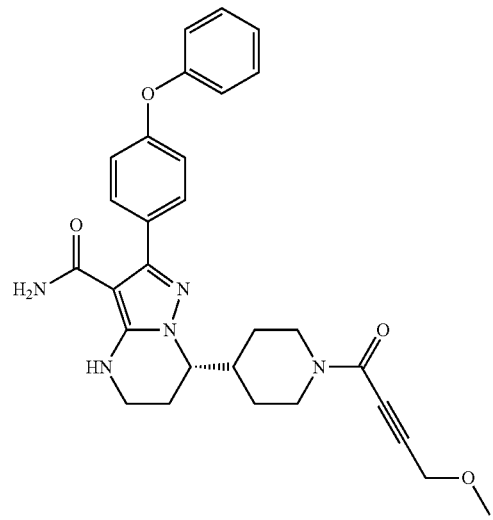 [SMILES: COCC#CC(=O)N1CCC([C@@H]2CCNc3c(C(N)=O)c(-c4ccc(Oc5ccccc5)cc4)nn32)CC1]
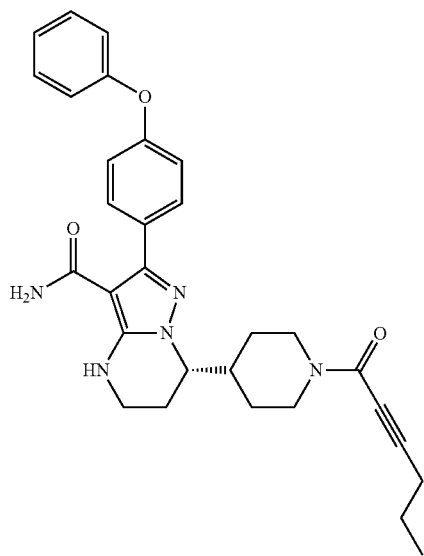 [SMILES: CCCC#CC(=O)N1CCC([C@@H]2CCNc3c(C(N)=O)c(-c4ccc(Oc5ccccc5)cc4)nn32)CC1]
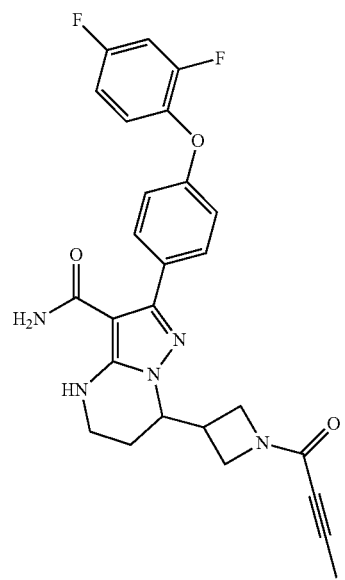 [SMILES: CC#CC(=O)N1CC(C2CCNc3c(C(N)=O)c(-c4ccc(Oc5ccc(F)cc5F)cc4)nn32)C1]

TABLE III-continued
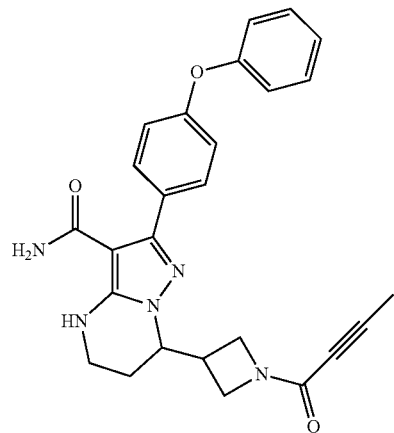 [SMILES: CC#CC(=O)N1CC(C2CCNc3c(C(N)=O)c(-c4ccc(Oc5ccccc5)cc4)nn32)C1]
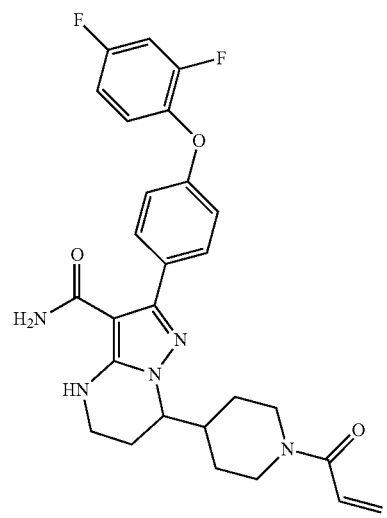 [SMILES: C=CC(=O)N1CCC(C2CCNc3c(C(N)=O)c(-c4ccc(Oc5ccc(F)cc5F)cc4)nn32)CC1]
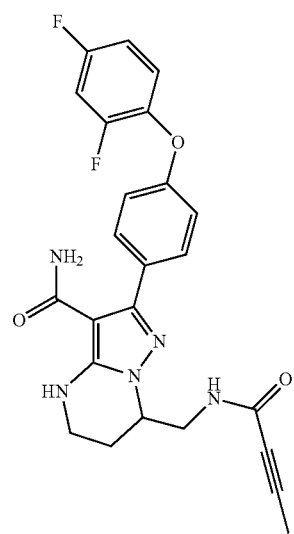 [SMILES: CC#CC(=O)NCC1CCNc2c(C(N)=O)c(-c3ccc(Oc4ccc(F)cc4F)cc3)nn21]

TABLE III-continued
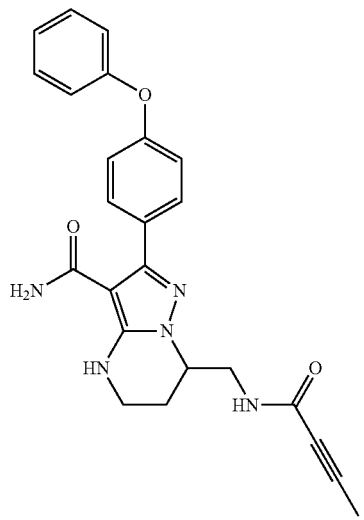 [SMILES: CC#CC(=O)NCC1CCNc2c(C(N)=O)c(-c3ccc(Oc4ccccc4)cc3)nn21]
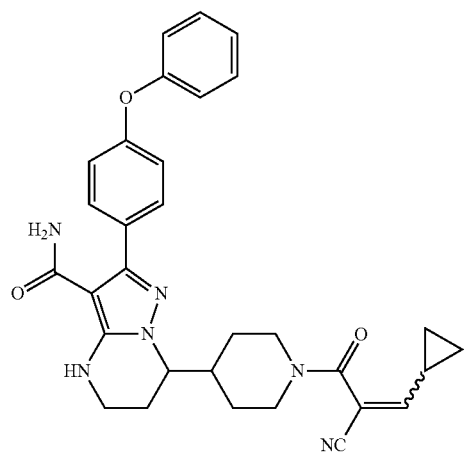 [SMILES: N#CC(=CC1CC1)C(=O)N1CCC(C2CCNc3c(C(N)=O)c(-c4ccc(Oc5ccccc5)cc4)nn32)CC1]
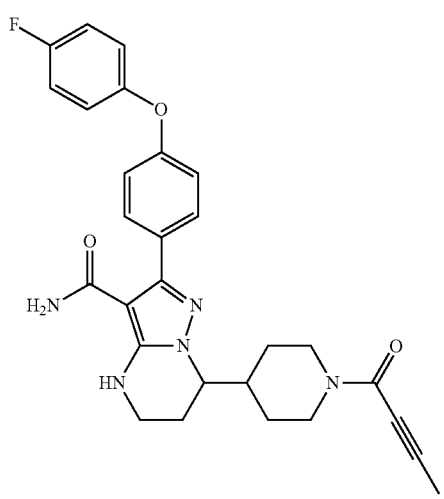 [SMILES: CC#CC(=O)N1CCC(C2CCNc3c(C(N)=O)c(-c4ccc(Oc5ccc(F)cc5)cc4)nn32)CC1]

TABLE III-continued

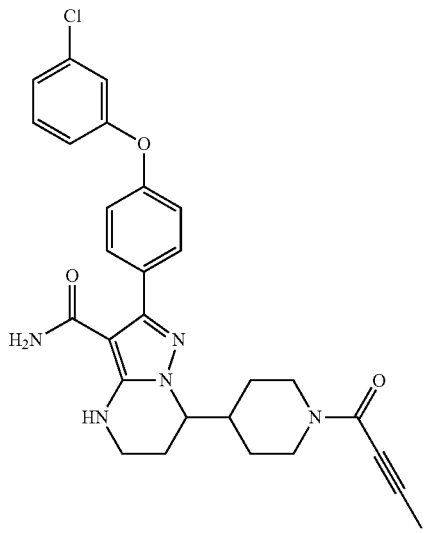 [SMILES: CC#CC(=O)N1CCC(C2CCNc3c(C(N)=O)c(-c4ccc(Oc5cccc(Cl)c5)cc4)nn32)CC1]

What is claimed is:

1. An oral dosage form comprising a pharmaceutically acceptable carrier and a compound of formula I:

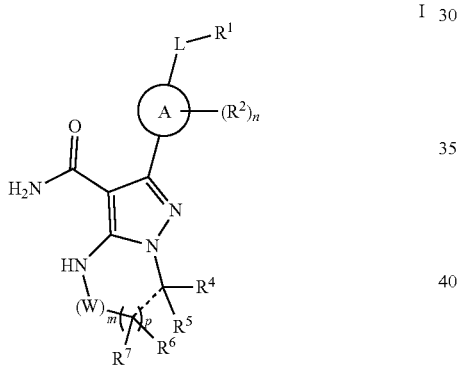

or a pharmaceutically acceptable salt or stereoisomer thereof, wherein:

A is a 5- or 6-membered aromatic ring, wherein the 5- or 6-membered aromatic ring comprises 0, 1, 2, or 3 heteroatoms independently selected from the group consisting of nitrogen, oxygen, and sulfur;

L is a bond, —$CH_2$—, —$NR^{12}$—, —O—, or —S—;

$R^1$ is H, halogen, CN, alkyl, heteroalkyl, alkenyl, alkynyl, $C(NR^{13})NR^{14}R^{15}$, $C(O)R^{13}$, $C(O)NR^{13}R^{14}$, $C(O)OR^{13}$, $NR^{13}R^{14}$, $NR^{13}C(O)R^{14}$, $NR^{13}C(O)NR^{14}R^{15}$, $NR^{13}C(O)OR^{14}$, $NR^{13}S(O)_2R^{14}$, $NR^{13}S(O)_2NR^{14}R^{15}$, $OR^{13}$, $S(O)_2R^{13}$, cycloalkyl, heterocyclyl, aryl, or heteroaryl, wherein the alkyl, alkenyl, alkynyl, cycloalkyl, heterocyclyl, aryl, or heteroaryl is optionally substituted with one or more independently selected $R^{16}$ substituents;

each $R^2$ is independently halogen, CN, alkyl, $C(NR^{13})NR^{14}R^{15}$, $C(O)R^{13}$, $C(O)NR^{13}R^{14}$, $C(O)OR^{13}$, $NR^{13}R^{14}$, $NR^{13}C(O)R^{14}$, $NR^{13}C(O)NR^{14}R^{15}$, $NR^{13}C(O)OR^{14}$, $NR^{13}S(O)_2R^{14}$, $NR^{13}S(O)_2NR^{14}R^{15}$, $OR^{13}$, S-alkyl, or $S(O)_2R^{13}$;

$R^4$ is H, halogen, CN, alkyl, heteroalkyl, alkenyl, alkynyl, $C(NR^{13})NR^{14}R^{15}$, $C(O)R^{13}$, $C(O)NR^{13}R^{14}$, $C(O)OR^{13}$, $NR^{13}R^{14}$, $NR^{13}C(O)R^{14}$, $NR^{13}C(O)NR^{14}R^{15}$, $NR^{13}C(O)OR^{14}$, $NR^{13}S(O)_2R^{14}$, $NR^{13}S(O)_2NR^{14}R^{15}$, $OR^{13}$, $S(O)_2R^{13}$, cycloalkyl, heterocyclyl, aryl, or heteroaryl, wherein the alkyl, alkenyl, alkynyl, cycloalkyl, heterocyclyl, aryl, or heteroaryl is optionally substituted with one or more independently selected $R^{16}$ substituents;

$R^5$ is H, halogen, CN, alkyl, heteroalkyl, alkenyl, alkynyl, $C(NR^{13})NR^{14}R^{15}$, $C(O)R^{13}$, $C(O)NR^{13}R^{14}$, $C(O)OR^{13}$, $NR^{13}R^{14}$, $NR^{13}C(O)R^{14}$, $NR^{13}C(O)NR^{14}R^{15}$, $NR^{13}C(O)OR^{14}$, $NR^{13}S(O)_2R^{14}$, $NR^{13}S(O)_2NR^{14}R^{15}$, $OR^{13}$, $S(O)_2R^{13}$, cycloalkyl, heterocyclyl, aryl, or heteroaryl, wherein the alkyl, alkenyl, alkynyl, cycloalkyl, heterocyclyl, aryl, or heteroaryl is optionally substituted with one or more independently selected $R^{16}$ substituents;

$R^6$ is H, halogen, CN, alkyl, heteroalkyl, alkenyl, alkynyl, $C(NR^{13})NR^{14}R^{15}$, $C(O)R^{13}$, $C(O)NR^{13}R^{14}$, $C(O)OR^{13}$, $NR^{13}R^{14}$, $NR^{13}C(O)R^{14}$, $NR^{13}C(O)NR^{14}R^{15}$, $NR^{13}C(O)OR^{14}$, $NR^{13}S(O)_2R^{14}$, $NR^{13}S(O)_2NR^{14}R^{15}$, $OR^{13}$, $S(O)_2R^{13}$, cycloalkyl, heterocyclyl, aryl, or heteroaryl, wherein the alkyl, alkenyl, alkynyl, cycloalkyl, heterocyclyl, aryl, or heteroaryl is optionally substituted with one or more independently selected $R^{16}$ substituents;

$R^7$ is H, halogen, CN, alkyl, heteroalkyl, alkenyl, alkynyl, $C(NR^{13})NR^{14}R^{15}$, $C(O)R^{13}$, $C(O)NR^{13}R^{14}$, $C(O)OR^{13}$, $NR^{13}R^{14}$, $NR^{13}C(O)R^{14}$, $NR^{13}C(O)NR^{14}R^{15}$, $NR^{13}C(O)OR^{14}$, $NR^{13}S(O)_2R^{14}$, $NR^{13}S(O)_2NR^{14}R^{15}$, $OR^{13}$, $S(O)_2R^{13}$, cycloalkyl, heterocyclyl, aryl, or heteroaryl, wherein the alkyl, alkenyl, alkynyl, cycloalkyl, heterocyclyl, aryl, or heteroaryl is optionally substituted with one or more independently selected $R^{16}$ substituents;

$R^{12}$ is H or lower alkyl;

each $R^{13}$ is independently H, alkyl, heteroalkyl, alkenyl, alkynyl, cycloalkyl, heterocyclyl, aryl, or heteroaryl;

each $R^{14}$ is independently H, alkyl, heteroalkyl, alkenyl, alkynyl, cycloalkyl, heterocyclyl, aryl, or heteroaryl;

each $R^{15}$ is independently H, alkyl, heteroalkyl, alkenyl, alkynyl, cycloalkyl, heterocyclyl, aryl, or heteroaryl; or each $R^{13}$ and $R^{14}$, together with the atom(s) to which they are attached, independently forms a cycloalkyl, heterocyclyl, aryl, or heteroaryl, wherein each cycloalkyl, heterocyclyl, aryl, or heteroaryl is optionally and independently substituted with one or more independently selected $R^{16}$ substituents; or each $R^{14}$ and $R^{15}$, together with the atom(s) to which they are attached, independently forms a cycloalkyl, heterocyclyl, aryl, or heteroaryl, wherein each cycloalkyl, heterocyclyl, aryl, or heteroaryl is optionally and independently substituted with one or more independently selected $R^{16}$ substituents;

each $R^{16}$ is independently halogen, CN, oxo, alkyl, alkenyl, alkynyl, C(NR')NR"R''', C(O)R', C(O)NR'R", C(O)OR', NR'R", NR'C(O)R", NR'C(O)NR'R", NR'C(O)OR", NR'S(O)$_2$R", NR'S(O)$_2$NR"R''', OR', S(O)$_2$R', S(O)$_2$aryl, cycloalkyl, heterocyclyl, aryl, or heteroaryl;

each R' is independently H, halogen, alkyl, alkenyl, alkynyl, cycloalkyl, heterocyclyl, aryl, or heteroaryl;

each R" is independently H, halogen, alkyl, alkenyl, alkynyl, cycloalkyl, heterocyclyl, aryl, or heteroaryl;

each R''' is independently H, halogen, alkyl, alkenyl, alkynyl, cycloalkyl, heterocyclyl, aryl, or heteroaryl; or each R' and R", together with the atom(s) to which they are attached, independently forms a cycloalkyl, heterocyclyl, aryl, or heteroaryl; or each R" and R''', together with the atom(s) to which they are attached, independently forms a cycloalkyl, heterocyclyl, aryl, or heteroaryl;

W is —CH$_2$— or —C(O)—;

m is 1;

n is 0, 1, 2, 3, or 4;

p is 1; and

— is a single or double bond;

wherein each alkyl, alkenyl, and alkynyl of each $R^{16}$, R', R", and R''' is optionally and independently substituted with one or more substituents independently selected from the group consisting of halogen, CN, oxo, C(NR$^a$)NR$^b$R$^c$, C(O)R$^a$, C(O)NR$^a$R$^b$, C(O)OR$^a$, NR$^a$R$^b$, NR$^a$C(O)R$^b$, NR$^a$C(O)NR$^a$R$^b$, NR$^a$C(O)OR$^b$, NR$^a$S(O)$_2$R$^b$, NR$^a$S(O)$_2$NR$^b$R$^c$, OR$^a$, S(O)$_2$R$^a$, S(O)$_2$aryl, cycloalkyl, heterocyclyl, aryl, and heteroaryl;

wherein each cycloalkyl, heterocyclyl, aryl, and heteroaryl of each $R^{16}$, R', R", and R''' is optionally and independently substituted with one or more substituents independently selected from the group consisting of halogen, CN, oxo, alkyl, alkenyl, alkynyl, C(NR$^a$)NR$^b$R$^c$, C(O)R$^a$, C(O)NR$^a$R$^b$, C(O)OR$^a$, NR$^a$R$^b$, NR$^a$C(O)R$^b$, NR$^a$C(O)NR$^a$R$^b$, NR$^a$C(O)OR$^b$, NR$^a$S(O)$_2$R$^b$, NR$^a$S(O)$_2$NR$^b$R$^c$, OR$^a$, S(O)$_2$R$^a$, S(O)$_2$aryl, cycloalkyl, heterocyclyl, aryl, and heteroaryl; and wherein each R$^a$, R$^b$, and R$^c$ is independently H, halogen, alkyl, alkenyl, alkynyl, cycloalkyl, heterocyclyl, aryl, or heteroaryl;

with the proviso that when = is a double bond, $R^5$ and $R^7$ are absent.

2. The oral dosage form of claim 1, wherein the oral dosage form comprises 10 mg to 500 mg of the compound of formula I, or a pharmaceutically acceptable salt or stereoisomer thereof.

3. The oral dosage form of claim 1, wherein the oral dosage form comprises 20 mg to 500 mg of the compound of formula I, or a pharmaceutically acceptable salt or stereoisomer thereof.

4. The oral dosage form of claim 1, wherein the oral dosage form is a tablet or a capsule.

5. The oral dosage form of claim 1, wherein A is phenyl.

6. The oral dosage form of claim 1, wherein L is —O—.

7. The oral dosage form of claim 1, wherein $R^1$ is aryl, wherein the aryl is optionally substituted with one or more independently selected $R^{16}$ substituents.

8. The oral dosage form of claim 1, wherein:

each $R^2$ is independently halogen, lower alkyl, or lower OR$^{13}$; and each $R^{13}$ is independently alkyl.

9. The oral dosage form of claim 1, wherein $R^4$ is

10. The oral dosage form of claim 1, wherein $R^4$ is:

11. The oral dosage form of claim 1, wherein:

$R^5$ is H;

$R^6$ is H; and $R^7$ is H.

12. The oral dosage form of claim 1, wherein W is —CH$_2$—.

13. The oral dosage form of claim 1, wherein — is a single bond.

14. The oral dosage form of claim 1, wherein the compound is of formula II:

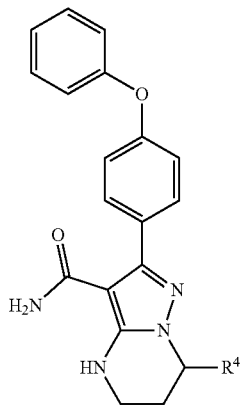

II or a pharmaceutically acceptable salt or stereoisomer thereof.

15. The oral dosage form of claim 1, wherein the compound is:

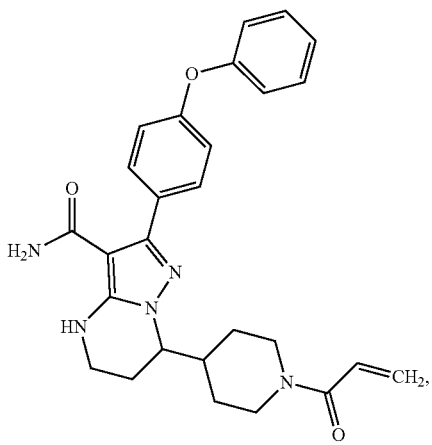 [SMILES: C=CC(=O)N1CCC(C2CCNc3c(C(N)=O)c(-c4ccc(Oc5ccccc5)cc4)nn32)CC1]

or a pharmaceutically acceptable salt or stereoisomer thereof.

16. The oral dosage form of claim 1, wherein the compound, or stereoisomer thereof, is:

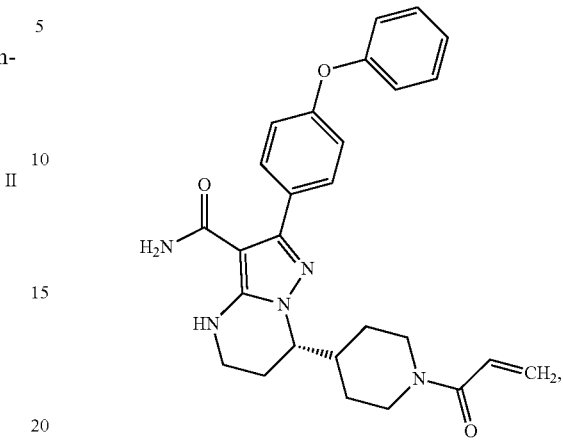

or a pharmaceutically acceptable salt thereof.

17. The oral dosage form of claim 1, wherein the compound, or stereoisomer thereof, is:

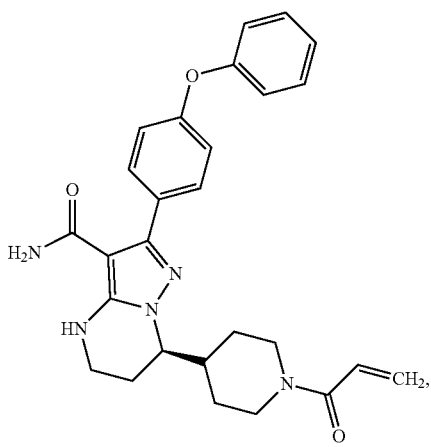 [SMILES: C=CC(=O)N1CCC([C@H]2CCNc3c(C(N)=O)c(-c4ccc(Oc5ccccc5)cc4)nn32)CC1]

or a pharmaceutically acceptable salt thereof.

18. A method for modulating Bruton's tyrosine kinase activity in a subject, comprising administering to the subject in need thereof a therapeutically effective amount of the oral dosage form of claim 1.

19. The method of claim 18, wherein the subject has a B-cell proliferative disorder selected from the group consisting of chronic lymphocytic leukemia, chronic lymphocytic lymphoma, diffuse large B-cell lymphoma, follicular lymphoma, mantle cell lymphoma, and non-Hodgkin's lymphoma.

* * * * *